US009714270B2

(12) United States Patent
Bhandari et al.

(10) Patent No.: US 9,714,270 B2
(45) Date of Patent: Jul. 25, 2017

(54) A4B7 INTEGRIN THIOETHER PEPTIDE ANTAGONISTS

(71) Applicant: Protagonist Therapeutics, Inc., Milpitas, CA (US)

(72) Inventors: Ashok Bhandari, Pleasanton, CA (US); Dinesh V. Patel, Fremont, CA (US); Genet Zemede, San Jose, CA (US); Brian Troy Frederick, Ben Lomond, CA (US); Larry C. Mattheakis, Cupertino, CA (US)

(73) Assignee: Protagonist Therapeutics, Inc., Milpitas, CA (US)

( * ) Notice: Subject to any disclaimer, the term of this patent is extended or adjusted under 35 U.S.C. 154(b) by 0 days.

(21) Appl. No.: 14/714,198

(22) Filed: May 15, 2015

(65) Prior Publication Data

US 2016/0031944 A1 Feb. 4, 2016

Related U.S. Application Data

(60) Provisional application No. 62/058,499, filed on Oct. 1, 2014, provisional application No. 62/058,501, filed on Oct. 1, 2014, provisional application No. 61/994,717, filed on May 16, 2014, provisional application No. 61/994,699, filed on May 16, 2014.

(51) Int. Cl.
C07K 7/00 (2006.01)
C07K 7/56 (2006.01)
C07K 14/705 (2006.01)
C07K 7/08 (2006.01)
A61K 38/12 (2006.01)
A61K 47/48 (2006.01)

(52) U.S. Cl.
CPC .............. *C07K 7/56* (2013.01); *A61K 38/12* (2013.01); *A61K 47/48023* (2013.01); *A61K 47/48061* (2013.01); *A61K 47/48215* (2013.01); *A61K 47/48246* (2013.01); *C07K 7/08* (2013.01); *C07K 14/70546* (2013.01)

(58) Field of Classification Search
CPC .................................. C07K 7/56; C07K 7/00
USPC ................................................. 530/327, 328
See application file for complete search history.

(56) References Cited

U.S. PATENT DOCUMENTS

| 4,684,620 | A | 8/1987 | Hruby et al. |
| 5,990,084 | A | 11/1999 | Richter et al. |
| 6,235,711 | B1 | 5/2001 | Dutta |
| 6,818,617 | B1 | 11/2004 | Niewiarowski |
| 8,536,140 | B2 | 9/2013 | Clandinin et al. |
| 8,796,418 | B2 | 8/2014 | Walensky et al. |
| 8,946,150 | B2 | 2/2015 | Gallagher et al. |
| 8,999,935 | B2 | 4/2015 | Huang |
| 9,169,292 | B2 | 10/2015 | Gallagher et al. |
| 9,273,093 | B2 | 3/2016 | Bhandari et al. |
| 9,518,091 | B2 | 12/2016 | Bhandari et al. |
| 2003/0166514 | A1 | 9/2003 | Jones et al. |
| 2004/0176293 | A1 | 9/2004 | Peterson et al. |
| 2006/0183884 | A1 | 8/2006 | Blaschuk et al. |
| 2007/0032417 | A1 | 2/2007 | Baell |
| 2007/0166308 | A1 | 7/2007 | Pullen et al. |
| 2007/0197430 | A1 | 8/2007 | Baell et al. |
| 2008/0260820 | A1 | 10/2008 | Borrelly et al. |
| 2008/0300180 | A1 | 12/2008 | Schambye et al. |
| 2009/0053819 | A1 | 2/2009 | Seymour et al. |
| 2009/0257952 | A1 | 10/2009 | Cochran et al. |
| 2010/0190710 | A1 | 7/2010 | Chemtob et al. |
| 2010/0196441 | A1 | 8/2010 | Sondermeijer et al. |
| 2010/0272731 | A1 | 10/2010 | Presta et al. |
| 2010/0280098 | A1 | 11/2010 | Juliano et al. |
| 2011/0059087 | A1 | 3/2011 | Lewis et al. |
| 2011/0086024 | A1 | 4/2011 | Arthos et al. |
| 2011/0282029 | A1 | 11/2011 | Holmes et al. |
| 2012/0071422 | A1 | 3/2012 | Gallagher et al. |
| 2013/0029907 | A1 | 1/2013 | Gallagher et al. |
| 2013/0172272 | A1 | 7/2013 | Gallagher et al. |
| 2013/0183755 | A1 | 7/2013 | Gallagher et al. |
| 2013/0310303 | A1 | 11/2013 | Eldar-Finkelman et al. |
| 2014/0193465 | A1 | 7/2014 | Bhandari et al. |
| 2014/0294901 | A1 | 10/2014 | Bhandari et al. |
| 2014/0294902 | A1 | 10/2014 | Bhandari et al. |
| 2014/0336110 | A1 | 11/2014 | Ganz et al. |
| 2015/0056301 | A1 | 2/2015 | Kawabe et al. |
| 2015/0157692 | A1 | 6/2015 | Fu |
| 2016/0145306 | A1 | 5/2016 | Bourne et al. |
| 2016/0152664 | A1 | 6/2016 | Bhandari et al. |
| 2016/0159862 | A1 | 6/2016 | Bhandari et al. |
| 2016/0222076 | A1 | 8/2016 | Smythe et al. |

FOREIGN PATENT DOCUMENTS

| DE | 10107707 A1 | 8/2002 |
| WO | WO 97/25351 A2 | 7/1997 |
| WO | WO 99/26615 A1 | 6/1999 |
| WO | WO 00/18789 A1 | 4/2000 |

(Continued)

OTHER PUBLICATIONS

Clark, Richard J., et al. "Design, synthesis, and characterization of cyclic analogues of the iron regulatory peptide hormone hepcidin." Peptide Science (2013); 100.5: 519-526.
Database EPO Proteins [Online] Dec. 3, 2010 (Dec. 3, 2010), "Sequence from Patent W02010124874." XP002761649, retrieved from EBI accession No. EPOP:HI656765 Database accession No. H1656765, 1 page.
Database USPTO Proteins [Online] Dec. 17, 2012 (Dec. 17, 2012), "Sequence from U.S. Pat. No. 8313950.", XP002761650, retrieved from EBI accession No. USPOP:AGA36544 Database accession No. AGA36544, 1 page.
Desbenoit, N., et al. "Reversible metalation of a bis-disulfide analogue of the Cys*-X-Cys* hepcidin binding site: structural characterisation of the related copper complex]." Annales Pharmaceutiques Francaises (2010); 68(6): 388-396. (with English summary).

(Continued)

Primary Examiner — David Lukton
(74) Attorney, Agent, or Firm — Cooley LLP

(57) ABSTRACT

The invention relates to thioether monomer and dimer peptide molecules which inhibit binding of α4β7 to the mucosal addressing cell adhesion molecule (MAdCAM) in vivo.

22 Claims, 8 Drawing Sheets

(56) References Cited

FOREIGN PATENT DOCUMENTS

| WO | WO 00/18790 A1 | 4/2000 |
|---|---|---|
| WO | WO 00/23474 A1 | 4/2000 |
| WO | WO 00/61580 A1 | 10/2000 |
| WO | WO 01/68586 A2 | 9/2001 |
| WO | WO 03/066678 A1 | 8/2003 |
| WO | WO 2008/097461 A2 | 8/2008 |
| WO | WO 2008/134659 A2 | 11/2008 |
| WO | WO 2008/140602 A2 | 11/2008 |
| WO | WO 2009/002947 A2 | 12/2008 |
| WO | WO 2009/027752 A2 | 3/2009 |
| WO | WO 2011/149942 A2 | 12/2011 |
| WO | WO 2014/059213 A1 | 4/2014 |
| WO | WO 2014/127316 A2 | 8/2014 |
| WO | WO 2014/145561 A2 | 9/2014 |
| WO | WO 2014/165448 A1 | 10/2014 |
| WO | WO 2014/165449 A1 | 10/2014 |
| WO | WO 2015/176035 A1 | 11/2015 |
| WO | WO 2015/200916 A2 | 12/2015 |
| WO | WO 2016/011208 A1 | 1/2016 |

OTHER PUBLICATIONS

Dolain, Christel, et al. "Inducing α-Helices in Short Oligopeptides through Binding by an Artificial Hydrophobic Cavity." Journal of the American Chemical Society (2010); 132.16: 5564-5565.
European Application No. 14763104.8, Extended European Search Report dated Sep. 23, 2016, 10 pages.
European Application No. 14779463.0, Extended European Search Report mailed Nov. 9, 2016, 9 pages.
European Application No. 14780207.8, Partial Supplementary European Search Report mailed Nov. 16, 2016, 6 pages.
U.S. Appl. No. 14/714,198, Office Action mailed Nov. 7, 2016, 6 pages.
U.S. Appl. No. 14/229,784 (abandoned).
U.S. Appl. No. 14/229,799 (abandoned).
U.S. Appl. No. 14/775,469 (pending).
U.S. Appl. No. 14/800,627 (pending).
U.S. Appl. No. 14/872,975 (pending).
U.S. Appl. No. 15/000,923 (pending).
U.S. Appl. No. 15/255,750 (pending).
U.S. Appl. No. 15/258,540 (pending).
U.S. Appl. No. 15/321,124 (pending).
U.S. Appl. No. 14/050,349 (allowed).
U.S. Appl. No. 14/229,784 (pending).
U.S. Appl. No. 14/229,799 (pending).
U.S. Appl. No. 15/046,325 (pending).
U.S. Appl. No. 15/046,325, filed Feb. 17, 2016, Bhandari et al.
PCT/US2015/053603, International Search Report and Written Opinion, mailed Feb. 12, 2016.
Pelton, J.T. et al., "Somatostatin Analogs with Affinity for Opiate Receptors in Rat Brain Binding Assay", Peptides, 6(Suppl 1): 159-163 (1985).
U.S. Appl. No. 14/050,349, Notice of Allowance dated Jan. 12, 2016.
U.S. Appl. No. 15/255,750, filed Sep. 2, 2016, Bhandari et al.
U.S. Appl. No. 15/258,540, filed Sep. 7, 2016, Bhandari et al.
Kitazume and Yamazaki, Experimental Methods in Organic Fluorine Chemistry, Gordon and Breach Science Publishers, 1998, p. 9, 3 pages.
SID 24885660, National Center for Biotechnology Information, PubChem Substance Database; SID=24885660, 5 pages. https://pubchem.ncbi.nlm.nih.gov/substance/24885660, available date: Jul. 16, 2007, accessed Jul. 21, 2016.
U.S. Appl. No. 15/046,325, Office Action mailed Aug. 1, 2016, 13 pages.
U.S. Appl. No. 14/800,627, Office Action mailed Aug. 25, 2016, 11 pages.
Gee et al. "Cyclic Peptides as Non-carboxyl-terminal Ligands of Syntrophin PDZ Domains," The Journal of Biological Chemistry, 273(34): 21980-21987 (1998).
PCT/US2015/053558, International Search Report and Written Opinion, mailed Feb. 19, 2016.
U.S. Appl. No. 15/000,923, filed Jan. 19, 2016, Bhandari et al.
Methods in Molecular Biology, vol. 35 Peptide Synthesis Protocols, Edited by M.W Pennington and B. M. Dunn Copyright, 1994 Humana Press Inc, Totowa, NJ, pp. 201-241.
Xie, Youmei et al., "Nerve Growth Factor (NGF) Loop 4 Dimeric Mimetics Activate ERK and AKT and Promote NGF-like Neurotrophic Effects", The Journal of Biological Chemistry, 275(38): 29868-29874 (2000).
U.S. Appl. No. 14/229,799, Office Action dated Mar. 4, 2016.
U.S. Appl. No. 14/229,784, Office Action dated Mar. 8, 2016.
European Application No. 13845982.1, Extended European Search Report dared May 13, 2016.
U.S. Appl. No. 15/321,124, filed Dec. 21, 2016, Bourne et al.
Ley, Klaus, et al. "Integrin-based therapeutics: biological basis, clinical use and new drugs." Nature Reviews Drug Discovery (2016); 15.3: 173-183.
PCT/US2015/038370, International Preliminary Report on Patentability, mailed Dec. 27, 2016, 4 pages.
PCT/US2015/031243, International Preliminary Report on Patentability, mailed Nov. 22, 2016, 8 pages.
PCT/US2015/040658, International Preliminary Report on Patentability, mailed Jan. 17, 2017, 5 pages.
PCT/US2016/042680, International Search Report and Written Opinion, mailed Jan. 13, 2017, 12 pages.
Shahidi, Neal, et al. "Vedolizumab for the treatment of ulcerative colitis." Expert Opinion on Biological Therapy (2016); 16.1 : 129-135.
U.S. Appl. No. 14/872,975, Office Action mailed Dec. 27, 2016, 14 pages.
U.S. Appl. No. 14/775,469, filed Mar. 17, 2014, Smythe et al.
U.S. Appl. No. 14/800,627, filed Jul. 15, 2015, Bourne et al.
U.S. Appl. No. 14/872,975, filed Oct. 1, 2015, Bhandari et al.
Chatterjee, J. et al., "N-Methylation of Peptides: a New Perspective in Medicinal Chemistry", Accounts of Chemical Research, 41(10): 1331-1342 (2008).
Definition of Isostere, Medical Definition and More from Merriam-Webster Dictionary, 3 pages, www.merriam-webster.com/medical/isostere accessed on Feb. 5, 2015.
Dubree, Nathan J.P. et al., "Selective a4B7 Integrin Antagonists and Their Potential as Antiinflammatory Agents", J. Med. Chem., 45: 3451-3457 (2002).
Dutta, Anand S., "Potent Cyclic Monomeric and Dimeric Peptide Inhibitors of VLA-4 (a4b1 Integrin)-Mediated Cell Adhesion Based on the Ile-Leu-Asp-Val Tetrapeptide", J. Peptide Sci., 6:321-341 (2000).
Janssen et al., "Comparison of a Monomeric and Dimeric Radiolabeled RGD-Peptide for Tumor Targeting", Cancer Biotherapy and Radiopharmaceuticals, 17(6): 641-646 (2002).
Haanstra, et al., "Antagonizing the a4B1 Integrin, but no a4B7, Inhibits Leukocytic Infiltration of the Central Nervous System in Rhesus Monkey Experimental Autoimmune Encephalomyelitis", Journal of Immunology, 90(5): 1961-1973 (2013).
Kelleman, A. et al., "Incorporation of thioether building blocks into an $α_vβ_3$-specific RGD peptide: Synthesis and biological activity", Biopolymers (Peptide Science), 71(6): 686-695 (2003).
Kluskens, L.D. et al., "Angiotensin-(1-7) with Thioether Bridge: An Angiotensin-Converting Enzyme-Resistant, Potent Angiotensin-(1-7) Analog", The Journal of Pharmacology and Experimental Therapeutics, 328(3): 849-855 (2009).
Liu, Shuang, "Radiolabeled Multimeric Cyclic RGD Peptides as Integrin avB3 Targeted Radiotracers for Tumor Imaging", School of Health Science, Purdue University, Molecular Pharmaceuticals, 3(5): 472-487 (2006).
PCT/US2013/064439, International Search Report and Written Opinion, mailed Jan. 24, 2014.
PCT/US2013/064439, International Preliminary Report on Patentability, dated Apr. 14, 2015.
PCT/US2014/030352, International Search Report and Written Opinion, mailed Nov. 28, 2014.
PCT/US2014/030352, International Preliminary Report on Patentability, dated Sep. 15, 2015.

(56) References Cited

OTHER PUBLICATIONS

PCT/US2014/032391, International Search Report, mailed Aug. 7, 2014.
PCT/US2014/032391, Written Opinion, mailed Aug. 7, 2014.
PCT/US2014/032391, International Preliminary Report on Patentability, dated Oct. 6, 2015.
PCT/US2014/032392, International Search Report and Written Opinion, mailed Sep. 15, 2014.
PCT/US2014/032392, International Preliminary Report on Patentability, dated Oct. 6, 2015.
PCT/US2015/031243, International Search Report and Written Opinion, mailed Aug. 5, 2015.
PCT/US2015/038370, International Search Report and Written Opinion, mailed Sep. 14, 2015.
PCT/US2015/040658, International Search Report and Written Opinion, mailed Oct. 28, 2015.
Soler-Ferran and Briskin, "Integrin $\alpha_4\beta_7$ Antagonists: Activities, Mechanisms of Action and Therapeutic Prospects", Current Immunology Reviews, 8(2): 118-134 (2012).
Temming, K. et al. "Rational Design of RGD-Albumin Conjugates for targeted Delivery of the VEGF-R Kinase Inhibitor PTK787 to Angiogenic Endothelium", ChemMedChem, 1: pp. 1200-1203 (2006).
Thermo Electron Corporation, Technical Information, "N-terminal and C-terminal Amidation of Peptides", 2 pages (2004).
Thumshirn, G. et al., "Multimeric Cyclic RGD Peptides as Potential Tools for Tumor Targeting: Solid Phase Peptide Synthesis and Chemoselective Oxime Ligation", Chem. Eur. J., 9: 2717-2725 (2003).
Waitemata District Health Board, "Crushing Guide for Oral Medication in Residential Aged Care", 2 pages (2011).
Yu and Gallagher, "A Naturally Occurring, Soluble Antagonist of Human IL-23 Inhibits the Development and In Vitro Function of Human Th17 Cells", The Journal of Immunology, 185: 7302-7308 (2010).
U.S. Appl. No. 14/050,349, Non-Final Office Action dated Feb. 27, 2015.
U.S. Appl. No. 14/229,799, Non-Final Office Action dated Jul. 24, 2015.
U.S. Appl. No. 14/229,784, Non-Final Office Action dated Aug. 13, 2015.
U.S. Appl. No. 14/050,349, Final Office Action dated Sep. 9, 2015.

| SEQ ID | Xaa¹ | Xaa² | Xaa³ | Xaa⁴ | Xaa⁵ | Xaa⁶ | Xaa⁷ | Xaa⁸ | Xaa⁹ | Xaa¹⁰ | Xaa¹¹ | Linker |
|---|---|---|---|---|---|---|---|---|---|---|---|---|
| 151 | 2-Me-Benzoyl | N-Me-R | S | D | T | L | Pen | W | b-H-E | k | NH₂)₂ | DIG |
| 152 | 2-Me-Benzoyl | N-Me-R | S | D | T | L | Pen | W | E | N-Me-k | NH₂)₂ | DIG |
| 228 | 2-Me-Benzoyl | N-Me-R | S | D | T | Nle | Pen | W | E | N-Me-k | NH₂)₂ | DIG |
| 229 | 2-Me-Benzoyl | N-Me-R | S | D | T | Nle | Pen | F | e | N-Me-k | NH₂)₂ | DIG |
| 158 | 2-Me-Benzoyl | N-Me-R | S | D | T | L | Pen | 1-Nal | e | k | NH₂)₂ | DIG |
| 159 | 2-Me-Benzoyl | N-Me-R | S | D | T | L | Pen | 2-Nal | e | k | NH₂)₂ | DIG |
| 164 | 2-Me-Benzoyl | N-Me-R | S | D | T | L | Pen | F | b-H-E | k | NH₂)₂ | DIG |
| 165 | 2-Me-Benzoyl | N-Me-R | S | D | T | L | Pen | Y | b-H-E | k | NH₂)₂ | DIG |
| 169 | 2-Me-Benzoyl | N-Me-R | S | D | T | L | Pen | Y | e | k | NH₂)₂ | DIG |

Thioether bond between Xaa¹ and Xaa⁷

Representative peptides with IC50 values <25nM in α4β7 ELISA and in Cell adhesion assay and with stability of >180min (half-life) in SIF (simulated intestinal fluids)

*FIG. 6*

| SEQ ID | Xaa¹ | Xaa² | Xaa³ | Xaa⁴ | Xaa⁵ | Xaa⁶ | Xaa⁷ | Xaa⁸ | Xaa⁹ | Xaa¹⁰ | Xaa¹¹ |
|---|---|---|---|---|---|---|---|---|---|---|---|
| 55 | 2-Me-Benzoyl | N-Me-R | S | D | T | L | C | W | E | k | NH₂ |
| 225 | 2-Me-Benzoyl | N-Me-R | S | D | T | Nle | Pen | F | e | N-Me-k | NH₂ |
| 69 | 2-Me-Benzoyl | N-Me-R | S | D | T | L | Pen | 1-Nal | e | N-Me-K | NH₂ |
| 82 | 2-Me-Benzoyl | N-Me-R | S | D | T | L | Pen | W | e | k(PEG8) | NH₂ |
| 89 | 2-Me-Benzoyl | N-Me-R | S | D | T | L | Pen | 1-Nal | E | K(Ac) | NH₂ |
| 91 | 2-Me-Benzoyl | N-Me-R | S | D | T | L | Pen | Y | e | k(Ac) | NH₂ |
| 94 | 2-Me-Benzoyl | N-Me-R | S | D | T | L | Pen | W | e | Dap | NH₂ |
| 95 | 2-Me-Benzoyl | N-Me-R | S | D | T | L | Pen | W | E | Dab | NH₂ |
| 96 | 2-Me-Benzoyl | N-Me-R | S | D | T | L | Pen | W | e | NH2 | |
| 224 | 2-Me-Benzoyl | N-Me-R | S | D | T | L | Pen | W | e | Dap(Ac) | NH₂ |
| 101 | 2-Me-Benzoyl | N-Me-R | S | D | T | L | Pen | W | e | F | NH₂ |
| 107 | 2-Me-Benzoyl | N-Me-R | S | D | T | L | Pen | W | e | f | NH₂ |

Thioether bond between Xaa¹ and Xaa⁷

Representative peptides with IC50 (α4β7) values for <50nM in ELISA and <300nM in Cell adhesion assay

FIG. 7

| SEQ ID | Xaa¹ | Xaa² | Xaa³ | Xaa⁴ | Xaa⁵ | Xaa⁶ | Xaa⁷ | Xaa⁸ | Xaa⁹ | Xaa¹⁰ | Xaa¹¹ |
|---|---|---|---|---|---|---|---|---|---|---|---|
| 62 | 2-Me-Benzoyl | N-Me-R | S | D | T | L | Pen | W | E | N-Me-k | NH₂ |
| 63 | 2-Me-Benzoyl | N-Me-R | S | D | T | L | Pen | W | Y | N-Me-K | NH₂ |
| 226 | 2-Me-Benzoyl | N-Me-R | S | D | T | Nle | Pen | W | E | N-Me-k | NH₂ |
| 227 | 2-Me-Benzoyl | N-Me-R | S | D | T | Nle | Pen | F | e | N-Me-k | NH₂ |
| 66 | 2-Me-Benzoyl | N-Me-R | S | D | T | L | c | W | b-H-E | k | NH₂ |
| 68 | 2-Me-Benzoyl | N-Me-R | S | D | T | L | Pen | 1-Nal | e | k | NH₂ |
| 69 | 2-Me-Benzoyl | N-Me-R | S | D | T | L | Pen | 1-Nal | e | N-Me-K | NH₂ |
| 70 | 2-Me-Benzoyl | N-Me-R | S | D | T | L | Pen | 2-Nal | b-H-E | k | NH₂ |
| 71 | 2-Me-Benzoyl | N-Me-R | S | D | T | L | Pen | f | 2-Nal | k | NH₂ |
| 72 | 2-Me-Benzoyl | N-Me-R | S | D | T | L | Pen | f | E | k | NH₂ |

Thioether bond between Xaa¹ and Xaa⁷

Representative peptides with stability of >180min (half-life) in SIF (simulated intestinal fluids)

*FIG. 8*

SEQUENCE LISTING

```
<160> NUMBER OF SEQ ID NOS: 394

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Absent, any naturally occurring amino acid,
      suitable isosteres, or corresponding D-amino acids
<220> FEATURE:
<221> NAME/KEY: misc_feature
<222> LOCATION: (1)..(4)
<223> OTHER INFORMATION: Optional Acetylation
<220> FEATURE:
<221> NAME/KEY: misc_feature
<222> LOCATION: (3)..(3)
<223> OTHER INFORMATION: Optional N(alpha)Methylation
<220> FEATURE:
<221> NAME/KEY: MOD_RES
<222> LOCATION: (4)..(4)
<223> OTHER INFORMATION: Absent, Modified Ser or HSer (modified to have
      one or two carbons for forming thioether bond with Xaa at pos.
      10), suitable isosteres or D-amino acids
<220> FEATURE:
<221> NAME/KEY: misc_feature
<222> LOCATION: (5)..(5)
<223> OTHER INFORMATION: Optional N(alpha)Methylation
<220> FEATURE:
<221> NAME/KEY: MOD_RES
<222> LOCATION: (5)..(5)
<223> OTHER INFORMATION: Arg, HArg, 4-Guan, Cit, Cav, Dap, Dab, suitable
```

```
        isosteres, Arg-Me-sym or Arg-Me-asym
<220> FEATURE:
<221> NAME/KEY: MOD_RES
<222> LOCATION: (6)..(6)
<223> OTHER INFORMATION: Ser, Gly or suitable isosteres
<220> FEATURE:
<221> NAME/KEY: misc_feature
<222> LOCATION: (7)..(9)
<223> OTHER INFORMATION: Optional N(alpha)Methylation
<220> FEATURE:
<221> NAME/KEY: MOD_RES
<222> LOCATION: (7)..(7)
<223> OTHER INFORMATION: Asp, D-Asp, Asp(OMe) or suitable isosteres for
        Asp
<220> FEATURE:
<221> NAME/KEY: MOD_RES
<222> LOCATION: (8)..(8)
<223> OTHER INFORMATION: Thr, Gln, Ser, Asp, Pro, Gly, His, Ala, Ile,
        Phe, Lys, Arg, Asn, Glu, Val, Tyr, Trp, Leu or Met
<220> FEATURE:
<221> NAME/KEY: MOD_RES
<222> LOCATION: (9)..(9)
<223> OTHER INFORMATION: Gln, Asn, Asp, Pro, Gly, Ala, Phe, Leu, Glu,
        Ile, Val, HLeu, n-Butyl Ala, n-Pentyl Ala, n-Hexyl Ala, Nle,
        cyclobutyl-Ala or suitable isosteres
<220> FEATURE:
<221> NAME/KEY: MOD_RES
<222> LOCATION: (10)..(10)
<223> OTHER INFORMATION: Cys, D-Cys, HCys, Pen or D-Pen
<220> FEATURE:
<221> NAME/KEY: misc_feature
<222> LOCATION: (11)..(14)
<223> OTHER INFORMATION: Optional Acetylation
<220> FEATURE:
<221> NAME/KEY: MOD_RES
<222> LOCATION: (11)..(11)
<223> OTHER INFORMATION: Absent, Gly, Gln, Asn, Asp, Ala, Ile, Leu, Val,
        Met, Thr, Lys, Trp, Tyr, His, Glu, Ser, Arg, Pro, Phe, Sar, 1-Nal,
        2-Nal, D-1-Nal, D-2-Nal, HPhe, Phe(4-F), O-Me-Tyr, dihydro-Trp,
        Dap, Dab, Dab(Ac), Orn, D-Orn, D-Dap, D-Dab, Bip, Ala
        (3,3diphenyl),
<220> FEATURE:
<221> NAME/KEY: MOD_RES
<222> LOCATION: (11)..(11)
<223> OTHER INFORMATION: continued from above; D-Phe, aromatic ring
        substituted Phe, aromatic ring substituted Trp, aromatic ring
        substituted His, hetero aromatic amino acids, 4-Me-Phe,
        corresponding D-amino acids or suitable isosteres
<220> FEATURE:
<221> NAME/KEY: MOD_RES
<222> LOCATION: (12)..(12)
<223> OTHER INFORMATION: Absent, Glu, Lys, Gln, Pro, Gly, His, Ala, Ile,
        Phe, Arg, Leu, Val, Tyr, Trp, Met, Gla, Ser, Asn, D-Glu, Beta-
        HGlu, 2-Nal, 1-Nal, D-Asp, Bip, Beta-HPhe, Beta-Glu, D-Tyr, D-Lys,
        D-Phe, Dap, Dab, Orn, D-Dap, D-Dap, suitable isosteres
<220> FEATURE:
<221> NAME/KEY: MOD_RES
<222> LOCATION: (12)..(12)
<223> OTHER INFORMATION: continued from above; or D-amino acids
<220> FEATURE:
<221> NAME/KEY: MOD_RES
<222> LOCATION: (13)..(13)
<223> OTHER INFORMATION: Absent, Gln, Pro, Gly, His, Ala, Ile, Phe, Lys,
        Arg, Leu, Val, Tyr, Trp, Met, Glu, Ser, Asn, Gla, Dap, Dab, Orn,
        D-Orn, D-Lys, D-N-Me-Lys, D-Dap, D-Dab, suitable isosteres or
        corresponding D-amino acids
<220> FEATURE:
<221> NAME/KEY: MOD_RES
<222> LOCATION: (14)..(14)
<223> OTHER INFORMATION: Absent, Gln, Pro, Gly, His, Ala, Ile, Phe, Lys,
        Arg, Leu, Val, Tyr, Trp, Met, Glu, Ser, Asn, Gla, Dap, Dab, Orn,
        D-Orn, D-Lys, D-N-Me-Lys, D-Dap, D-Dab, suitable isosteres,
        corresponding D-amino acids or corresponding N-Methyl amino acids

<400> SEQUENCE: 1

Xaa Xaa Xaa Xaa Xaa Xaa Xaa Xaa Xaa Xaa Xaa Xaa Xaa Xaa
1               5                   10
```

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Xaa at position 6
<220> FEATURE:
<221> NAME/KEY: MOD_RES
<222> LOCATION: (1)..(1)
<223> OTHER INFORMATION: Arg, HArg, 4-Guan, Cit, Cav, Dap, Dab, suitable
      isosteres, N-Me-Arg, Arg-Me-sym or Arg-Me-asym
<220> FEATURE:
<221> NAME/KEY: MOD_RES
<222> LOCATION: (2)..(2)
<223> OTHER INFORMATION: Ser, Gly or suitable isosteres
<220> FEATURE:
<221> NAME/KEY: MOD_RES
<222> LOCATION: (3)..(3)
<223> OTHER INFORMATION: Asp, D-Asp, Asp(OMe) or and suitable isosteres
      for Asp
<220> FEATURE:
<221> NAME/KEY: misc_feature
<222> LOCATION: (3)..(5)
<223> OTHER INFORMATION: Optional N(alpha)Methylation
<220> FEATURE:
<221> NAME/KEY: MOD_RES
<222> LOCATION: (4)..(4)
<223> OTHER INFORMATION: Thr, Gln, Ser, Asp, Pro, Gly, His, Ala, Ile,
      Phe, Lys, Arg, Asn, Glu, Val, Tyr, Trp, Leu or Met
<220> FEATURE:
<221> NAME/KEY: MOD_RES
<222> LOCATION: (5)..(5)
<223> OTHER INFORMATION: Gln, Asn, Asp, Pro, Gly, Ala, Phe, Leu, Glu,
      Ile, Val, HLeu, n-Butyl Ala, n-Pentyl Ala, n-Hexyl Ala, Nle,
      cyclobutyl-Ala or suitable isosteres
<220> FEATURE:
<221> NAME/KEY: MOD_RES
<222> LOCATION: (6)..(6)
<223> OTHER INFORMATION: Cys, D-Cys, HCys, Pen or D-Pen
<220> FEATURE:
<221> NAME/KEY: MOD_RES
<222> LOCATION: (7)..(7)
<223> OTHER INFORMATION: Absent, Gly, Gln, Asn, Asp, Ala, Ile, Leu, Val,
      Met, Thr, Lys, Trp, Tyr, His, Glu, Ser, Arg, Pro, Phe, Sar, 1-Nal,
      2-Nal, D-1-Nal, D-2-Nal, HPhe, Phe(4-F), O-Me-Tyr, dihydro-Trp,
      Dap, Dab, Dab(Ac), Orn, D-Orn, D-Dap, D-Dab, Bip, Ala
      (3,3diphenyl),
<220> FEATURE:
<221> NAME/KEY: MOD_RES
<222> LOCATION: (7)..(7)
<223> OTHER INFORMATION: continued from above; D-Phe, D-Tyr, aromatic
      ring substituted Phe, aromatic ring substituted Trp, aromatic
      ring substituted His, hetero aromatic amino acids, 4-Me-Phe or
      corresponding D-amino acids
<220> FEATURE:
<221> NAME/KEY: misc_feature
<222> LOCATION: (7)..(9)
<223> OTHER INFORMATION: Optional N(alpha)Methylation
<220> FEATURE:
<221> NAME/KEY: misc_feature
<222> LOCATION: (7)..(9)
<223> OTHER INFORMATION: Optional Acetylation
<220> FEATURE:
<221> NAME/KEY: MOD_RES
<222> LOCATION: (8)..(8)
<223> OTHER INFORMATION: Absent, Glu, Lys, Gln, Pro, Gly, His, Ala, Ile,
      Phe, Arg, Leu, Val, Tyr, Trp, Met, Gla, Ser, Asn, D-Glu, Beta-
      HGlu, 2-Nal, 1-Nal, D-Asp, Bip, Beta-HPhe, Beta-Glu, D-Tyr, D-Lys,
      D-Phe, Dap, Dab, Orn, D-Dap, D-Dap,
<220> FEATURE:
<221> NAME/KEY: MOD_RES
<222> LOCATION: (8)..(8)
<223> OTHER INFORMATION: continued from above; suitable isosteres or

```
                          D-amino acids
<220> FEATURE:
<221> NAME/KEY: MOD_RES
<222> LOCATION: (9)..(9)
<223> OTHER INFORMATION: Absent, Gln, Pro, Gly, His, Ala, Ile, Phe, Lys,
      Arg, Leu, Val, Tyr, Trp, Met, Glu, Ser, Asn, Gla, Dap, Dab, Orn,
      D-Orn, D-Lys, D-Dap, D-Dab, suitable isosteres or corresponding
      D-amino acids
<220> FEATURE:
<221> NAME/KEY: MOD_RES
<222> LOCATION: (10)..(10)
<223> OTHER INFORMATION: Absent, Gln, Pro, Gly, His, Ala, Ile, Phe, Lys,
      Arg, Leu, Val, Tyr, Trp, Met, Glu, Ser, Asn, Gla, Dap, Dab, Orn,
      D-Orn, D-Lys, D-N-Me-Lys, D-Dap, D-Dab, suitable isosteres,
      corresponding D-amino acids or corresponding N-Methyl amino acids

<400> SEQUENCE: 2

Xaa Xaa Xaa Xaa Xaa Xaa Xaa Xaa Xaa Xaa
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Cys at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (7)..(8)
<223> OTHER INFORMATION: Any naturally occurring amino acid

<400> SEQUENCE: 3

Arg Xaa Asp Xaa Xaa Cys Xaa Xaa
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Xaa at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
```

```
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(8)
<223> OTHER INFORMATION: Any naturally occurring amino acid

<400> SEQUENCE: 4

Arg Xaa Asp Xaa Xaa Xaa Xaa Xaa
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Cys at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (7)..(8)
<223> OTHER INFORMATION: Any naturally occurring amino acid

<400> SEQUENCE: 5

Arg Xaa Asp Xaa Xaa Cys Xaa Xaa
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Xaa at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(8)
```

```
<223> OTHER INFORMATION: Any naturally occurring amino acid

<400> SEQUENCE: 6

Arg Xaa Asp Xaa Xaa Xaa Xaa Xaa
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Cys at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (7)..(9)
<223> OTHER INFORMATION: Any naturally occurring amino acid

<400> SEQUENCE: 7

Arg Xaa Asp Xaa Xaa Cys Xaa Xaa Xaa
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Xaa at position 6
<220> FEATURE:
<221> NAME/KEY: MOD_RES
<222> LOCATION: (1)..(1)
<223> OTHER INFORMATION: Optional N(alpha)Methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(9)
<223> OTHER INFORMATION: Any naturally occurring amino acid

<400> SEQUENCE: 8

Arg Xaa Asp Xaa Xaa Xaa Xaa Xaa Xaa
1               5
```

```
<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Cys at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (7)..(9)
<223> OTHER INFORMATION: Any naturally occurring amino acid

<400> SEQUENCE: 9

Arg Xaa Asp Xaa Xaa Cys Xaa Xaa Xaa
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Xaa at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(9)
<223> OTHER INFORMATION: Any naturally occurring amino acid

<400> SEQUENCE: 10

Arg Xaa Asp Xaa Xaa Xaa Xaa Xaa Xaa
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
```

-continued

```
      peptide
<220> FEATURE:
<223> OTHER INFORMATION: N-term Aromatic acid group, 2-methylbenzoyl,
      propionyl, isobutyryl, acetyl or butyryl forming a thioether bond
      with Cys at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (7)..(9)
<223> OTHER INFORMATION: Any naturally occurring amino acid

<400> SEQUENCE: 11

Arg Xaa Asp Xaa Xaa Cys Xaa Xaa Xaa
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Xaa at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(4)
<223> OTHER INFORMATION: Any naturally occurring amino acid
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(9)
<223> OTHER INFORMATION: Any naturally occurring amino acid

<400> SEQUENCE: 12

Arg Xaa Asp Xaa Xaa Xaa Xaa Xaa Xaa
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Cys at position 6
<220> FEATURE:
<221> NAME/KEY: misc_feature
```

```
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (7)..(9)
<223> OTHER INFORMATION: Any naturally occurring amino acid

<400> SEQUENCE: 13

Arg Xaa Asp Xaa Xaa Cys Xaa Xaa Xaa
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Xaa at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(9)
<223> OTHER INFORMATION: Any naturally occurring amino acid

<400> SEQUENCE: 14

Arg Xaa Asp Xaa Xaa Xaa Xaa Xaa Xaa
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Cys at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
```

```
<221> NAME/KEY: MOD_RES
<222> LOCATION: (4)..(5)
<223> OTHER INFORMATION: Any naturally occurring amino acid

<400> SEQUENCE: 15

Arg Xaa Asp Xaa Xaa Cys
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Cys at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (7)..(7)
<223> OTHER INFORMATION: Any naturally occurring amino acid

<400> SEQUENCE: 16

Arg Xaa Asp Xaa Xaa Cys Xaa
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Xaa at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Any naturally occurring amino acid

<400> SEQUENCE: 17

Arg Xaa Asp Xaa Xaa Xaa Xaa
```

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Cys at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (7)..(7)
<223> OTHER INFORMATION: Any naturally occurring amino acid

<400> SEQUENCE: 18

Arg Xaa Asp Xaa Xaa Cys Xaa
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Xaa at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Any naturally occurring amino acid

<400> SEQUENCE: 19

Arg Xaa Asp Xaa Xaa Xaa Xaa
1               5

<210> SEQ ID NO 20
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Cys at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (7)..(7)
<223> OTHER INFORMATION: Any naturally occurring amino acid

<400> SEQUENCE: 20

Arg Xaa Asp Xaa Xaa Cys Xaa
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Xaa at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Any naturally occurring amino acid

<400> SEQUENCE: 21

Arg Xaa Asp Xaa Xaa Xaa Xaa
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Me-Benzoyl with a thioether bond
      between the N-term and the residue at position 6
<220> FEATURE:
```

```
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Lys

<400> SEQUENCE: 22

Arg Ser Asp Thr Leu Xaa Trp Lys
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Xaa at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (5)..(5)
<223> OTHER INFORMATION: Leu or Nle
<220> FEATURE:
<221> NAME/KEY: MOD_RES
<222> LOCATION: (6)..(6)
<223> OTHER INFORMATION: Cys, Pen, HCys or D-Cys
<220> FEATURE:
<221> NAME/KEY: MOD_RES
<222> LOCATION: (7)..(7)
<223> OTHER INFORMATION: Trp, Phe, 1-Nal, 2-Nal, D-Phe, Tyr or Phe(CF3)
<220> FEATURE:
<221> NAME/KEY: MOD_RES
<222> LOCATION: (8)..(8)
<223> OTHER INFORMATION: Glu, D-Glu, Beta-HGlu, Tyr or 2-Nal
<220> FEATURE:
<221> NAME/KEY: MOD_RES
<222> LOCATION: (9)..(9)
<223> OTHER INFORMATION: D-Lys, Lys, Dap, Dab, Leu, Ser, Phe, His, Gln,
      Tyr, D-Leu, D-Ser, D-Phe, D-Glu, D-Tyr, D-His or Glu
<220> FEATURE:
<221> NAME/KEY: misc_feature
<222> LOCATION: (9)..(9)
<223> OTHER INFORMATION: Optional N(alpha)methylation
<220> FEATURE:
<221> NAME/KEY: misc_feature
<222> LOCATION: (9)..(9)
<223> OTHER INFORMATION: Optional acetylation

<400> SEQUENCE: 23

Arg Ser Asp Thr Xaa Xaa Xaa Xaa Xaa
1               5

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
```

```
       with Xaa at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (5)..(5)
<223> OTHER INFORMATION: Any naturally occurring amino acid
<220> FEATURE:
<221> NAME/KEY: MOD_RES
<222> LOCATION: (6)..(6)
<223> OTHER INFORMATION: Cys, Pen, HCys or D-Cys
<220> FEATURE:
<221> NAME/KEY: MOD_RES
<222> LOCATION: (7)..(7)
<223> OTHER INFORMATION: Trp, Phe, 1-Nal, 2-Nal, D-Phe, Tyr or Phe(CF3)
<220> FEATURE:
<221> NAME/KEY: MOD_RES
<222> LOCATION: (8)..(8)
<223> OTHER INFORMATION: Glu, D-Glu, Beta-HGlu, Tyr or 2-Nal
<220> FEATURE:
<221> NAME/KEY: MOD_RES
<222> LOCATION: (9)..(9)
<223> OTHER INFORMATION: Leu, Ser, Phe, His, Gln, Tyr, D-Leu, D-Ser,
      D-Phe, D-Val, D-Glu, D-Tyr, D-His, D-Glu, Glu, Asp or D-Asp
<220> FEATURE:
<221> NAME/KEY: MOD_RES
<222> LOCATION: (10)..(10)
<223> OTHER INFORMATION: D-Lys, Lys, Dap, Dab, Leu, Ser, Phe, His, Gln,
      Tyr, D-Leu, D-Ser, D-Phe, D-Glu, D-Tyr, D-His or Glu
<220> FEATURE:
<221> NAME/KEY: misc_feature
<222> LOCATION: (10)..(10)
<223> OTHER INFORMATION: Optional N(alpha)methylation
<220> FEATURE:
<221> NAME/KEY: misc_feature
<222> LOCATION: (10)..(10)
<223> OTHER INFORMATION: Optional acetylation

<400> SEQUENCE: 24

Arg Ser Asp Thr Xaa Xaa Xaa Xaa Xaa Xaa
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Cys at position 6
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (7)..(10)
<223> OTHER INFORMATION: Any naturally occurring amino acid

<400> SEQUENCE: 25

Arg Xaa Asp Xaa Xaa Cys Xaa Xaa Xaa Xaa
1               5                   10

<210> SEQ ID NO 26
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Xaa at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(11)
<223> OTHER INFORMATION: Any naturally occurring amino acid

<400> SEQUENCE: 26

Arg Xaa Asp Xaa Xaa Xaa Xaa Xaa Xaa Xaa Xaa
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Cys at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (7)..(10)
<223> OTHER INFORMATION: Any naturally occurring amino acid

<400> SEQUENCE: 27

Arg Xaa Asp Xaa Xaa Cys Xaa Xaa Xaa Xaa
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
```

```
     with Xaa at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(10)
<223> OTHER INFORMATION: Any naturally occurring amino acid

<400> SEQUENCE: 28

Arg Xaa Asp Xaa Xaa Xaa Xaa Xaa Xaa Xaa
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Cys at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (7)..(10)
<223> OTHER INFORMATION: Any naturally occurring amino acid

<400> SEQUENCE: 29

Arg Xaa Asp Xaa Xaa Cys Xaa Xaa Xaa Xaa
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Xaa at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
```

```
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(10)
<223> OTHER INFORMATION: Any naturally occurring amino acid

<400> SEQUENCE: 30

Arg Xaa Asp Xaa Xaa Xaa Xaa Xaa Xaa Xaa
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Cys at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (7)..(10)
<223> OTHER INFORMATION: Any naturally occurring amino acid

<400> SEQUENCE: 31

Arg Xaa Asp Xaa Xaa Cys Xaa Xaa Xaa Xaa
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Aromatic acid group, 2-methylbenzoyl,
      propionyl, isobutyryl, acetyl or butyryl forming a thioether bond
      with Xaa at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (4)..(5)
<223> OTHER INFORMATION: Any naturally occurring amino acid
<220> FEATURE:
```

```
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(10)
<223> OTHER INFORMATION: Any naturally occurring amino acid

<400> SEQUENCE: 32

Arg Xaa Asp Xaa Xaa Xaa Xaa Xaa Xaa Xaa
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Absent or any amino acid
<220> FEATURE:
<221> NAME/KEY: misc_feature
<222> LOCATION: (4)..(10)
<223> OTHER INFORMATION: Thioether bond between position 4 and Xaa at
      position 10
<220> FEATURE:
<221> NAME/KEY: MOD_RES
<222> LOCATION: (5)..(5)
<223> OTHER INFORMATION: N(alpha)-Me-Arg, Arg, HomoArg, Dap, Dab, Arg-
      Me-sym, Arg-Me-asym, 4-Guan, Cit, Cav, N-Me-Lys, Phe(4-quanidino),
      Phe(4-carbamoyl amino), Phe(4-NH2), N-Me-HomoArg, Tyr, His or
      suitable isostere replacements
<220> FEATURE:
<221> NAME/KEY: MOD_RES
<222> LOCATION: (6)..(6)
<223> OTHER INFORMATION: Ser, Gly, Thr, Ile or suitable isostere
      replacements
<220> FEATURE:
<221> NAME/KEY: MOD_RES
<222> LOCATION: (7)..(7)
<223> OTHER INFORMATION: Asp, N-Me-Asp, Asp(OMe), D-Asp or a suitable
      isostere replacements
<220> FEATURE:
<221> NAME/KEY: MOD_RES
<222> LOCATION: (8)..(8)
<223> OTHER INFORMATION: Thr, Gln, Ser, Asp, Pro, Gly, His, Ala, Ile,
      Phe, Lys, Arg, Asn, Glu, Val, Tyr, Trp, Leu, Met, HomoLeu, Nle or
      an N-Methyl amino acid including N-Me-Thr
<220> FEATURE:
<221> NAME/KEY: MOD_RES
<222> LOCATION: (9)..(9)
<223> OTHER INFORMATION: Gln, Asn, Asp, Pro, Gly, Ala, Phe, Leu, Glu,
      Ile, Val, HLeu, n-Butyl Ala, n-Pentyl Ala, n-Hexyl Ala, Nle,
      cyclobutyl-Ala, Cpa, Aoc, N-Me-Leu or a suitable isostere
      replacement
<220> FEATURE:
<221> NAME/KEY: MOD_RES
<222> LOCATION: (10)..(10)
<223> OTHER INFORMATION: Cys, N-Me-Cys, D-Cys, HCys, Pen, D-Pen or
      Pen(=O)
<220> FEATURE:
<221> NAME/KEY: MOD_RES
<222> LOCATION: (11)..(11)
<223> OTHER INFORMATION: Absent, or Trp, Phe, 2-Nal, 1-Nal, Tyr, His,
      Phe(4-F), Phe(4-CF3), Phe (4-CH3), Phe (4-tBu), Bip, Phe(4-COOH),
      Gly, 3,3-DiPhenylGly, 3,3 diPhenyl Ala, Tic, b-homo-Trp, D-1-Nal,
      D-2-Nal, Phe(2,4-diCl), Phe(3,4-diCl), Phe(4-carbomyl)
<220> FEATURE:
<221> NAME/KEY: MOD_RES
<222> LOCATION: (11)..(11)
<223> OTHER INFORMATION: continued from above; Phe(2-carbomyl), Tyr(Me),
      HomoPhe, N-Me-Phe, N-Me-Tyr, Ser, Sar, Dihydro Trp, Ile, Leu, Ser,
      Arg, Thr, Sar, and Ser, aromatic amino acids, substituted aromatic
      amino acids, Gly, Gln, Asn, Asp, Ala, Ile, Leu, Val, Met, Thr,
```

```
            Lys, Trp, Tyr,
<220> FEATURE:
<221> NAME/KEY: MOD_RES
<222> LOCATION: (11)..(11)
<223> OTHER INFORMATION: continued from above; Glu, Ser, Arg, Pro, Phe,
      Sar, 1-Nal, 2-Nal, D-1-Nal, D-2-Nal, HPhe, D-Phe, D-Tyr, Phe(4-F),
      O-Me-Tyr, dihydro-Trp, Dap, Dab, Dab(Ac), Orn, D-Orn, N-Me-Orn,
      N-Me-Dap, D-Dap, D-Dab, Bip, Ala(3,3diphenyl), Biphenyl-Ala,
<220> FEATURE:
<221> NAME/KEY: MOD_RES
<222> LOCATION: (11)..(11)
<223> OTHER INFORMATION: continued from above; aromatic ring substituted
      Phe, aromatic ring substituted Trp, aromatic ring substituted His,
      hetero aromatic amino acids, N-Me-Lys, N-Me-Lys(Ac), 4-Me-Phe,
      Phe(4tBu), Phe(4-OMe), Phe(4-COOH), Phe(2-carbomyl), Phe
      (3-carbomyl),
<220> FEATURE:
<221> NAME/KEY: MOD_RES
<222> LOCATION: (11)..(11)
<223> OTHER INFORMATION: continued from above; Phe(2,4-diCl), Phe(3,4-
      diCl), Aic, N-Me-Tyr, N-Me-Phe, Tic, Phe(4CF3), or a
      corresponding D-amino acid or suitable isostere replacement
<220> FEATURE:
<221> NAME/KEY: MOD_RES
<222> LOCATION: (12)..(12)
<223> OTHER INFORMATION: Absent, or an aromatic amino acid, a
      substituted aromatic amino acid, Glu, D-Glu, HomoGlu, Beta-Homo-
      Glu, Asp, D-HomoGlu, Pro, Gly, His, Ala, Ile, Phe, Arg, Leu,Lys,
      Gln, Val, Tyr, Trp, Met, Gla, Ser, Asn, D-Glu, Beta-HGlu, 2-Nal,
      1-Nal, D-Asp, Bip,
<220> FEATURE:
<221> NAME/KEY: MOD_RES
<222> LOCATION: (12)..(12)
<223> OTHER INFORMATION: Continued from above; Beta-HPhe, Beta-Glu,
      D-Tyr, D-Phe, D-Lys, Dap, Dab, Orn, D-Orn, N-Me-Orn, N-Me-Dap,
      N-Me-Dab, N-Me Lys, D-Dap, D-Dab, D-His, Phe(4-COOH), Tic, D-Trp,
      D-Leu, D-Arg D-Thr, a suitable isostere or a corresponding
      D-amino acid
<220> FEATURE:
<221> NAME/KEY: MOD_RES
<222> LOCATION: (13)..(13)
<223> OTHER INFORMATION: Absent or any amino acid
<220> FEATURE:
<221> NAME/KEY: MOD_RES
<222> LOCATION: (14)..(14)
<223> OTHER INFORMATION: Absent, any amino acid, or any amino acid with
      an amine side chain, Lys, D-Lys, N-Me-Lys, D-N-Me-Lys, Orn,
      N-Me-Orn, Dab, N-Me-Dab, Dap, N-Me-Dap, Homo-Lys, D-Dap, D-Dab,
      D-Orn, Gln, Pro, Gly, His, Ala, Ile, Phe, Lys, Arg, Leu, Val, Tyr,
      Trp, Met, Glu,
<220> FEATURE:
<221> NAME/KEY: MOD_RES
<222> LOCATION: (14)..(14)
<223> OTHER INFORMATION: continued from above; Asn, Gla, Cys, HomoCys, a
      suitable isostere, a corresponding D-amino acid or corresponding
      N-Methyl amino acid

<400> SEQUENCE: 33

Xaa Xaa Xaa Xaa Xaa Xaa Xaa Xaa Xaa Xaa Xaa Xaa Xaa Xaa
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Absent, any naturally occurring amino acid, a
      suitable isostere or corresponding D-amino acids
<220> FEATURE:
<221> NAME/KEY: MOD_RES
<222> LOCATION: (4)..(4)
<223> OTHER INFORMATION: Absent or any amino acid
```

```
<220> FEATURE:
<221> NAME/KEY: misc_feature
<222> LOCATION: (4)..(10)
<223> OTHER INFORMATION: Thioether bond between position 4 and Xaa at
      position 10
<220> FEATURE:
<221> NAME/KEY: MOD_RES
<222> LOCATION: (5)..(5)
<223> OTHER INFORMATION: N(alpha)-Me-Arg, Arg,  HomoArg, Dap, Dab, Arg-
      Me-sym, Arg-Me-asym, 4-Guan, Cit, Cav, N-Me-Lys, Phe (4-
      quanidino), Phe (4-carbomyl amino), Phe(4-NH2), N-Me-Homo-Arg,
      Tyr and His or suitable isostere replacements
<220> FEATURE:
<221> NAME/KEY: MOD_RES
<222> LOCATION: (6)..(6)
<223> OTHER INFORMATION: Ser, Gly, Thr, Ile or suitable isostere
      replacements
<220> FEATURE:
<221> NAME/KEY: MOD_RES
<222> LOCATION: (7)..(7)
<223> OTHER INFORMATION: Asp, N-Me-Asp, Asp(OMe), D-Asp or a suitable
      isostere replacement
<220> FEATURE:
<221> NAME/KEY: MOD_RES
<222> LOCATION: (8)..(8)
<223> OTHER INFORMATION: Thr, Gln, Ser, Asp, Pro, Gly, His, Ala, Ile,
      Phe, Lys, Arg, Asn, Glu, Val, Tyr, Trp, Leu, Met, hLeu, Nle or
      N-Methyl amino acids including N-Me-Thr
<220> FEATURE:
<221> NAME/KEY: MOD_RES
<222> LOCATION: (9)..(9)
<223> OTHER INFORMATION: Gln, Asn, Asp, Pro, Gly, Ala, Phe, Leu, Glu,
      Ile, Val, HomoLeu, n-Butyl Ala, n-Pentyl Ala, n-Hexyl Ala, Nle,
      cyclobutyl-Ala, N-Me-Leu, Cpa, Aoc or suitable isostere
      replacements
<220> FEATURE:
<221> NAME/KEY: MOD_RES
<222> LOCATION: (10)..(10)
<223> OTHER INFORMATION: Cys, N-Me-Cys, D-Cys, HomoCys, Pen, D-Pen,
      modified HomoSer or modified Ser
<220> FEATURE:
<221> NAME/KEY: MOD_RES
<222> LOCATION: (11)..(11)
<223> OTHER INFORMATION: Absent, aromatic amino acids, substituted
      aromatic amino acids, Tic, corresponding D-amino acids or
      suitable isostere replacements
<220> FEATURE:
<221> NAME/KEY: MOD_RES
<222> LOCATION: (12)..(12)
<223> OTHER INFORMATION: Absent, aromatic amino acids, substituted
      aromatic amino acids, Glu, D-Glu, homoGlu, Asp, D-Asp, D-homoGlu,
      Gla, beta-Homo-Glu, Tic or corresponding D-amino acids and
      suitable isosteres
<220> FEATURE:
<221> NAME/KEY: MOD_RES
<222> LOCATION: (13)..(13)
<223> OTHER INFORMATION: Absent, Gln, Pro, Gly, His, Ala, Ile, Phe, Lys,
      Arg, Leu, Val, Tyr, Trp, Met, Glu, Ser, Asn, Gla, Dap, Dab, Orn,
      D-Orn, D-Lys, N-Me-Orn, N-Me-Dap, N-Me-Dab, N-Me-Lys, D-N-Me-Lys,
      D-Dap, D-Dab, suitable isosteres or corresponding D-amino acids
<220> FEATURE:
<221> NAME/KEY: MOD_RES
<222> LOCATION: (14)..(14)
<223> OTHER INFORMATION: Absent, any amino acid, any amino acid with an
      amine side chain, Lys, D-Lys, N-Me-Lys, D-N-Me-Lys, Orn, N-Me-Orn,
      Dab, N-Me-Dab, Dap, N-Me-Dap, Homo-Lys, D-Dap, D-Dab, D-Orn, Gln,
      Pro, Gly, His, Ala, Ile, Phe, Lys, Arg, Leu, Val, Tyr, Trp, Met,
      Glu, Ser, Asn,
<220> FEATURE:
<221> NAME/KEY: MOD_RES
<222> LOCATION: (14)..(14)
<223> OTHER INFORMATION: continued from above; Gla, Cys, HomoCys, Pen,
      suitable isosteres, corresponding D-amino acids or corresponding
      N-Methyl amino acids

<400> SEQUENCE: 34

Xaa Xaa Xaa Xaa Xaa Xaa Xaa Xaa Xaa Xaa Xaa Xaa Xaa Xaa
1               5                   10
```

```
<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Absent or any amino acid
<220> FEATURE:
<221> NAME/KEY: misc_feature
<222> LOCATION: (1)..(3)
<223> OTHER INFORMATION: Optional acetylation
<220> FEATURE:
<221> NAME/KEY: MOD_RES
<222> LOCATION: (4)..(4)
<223> OTHER INFORMATION: Absent or Cys, HomoCys, Pen, Homo-Ser-Cl or
      Homo-Ser
<220> FEATURE:
<221> NAME/KEY: misc_feature
<222> LOCATION: (4)..(10)
<223> OTHER INFORMATION: Thioether bond between position 4 and Xaa at
      position 10
<220> FEATURE:
<221> NAME/KEY: MOD_RES
<222> LOCATION: (5)..(5)
<223> OTHER INFORMATION: N-Me-Arg, Arg, N-Me-Lys, Phe (4-quanidino), Phe
      (4-carbonylamino), Cit, Phe(4-NH2), N-Me-Homo-Arg, Homo-Arg, Tyr
      and His
<220> FEATURE:
<221> NAME/KEY: MOD_RES
<222> LOCATION: (6)..(6)
<223> OTHER INFORMATION: Ser, Gly, Ile or Thr
<220> FEATURE:
<221> NAME/KEY: MOD_RES
<222> LOCATION: (7)..(7)
<223> OTHER INFORMATION: Asp or D-Asp
<220> FEATURE:
<221> NAME/KEY: MOD_RES
<222> LOCATION: (8)..(8)
<223> OTHER INFORMATION: Thr, Val, Ile, Leu, hLeu and Nle
<220> FEATURE:
<221> NAME/KEY: MOD_RES
<222> LOCATION: (9)..(9)
<223> OTHER INFORMATION: Leu, Nle, Cpa, Cba, HomoLeu, Aoc or N-Me-Leu
<220> FEATURE:
<221> NAME/KEY: MOD_RES
<222> LOCATION: (10)..(10)
<223> OTHER INFORMATION: Cys, D-Cys, HomoCys, Pen, modified HomoSer or
      modified Ser
<220> FEATURE:
<221> NAME/KEY: MOD_RES
<222> LOCATION: (11)..(11)
<223> OTHER INFORMATION: Absent, aromatic amino acids or substituted
      aromatic amino acids
<220> FEATURE:
<221> NAME/KEY: MOD_RES
<222> LOCATION: (12)..(12)
<223> OTHER INFORMATION: Absent, aromatic amino acids, substituted
      aromatic amino acids, Glu, D-Glu, homoGlu, Asp, D-Asp, D-homoGlu,
      Gla, beta-Homo-Glu, and corresponding D-amino acids and suitable
      isosteres
<220> FEATURE:
<221> NAME/KEY: MOD_RES
<222> LOCATION: (13)..(13)
<223> OTHER INFORMATION: May or may not be present
<220> FEATURE:
<221> NAME/KEY: MOD_RES
<222> LOCATION: (14)..(14)
<223> OTHER INFORMATION: Any amino acid, any amino acid with an amine
      side chain, Lys, D-Lys, N-Me-Lys, D-N-Me-Lys, Orn, N-Me-Orn, Dab,
      N-Me-Dab, Dap, N-Me-Dap, Homo-Lys, D-Dap, D-Dab, D-Orn, Gln, Pro,
      Gly, His, Ala, Ile, Phe, Lys, Arg, Leu, Val, Tyr, Trp, Met, Glu,
      Ser, Asn, Gla,
<220> FEATURE:
```

```
<221> NAME/KEY: MOD_RES
<222> LOCATION: (14)..(14)
<223> OTHER INFORMATION: continued from above; HomoCys, Pen, suitable
      isosteres, corresponding D-amino acids or corresponding N-Methyl
      amino acids

<400> SEQUENCE: 35

Xaa Xaa Xaa Xaa Xaa Xaa Asp Xaa Xaa Xaa Xaa Xaa Pro Xaa
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Absent or any amino acid
<220> FEATURE:
<221> NAME/KEY: MOD_RES
<222> LOCATION: (4)..(4)
<223> OTHER INFORMATION: Absent, modified HomoSer or Homo-Ser-Cl
<220> FEATURE:
<221> NAME/KEY: misc_feature
<222> LOCATION: (4)..(10)
<223> OTHER INFORMATION: Thioether bond between position 4 and Xaa at
      position 10
<220> FEATURE:
<221> NAME/KEY: MOD_RES
<222> LOCATION: (5)..(5)
<223> OTHER INFORMATION: N-Me-Arg, Arg, N-Me-Lys, Phe (4-quanidino),
      Phe(4-carbonylamino), Cit, Phe(4-NH2), N-Me-Homo-Arg, Homo-Arg,
      Tyr and His
<220> FEATURE:
<221> NAME/KEY: MOD_RES
<222> LOCATION: (6)..(6)
<223> OTHER INFORMATION: Ser, Gly, Thr or Ile
<220> FEATURE:
<221> NAME/KEY: MOD_RES
<222> LOCATION: (7)..(7)
<223> OTHER INFORMATION: Asp or D-Asp
<220> FEATURE:
<221> NAME/KEY: MOD_RES
<222> LOCATION: (8)..(8)
<223> OTHER INFORMATION: Thr, Val, Ile, Leu, hLeu, Nle or Val
<220> FEATURE:
<221> NAME/KEY: MOD_RES
<222> LOCATION: (9)..(9)
<223> OTHER INFORMATION: Leu, Nle, Cpa, Cba, HomoLeu, Aoc or N-Me-Leu
<220> FEATURE:
<221> NAME/KEY: MOD_RES
<222> LOCATION: (10)..(10)
<223> OTHER INFORMATION: Pen, Cys, D-Cys or HomoCys
<220> FEATURE:
<221> NAME/KEY: MOD_RES
<222> LOCATION: (11)..(11)
<223> OTHER INFORMATION: Trp, Phe, 2-Nal, 1-Nal, Tyr, His, Phe(4-F),
      Phe(4-CF3), Phe (4-CH3), Phe (4-tBu), Bip, Phe(4-COOH), Gly, 3,3-
      DiPhenylGly, 3,3 diPhenyl-Ala, Tic, b-homo-Trp, D-1-Nal, D-2-Nal,
      Phe(2,4-diCl), Phe(3,4-diCl), Phe(4-carbomyl), Phe(3-Carbomyl),
<220> FEATURE:
<221> NAME/KEY: MOD_RES
<222> LOCATION: (11)..(11)
<223> OTHER INFORMATION: continued from above; Phe, Tyr(Me), HomoPhe,
      N-Me-Phe, N-Me-Tyr, Ser, Sar, Dihydro Trp, Ilu, Leu, Arg or Thr
<220> FEATURE:
<221> NAME/KEY: MOD_RES
<222> LOCATION: (12)..(12)
<223> OTHER INFORMATION: Absent or any aromatic amino acid, Glu, D-Glu,
      homoGlu, Asp, D-Asp, D-homoGlu, D-Asp, Gla, beta-homo-Glu,
      corresponding D-amino acid or isosteres
<220> FEATURE:
<221> NAME/KEY: MOD_RES
<222> LOCATION: (13)..(13)
```

```
<223> OTHER INFORMATION: Absent or any amino acid
<220> FEATURE:
<221> NAME/KEY: MOD_RES
<222> LOCATION: (14)..(14)
<223> OTHER INFORMATION: Any amino acid, any amino acid with a free
      amino group on a side chain, Lys, D-Lys, N-Me-Lys, D-N-Me-Lys,
      Orn, Dab, Dap, Homo-Lys, D-Dap, D-Dab, Cys, HomoCys, Pen or D-Orn

<400> SEQUENCE: 36

Xaa Xaa Xaa Xaa Xaa Xaa Asp Xaa Xaa Xaa Xaa Xaa Xaa Xaa
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Absent or any amino acid
<220> FEATURE:
<221> NAME/KEY: MOD_RES
<222> LOCATION: (4)..(4)
<223> OTHER INFORMATION: Absent, modified HomoSer or Homo-Ser-Cl
<220> FEATURE:
<221> NAME/KEY: misc_feature
<222> LOCATION: (4)..(10)
<223> OTHER INFORMATION: Thioether bond between position 4 and Xaa at
      position 10
<220> FEATURE:
<221> NAME/KEY: MOD_RES
<222> LOCATION: (5)..(5)
<223> OTHER INFORMATION: N-Me-Arg
<220> FEATURE:
<221> NAME/KEY: MOD_RES
<222> LOCATION: (6)..(6)
<223> OTHER INFORMATION: Ser, Gly, Thr, or Ile
<220> FEATURE:
<221> NAME/KEY: MOD_RES
<222> LOCATION: (7)..(7)
<223> OTHER INFORMATION: Asp or D-Asp
<220> FEATURE:
<221> NAME/KEY: MOD_RES
<222> LOCATION: (8)..(8)
<223> OTHER INFORMATION: Thr, Val, Ile, Leu, hLeu and Nle
<220> FEATURE:
<221> NAME/KEY: MOD_RES
<222> LOCATION: (9)..(9)
<223> OTHER INFORMATION: Leu, Nle, Cpa, Cba, HomoLeu, Aoc or N-Me-Leu
<220> FEATURE:
<221> NAME/KEY: MOD_RES
<222> LOCATION: (10)..(10)
<223> OTHER INFORMATION: Pen, Cys, D-Cys or HomoCys
<220> FEATURE:
<221> NAME/KEY: MOD_RES
<222> LOCATION: (11)..(11)
<223> OTHER INFORMATION: Trp, Phe, 2-Nal, 1-Nal, Tyr, His, Phe(4-F),
      Phe(4-CF3), Phe (4-CH3), Phe(4-tBu), Bip, Phe(4-COOH), Gly, 3,3-
      DiPhenylGly, 3,3 diPhenyl Ala, Tic, b-homo-Trp, D-1-Nal, D-2-Nal,
      Phe(2,4-diCl), Phe(3,4-diCl), Phe(4-carbomyl), Phe(3-Carbomyl),
      Tyr(Me),
<220> FEATURE:
<221> NAME/KEY: MOD_RES
<222> LOCATION: (11)..(11)
<223> OTHER INFORMATION: continued from above; N-Me-Phe, N-Me-Tyr, Ser,
      Sar, Dihydro Trp, Ile, Leu, Ser, Arg, Thr, Sar, Ser and any
      substituted aromatic amino acid or corresponding D-amino acids
<220> FEATURE:
<221> NAME/KEY: MOD_RES
<222> LOCATION: (12)..(12)
<223> OTHER INFORMATION: any aromatic amino acid, Glu, D-Glu, homoGlu,
      Asp, D-Asp, D-homoGlu, Gla, beta-homo-Glu, corresponding D-amino
      acid and isostere
<220> FEATURE:
```

-continued

```
<221> NAME/KEY: MOD_RES
<222> LOCATION: (13)..(13)
<223> OTHER INFORMATION: Any amino acid, Lys, D-Lys, N-Me-Lys, D-N-Me-
      Lys, Orn, Dab, Dap, Homo-Lys, D-Dap, D-Dab, Cys, HomoCys, Pen or
      D-Orn

<400> SEQUENCE: 37

Xaa Xaa Xaa Xaa Arg Xaa Asp Xaa Xaa Xaa Xaa Xaa Xaa
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Absent or any amino acid
<220> FEATURE:
<221> NAME/KEY: MOD_RES
<222> LOCATION: (4)..(4)
<223> OTHER INFORMATION: Absent, modified HomoSer or Homo-Ser-Cl
<220> FEATURE:
<221> NAME/KEY: misc_feature
<222> LOCATION: (4)..(10)
<223> OTHER INFORMATION: Thioether bond between position 4 and Xaa at
      position 10
<220> FEATURE:
<221> NAME/KEY: MOD_RES
<222> LOCATION: (5)..(5)
<223> OTHER INFORMATION: N-Me-Arg
<220> FEATURE:
<221> NAME/KEY: MOD_RES
<222> LOCATION: (6)..(6)
<223> OTHER INFORMATION: Ser, Gly, Thr, or Ile
<220> FEATURE:
<221> NAME/KEY: MOD_RES
<222> LOCATION: (7)..(7)
<223> OTHER INFORMATION: Asp or D-Asp
<220> FEATURE:
<221> NAME/KEY: MOD_RES
<222> LOCATION: (8)..(8)
<223> OTHER INFORMATION: Thr, Val, Ile, Leu, hLeu or Nle
<220> FEATURE:
<221> NAME/KEY: MOD_RES
<222> LOCATION: (9)..(9)
<223> OTHER INFORMATION: Leu, Nle, Cpa, Cba, HomoLeu, Aoc or N-Me-Leu
<220> FEATURE:
<221> NAME/KEY: MOD_RES
<222> LOCATION: (10)..(10)
<223> OTHER INFORMATION: Pen, Cys, D-Cys or HomoCys
<220> FEATURE:
<221> NAME/KEY: MOD_RES
<222> LOCATION: (11)..(11)
<223> OTHER INFORMATION: Trp, Phe, 2-Nal, 1-Nal, Tyr, His, Phe(4-F),
      Phe(4-CF3), Phe (4-CH3), Phe (4-tBu), Bip, Phe(4-COOH), Gly, 3,3-
      DiPhenylGly, 3,3 diPhenyl-Ala, Tic, b-homo-Trp, D-1-Nal, D-2-Nal,
      Phe(2,4-diCl), Phe(3,4-diCl), Phe(4-carbomyl), Phe(3-Carbomyl),
<220> FEATURE:
<221> NAME/KEY: MOD_RES
<222> LOCATION: (11)..(11)
<223> OTHER INFORMATION: continued from above; Tyr(Me), N-Me-Phe, N-Me-
      Tyr, Sar, Dihydro Trp, Ile, Leu, Ser, Arg or Thr
<220> FEATURE:
<221> NAME/KEY: MOD_RES
<222> LOCATION: (12)..(12)
<223> OTHER INFORMATION: Any aromatic amino acid, Glu, D-Glu, homoGlu,
      Asp, D-Asp, D-homoGlu, Gla, beta-homo-Glu, corresponding D-amino
      acid or isosteres
<220> FEATURE:
<221> NAME/KEY: MOD_RES
<222> LOCATION: (13)..(13)
<223> OTHER INFORMATION: Any amino acid, Lys, D-Lys, N-Me-Lys, D-N-Me-
      Lys, Orn, Dab, Dap, Homo-Lys, D-Dap, D-Dab, Cys, HomoCys, Pen or
```

```
         D-Orn

<400> SEQUENCE: 38

Xaa Xaa Xaa Xaa Arg Xaa Asp Xaa Xaa Xaa Xaa Xaa Xaa
1               5                   10
```

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Absent or any amino acid
<220> FEATURE:
<221> NAME/KEY: MOD_RES
<222> LOCATION: (4)..(4)
<223> OTHER INFORMATION: Absent, modified HomoSer or Homo-Ser-Cl
<220> FEATURE:
<221> NAME/KEY: misc_feature
<222> LOCATION: (4)..(10)
<223> OTHER INFORMATION: Thioether bond between position 4 and Xaa at
      position 10
<220> FEATURE:
<221> NAME/KEY: MOD_RES
<222> LOCATION: (5)..(5)
<223> OTHER INFORMATION: N-Me-Arg
<220> FEATURE:
<221> NAME/KEY: MOD_RES
<222> LOCATION: (7)..(7)
<223> OTHER INFORMATION: Asp or D-Asp
<220> FEATURE:
<221> NAME/KEY: MOD_RES
<222> LOCATION: (8)..(8)
<223> OTHER INFORMATION: Thr or Val
<220> FEATURE:
<221> NAME/KEY: MOD_RES
<222> LOCATION: (9)..(9)
<223> OTHER INFORMATION: Leu, Nle, Cpa, Cba, HomoLeu, Aoc or N-Me-Leu
<220> FEATURE:
<221> NAME/KEY: MOD_RES
<222> LOCATION: (10)..(10)
<223> OTHER INFORMATION: Pen, Cys, D-Cys or HomoCys
<220> FEATURE:
<221> NAME/KEY: MOD_RES
<222> LOCATION: (11)..(11)
<223> OTHER INFORMATION: Trp, Phe, 2-Nal, 1-Nal, Tyr, His, Phe(4-F),
      Phe(4-CF3), Phe (4-CH3), Phe (4-tBu), Bip, Phe(4-COOH), Gly, 3,3-
      DiPhenylGly, 3,3 diPhenyl-Ala, Tic, b-homo-Trp, D-1-Nal, D-2-Nal,
      Phe(2,4-diCl), Phe(3,4-diCl), Phe(4-carbomyl), Phe(3-Carbomyl),
<220> FEATURE:
<221> NAME/KEY: MOD_RES
<222> LOCATION: (11)..(11)
<223> OTHER INFORMATION: continued from above; Tyr(Me), N-Me-Phe, N-Me-
      Tyr, Ser, Sar, Dihydro-Trp, Ile, Leu, Arg or Thr
<220> FEATURE:
<221> NAME/KEY: MOD_RES
<222> LOCATION: (12)..(12)
<223> OTHER INFORMATION: Any aromatic amino acid, Glu, D-Glu, homoGlu,
      Asp, D-Asp, D-homoGlu, Gla, beta-homo-Glu, corresponding D-amino
      acid or isosteres
<220> FEATURE:
<221> NAME/KEY: MOD_RES
<222> LOCATION: (13)..(13)
<223> OTHER INFORMATION: Any amino acid, Lys, D-Lys, N-Me-Lys, D-N-Me-
      Lys, Orn, Dab, Dap, Homo-Lys, D-Dap, D-Dab, Cys, HomoCys, Pen or
      D-Orn

```
<400> SEQUENCE: 39

Xaa Xaa Xaa Xaa Arg Ser Asp Xaa Xaa Xaa Xaa Xaa Xaa
1               5                   10
```

```
<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Absent or any amino acid
<220> FEATURE:
<221> NAME/KEY: MOD_RES
<222> LOCATION: (4)..(4)
<223> OTHER INFORMATION: Absent, modified HomoSer or Homo-Ser-Cl
<220> FEATURE:
<221> NAME/KEY: misc_feature
<222> LOCATION: (4)..(10)
<223> OTHER INFORMATION: Thioether bond between position 4 and Xaa at
      position 10
<220> FEATURE:
<221> NAME/KEY: MOD_RES
<222> LOCATION: (5)..(5)
<223> OTHER INFORMATION: N-Me-Arg
<220> FEATURE:
<221> NAME/KEY: MOD_RES
<222> LOCATION: (7)..(7)
<223> OTHER INFORMATION: Asp or D-Asp
<220> FEATURE:
<221> NAME/KEY: MOD_RES
<222> LOCATION: (8)..(8)
<223> OTHER INFORMATION: Thr or Val
<220> FEATURE:
<221> NAME/KEY: MOD_RES
<222> LOCATION: (9)..(9)
<223> OTHER INFORMATION: Leu, Nle, Cpa, Cba, HomoLeu, Aoc or N-Me-Leu
<220> FEATURE:
<221> NAME/KEY: MOD_RES
<222> LOCATION: (10)..(10)
<223> OTHER INFORMATION: Pen, Cys, D-Cys or HomoCys
<220> FEATURE:
<221> NAME/KEY: MOD_RES
<222> LOCATION: (11)..(11)
<223> OTHER INFORMATION: Trp, Phe, 2-Nal, 1-Nal, Tyr, His, Phe(4-F),
      Phe(4-CF3), Phe (4-CH3), Phe(4-tBu), Bip, Phe(4-COOH), Gly, 3,3-
      DiPhenyl-Gly, 3,3 diPhenyl-Ala, Tic, b-homo-Trp, D-1-Nal, D-2-Nal,
      Phe(2,4-diCl), Phe(3,4-diCl), Phe(4-carbomyl), Phe(3-Carbomyl),
<220> FEATURE:
<221> NAME/KEY: MOD_RES
<222> LOCATION: (11)..(11)
<223> OTHER INFORMATION: continued from above; Tyr(Me), N-Me-Phe, N-Me-
      Tyr, Ser, Sar, Dihydro Trp, Ile, Leu, Arg or Thr
<220> FEATURE:
<221> NAME/KEY: MOD_RES
<222> LOCATION: (12)..(12)
<223> OTHER INFORMATION: Absent or any aromatic amino acid, Glu, D-Glu
      or beta-homo-Glu
<220> FEATURE:
<221> NAME/KEY: MOD_RES
<222> LOCATION: (13)..(13)
<223> OTHER INFORMATION: Any amino acid, Lys, D-Lys, N-Me-Lys, D-N-Me-
      Lys, Orn, Dab, Dap, Homo-Lys, D-Dap, D-Dab, Cys, HomoCys, Pen or
      D-Orn

<400> SEQUENCE: 40

Xaa Xaa Xaa Xaa Arg Ser Asp Xaa Xaa Xaa Xaa Xaa
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(3)
<223> OTHER INFORMATION: Absent or any amino acid
<220> FEATURE:
<221> NAME/KEY: MOD_RES
<222> LOCATION: (4)..(4)
<223> OTHER INFORMATION: Absent, modified HomoSer or Homo-Ser-Cl
<220> FEATURE:
<221> NAME/KEY: misc_feature
<222> LOCATION: (4)..(10)
<223> OTHER INFORMATION: Thioether bond between position 4 and Xaa at
      position 10
<220> FEATURE:
<221> NAME/KEY: MOD_RES
<222> LOCATION: (5)..(5)
<223> OTHER INFORMATION: N-Me-Arg
<220> FEATURE:
<221> NAME/KEY: MOD_RES
<222> LOCATION: (7)..(7)
<223> OTHER INFORMATION: Asp or D-Asp
<220> FEATURE:
<221> NAME/KEY: MOD_RES
<222> LOCATION: (8)..(8)
<223> OTHER INFORMATION: Thr or Val
<220> FEATURE:
<221> NAME/KEY: MOD_RES
<222> LOCATION: (10)..(10)
<223> OTHER INFORMATION: Pen, Cys, D-Cys or HomoCys
<220> FEATURE:
<221> NAME/KEY: MOD_RES
<222> LOCATION: (11)..(11)
<223> OTHER INFORMATION: Trp, Phe, 2-Nal, 1-Nal, Tyr, His, Phe(4-F), Phe
      (4-CF3), Phe (4-CH3), Phe (4-tBu), Bip, Phe(4-COOH), Gly, 3,3-
      DiPhenylGly, 3,3 diPhenyl-Ala, Tic, b-homo-Trp, D-1-Nal, D-2-Nal,
      Phe(2,4-diCl), Phe(3,4-diCl), Phe(4-carbomyl), Phe(3-Carbomyl),
<220> FEATURE:
<221> NAME/KEY: MOD_RES
<222> LOCATION: (11)..(11)
<223> OTHER INFORMATION: continued from above; Tyr(Me), N-Me-Phe, N-Me-
      Tyr, Ser, Sar, Dihydro Trp, Ile, Leu, Arg or Thr
<220> FEATURE:
<221> NAME/KEY: MOD_RES
<222> LOCATION: (12)..(12)
<223> OTHER INFORMATION: Any aromatic amino acid, Glu, D-Glu, beta-homo-
      Glu, corresponding D-amino acid and isosteres
<220> FEATURE:
<221> NAME/KEY: MOD_RES
<222> LOCATION: (13)..(13)
<223> OTHER INFORMATION: Any amino acid or Lys, D-Lys, N-Me-Lys, D-N-Me-
      Lys, Orn, Dab, Dap, Homo-Lys, D-Dap, D-Dab, Cys, HomoCys, Pen, or
      D-Orn

<400> SEQUENCE: 41

Xaa Xaa Xaa Xaa Arg Ser Asp Xaa Leu Xaa Xaa Xaa Xaa
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Absent or any amino acid
<220> FEATURE:
<221> NAME/KEY: MOD_RES
<222> LOCATION: (4)..(4)
<223> OTHER INFORMATION: Absent, modified HomoSer or Homo-Ser-Cl
<220> FEATURE:
<221> NAME/KEY: misc_feature
<222> LOCATION: (4)..(10)
<223> OTHER INFORMATION: Thioether bond between position 4 and Xaa at
      position 10
<220> FEATURE:
<221> NAME/KEY: MOD_RES
```

```
<222> LOCATION: (5)..(5)
<223> OTHER INFORMATION: N-Me-Arg
<220> FEATURE:
<221> NAME/KEY: MOD_RES
<222> LOCATION: (7)..(7)
<223> OTHER INFORMATION: Asp or D-Asp
<220> FEATURE:
<221> NAME/KEY: MOD_RES
<222> LOCATION: (8)..(8)
<223> OTHER INFORMATION: Thr or Val
<220> FEATURE:
<221> NAME/KEY: MOD_RES
<222> LOCATION: (10)..(10)
<223> OTHER INFORMATION: Pen, Cys, D-Cys or HomoCys
<220> FEATURE:
<221> NAME/KEY: MOD_RES
<222> LOCATION: (11)..(11)
<223> OTHER INFORMATION: Trp, Phe, 2-Nal, 1-Nal, Tyr, His, Phe(4-F), Phe
      (4-CF3), Phe (4-CH3), Phe (4-tBu), Bip, Phe(4-COOH), Gly, 3,3-
      DiPhenylGly, 3,3 diPhenyl Ala, Tic, b-homo-Trp, D-1-Nal, D-2-Nal,
      Phe(2,4-diCl), Phe(3,4-diCl), Phe(4-carbomyl), Phe(3-Carbomyl),
      Tyr(Me),
<220> FEATURE:
<221> NAME/KEY: MOD_RES
<222> LOCATION: (11)..(11)
<223> OTHER INFORMATION: continued from above; N-Me-Phe, N-Me-Tyr, Ser,
      Sar, Dihydro Trp, Ile, Leu, Arg or Thr
<220> FEATURE:
<221> NAME/KEY: MOD_RES
<222> LOCATION: (12)..(12)
<223> OTHER INFORMATION: Any aromatic amino acid, Glu, D-Glu or beta-
      Homo-Glu
<220> FEATURE:
<221> NAME/KEY: MOD_RES
<222> LOCATION: (13)..(13)
<223> OTHER INFORMATION: Any amino acid, Lys, D-Lys, N-Me-Lys, D-N-Me-
      Lys, Orn, Dab, Dap, Homo-Lys, D-Dap, D-Dab, Cys, HomoCys, Pen or
      D-Orn

<400> SEQUENCE: 42

Xaa Xaa Xaa Xaa Arg Ser Asp Xaa Leu Xaa Xaa Xaa Xaa
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Absent or any amino acid
<220> FEATURE:
<221> NAME/KEY: MOD_RES
<222> LOCATION: (4)..(4)
<223> OTHER INFORMATION: Absent, modified HomoSer or Homo-Ser-Cl
<220> FEATURE:
<221> NAME/KEY: misc_feature
<222> LOCATION: (4)..(10)
<223> OTHER INFORMATION: Thioether bond between position 4 and Xaa at
      position 10
<220> FEATURE:
<221> NAME/KEY: MOD_RES
<222> LOCATION: (5)..(5)
<223> OTHER INFORMATION: N-Me-Arg
<220> FEATURE:
<221> NAME/KEY: MOD_RES
<222> LOCATION: (7)..(7)
<223> OTHER INFORMATION: Asp or D-Asp
<220> FEATURE:
<221> NAME/KEY: MOD_RES
<222> LOCATION: (8)..(8)
<223> OTHER INFORMATION: Thr or Val
<220> FEATURE:
<221> NAME/KEY: MOD_RES
```

```
<222> LOCATION: (10)..(10)
<223> OTHER INFORMATION: Pen, Cys, D-Cys or HomoCys
<220> FEATURE:
<221> NAME/KEY: MOD_RES
<222> LOCATION: (11)..(11)
<223> OTHER INFORMATION: Trp, Phe, 2-Nal, 1-Nal, Tyr, His, Phe(4-F), Phe
      (4-CF3), Phe (4-CH3), Phe (4-tBu), Bip, Phe(4-COOH), Gly, 3,3-
      DiPhenylGly, 3,3 diPhenyl Ala, Tic, b-homo-Trp, D-1-Nal, D-2-Nal,
      Phe(2,4-diCl), Phe(3,4-diCl), Phe(4-carbomyl), Phe(3-Carbomyl),
      Tyr(Me),
<220> FEATURE:
<221> NAME/KEY: MOD_RES
<222> LOCATION: (11)..(11)
<223> OTHER INFORMATION: continued from above; N-Me-Phe, N-Me-Tyr, Ser,
      Sar, Dihydro Trp, Ile, Leu, Arg or Thr
<220> FEATURE:
<221> NAME/KEY: MOD_RES
<222> LOCATION: (12)..(12)
<223> OTHER INFORMATION: Any aromatic amino acid, Glu, D-Glu or Beta-
      Homo-Glu
<220> FEATURE:
<221> NAME/KEY: MOD_RES
<222> LOCATION: (13)..(13)
<223> OTHER INFORMATION: Any amino acid, D-Lys, N-Me-Lys or D-N-Me-Lys

<400> SEQUENCE: 43

Xaa Xaa Xaa Xaa Arg Ser Asp Xaa Leu Xaa Xaa Xaa Xaa
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Absent or any amino acid
<220> FEATURE:
<221> NAME/KEY: MOD_RES
<222> LOCATION: (4)..(4)
<223> OTHER INFORMATION: Absent, modified HomoSer or Homo-Ser-Cl
<220> FEATURE:
<221> NAME/KEY: misc_feature
<222> LOCATION: (4)..(10)
<223> OTHER INFORMATION: Thioether bond between position 4 and Xaa at
      position 10
<220> FEATURE:
<221> NAME/KEY: MOD_RES
<222> LOCATION: (5)..(5)
<223> OTHER INFORMATION: N-Me-Arg
<220> FEATURE:
<221> NAME/KEY: MOD_RES
<222> LOCATION: (7)..(7)
<223> OTHER INFORMATION: Asp or D-Asp
<220> FEATURE:
<221> NAME/KEY: MOD_RES
<222> LOCATION: (8)..(8)
<223> OTHER INFORMATION: Thr or Val
<220> FEATURE:
<221> NAME/KEY: MOD_RES
<222> LOCATION: (10)..(10)
<223> OTHER INFORMATION: Pen, Cys, D-Cys or HomoCys
<220> FEATURE:
<221> NAME/KEY: MOD_RES
<222> LOCATION: (11)..(11)
<223> OTHER INFORMATION: Trp, Phe, 2-Nal, 1-Nal, Tyr, His, Phe(4-F), Phe
      (4-CF3), Phe (4-CH3), Phe (4-tBu), Bip, Phe(4-COOH), Gly, 3,3-
      DiPhenylGly, 3,3 diPhenylAla, Tic, b-homo-Trp, D-1-Nal, D-2-Nal,
      Phe(2,4-diCl), Phe(3,4-diCl), Phe(4-carbomyl), Phe(3-Carbomyl),
<220> FEATURE:
<221> NAME/KEY: MOD_RES
<222> LOCATION: (11)..(11)
<223> OTHER INFORMATION: continued from above; Tyr(Me) or HomoPhe
<220> FEATURE:
```

```
<221> NAME/KEY: MOD_RES
<222> LOCATION: (12)..(12)
<223> OTHER INFORMATION: Any aromatic amino acid, Glu, D-Glu, and beta-
      homo-Glu

<400> SEQUENCE: 44

Xaa Xaa Xaa Xaa Arg Ser Asp Xaa Leu Xaa Xaa Xaa
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Absent, Modified Ser or modified HomoSer
<220> FEATURE:
<221> NAME/KEY: misc_feature
<222> LOCATION: (1)..(7)
<223> OTHER INFORMATION: Thioether bond between position 1 and Xaa at
      position 7
<220> FEATURE:
<221> NAME/KEY: MOD_RES
<222> LOCATION: (2)..(2)
<223> OTHER INFORMATION: N(alpha)-Me-Arg, Arg, HArg, Dap, Dab, Arg-Me-
      sym, Arg-Me-asym, 4-Guan, Cit, Cav or suitable isostere
      replacements
<220> FEATURE:
<221> NAME/KEY: MOD_RES
<222> LOCATION: (3)..(3)
<223> OTHER INFORMATION: Ser, Gly, Thr, Ile or suitable isostere
      replacements
<220> FEATURE:
<221> NAME/KEY: MOD_RES
<222> LOCATION: (4)..(4)
<223> OTHER INFORMATION: Asp, N-Me-Asp, D-Asp or suitable isostere
      replacements
<220> FEATURE:
<221> NAME/KEY: MOD_RES
<222> LOCATION: (5)..(5)
<223> OTHER INFORMATION: Thr, Gln, Ser, Asp, Pro, Gly, His, Ala, Ile,
      Phe, Lys, Arg, Asn, Glu, Val, Tyr, Trp, Leu, Met or N-Methyl amino
      acids including N-Me-Thr
<220> FEATURE:
<221> NAME/KEY: MOD_RES
<222> LOCATION: (6)..(6)
<223> OTHER INFORMATION: Gln, Asn, Asp, Pro, Gly, Ala, Phe, Leu, Glu,
      Ile, Val, HLeu, n-Butyl Ala, n-Pentyl Ala, n-Hexyl Ala, Nle,
      cyclobutyl-Ala, N-Me-Leu or suitable isostere replacements
<220> FEATURE:
<221> NAME/KEY: MOD_RES
<222> LOCATION: (7)..(7)
<223> OTHER INFORMATION: Cys, N-Me-Cys, D-Cys, HCys, Pen, D-Pen or Pen
      (=O)
<220> FEATURE:
<221> NAME/KEY: MOD_RES
<222> LOCATION: (8)..(8)
<223> OTHER INFORMATION: Absent, Gly, Gln, Asn, Asp, Ala, Ile, Leu, Val,
      Met, Thr, Lys, Trp, Tyr, His, Glu, Ser, Arg, Pro, Phe, Sar, 1-Nal,
      2-Nal, D-1-Nal, D-2-Nal, D-Phe, D-Tyr, HPhe, Phe(4-F), O-Me-Tyr,
      dihydro-Trp, Dap, Dab, Dab(Ac), Orn, D-Orn, N-Me-Orn, N-Me-Dap,
<220> FEATURE:
<221> NAME/KEY: MOD_RES
<222> LOCATION: (8)..(8)
<223> OTHER INFORMATION: continued from above; D-N-Me-Lys, D-Dap, D-Dab,
      Bip, Ala(3,3diphenyl), Biphenyl-Ala, Phe(4tBu), Phe(4-OMe),
      Phe(4-COOH), Phe(2-carbomyl), Phe(3-carbomyl), Phe(CF3),
      Phe(2,4-diCl), Phe(3,4-diCl), Aic, N-Me-Tyr, N-Me-Phe, Tic,
<220> FEATURE:
<221> NAME/KEY: MOD_RES
<222> LOCATION: (8)..(8)
<223> OTHER INFORMATION: continued from above; Phe(4CF3), aromatic ring
      substituted Phe, aromatic ring substituted Trp, aromatic ring
```

```
                substituted His, hetero aromatic amino acids, N-Me-Lys, N-Me-Lys
                (Ac), 4-Me-Phe, or corresponding D-amino acids and suitable
                isostere replacements
<220> FEATURE:
<221> NAME/KEY: MOD_RES
<222> LOCATION: (9)..(9)
<223> OTHER INFORMATION: Absent, Glu, Lys, Gln, Pro, Gly, His, Ala, Ile,
      Phe, Lys, Arg, Leu, Val, Tyr, Trp, Met, Gla, Ser, Asn, D-Glu,
      Beta-HGlu, 2-Nal, 1-Nal, D-1-Nal, D-2-Nal, D-Phe, D-Tyr, D-Asp,
      Bip, Beta-HPhe, Beta-Glu, D-Tyr, D-Lys, Dap, Dab, Orn, D-Orn,
      N-Me-Orn, N-Me-Dap,
<220> FEATURE:
<221> NAME/KEY: MOD_RES
<222> LOCATION: (9)..(9)
<223> OTHER INFORMATION: continued from above; N-Me-Dab, N-Me Lys, D-N-
      Me-Lys D-Dap, D-Dab, O-Me-Glu, suitable isosteres or corresponding
      D-amino acids
<220> FEATURE:
<221> NAME/KEY: MOD_RES
<222> LOCATION: (10)..(10)
<223> OTHER INFORMATION: Absent, Gln, Pro, Gly, His, Ala, Ile, Phe, Lys,
      Arg, Leu, Val, Tyr, Trp, Met, Glu, Ser, Asn, Gla, Dap, Dab, Orn,
      D-Orn, D-Lys, N-Me-Orn, N-Me-Dap, N-Me-Dab, D-N-Me-Lys N-Me-Lys,
      D-Dap, D-Dab, suitable isosteres, or corresponding D-amino acids
<220> FEATURE:
<221> NAME/KEY: MOD_RES
<222> LOCATION: (11)..(11)
<223> OTHER INFORMATION: Absent or any amino acid

<400> SEQUENCE: 45

Xaa Xaa Xaa Xaa Xaa Xaa Xaa Xaa Xaa Xaa Xaa
1               5                   10

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-methylbenzoyl forming a thioether bond
      between the N-term and position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (2)..(2)
<223> OTHER INFORMATION: Ser, Gly, Thr, or Ile
<220> FEATURE:
<221> NAME/KEY: MOD_RES
<222> LOCATION: (5)..(5)
<223> OTHER INFORMATION: Leu or Nle
<220> FEATURE:
<221> NAME/KEY: MOD_RES
<222> LOCATION: (6)..(6)
<223> OTHER INFORMATION: Pen, Cys or D-Cys
<220> FEATURE:
<221> NAME/KEY: MOD_RES
<222> LOCATION: (7)..(7)
<223> OTHER INFORMATION: Phe, D-Phe, Tyr, Bip, Tic, 1-Nal, 2-Nal or Trp
<220> FEATURE:
<221> NAME/KEY: MOD_RES
<222> LOCATION: (8)..(8)
<223> OTHER INFORMATION: D-Glu, Glu, Tyr, b-homo-Glu, or 2-Nal
<220> FEATURE:
<221> NAME/KEY: MOD_RES
<222> LOCATION: (9)..(9)
<223> OTHER INFORMATION: D-Lys, D-N-Me-Lys, Dap, Phe, D-Phe or absent

<400> SEQUENCE: 46

Arg Xaa Asp Thr Xaa Xaa Xaa Xaa Xaa
1               5
```

```
<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-methylbenzoyl forming a thioether bond
      between the N-term and position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (5)..(5)
<223> OTHER INFORMATION: Leu or Nle
<220> FEATURE:
<221> NAME/KEY: MOD_RES
<222> LOCATION: (6)..(6)
<223> OTHER INFORMATION: Pen, Cys, homoCys, Pen(=O) or D-Cys
<220> FEATURE:
<221> NAME/KEY: MOD_RES
<222> LOCATION: (7)..(7)
<223> OTHER INFORMATION: Phe, D-Phe, Tyr, D-Tyr, His, Bip, Tic, 1-Nal,
      2-Nal, Phe(CH3), Phe(2,4-diCl), Phe(3,4-diCl), Aic, N-Me-Tyr, N-
      Me-Phe, Phe(2-carbomyl), Phe(3-carbomyl), Phe(4-COOH), Phe(4OMe),
      Phe(4tBu), Phe-(4-F), Phe(4CF3) or Trp
<220> FEATURE:
<221> NAME/KEY: MOD_RES
<222> LOCATION: (8)..(8)
<223> OTHER INFORMATION: Absent, Glu, Beta-homo-Glu, Bip, O-Me-Glu,
      D-Lys, D-Phe, Tyr, 2-Nal, D-Tyr, Pro, Tic, D-Glu, D-Thr, D-Arg,
      D-Leu, D-Trp, Phe(4-COOH), D-His, Pro, D-Pro or Glu(OMe)
<220> FEATURE:
<221> NAME/KEY: MOD_RES
<222> LOCATION: (9)..(9)
<223> OTHER INFORMATION: Absent or any amino acid residue

<400> SEQUENCE: 47

Arg Ser Asp Thr Xaa Xaa Xaa Xaa Xaa
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-methylbenzoyl forming a thioether bond
      between the N-term and position 6
<220> FEATURE:
<221> NAME/KEY: MOD_RES
<222> LOCATION: (1)..(1)
<223> OTHER INFORMATION: N-methyl-Arg
<220> FEATURE:
<221> NAME/KEY: MOD_RES
<222> LOCATION: (2)..(2)
<223> OTHER INFORMATION: Ser, Gly, Thr or Ile
<220> FEATURE:
<221> NAME/KEY: MOD_RES
<222> LOCATION: (5)..(5)
<223> OTHER INFORMATION: Leu or Nle
<220> FEATURE:
<221> NAME/KEY: MOD_RES
<222> LOCATION: (6)..(6)
<223> OTHER INFORMATION: Cys, D-Cys, Hcys or Pen
<220> FEATURE:
<221> NAME/KEY: MOD_RES
<222> LOCATION: (7)..(7)
<223> OTHER INFORMATION: Trp, Tic, Bip, 1-Nal, 2-Nal, Phe(4tBu) or Phe
      (4-COOH)
<220> FEATURE:
```

```
<221> NAME/KEY: MOD_RES
<222> LOCATION: (8)..(8)
<223> OTHER INFORMATION: Glu, Beta-Homo-Glu or D-Glu
<220> FEATURE:
<221> NAME/KEY: MOD_RES
<222> LOCATION: (9)..(9)
<223> OTHER INFORMATION: Any amino acid

<400> SEQUENCE: 48

Arg Xaa Asp Thr Xaa Xaa Xaa Xaa Xaa
1               5

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Absent or any amino acid
<220> FEATURE:
<221> NAME/KEY: misc_feature
<222> LOCATION: (4)..(10)
<223> OTHER INFORMATION: Thioether linkage between position 4 and
      position 10
<220> FEATURE:
<221> NAME/KEY: MOD_RES
<222> LOCATION: (5)..(5)
<223> OTHER INFORMATION: N(alpha)-Me-Arg, Arg, HomoArg, Dap, Dab, Arg-
      Me-sym, Arg-Me-asym, 4-Guan, Cit, Cav, N-Me-Lys, Phe(4-quanidino),
      Phe(4-carbamoyl amino), Phe(4-NH2), N-Me-HomoArg, Tyr, His or
      suitable isostere replacements
<220> FEATURE:
<221> NAME/KEY: MOD_RES
<222> LOCATION: (6)..(6)
<223> OTHER INFORMATION: Ser, Gly, Thr, Ile or suitable isostere
      replacements
<220> FEATURE:
<221> NAME/KEY: MOD_RES
<222> LOCATION: (7)..(7)
<223> OTHER INFORMATION: Asp, N-Me-Asp, Asp(OMe), D-Asp or suitable
      isostere replacements
<220> FEATURE:
<221> NAME/KEY: MOD_RES
<222> LOCATION: (8)..(8)
<223> OTHER INFORMATION: Thr, Gln, Ser, Asp, Pro, Gly, His, Ala, Ile,
      Phe, Lys, Arg, Asn, Glu, Val, Tyr, Trp, Leu, Met, HomoLeu, Nle or
      N-Methyl amino acids including N-Me-Thr
<220> FEATURE:
<221> NAME/KEY: MOD_RES
<222> LOCATION: (9)..(9)
<223> OTHER INFORMATION: Gln, Asn, Asp, Pro, Gly, Ala, Phe, Leu, Glu,
      Ile, Val, HLeu, n-Butyl Ala, n-Pentyl Ala, n-Hexyl Ala, Nle,
      cyclobutyl-Ala, Cpa, Aoc, N-Me-Leu or suitable isostere
      replacements
<220> FEATURE:
<221> NAME/KEY: MOD_RES
<222> LOCATION: (10)..(10)
<223> OTHER INFORMATION: Cys, N-Me-Cys, D-Cys, HCys, Pen, D-Pen or Pen
      (=O)
<220> FEATURE:
<221> NAME/KEY: MOD_RES
<222> LOCATION: (11)..(11)
<223> OTHER INFORMATION: Trp, Phe, 2-Nal, 1-Nal, Tyr, His, Phe(4-F), Phe
      (4-CF3), Phe(4-CH3), Phe(4-tBu), Bip, Phe(4-COOH), Gly,
      3,3-DiPhenylGly, 3,3 diPhenyl Ala, Tic, b-homo-Trp, D-1-Nal,
      D-2-Nal, Phe(2,4-diCl), Phe(3,4-diCl), Phe(4-carbomyl),
<220> FEATURE:
<221> NAME/KEY: MOD_RES
<222> LOCATION: (11)..(11)
<223> OTHER INFORMATION: continued from above; Phe(3-Carbomyl), Phe (2-
      carbomyl), Tyr(Me), HomoPhe, N-Me-Phe, N-Me-Tyr, Ser, Sar, Dihydro
      Trp, Ile, Leu, Arg, Thr, aromatic amino acids, substituted
      aromatic amino acids, Gly, Gln, Asn, Asp, Ala, Ile, Leu, Val, Met,
```

```
        Thr,
<220> FEATURE:
<221> NAME/KEY: MOD_RES
<222> LOCATION: (11)..(11)
<223> OTHER INFORMATION: continued from above; Lys, Trp, Tyr, His, Glu,
      Ser, Arg, Pro, Phe, 1-Nal, 2-Nal, D-1-Nal, D-2-Nal, HPhe, D-Phe,
      D-Tyr, Phe(4-F), O-Me-Tyr, dihydro-Trp, Dap, Dab, Dab(Ac), Orn, D-
      Orn, N-Me-Orn, N-Me-Dap, D-Dap, D-Dab, Bip, Ala(3,3diphenyl),
      Biphenyl-Ala,
<220> FEATURE:
<221> NAME/KEY: MOD_RES
<222> LOCATION: (11)..(11)
<223> OTHER INFORMATION: continued from above; aromatic ring substituted
      Phe, aromatic ring substituted Trp, aromatic ring substituted His,
      hetero aromatic amino acids, N-Me-Lys, N-Me-Lys(Ac), 4-Me-Phe, Phe
      (4tBu), Phe(4-OMe), Phe(4-COOH), Phe(2-carbomyl), Phe(3-carbomyl),
<220> FEATURE:
<221> NAME/KEY: MOD_RES
<222> LOCATION: (11)..(11)
<223> OTHER INFORMATION: continued from above; Phe(CF3), Phe(2,4-diCl),
      Phe(3,4-diCl), Aic, N-Me-Tyr, N-Me-Phe, Tic, Phe(4CF3), Bpa, Phe
      (3-Me), Phe(2-Me), Phe(2-CF3), Beta-Me-Phe, or corresponding D-
      amino acids and suitable isostere replacements or absent
<220> FEATURE:
<221> NAME/KEY: MOD_RES
<222> LOCATION: (12)..(12)
<223> OTHER INFORMATION: Any aromatic amino acids, substituted aromatic
      amino acids, Glu, D-Glu, HomoGlu, Beta-Homo-Glu, Asp, D-HomoGlu,
      Lys, Gln, Pro, Gly, His, Ala, Ile, Phe, Arg, Leu, Val, Tyr, Trp,
      Met, Gla, Ser, Asn, D-Glu, Beta-HGlu, 2-Nal, 1-Nal, D-Asp, Bip,
      Beta-HPhe,
<220> FEATURE:
<221> NAME/KEY: MOD_RES
<222> LOCATION: (12)..(12)
<223> OTHER INFORMATION: continued from above; Beta-Glu, D-Tyr, D-Phe,
      D-Lys, Dap, Dab, Orn, D-Orn, N-Me-Orn, N-Me-Dap, N-Me-Dab, N-Me-
      Lys, D-Dap, D-Dab, D-His, Phe(4-COOH), Tic, D-Trp, D-Leu, D-Arg,
      D-Thr, N-Me-Glu, N-Me-Asp, alpha-H-Glu, suitable isosteres,
<220> FEATURE:
<221> NAME/KEY: MOD_RES
<222> LOCATION: (12)..(12)
<223> OTHER INFORMATION: continued from above; corresponding D-amino
      acids or absent
<220> FEATURE:
<221> NAME/KEY: MOD_RES
<222> LOCATION: (13)..(13)
<223> OTHER INFORMATION: Absent or any amino acid
<220> FEATURE:
<221> NAME/KEY: MOD_RES
<222> LOCATION: (14)..(14)
<223> OTHER INFORMATION: Absent, any amino acid, any amino acid with an
      amine side chain, Lys, D-Lys, N-Me-Lys, D-N-Me-Lys, Orn, N-Me-Orn,
      Dab, N-Me-Dab, Dap, N-Me-Dap, Homo-Lys, D-Dap, D-Dab, D-Orn, Gln,
      Pro, Gly, His, Ala, Ile, Phe, Lys, Arg, Leu, Val, Tyr, Trp, Met,
      Glu, Ser, Asn,
<220> FEATURE:
<221> NAME/KEY: MOD_RES
<222> LOCATION: (14)..(14)
<223> OTHER INFORMATION: Continued from above;  Gla, Cys, HomoCys,
      suitable isosteres, corresponding D-amino acids or corresponding
      N-Methyl amino acids

<400> SEQUENCE: 49

Xaa Xaa Xaa Xaa Xaa Xaa Xaa Xaa Xaa Xaa Xaa Xaa Xaa Xaa
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Me-benzoyl forming a thioether bond
      with the Xaa at position 6
<220> FEATURE:
```

```
<221> NAME/KEY: MOD_RES
<222> LOCATION: (1)..(1)
<223> OTHER INFORMATION: N(alpha)-Me-Arg, Arg, HArg, Dap, Dab, Arg-Me-
      sym, Arg-Me-asym, 4-Guan, Cit, Cav or suitable isostere
      replacements
<220> FEATURE:
<221> NAME/KEY: MOD_RES
<222> LOCATION: (2)..(2)
<223> OTHER INFORMATION: Ser, Gly or suitable isostere replacements
<220> FEATURE:
<221> NAME/KEY: MOD_RES
<222> LOCATION: (3)..(3)
<223> OTHER INFORMATION: Asp, N-Me-Asp, Asp(OMe), D-Asp or suitable
      isostere replacements
<220> FEATURE:
<221> NAME/KEY: MOD_RES
<222> LOCATION: (4)..(4)
<223> OTHER INFORMATION: Thr, Gln, Ser, Asp, Pro, Gly, His, Ala, Ile,
      Phe, Lys, Arg, Asn, Glu, Val, Tyr, Trp, Leu, Met, and N-Methyl
      amino acids including N-Me-Thr or suitable isostere replacements
<220> FEATURE:
<221> NAME/KEY: MOD_RES
<222> LOCATION: (5)..(5)
<223> OTHER INFORMATION: Gln, Asn, Asp, Pro, Gly, Ala, Phe, Leu, Glu,
      Ile, Val, HLeu, n-Butyl Ala, n-Pentyl Ala, n-Hexyl Ala, Nle,
      cyclobutyl-Ala, N-Me-Leu or suitable isostere replacements
<220> FEATURE:
<221> NAME/KEY: MOD_RES
<222> LOCATION: (6)..(6)
<223> OTHER INFORMATION: Cys, N-Me-Cys, D-Cys, HCys, Pen or D-Pen
<220> FEATURE:
<221> NAME/KEY: MOD_RES
<222> LOCATION: (7)..(7)
<223> OTHER INFORMATION: Absent, Gly, Gln, Asn, Asp, Ala, Ile, Leu, Val,
      Met, Thr, Lys, Trp, Tyr, His, Glu, Ser, Arg, Pro, Phe, Sar, 1-Nal,
      2-Nal, HPhe, Phe(4-F), O-Me-Tyr, dihydro-Trp, Dap, Dab, Dab(Ac),
      Orn, D-Orn, N-Me-Orn, N-Me-Dap, D-Dap, D-Dab, Bip, Ala
      (3,3diphenyl),
<220> FEATURE:
<221> NAME/KEY: MOD_RES
<222> LOCATION: (7)..(7)
<223> OTHER INFORMATION: continued from above; Biphenyl-Ala, aromatic
      ring substituted Phe, aromatic ring substituted Trp, aromatic
      ring substituted His, hetero aromatic amino acids, N-Me-Lys, N-Me-
      Lys(Ac), Bpa, Phe(3-Me), Phe(2-Me), Phe(2-CF3), beta-Me-Phe, 4-
      Me-Phe,
<220> FEATURE:
<221> NAME/KEY: MOD_RES
<222> LOCATION: (7)..(7)
<223> OTHER INFORMATION: continued from above; corresponding D-amino
      acids and suitable isostere replacements
<220> FEATURE:
<221> NAME/KEY: MOD_RES
<222> LOCATION: (8)..(8)
<223> OTHER INFORMATION: Absent, Glu, Lys, Gln, Pro, Gly, His, Ala,
      Ile, Phe, Lys, Arg, Leu, Val, Tyr, Trp, Met, Gla, Ser, Asn, D-Glu,
      Beta-HGlu, 2-Nal, 1-Nal, D-Asp, Bip, Beta-HPhe, Beta-Glu, D-Tyr,
      D-Lys, Dap, Dab, Orn, D-Orn, N-Me-Orn, N-Me-Dap, N-Me-Dab,
<220> FEATURE:
<221> NAME/KEY: MOD_RES
<222> LOCATION: (8)..(8)
<223> OTHER INFORMATION: continued from above; N-Me-Lys, D-Dap, D-Dab,
      Glu, N-Me-Asp, alpha-H-Glu, suitable isosteres or corresponding D-
      amino acids
<220> FEATURE:
<221> NAME/KEY: MOD_RES
<222> LOCATION: (9)..(9)
<223> OTHER INFORMATION: Absent, Gln, Pro, Gly, His, Ala, Ile, Phe, Lys,
      Arg, Leu, Val, Tyr, Trp, Met, Glu, Ser, Asn, Gla, Dap, Dab, Orn,
      D-Orn, D-Lys, N-Me-Orn, N-Me-Dap, N-Me-Dab, N-Me-Lys, D-Dap, D-
      Dab, suitable isosteres or corresponding D-amino acids
<220> FEATURE:
<221> NAME/KEY: MOD_RES
<222> LOCATION: (10)..(10)
<223> OTHER INFORMATION: Absent, Gln, Pro, Gly, His, Ala, Ile, Phe, Lys,
      Arg, Leu, Val, Tyr, Trp, Met, Glu, Ser, Asn, Gla, Dap, Dab, Orn,
      D-Orn, D-Lys, N-Me-Orn, N-Me-Dap, N-Me-Dab, N-Me-Lys, D-Dap, D-
      Dab, suitable isosteres or corresponding D-amino acids
```

```
<400> SEQUENCE: 50

Xaa Xaa Xaa Xaa Xaa Xaa Xaa Xaa Xaa Xaa
1               5                   10

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Propionyl
<220> FEATURE:
<221> NAME/KEY: misc_feature
<222> LOCATION: (1)..(6)
<223> OTHER INFORMATION: Thioether linkage between N-term and residue
      at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term NH2

<400> SEQUENCE: 51

Arg Ser Asp Thr Leu Cys Trp Lys
1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Alpha-bromoispbutyryl with a thioether
      bond between the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term NH2

<400> SEQUENCE: 52

Arg Ser Asp Thr Leu Cys Trp Lys
1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl with a thioether bond between the
      N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
```

```
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term NH2

<400> SEQUENCE: 53

Arg Ser Asp Thr Leu Xaa Trp Lys
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Propionyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term NH2

<400> SEQUENCE: 54

Arg Ser Asp Thr Leu Xaa Trp Lys
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 55

Arg Ser Asp Thr Leu Cys Trp Glu Lys
1               5

<210> SEQ ID NO 56
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 56

Arg Ser Asp Thr Leu Xaa Trp Glu Lys
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Propionyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Homo-Cys
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term NH2

<400> SEQUENCE: 57

Arg Ser Asp Thr Leu Cys Trp Lys
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Butyryl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term NH2

<400> SEQUENCE: 58
```

```
Arg Ser Asp Thr Leu Cys Trp Lys
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term NH2

<400> SEQUENCE: 59

Arg Ser Asp Thr Leu Cys Trp Lys
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 60

Arg Ser Asp Thr Leu Xaa Trp Glu Lys
1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
```

```
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 61

Arg Ser Asp Thr Leu Xaa Trp Glu Lys
1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: D-N-Me-Lys
<220> FEATURE:
<223> OTHER INFORMATION: C-term NH2

<400> SEQUENCE: 62

Arg Ser Asp Thr Leu Xaa Trp Glu Lys
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: N-Me-Lys
<220> FEATURE:
<223> OTHER INFORMATION: C-term NH2

<400> SEQUENCE: 63

Arg Ser Asp Thr Leu Xaa Trp Tyr Lys
1               5
```

```
<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (5)..(5)
<223> OTHER INFORMATION: Nle
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 64

Arg Ser Asp Thr Leu Xaa Trp Glu Lys
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 65

Arg Ser Asp Thr Leu Xaa Phe Glu Lys
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: D-Cys
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 66

Arg Ser Asp Thr Leu Cys Trp Glu Lys
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Homo-Cys
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 67

Arg Ser Asp Thr Leu Cys Trp Glu Lys
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
```

-continued

```
<222> LOCATION: (7)..(7)
<223> OTHER INFORMATION: 1-Nal
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 68

Arg Ser Asp Thr Leu Xaa Xaa Glu Lys
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: N-Me-Lys
<220> FEATURE:
<223> OTHER INFORMATION: C-term NH2

<400> SEQUENCE: 69

Arg Ser Asp Thr Leu Xaa Xaa Glu Lys
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
```

```
<223> OTHER INFORMATION: 2-Nal
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 70

Arg Ser Asp Thr Leu Xaa Xaa Glu Lys
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 71

Arg Ser Asp Thr Leu Xaa Phe Xaa Lys
1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: D-Phe
```

```
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 72

Arg Ser Asp Thr Leu Xaa Phe Glu Lys
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 73

Arg Ser Asp Thr Leu Xaa Phe Glu Lys
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 74
```

```
Arg Ser Asp Thr Leu Xaa Tyr Glu Lys
1               5
```

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 75

```
Arg Ser Asp Thr Leu Xaa Xaa Glu Lys
1               5
```

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(CF3)
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 76

```
Arg Ser Asp Thr Leu Xaa Phe Glu Lys
1               5
```

<210> SEQ ID NO 77

```
-continued

<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 77

Arg Ser Asp Thr Leu Xaa Xaa Glu Lys
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 78

Arg Ser Asp Thr Leu Xaa Tyr Glu Lys
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
```

```
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 79

Arg Ser Asp Thr Leu Xaa Tyr Glu Lys
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: D-Lys(Ac)
<220> FEATURE:
<223> OTHER INFORMATION: C-term NH2

<400> SEQUENCE: 80

Arg Ser Asp Thr Leu Xaa Trp Glu Lys
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys(Ac)
<220> FEATURE:
```

<223> OTHER INFORMATION: C-term NH2

<400> SEQUENCE: 81

Arg Ser Asp Thr Leu Xaa Trp Glu Lys
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys(PEG8)
<220> FEATURE:
<223> OTHER INFORMATION: C-term NH2

<400> SEQUENCE: 82

Arg Ser Asp Thr Leu Xaa Trp Glu Lys
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-Lys(Ac)
<220> FEATURE:
<223> OTHER INFORMATION: C-term NH2

<400> SEQUENCE: 83

Arg Ser Asp Thr Leu Xaa Trp Glu Lys
1               5

<210> SEQ ID NO 84

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: D-N-Me-Lys(Ac)
<220> FEATURE:
<223> OTHER INFORMATION: C-term NH2

<400> SEQUENCE: 84

Arg Ser Asp Thr Leu Xaa Trp Glu Lys
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: N-Me-Lys(Ac)
<220> FEATURE:
<223> OTHER INFORMATION: C-term NH2

<400> SEQUENCE: 85

Arg Ser Asp Thr Leu Xaa Trp Tyr Lys
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (5)..(5)
<223> OTHER INFORMATION: Nle
```

```
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: D-Lys(Ac)
<220> FEATURE:
<223> OTHER INFORMATION: C-term NH2

<400> SEQUENCE: 86

Arg Ser Asp Thr Leu Xaa Trp Glu Lys
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys(Ac)
<220> FEATURE:
<223> OTHER INFORMATION: C-term NH2

<400> SEQUENCE: 87

Arg Ser Asp Thr Leu Xaa Phe Glu Lys
1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(CF3)
<220> FEATURE:
<221> NAME/KEY: MOD_RES
<222> LOCATION: (9)..(9)
<223> OTHER INFORMATION: D-Lys(Ac)
<220> FEATURE:
```

<223> OTHER INFORMATION: C-term NH2

<400> SEQUENCE: 88

Arg Ser Asp Thr Leu Xaa Phe Glu Lys
1               5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (9)..(9)
<223> OTHER INFORMATION: D-Lys(Ac)
<220> FEATURE:
<223> OTHER INFORMATION: C-term NH2

<400> SEQUENCE: 89

Arg Ser Asp Thr Leu Xaa Xaa Glu Lys
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: D-Lys(Ac)
<220> FEATURE:
<223> OTHER INFORMATION: C-term NH2

<400> SEQUENCE: 90

Arg Ser Asp Thr Leu Xaa Tyr Glu Lys
1               5

<210> SEQ ID NO 91
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys(Ac)
<220> FEATURE:
<223> OTHER INFORMATION: C-term NH2

<400> SEQUENCE: 91

Arg Ser Asp Thr Leu Xaa Tyr Glu Lys
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: Dap
<220> FEATURE:
<223> OTHER INFORMATION: C-term NH2

<400> SEQUENCE: 92

Arg Ser Asp Thr Leu Xaa Trp Glu Xaa
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
```

```
<220> FEATURE:
<221> NAME/KEY: MOD_RES
<222> LOCATION: (9)..(9)
<223> OTHER INFORMATION: Dab
<220> FEATURE:
<223> OTHER INFORMATION: C-term NH2

<400> SEQUENCE: 93

Arg Ser Asp Thr Leu Xaa Trp Glu Xaa
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: Dap
<220> FEATURE:
<223> OTHER INFORMATION: C-term NH2

<400> SEQUENCE: 94

Arg Ser Asp Thr Leu Xaa Trp Glu Xaa
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: Dab
<220> FEATURE:
<223> OTHER INFORMATION: C-term NH2

<400> SEQUENCE: 95
```

Arg Ser Asp Thr Leu Xaa Trp Glu Xaa
1               5

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<223> OTHER INFORMATION: C-term NH2

<400> SEQUENCE: 96

Arg Ser Asp Thr Leu Xaa Trp Glu
1               5

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<223> OTHER INFORMATION: C-term NH2

<400> SEQUENCE: 97

Arg Ser Asp Thr Leu Xaa Trp Glu
1               5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)

```
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<223> OTHER INFORMATION: C-term NH2

<400> SEQUENCE: 98

Arg Ser Asp Thr Leu Xaa Trp Glu
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<223> OTHER INFORMATION: C-term NH2

<400> SEQUENCE: 99

Arg Ser Asp Thr Leu Xaa Trp Glu Leu
1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<223> OTHER INFORMATION: C-term NH2

<400> SEQUENCE: 100

Arg Ser Asp Thr Leu Xaa Trp Glu Ser
1               5

<210> SEQ ID NO 101
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<223> OTHER INFORMATION: C-term NH2

<400> SEQUENCE: 101

Arg Ser Asp Thr Leu Xaa Trp Glu Phe
1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<223> OTHER INFORMATION: C-term NH2

<400> SEQUENCE: 102

Arg Ser Asp Thr Leu Xaa Trp Glu His
1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
```

```
<222> LOCATION: (8)..(8)
<223> OTHER INFORMATION: D-Glu
<220> FEATURE:
<223> OTHER INFORMATION: C-term NH2

<400> SEQUENCE: 103

Arg Ser Asp Thr Leu Xaa Trp Glu Gln
1               5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<223> OTHER INFORMATION: C-term NH2

<400> SEQUENCE: 104

Arg Ser Asp Thr Leu Xaa Trp Glu Tyr
1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 105

Arg Ser Asp Thr Leu Xaa Trp Glu Leu
1               5

<210> SEQ ID NO 106
<211> LENGTH: 9
```

-continued

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Ser
<220> FEATURE:
<223> OTHER INFORMATION: C-term NH2

<400> SEQUENCE: 106

Arg Ser Asp Thr Leu Xaa Trp Glu Ser
1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Phe
<220> FEATURE:
<223> OTHER INFORMATION: C-term NH2

<400> SEQUENCE: 107

Arg Ser Asp Thr Leu Xaa Trp Glu Phe
1               5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
```

```
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Glu
<220> FEATURE:
<223> OTHER INFORMATION: C-term NH2

<400> SEQUENCE: 108

Arg Ser Asp Thr Leu Xaa Trp Glu Glu
1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-His
<220> FEATURE:
<223> OTHER INFORMATION: C-term NH2

<400> SEQUENCE: 109

Arg Ser Asp Thr Leu Xaa Trp Glu His
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
```

```
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Tyr
<220> FEATURE:
<223> OTHER INFORMATION: C-term NH2

<400> SEQUENCE: 110

Arg Ser Asp Thr Leu Xaa Trp Glu Tyr
1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 3-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 111

Arg Ser Asp Thr Leu Xaa Trp Glu Lys
1               5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 4-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2
```

```
<400> SEQUENCE: 112

Arg Ser Asp Thr Leu Xaa Trp Glu Lys
1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<223> OTHER INFORMATION: C-term NH2

<400> SEQUENCE: 113

Arg Ser Asp Thr Leu Xaa Trp Glu Glu
1               5

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: D-Glu
<220> FEATURE:
<223> OTHER INFORMATION: C-term NH2

<400> SEQUENCE: 114

Arg Ser Asp Thr Leu Xaa Xaa Glu
1               5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: Glu(OMe)
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 115

Arg Ser Asp Thr Leu Xaa Trp Glu Lys
1               5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<223> OTHER INFORMATION: C-term NH2

<400> SEQUENCE: 116

Arg Ser Asp Thr Leu Xaa Xaa
1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
```

```
<222> LOCATION: (9)..(9)
<223> OTHER INFORMATION: D-Lys
<220> FEATURE:
<223> OTHER INFORMATION: C-term NH2

<400> SEQUENCE: 117

Arg Ser Asp Thr Leu Cys Xaa Glu Lys
1               5

<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term OH

<400> SEQUENCE: 118

Arg Ser Asp Thr Leu Cys Xaa Lys
1               5

<210> SEQ ID NO 119
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Atc
<220> FEATURE:
<221> NAME/KEY: MOD_RES
<222> LOCATION: (8)..(8)
<223> OTHER INFORMATION: Beta-Homo-Glu
<220> FEATURE:
<223> OTHER INFORMATION: C-term NH2

<400> SEQUENCE: 119

Arg Ser Asp Thr Leu Xaa Xaa Glu
1               5

<210> SEQ ID NO 120
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: erythro-Beta-phenyl-Ser
<220> FEATURE:
<221> NAME/KEY: MOD_RES
<222> LOCATION: (8)..(8)
<223> OTHER INFORMATION: Beta-Homo-Glu
<220> FEATURE:
<223> OTHER INFORMATION: C-term NH2

<400> SEQUENCE: 120

Arg Ser Asp Thr Leu Xaa Ser Glu
1               5

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: erythro-Beta-phenyl-Ser
<220> FEATURE:
<221> NAME/KEY: MOD_RES
<222> LOCATION: (8)..(8)
<223> OTHER INFORMATION: Beta-Homo-Glu
<220> FEATURE:
<223> OTHER INFORMATION: C-term NH2

<400> SEQUENCE: 121

Arg Ser Asp Thr Leu Xaa Ser Glu
1               5

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
```

```
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: threo-Beta-phenyl-Ser
<220> FEATURE:
<221> NAME/KEY: MOD_RES
<222> LOCATION: (8)..(8)
<223> OTHER INFORMATION: Beta-Homo-Glu
<220> FEATURE:
<223> OTHER INFORMATION: C-term NH2

<400> SEQUENCE: 122

Arg Ser Asp Thr Leu Xaa Ser Glu
1               5

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: threo-Beta-phenyl-Ser
<220> FEATURE:
<221> NAME/KEY: MOD_RES
<222> LOCATION: (8)..(8)
<223> OTHER INFORMATION: Beta-Homo-Glu
<220> FEATURE:
<223> OTHER INFORMATION: C-term NH2

<400> SEQUENCE: 123

Arg Ser Asp Thr Leu Xaa Ser Glu
1               5

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
```

```
<222> LOCATION: (7)..(7)
<223> OTHER INFORMATION: Bpa
<220> FEATURE:
<221> NAME/KEY: MOD_RES
<222> LOCATION: (8)..(8)
<223> OTHER INFORMATION: Beta-Homo-Glu
<220> FEATURE:
<223> OTHER INFORMATION: C-term NH2

<400> SEQUENCE: 124

Arg Ser Asp Thr Leu Xaa Xaa Glu
1               5

<210> SEQ ID NO 125
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(3-Me)
<220> FEATURE:
<221> NAME/KEY: MOD_RES
<222> LOCATION: (8)..(8)
<223> OTHER INFORMATION: Beta-Homo-Glu
<220> FEATURE:
<223> OTHER INFORMATION: C-term NH2

<400> SEQUENCE: 125

Arg Ser Asp Thr Leu Xaa Phe Glu
1               5

<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(2-Me)
<220> FEATURE:
<221> NAME/KEY: MOD_RES
<222> LOCATION: (8)..(8)
<223> OTHER INFORMATION: Beta-Homo-Glu
<220> FEATURE:
<223> OTHER INFORMATION: C-term NH2
```

```
<400> SEQUENCE: 126

Arg Ser Asp Thr Leu Xaa Phe Glu
1               5

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(2-CF3)
<220> FEATURE:
<221> NAME/KEY: MOD_RES
<222> LOCATION: (8)..(8)
<223> OTHER INFORMATION: Beta-Homo-Glu
<220> FEATURE:
<223> OTHER INFORMATION: C-term NH2

<400> SEQUENCE: 127

Arg Ser Asp Thr Leu Xaa Phe Glu
1               5

<210> SEQ ID NO 128
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: beta-Me-Phe
<220> FEATURE:
<221> NAME/KEY: MOD_RES
<222> LOCATION: (8)..(8)
<223> OTHER INFORMATION: Beta-Homo-Glu
<220> FEATURE:
<223> OTHER INFORMATION: C-term NH2

<400> SEQUENCE: 128

Arg Ser Asp Thr Leu Xaa Phe Glu
1               5

<210> SEQ ID NO 129
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Beta-Me-Phe
<220> FEATURE:
<221> NAME/KEY: MOD_RES
<222> LOCATION: (8)..(8)
<223> OTHER INFORMATION: Beta-Homo-Glu
<220> FEATURE:
<223> OTHER INFORMATION: C-term NH2

<400> SEQUENCE: 129

Arg Ser Asp Thr Leu Xaa Phe Glu
1               5

<210> SEQ ID NO 130
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: beta-dimethyl-Phe
<220> FEATURE:
<221> NAME/KEY: MOD_RES
<222> LOCATION: (8)..(8)
<223> OTHER INFORMATION: Beta-Homo-Glu
<220> FEATURE:
<223> OTHER INFORMATION: C-term NH2

<400> SEQUENCE: 130

Arg Ser Asp Thr Leu Xaa Phe Glu
1               5

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
```

```
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: beta-dimethyl-Phe
<220> FEATURE:
<221> NAME/KEY: MOD_RES
<222> LOCATION: (8)..(8)
<223> OTHER INFORMATION: Beta-Homo-Glu
<220> FEATURE:
<223> OTHER INFORMATION: C-term NH2

<400> SEQUENCE: 131

Arg Ser Asp Thr Leu Xaa Phe Glu
1               5

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 4-Me-Phe
<220> FEATURE:
<221> NAME/KEY: MOD_RES
<222> LOCATION: (8)..(8)
<223> OTHER INFORMATION: Beta-Homo-Glu
<220> FEATURE:
<223> OTHER INFORMATION: C-term NH2

<400> SEQUENCE: 132

Arg Ser Asp Thr Leu Xaa Phe Glu
1               5

<210> SEQ ID NO 133
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
```

```
<223> OTHER INFORMATION: Bip
<220> FEATURE:
<221> NAME/KEY: MOD_RES
<222> LOCATION: (8)..(8)
<223> OTHER INFORMATION: Beta-Homo-Glu
<220> FEATURE:
<223> OTHER INFORMATION: C-term NH2

<400> SEQUENCE: 133

Arg Ser Asp Thr Leu Xaa Xaa Glu
1               5

<210> SEQ ID NO 134
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
<221> NAME/KEY: MOD_RES
<222> LOCATION: (8)..(8)
<223> OTHER INFORMATION: Beta-Homo-Glu
<220> FEATURE:
<223> OTHER INFORMATION: C-term NH2

<400> SEQUENCE: 134

Arg Ser Asp Thr Leu Xaa Phe Glu
1               5

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
<221> NAME/KEY: MOD_RES
<222> LOCATION: (8)..(8)
<223> OTHER INFORMATION: N-Me-Glu
<220> FEATURE:
<223> OTHER INFORMATION: C-term NH2

<400> SEQUENCE: 135
```

Arg Ser Asp Thr Leu Xaa Phe Glu
1               5

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
<221> NAME/KEY: MOD_RES
<222> LOCATION: (8)..(8)
<223> OTHER INFORMATION: N-Me-Asp
<220> FEATURE:
<223> OTHER INFORMATION: C-term NH2

<400> SEQUENCE: 136

Arg Ser Asp Thr Leu Xaa Phe Asp
1               5

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
<221> NAME/KEY: MOD_RES
<222> LOCATION: (8)..(8)
<223> OTHER INFORMATION: alpha-Homo-Glu
<220> FEATURE:
<223> OTHER INFORMATION: C-term NH2

<400> SEQUENCE: 137

Arg Ser Asp Thr Leu Xaa Phe Glu
1               5

<210> SEQ ID NO 138
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: Cit
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
<221> NAME/KEY: MOD_RES
<222> LOCATION: (8)..(8)
<223> OTHER INFORMATION: Beta-Homo-Glu
<220> FEATURE:
<223> OTHER INFORMATION: C-term NH2

<400> SEQUENCE: 138

Xaa Ser Asp Thr Leu Xaa Phe Glu
1               5

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
<221> NAME/KEY: MOD_RES
<222> LOCATION: (8)..(8)
<223> OTHER INFORMATION: Beta-Homo-Glu
<220> FEATURE:
<223> OTHER INFORMATION: C-term NH2

<400> SEQUENCE: 139

Arg Ala Asp Thr Leu Xaa Phe Glu
1               5

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond
      between the N-term and the residue at position 6
<220> FEATURE:
<221> NAME/KEY: MOD_RES
<222> LOCATION: (1)..(1)
```

<223> OTHER INFORMATION: N-Me-Arg
<220> FEATURE:
<221> NAME/KEY: MOD_RES
<222> LOCATION: (2)..(2)
<223> OTHER INFORMATION: Abu
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
<221> NAME/KEY: MOD_RES
<222> LOCATION: (8)..(8)
<223> OTHER INFORMATION: Beta-Homo-Glu
<220> FEATURE:
<223> OTHER INFORMATION: C-term NH2

<400> SEQUENCE: 140

Arg Xaa Asp Thr Leu Xaa Phe Glu
1               5

<210> SEQ ID NO 141
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (2)..(2)
<223> OTHER INFORMATION: Tbu
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
<221> NAME/KEY: MOD_RES
<222> LOCATION: (8)..(8)
<223> OTHER INFORMATION: Beta-Homo-Glu
<220> FEATURE:
<223> OTHER INFORMATION: C-term NH2

<400> SEQUENCE: 141

Arg Xaa Asp Thr Leu Xaa Phe Glu
1               5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg

```
-continued

<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
<221> NAME/KEY: MOD_RES
<222> LOCATION: (8)..(8)
<223> OTHER INFORMATION: N-Me-Glu
<220> FEATURE:
<223> OTHER INFORMATION: C-term NH2

<400> SEQUENCE: 142

Arg Ser Asp Thr Leu Xaa Phe Glu
1               5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term NH2

<400> SEQUENCE: 143

Arg Ser Asp Thr Leu Cys Trp Lys
1               5

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Propionyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term NH2

<400> SEQUENCE: 144

Arg Ser Asp Thr Leu Cys Trp Lys
1               5

<210> SEQ ID NO 145
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 145

Arg Ser Asp Thr Leu Cys Trp Glu Lys
1               5

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 146

Arg Ser Asp Thr Leu Xaa Trp Glu Lys
1               5

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term NH2
```

```
<400> SEQUENCE: 147

Arg Ser Asp Thr Leu Xaa Trp Lys
1               5

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Propionyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term NH2

<400> SEQUENCE: 148

Arg Ser Asp Thr Leu Xaa Trp Lys
1               5

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Propionyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: homo-Cys
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term NH2

<400> SEQUENCE: 149

Arg Ser Asp Thr Leu Cys Trp Lys
1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
```

```
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 150

Arg Ser Asp Thr Leu Xaa Trp Glu Lys
1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 151

Arg Ser Asp Thr Leu Xaa Trp Glu Lys
1               5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
```

```
<222> LOCATION: (9)..(9)
<223> OTHER INFORMATION: D-N-Me-Lys
<220> FEATURE:
<223> OTHER INFORMATION: C-term NH2

<400> SEQUENCE: 152

Arg Ser Asp Thr Leu Xaa Trp Glu Lys
1               5

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: N-Me-Lys
<220> FEATURE:
<223> OTHER INFORMATION: C-term NH2

<400> SEQUENCE: 153

Arg Ser Asp Thr Leu Xaa Trp Tyr Lys
1               5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (5)..(5)
<223> OTHER INFORMATION: Nle
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 154

Arg Ser Asp Thr Leu Xaa Trp Glu Lys
1               5

<210> SEQ ID NO 155
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 155

Arg Ser Asp Thr Leu Xaa Phe Glu Lys
1               5

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: D-Cys
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 156

Arg Ser Asp Thr Leu Cys Trp Glu Lys
1               5

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
```

```
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Homo-Cys
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 157

Arg Ser Asp Thr Leu Cys Trp Glu Lys
1               5

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 158

Arg Ser Asp Thr Leu Xaa Xaa Glu Lys
1               5

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
```

```
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 159

Arg Ser Asp Thr Leu Xaa Xaa Glu Lys
1               5

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: N-Me-Lys
<220> FEATURE:
<223> OTHER INFORMATION: C-term NH2

<400> SEQUENCE: 160

Arg Ser Asp Thr Leu Xaa Xaa Glu Lys
1               5

<210> SEQ ID NO 161
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
```

```
<223> OTHER INFORMATION: 2-Nal
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 161

Arg Ser Asp Thr Leu Xaa Xaa Glu Lys
1               5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 162

Arg Ser Asp Thr Leu Xaa Phe Xaa Lys
1               5

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: D-Phe
```

```
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 163

Arg Ser Asp Thr Leu Xaa Phe Glu Lys
1               5

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 164

Arg Ser Asp Thr Leu Xaa Phe Glu Lys
1               5

<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 165
```

```
Arg Ser Asp Thr Leu Xaa Tyr Glu Lys
1               5
```

```
<210> SEQ ID NO 166
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(CF3)
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 166

Arg Ser Asp Thr Leu Xaa Phe Glu Lys
1               5
```

```
<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 167

Arg Ser Asp Thr Leu Xaa Xaa Glu Lys
1               5
```

```
<210> SEQ ID NO 168
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 168

Arg Ser Asp Thr Leu Xaa Tyr Glu Lys
1               5

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 169

Arg Ser Asp Thr Leu Xaa Tyr Glu Lys
1               5

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen

```
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 170

Arg Ser Asp Thr Leu Xaa Trp Glu Lys
1               5

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 171

Arg Ser Asp Thr Leu Xaa Trp Glu Lys
1               5

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen(=O)
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: D-Glu
<220> FEATURE:
```

```
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 172

Arg Ser Asp Thr Leu Xaa Xaa Glu Lys
1               5

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen(=O)
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 173

Arg Ser Asp Thr Leu Xaa Xaa Glu Lys
1               5

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2
```

<400> SEQUENCE: 174

Arg Ser Asp Thr Leu Xaa Trp Glu Lys
1               5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 175

Arg Ser Asp Thr Leu Xaa Trp Glu Lys
1               5

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(2,4-diCl)
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 176

Arg Ser Asp Thr Leu Xaa Phe Glu Lys
1               5

```
<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(3,4-diCl)
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 177

Arg Ser Asp Thr Leu Xaa Phe Glu Lys
1               5

<210> SEQ ID NO 178
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Bip
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 178

Arg Ser Asp Thr Leu Xaa Xaa Glu Lys
1               5
```

```
<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: D-Cys
<220> FEATURE:
<221> NAME/KEY: MOD_RES
<222> LOCATION: (7)..(7)
<223> OTHER INFORMATION: Aic
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 179

Arg Ser Asp Thr Leu Cys Xaa Glu Lys
1               5

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (7)..(7)
<223> OTHER INFORMATION: Aic
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 180

Arg Ser Asp Thr Leu Cys Xaa Glu Lys
1               5

<210> SEQ ID NO 181
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: D-Pen
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 181

Arg Ser Asp Thr Leu Xaa Trp Glu Lys
1               5

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (7)..(7)
<223> OTHER INFORMATION: N-Me-Tyr
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 182

Arg Ser Asp Thr Leu Cys Tyr Glu Lys
1               5

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (7)..(7)
<223> OTHER INFORMATION: N-Me-Phe
<220> FEATURE:
<221> NAME/KEY: MOD_RES
<222> LOCATION: (9)..(9)
```

```
<223> OTHER INFORMATION: D-Lys
<220> FEATURE:
<223> OTHER INFORMATION: C-term NH2

<400> SEQUENCE: 183

Arg Ser Asp Thr Leu Cys Phe Glu Lys
1               5

<210> SEQ ID NO 184
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 184

Arg Ser Asp Thr Leu Cys Xaa Glu Lys
1               5

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: D-Cys
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 185
```

```
Arg Ser Asp Thr Leu Cys Xaa Glu Lys
1               5

<210> SEQ ID NO 186
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 186

Arg Ser Asp Thr Leu Cys Phe Glu Lys
1               5

<210> SEQ ID NO 187
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 187

Arg Ser Asp Thr Leu Cys Phe Glu Lys
1               5

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: D-Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 188

Arg Ser Asp Thr Leu Xaa Tyr Glu Lys
1               5

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 189

Arg Ser Glu Thr Leu Xaa Phe Glu Lys
1               5

<210> SEQ ID NO 190
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
```

```
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (10)..(10)
<223> OTHER INFORMATION: D-Lys
<220> FEATURE:
<223> OTHER INFORMATION: C-term NH2

<400> SEQUENCE: 190

Arg Ser Asp Thr Leu Xaa Trp Glu Leu Lys
1               5                   10

<210> SEQ ID NO 191
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (10)..(10)
<223> OTHER INFORMATION: D-Lys
<220> FEATURE:
<223> OTHER INFORMATION: C-term NH2

<400> SEQUENCE: 191

Arg Ser Asp Thr Leu Xaa Trp Glu Ser Lys
1               5                   10

<210> SEQ ID NO 192
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (10)..(10)
<223> OTHER INFORMATION: D-Lys
```

```
<220> FEATURE:
<223> OTHER INFORMATION: C-term NH2

<400> SEQUENCE: 192

Arg Ser Asp Thr Leu Xaa Trp Glu Phe Lys
1               5                   10

<210> SEQ ID NO 193
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (10)..(10)
<223> OTHER INFORMATION: D-Lys
<220> FEATURE:
<223> OTHER INFORMATION: C-term NH2

<400> SEQUENCE: 193

Arg Ser Asp Thr Leu Xaa Trp Glu His Lys
1               5                   10

<210> SEQ ID NO 194
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (10)..(10)
<223> OTHER INFORMATION: D-Lys
<220> FEATURE:
<223> OTHER INFORMATION: C-term NH2

<400> SEQUENCE: 194

Arg Ser Asp Thr Leu Xaa Trp Glu Glu Lys
1               5                   10
```

```
<210> SEQ ID NO 195
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (10)..(10)
<223> OTHER INFORMATION: D-Lys
<220> FEATURE:
<223> OTHER INFORMATION: C-term NH2

<400> SEQUENCE: 195

Arg Ser Asp Thr Leu Xaa Trp Glu Tyr Lys
1               5                   10

<210> SEQ ID NO 196
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Leu
<220> FEATURE:
<221> NAME/KEY: MOD_RES
<222> LOCATION: (10)..(10)
<223> OTHER INFORMATION: D-Lys
<220> FEATURE:
<223> OTHER INFORMATION: C-term NH2

<400> SEQUENCE: 196

Arg Ser Asp Thr Leu Xaa Trp Glu Leu Lys
1               5                   10

<210> SEQ ID NO 197
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Ser
<220> FEATURE:
<221> NAME/KEY: MOD_RES
<222> LOCATION: (10)..(10)
<223> OTHER INFORMATION: D-Lys
<220> FEATURE:
<223> OTHER INFORMATION: C-term NH2

<400> SEQUENCE: 197

Arg Ser Asp Thr Leu Xaa Trp Glu Ser Lys
1               5                   10

<210> SEQ ID NO 198
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Phe
<220> FEATURE:
<221> NAME/KEY: MOD_RES
<222> LOCATION: (10)..(10)
<223> OTHER INFORMATION: D-Lys
<220> FEATURE:
<223> OTHER INFORMATION: C-term NH2

<400> SEQUENCE: 198

Arg Ser Asp Thr Leu Xaa Trp Glu Phe Lys
1               5                   10

<210> SEQ ID NO 199
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-His
<220> FEATURE:
<221> NAME/KEY: MOD_RES
<222> LOCATION: (10)..(10)
<223> OTHER INFORMATION: D-Lys
<220> FEATURE:
<223> OTHER INFORMATION: C-term NH2

<400> SEQUENCE: 199

Arg Ser Asp Thr Leu Xaa Trp Glu His Lys
1               5                   10

<210> SEQ ID NO 200
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys
<220> FEATURE:
<223> OTHER INFORMATION: C-term NH2

<400> SEQUENCE: 200

Arg Ser Asp Thr Leu Xaa Trp Glu Glu Lys
1               5                   10

<210> SEQ ID NO 201
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Tyr
<220> FEATURE:
<221> NAME/KEY: MOD_RES
<222> LOCATION: (10)..(10)
<223> OTHER INFORMATION: D-Lys
<220> FEATURE:
<223> OTHER INFORMATION: C-term NH2

<400> SEQUENCE: 201

Arg Ser Asp Thr Leu Xaa Trp Glu Tyr Lys
1               5                   10

<210> SEQ ID NO 202
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 202

Arg Ser Asp Thr Leu Xaa Trp Xaa Lys
1               5

<210> SEQ ID NO 203
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
```

```
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 203

Arg Ser Asp Thr Leu Xaa Phe Xaa Lys
1               5

<210> SEQ ID NO 204
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 204

Arg Ser Asp Thr Leu Xaa Phe Glu Lys
1               5

<210> SEQ ID NO 205
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
```

```
<223> OTHER INFORMATION: Bip
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 205

Arg Ser Asp Thr Leu Cys Xaa Xaa Lys
1               5

<210> SEQ ID NO 206
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 206

Arg Ser Asp Thr Leu Xaa Xaa Xaa Lys
1               5

<210> SEQ ID NO 207
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
```

```
<220> FEATURE:
<223> OTHER INFORMATION: C-term NH2

<400> SEQUENCE: 207

Arg Ser Asp Thr Leu Cys Xaa Glu Lys
1               5

<210> SEQ ID NO 208
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Bip
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 208

Arg Ser Asp Thr Leu Xaa Xaa Glu Lys
1               5

<210> SEQ ID NO 209
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 209
```

Arg Ser Asp Thr Leu Xaa Trp Glu Lys
1               5

<210> SEQ ID NO 210
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: Glu(OMe)
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 210

Arg Ser Asp Thr Leu Xaa Trp Glu Lys
1               5

<210> SEQ ID NO 211
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Glu(OMe)
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 211

Arg Ser Asp Thr Leu Cys Xaa Glu Lys
1               5

<210> SEQ ID NO 212
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 212

Arg Ser Asp Thr Leu Xaa Trp Glu Lys
1               5

<210> SEQ ID NO 213
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 213

Arg Ser Asp Thr Leu Xaa Trp Glu Lys
1               5

<210> SEQ ID NO 214
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg

```
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 214

Arg Ser Asp Thr Leu Xaa Trp Glu Lys
1               5

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 215

Arg Ser Asp Thr Leu Xaa Trp Glu Lys
1               5

<210> SEQ ID NO 216
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: D-Lys
<220> FEATURE:
```

<223> OTHER INFORMATION: C-term NH2

<400> SEQUENCE: 216

Arg Ser Asp Thr Leu Cys Xaa Lys
1               5

<210> SEQ ID NO 217
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 217

Arg Ser Asp Thr Leu Xaa Trp Glu Lys
1               5

<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 218

Arg Ser Asp Thr Leu Xaa Trp Glu Lys
1               5

<210> SEQ ID NO 219

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 219

Arg Ser Asp Thr Leu Cys Xaa Glu Lys
1               5

<210> SEQ ID NO 220
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Glu(OMe)
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 220

Arg Ser Asp Thr Leu Cys Xaa Glu Lys
1               5

<210> SEQ ID NO 221
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
```

```
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term NH2

<400> SEQUENCE: 221

Arg Ser Asp Thr Leu Cys Xaa Lys
1               5

<210> SEQ ID NO 222
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 222

Arg Ser Asp Thr Leu Xaa Phe Glu Lys
1               5

<210> SEQ ID NO 223
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
```

```
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 223

Arg Ser Asp Thr Leu Xaa Phe Glu Lys
1               5

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: Dap
<220> FEATURE:
<223> OTHER INFORMATION: C-term Ac

<400> SEQUENCE: 224

Arg Ser Asp Thr Leu Xaa Trp Glu Xaa
1               5

<210> SEQ ID NO 225
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (5)..(5)
<223> OTHER INFORMATION: Nle
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
```

```
<222> LOCATION: (9)..(9)
<223> OTHER INFORMATION: D-N-Me-Lys
<220> FEATURE:
<223> OTHER INFORMATION: C-term NH2

<400> SEQUENCE: 225

Arg Ser Asp Thr Leu Xaa Phe Glu Lys
1               5

<210> SEQ ID NO 226
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (5)..(5)
<223> OTHER INFORMATION: Nle
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: N-Me-Lys
<220> FEATURE:
<223> OTHER INFORMATION: C-term NH2

<400> SEQUENCE: 226

Arg Ser Asp Thr Leu Xaa Trp Glu Lys
1               5

<210> SEQ ID NO 227
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (5)..(5)
<223> OTHER INFORMATION: Nle
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-N-Me-Lys
<220> FEATURE:
<223> OTHER INFORMATION: C-term NH2
```

```
<400> SEQUENCE: 227

Arg Ser Asp Thr Leu Xaa Phe Glu Lys
1               5

<210> SEQ ID NO 228
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (5)..(5)
<223> OTHER INFORMATION: Nle
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: D-N-Me-Lys
<220> FEATURE:
<223> OTHER INFORMATION: C-term NH2

<400> SEQUENCE: 228

Arg Ser Asp Thr Leu Xaa Trp Glu Lys
1               5

<210> SEQ ID NO 229
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (5)..(5)
<223> OTHER INFORMATION: Nle
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-N-Me-Lys
<220> FEATURE:
<223> OTHER INFORMATION: C-term NH2

<400> SEQUENCE: 229

Arg Ser Asp Thr Leu Xaa Phe Glu Lys
1               5
```

```
<210> SEQ ID NO 230
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term C(thioether propane) with a thioether
      bond between the N-term and the C-term
<220> FEATURE:
<221> NAME/KEY: MOD_RES
<222> LOCATION: (1)..(1)
<223> OTHER INFORMATION: N-Me-Arg
<220> FEATURE:
<223> OTHER INFORMATION: C-term C(thioether propane)

<400> SEQUENCE: 230

Arg Ser Asp Thr Leu
1               5

<210> SEQ ID NO 231
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: Dab
<220> FEATURE:
<223> OTHER INFORMATION: C-term Ac

<400> SEQUENCE: 231

Arg Ser Asp Thr Leu Xaa Trp Glu Xaa
1               5

<210> SEQ ID NO 232
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
```

```
<222> LOCATION: (9)..(9)
<223> OTHER INFORMATION: Dab
<220> FEATURE:
<223> OTHER INFORMATION: C-term Ac

<400> SEQUENCE: 232

Arg Ser Asp Thr Leu Xaa Trp Glu Xaa
1               5

<210> SEQ ID NO 233
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: Dab
<220> FEATURE:
<223> OTHER INFORMATION: C-term NH2

<400> SEQUENCE: 233

Arg Ser Asp Thr Leu Xaa Trp Glu Xaa
1               5

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: Dab
<220> FEATURE:
<223> OTHER INFORMATION: C-term Ac

<400> SEQUENCE: 234

Arg Ser Asp Thr Leu Xaa Trp Glu Xaa
1               5

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                              peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 235

Arg Ser Asp Thr Leu Cys Xaa Glu Lys
1               5

<210> SEQ ID NO 236
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Phe
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 236

Arg Ser Asp Thr Leu Xaa Trp Phe Lys
1               5

<210> SEQ ID NO 237
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
```

```
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Tyr
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 237

Arg Ser Asp Thr Leu Xaa Trp Tyr Lys
1               5

<210> SEQ ID NO 238
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 238

Arg Ser Asp Thr Leu Cys Xaa Glu Lys
1               5

<210> SEQ ID NO 239
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2
```

<400> SEQUENCE: 239

Arg Ser Asp Thr Leu Xaa Trp Pro Lys
1               5

<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<223> OTHER INFORMATION: C-term NH2

<400> SEQUENCE: 240

Arg Ser Asp Thr Leu Xaa Trp Pro Lys
1               5

<210> SEQ ID NO 241
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Pro
<220> FEATURE:
<223> OTHER INFORMATION: C-term NH2

<400> SEQUENCE: 241

Arg Ser Asp Thr Leu Xaa Trp Pro Lys
1               5

<210> SEQ ID NO 242
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(2-carbamoyl)
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 242

Arg Ser Asp Thr Leu Xaa Phe Glu Lys
1               5

<210> SEQ ID NO 243
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(3-carbamoyl)
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 243

Arg Ser Asp Thr Leu Xaa Phe Glu Lys
1               5

<210> SEQ ID NO 244
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:

```
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-COOH)
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 244

Arg Ser Asp Thr Leu Xaa Phe Glu Lys
1               5

<210> SEQ ID NO 245
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(2,4-Cl)
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 245

Arg Ser Asp Thr Leu Xaa Phe Glu Lys
1               5

<210> SEQ ID NO 246
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
```

```
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(3,4-Cl)
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 246

Arg Ser Asp Thr Leu Xaa Phe Glu Lys
1               5

<210> SEQ ID NO 247
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-OMe)
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 247

Arg Ser Asp Thr Leu Xaa Phe Glu Lys
1               5

<210> SEQ ID NO 248
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
```

<223> OTHER INFORMATION: Pen
<220> FEATURE:
<221> NAME/KEY: MOD_RES
<222> LOCATION: (8)..(8)
<223> OTHER INFORMATION: D-His
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 248

Arg Ser Asp Thr Leu Xaa Trp His Lys
1               5

<210> SEQ ID NO 249
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: Phe(4-COOH)
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 249

Arg Ser Asp Thr Leu Xaa Trp Phe Lys
1               5

<210> SEQ ID NO 250
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
<221> NAME/KEY: MOD_RES
<222> LOCATION: (8)..(8)
<223> OTHER INFORMATION: D-Glu

```
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 250

Arg Ser Asp Thr Leu Xaa Phe Glu Lys
1               5

<210> SEQ ID NO 251
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-F)
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 251

Arg Ser Asp Thr Leu Xaa Phe Glu Lys
1               5

<210> SEQ ID NO 252
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Bip
<220> FEATURE:
<221> NAME/KEY: MOD_RES
<222> LOCATION: (8)..(8)
<223> OTHER INFORMATION: D-Glu
<220> FEATURE:
```

<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 252

Arg Ser Asp Thr Leu Xaa Xaa Glu Lys
1               5

<210> SEQ ID NO 253
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: Tic
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 253

Arg Ser Asp Thr Leu Xaa Trp Xaa Lys
1               5

<210> SEQ ID NO 254
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Trp
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 254

Arg Ser Asp Thr Leu Xaa Trp Trp Lys

<210> SEQ ID NO 255
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (8)..(8)
<223> OTHER INFORMATION: D-Phe
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 255

Arg Ser Asp Thr Leu Xaa Xaa Phe Lys
1               5

<210> SEQ ID NO 256
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (8)..(8)
<223> OTHER INFORMATION: D-His
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 256

Arg Ser Asp Thr Leu Xaa Xaa His Lys
1               5

```
<210> SEQ ID NO 257
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (8)..(8)
<223> OTHER INFORMATION: D-Leu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 257

Arg Ser Asp Thr Leu Xaa Xaa Leu Lys
1               5

<210> SEQ ID NO 258
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 258

Arg Ser Asp Thr Leu Xaa Xaa Arg Lys
1               5
```

```
<210> SEQ ID NO 259
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (8)..(8)
<223> OTHER INFORMATION: Tic
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 259

Arg Ser Asp Thr Leu Xaa Xaa Xaa Lys
1               5

<210> SEQ ID NO 260
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (8)..(8)
<223> OTHER INFORMATION: D-Thr
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 260

Arg Ser Asp Thr Leu Xaa Xaa Thr Lys
1               5
```

```
<210> SEQ ID NO 261
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: D-Phe
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 261

Arg Ser Asp Thr Leu Xaa Xaa Phe Lys
1               5

<210> SEQ ID NO 262
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: D-His
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 262

Arg Ser Asp Thr Leu Xaa Xaa His Lys
1               5

<210> SEQ ID NO 263
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: D-Leu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 263

Arg Ser Asp Thr Leu Xaa Xaa Leu Lys
1               5

<210> SEQ ID NO 264
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 264

Arg Ser Asp Thr Leu Xaa Xaa Arg Lys
1               5

<210> SEQ ID NO 265
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: Tic
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 265

Arg Ser Asp Thr Leu Xaa Xaa Xaa Lys
1               5

<210> SEQ ID NO 266
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4CF3)
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 266

Arg Ser Asp Thr Leu Xaa Phe Glu Lys
1               5

<210> SEQ ID NO 267
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 267

Arg Ser Asp Thr Leu Xaa Tyr Glu Lys
1               5

<210> SEQ ID NO 268
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 268

Arg Ser Asp Thr Leu Xaa His Glu Lys
1               5

<210> SEQ ID NO 269
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
```

```
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 269

Arg Ser Asp Thr Leu Xaa Phe Glu Lys
1               5

<210> SEQ ID NO 270
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
<221> NAME/KEY: MOD_RES
<222> LOCATION: (8)..(8)
<223> OTHER INFORMATION: beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 270

Arg Ser Asp Thr Leu Xaa Phe Glu Lys
1               5

<210> SEQ ID NO 271
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
```

```
<223> OTHER INFORMATION: Pen
<220> FEATURE:
<221> NAME/KEY: MOD_RES
<222> LOCATION: (7)..(7)
<223> OTHER INFORMATION: Phe(4-COOH)
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 271

Arg Ser Asp Thr Leu Xaa Phe Glu Lys
1               5

<210> SEQ ID NO 272
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-COOH)
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 272

Arg Ser Asp Thr Leu Xaa Phe Glu Lys
1               5

<210> SEQ ID NO 273
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-COOH)
<220> FEATURE:
<221> NAME/KEY: MOD_RES
<222> LOCATION: (9)..(9)
<223> OTHER INFORMATION: D-Lys
```

```
<220> FEATURE:
<223> OTHER INFORMATION: C-term NH2

<400> SEQUENCE: 273

Arg Ser Asp Thr Leu Xaa Phe Glu Lys
1               5

<210> SEQ ID NO 274
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-COOH)
<220> FEATURE:
<221> NAME/KEY: MOD_RES
<222> LOCATION: (8)..(8)
<223> OTHER INFORMATION: beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 274

Arg Ser Asp Thr Leu Xaa Phe Glu Lys
1               5

<210> SEQ ID NO 275
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-COOH)
<220> FEATURE:
<221> NAME/KEY: MOD_RES
<222> LOCATION: (8)..(8)
<223> OTHER INFORMATION: beta-Homo-Glu
<220> FEATURE:
<221> NAME/KEY: MOD_RES
<222> LOCATION: (9)..(9)
<223> OTHER INFORMATION: D-Lys
<220> FEATURE:
```

<223> OTHER INFORMATION: C-term NH2

<400> SEQUENCE: 275

Arg Ser Asp Thr Leu Xaa Phe Glu Lys
1               5

<210> SEQ ID NO 276
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-COOH)
<220> FEATURE:
<221> NAME/KEY: MOD_RES
<222> LOCATION: (8)..(8)
<223> OTHER INFORMATION: beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 276

Arg Ser Asp Thr Leu Xaa Phe Glu Lys
1               5

<210> SEQ ID NO 277
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Bip
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 277

Arg Ser Asp Thr Leu Xaa Xaa Glu Lys

```
1               5

<210> SEQ ID NO 278
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Bip
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 278

Arg Ser Asp Thr Leu Xaa Xaa Glu Lys
1               5

<210> SEQ ID NO 279
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 279

Arg Ser Asp Thr Leu Xaa Xaa Glu Lys
1               5

<210> SEQ ID NO 280
<211> LENGTH: 9
```

```
-continued

<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 280

Arg Ser Asp Thr Leu Xaa Xaa Glu Lys
1               5

<210> SEQ ID NO 281
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 281

Arg Ser Asp Thr Leu Xaa Xaa Glu Lys
1               5

<210> SEQ ID NO 282
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
-continued

<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (8)..(8)
<223> OTHER INFORMATION: beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 282

Arg Ser Asp Thr Leu Xaa Xaa Glu Lys
1               5

<210> SEQ ID NO 283
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term NH2

<400> SEQUENCE: 283

Arg Ser Asp Thr Leu Xaa Xaa Lys
1               5

<210> SEQ ID NO 284
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
```

```
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term NH2

<400> SEQUENCE: 284

Arg Ser Asp Thr Leu Xaa Xaa Lys
1               5

<210> SEQ ID NO 285
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
<221> NAME/KEY: MOD_RES
<222> LOCATION: (9)..(9)
<223> OTHER INFORMATION: N-Me-Lys
<220> FEATURE:
<223> OTHER INFORMATION: C-term NH2

<400> SEQUENCE: 285

Arg Ser Asp Thr Leu Xaa Phe Glu Lys
1               5

<210> SEQ ID NO 286
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
```

```
<223> OTHER INFORMATION: Phe(4-tBu)
<220> FEATURE:
<221> NAME/KEY: MOD_RES
<222> LOCATION: (9)..(9)
<223> OTHER INFORMATION: D-N-Me-Lys
<220> FEATURE:
<223> OTHER INFORMATION: C-term NH2

<400> SEQUENCE: 286

Arg Ser Asp Thr Leu Xaa Phe Glu Lys
1               5

<210> SEQ ID NO 287
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: N-Me-Lys
<220> FEATURE:
<223> OTHER INFORMATION: C-term NH2

<400> SEQUENCE: 287

Arg Ser Asp Thr Leu Xaa Phe Glu Lys
1               5

<210> SEQ ID NO 288
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
<221> NAME/KEY: MOD_RES
<222> LOCATION: (8)..(8)
<223> OTHER INFORMATION: Beta-Homo-Glu
```

```
<220> FEATURE:
<221> NAME/KEY: MOD_RES
<222> LOCATION: (9)..(9)
<223> OTHER INFORMATION: D-N-Me-Lys
<220> FEATURE:
<223> OTHER INFORMATION: C-term NH2

<400> SEQUENCE: 288

Arg Ser Asp Thr Leu Xaa Phe Glu Lys
1               5

<210> SEQ ID NO 289
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Bip
<220> FEATURE:
<221> NAME/KEY: MOD_RES
<222> LOCATION: (9)..(9)
<223> OTHER INFORMATION: N-Me-Lys
<220> FEATURE:
<223> OTHER INFORMATION: C-term NH2

<400> SEQUENCE: 289

Arg Ser Asp Thr Leu Xaa Xaa Glu Lys
1               5

<210> SEQ ID NO 290
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Bip
<220> FEATURE:
<221> NAME/KEY: MOD_RES
<222> LOCATION: (9)..(9)
<223> OTHER INFORMATION: D-N-Me-Lys
<220> FEATURE:
<223> OTHER INFORMATION: C-term NH2

<400> SEQUENCE: 290
```

```
Arg Ser Asp Thr Leu Xaa Xaa Glu Lys
1               5

<210> SEQ ID NO 291
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Bip
<220> FEATURE:
<221> NAME/KEY: MOD_RES
<222> LOCATION: (8)..(8)
<223> OTHER INFORMATION: beta-Homo-Glu
<220> FEATURE:
<221> NAME/KEY: MOD_RES
<222> LOCATION: (9)..(9)
<223> OTHER INFORMATION: N-Me-Lys
<220> FEATURE:
<223> OTHER INFORMATION: C-term NH2

<400> SEQUENCE: 291

Arg Ser Asp Thr Leu Xaa Xaa Glu Lys
1               5

<210> SEQ ID NO 292
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Bip
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-N-Me-Lys
<220> FEATURE:
<223> OTHER INFORMATION: C-term NH2

<400> SEQUENCE: 292

Arg Ser Asp Thr Leu Xaa Xaa Glu Lys
```

```
1               5
```

<210> SEQ ID NO 293
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (9)..(9)
<223> OTHER INFORMATION: N-Me-Lys
<220> FEATURE:
<223> OTHER INFORMATION: C-term NH2

<400> SEQUENCE: 293

```
Arg Ser Asp Thr Leu Xaa Xaa Glu Lys
1               5
```

<210> SEQ ID NO 294
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (9)..(9)
<223> OTHER INFORMATION: D-N-Me-Lys
<220> FEATURE:
<223> OTHER INFORMATION: C-term NH2

<400> SEQUENCE: 294

```
Arg Ser Asp Thr Leu Xaa Xaa Glu Lys
1               5
```

<210> SEQ ID NO 295
<211> LENGTH: 9
<212> TYPE: PRT
<213> ORGANISM: Artificial Sequence
<220> FEATURE:
<223> OTHER INFORMATION: Description of Artificial Sequence: Synthetic

```
                                   peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: N-Me-Lys
<220> FEATURE:
<223> OTHER INFORMATION: C-term NH2

<400> SEQUENCE: 295

Arg Ser Asp Thr Leu Xaa Xaa Glu Lys
1               5

<210> SEQ ID NO 296
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-N-Me-Lys
<220> FEATURE:
<223> OTHER INFORMATION: C-term NH2

<400> SEQUENCE: 296

Arg Ser Asp Thr Leu Xaa Xaa Glu Lys
1               5

<210> SEQ ID NO 297
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (9)..(9)
<223> OTHER INFORMATION: N-Me-Lys
<220> FEATURE:
<223> OTHER INFORMATION: C-term NH2

<400> SEQUENCE: 297

Arg Ser Asp Thr Leu Xaa Xaa Glu Lys
1               5

<210> SEQ ID NO 298
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (9)..(9)
<223> OTHER INFORMATION: D-N-Me-Lys
<220> FEATURE:
<223> OTHER INFORMATION: C-term NH2

<400> SEQUENCE: 298

Arg Ser Asp Thr Leu Xaa Xaa Glu Lys
1               5

<210> SEQ ID NO 299
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
```

```
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: N-Me-Lys
<220> FEATURE:
<223> OTHER INFORMATION: C-term NH2

<400> SEQUENCE: 299

Arg Ser Asp Thr Leu Xaa Xaa Glu Lys
1               5

<210> SEQ ID NO 300
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-N-Me-Lys
<220> FEATURE:
<223> OTHER INFORMATION: C-term NH2

<400> SEQUENCE: 300

Arg Ser Asp Thr Leu Xaa Xaa Glu Lys
1               5

<210> SEQ ID NO 301
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Butyryl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (8)..(8)
```

```
<223> OTHER INFORMATION: D-Lys
<220> FEATURE:
<223> OTHER INFORMATION: C-term NH2

<400> SEQUENCE: 301

Arg Ser Asp Thr Leu Cys Trp Lys
1               5

<210> SEQ ID NO 302
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: D-Cys
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 302

Arg Ser Asp Thr Leu Cys Trp Glu Lys
1               5

<210> SEQ ID NO 303
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Homo-Cys
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 303

Arg Ser Asp Thr Leu Cys Trp Glu Lys
1               5

<210> SEQ ID NO 304
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: Dap
<220> FEATURE:
<223> OTHER INFORMATION: C-term Ac

<400> SEQUENCE: 304

Arg Ser Asp Thr Leu Xaa Trp Glu Xaa
1               5

<210> SEQ ID NO 305
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: Dab
<220> FEATURE:
<223> OTHER INFORMATION: C-term Ac

<400> SEQUENCE: 305

Arg Ser Asp Thr Leu Xaa Trp Glu Xaa
1               5

<210> SEQ ID NO 306
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
```

```
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: Dap
<220> FEATURE:
<223> OTHER INFORMATION: C-term Ac

<400> SEQUENCE: 306

Arg Ser Asp Thr Leu Xaa Trp Glu Xaa
1               5

<210> SEQ ID NO 307
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: Dab
<220> FEATURE:
<223> OTHER INFORMATION: C-term Ac

<400> SEQUENCE: 307

Arg Ser Asp Thr Leu Xaa Trp Glu Xaa
1               5

<210> SEQ ID NO 308
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2
```

```
<400> SEQUENCE: 308

Arg Ser Asp Thr Leu Xaa Trp Glu Lys
1               5

<210> SEQ ID NO 309
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<223> OTHER INFORMATION: C-term NH2

<400> SEQUENCE: 309

Arg Ser Asp Thr Leu Xaa Trp Glu
1               5

<210> SEQ ID NO 310
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 3-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 310

Arg Ser Asp Thr Leu Xaa Trp Glu Lys
1               5

<210> SEQ ID NO 311
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term 4-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 311

Arg Ser Asp Thr Leu Xaa Trp Glu Lys
1               5

<210> SEQ ID NO 312
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 312

Arg Ser Asp Thr Leu Xaa Trp Glu Lys
1               5

<210> SEQ ID NO 313
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
```

```
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term OH

<400> SEQUENCE: 313

Arg Ser Asp Thr Leu Cys Xaa Lys
1               5

<210> SEQ ID NO 314
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: Glu(OMe)
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 314

Arg Ser Asp Thr Leu Xaa Trp Glu Lys
1               5

<210> SEQ ID NO 315
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (8)..(8)
<223> OTHER INFORMATION: D-Phe
<220> FEATURE:
<221> NAME/KEY: MOD_RES
<222> LOCATION: (9)..(9)
```

```
<223> OTHER INFORMATION: D-Lys
<220> FEATURE:
<223> OTHER INFORMATION: C-term NH2

<400> SEQUENCE: 315

Arg Ser Asp Thr Leu Xaa Xaa Phe Lys
1               5

<210> SEQ ID NO 316
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (8)..(8)
<223> OTHER INFORMATION: D-His
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 316

Arg Ser Asp Thr Leu Xaa Xaa His Lys
1               5

<210> SEQ ID NO 317
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (8)..(8)
<223> OTHER INFORMATION: D-Leu
<220> FEATURE:
<221> NAME/KEY: MOD_RES
<222> LOCATION: (9)..(9)
<223> OTHER INFORMATION: D-Lys
```

<220> FEATURE:
<223> OTHER INFORMATION: C-term NH2

<400> SEQUENCE: 317

Arg Ser Asp Thr Leu Xaa Xaa Leu Lys
1               5

<210> SEQ ID NO 318
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 318

Arg Ser Asp Thr Leu Xaa Xaa Arg Lys
1               5

<210> SEQ ID NO 319
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (8)..(8)
<223> OTHER INFORMATION: Tic
<220> FEATURE:
<221> NAME/KEY: MOD_RES
<222> LOCATION: (9)..(9)
<223> OTHER INFORMATION: D-Lys
<220> FEATURE:

<223> OTHER INFORMATION: C-term NH2

<400> SEQUENCE: 319

Arg Ser Asp Thr Leu Xaa Xaa Xaa Lys
1               5

<210> SEQ ID NO 320
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (8)..(8)
<223> OTHER INFORMATION: D-Thr
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 320

Arg Ser Asp Thr Leu Xaa Xaa Thr Lys
1               5

<210> SEQ ID NO 321
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 321

Arg Ser Asp Thr Leu Xaa Xaa Glu Lys

<210> SEQ ID NO 322
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 322

Arg Ser Asp Thr Leu Xaa Xaa Glu Lys
1               5

<210> SEQ ID NO 323
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (9)..(9)
<223> OTHER INFORMATION: N-Me-Lys
<220> FEATURE:
<223> OTHER INFORMATION: C-term NH2

<400> SEQUENCE: 323

Arg Ser Asp Thr Leu Xaa Xaa Glu Lys
1               5

<210> SEQ ID NO 324
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (9)..(9)
<223> OTHER INFORMATION: D-N-Me-Lys
<220> FEATURE:
<223> OTHER INFORMATION: C-term NH2

<400> SEQUENCE: 324

Arg Ser Asp Thr Leu Xaa Xaa Glu Lys
1               5

<210> SEQ ID NO 325
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: N-Me-Lys
<220> FEATURE:
<223> OTHER INFORMATION: C-term NH2

<400> SEQUENCE: 325

Arg Ser Asp Thr Leu Xaa Xaa Glu Lys
1               5

<210> SEQ ID NO 326
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 1-Nal
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-N-Me-Lys
<220> FEATURE:
<223> OTHER INFORMATION: C-term NH2

<400> SEQUENCE: 326

Arg Ser Asp Thr Leu Xaa Xaa Glu Lys
1               5

<210> SEQ ID NO 327
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: D-Phe
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 327

Arg Ser Asp Thr Leu Xaa Xaa Phe Lys
1               5

<210> SEQ ID NO 328
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: D-His
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 328

Arg Ser Asp Thr Leu Xaa Xaa His Lys
1               5

<210> SEQ ID NO 329
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: D-Leu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 329

Arg Ser Asp Thr Leu Xaa Xaa Leu Lys
1               5

<210> SEQ ID NO 330
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
```

```
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 330

Arg Ser Asp Thr Leu Xaa Xaa Arg Lys
1               5

<210> SEQ ID NO 331
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: Tic
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 331

Arg Ser Asp Thr Leu Xaa Xaa Xaa Lys
1               5

<210> SEQ ID NO 332
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
```

```
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 332

Arg Ser Asp Thr Leu Xaa Xaa Glu Lys
1               5

<210> SEQ ID NO 333
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 333

Arg Ser Asp Thr Leu Xaa Xaa Glu Lys
1               5

<210> SEQ ID NO 334
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
```

```
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term NH2

<400> SEQUENCE: 334

Arg Ser Asp Thr Leu Xaa Xaa Lys
1               5

<210> SEQ ID NO 335
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term NH2

<400> SEQUENCE: 335

Arg Ser Asp Thr Leu Xaa Xaa Lys
1               5

<210> SEQ ID NO 336
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
```

```
<222> LOCATION: (9)..(9)
<223> OTHER INFORMATION: N-Me-Lys
<220> FEATURE:
<223> OTHER INFORMATION: C-term NH2

<400> SEQUENCE: 336

Arg Ser Asp Thr Leu Xaa Xaa Glu Lys
1               5

<210> SEQ ID NO 337
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (9)..(9)
<223> OTHER INFORMATION: D-N-Me-Lys
<220> FEATURE:
<223> OTHER INFORMATION: C-term NH2

<400> SEQUENCE: 337

Arg Ser Asp Thr Leu Xaa Xaa Glu Lys
1               5

<210> SEQ ID NO 338
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: N-Me-Lys
<220> FEATURE:
<223> OTHER INFORMATION: C-term NH2
```

```
<400> SEQUENCE: 338

Arg Ser Asp Thr Leu Xaa Xaa Glu Lys
1               5

<210> SEQ ID NO 339
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: 2-Nal
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-N-Me-Lys
<220> FEATURE:
<223> OTHER INFORMATION: C-term NH2

<400> SEQUENCE: 339

Arg Ser Asp Thr Leu Xaa Xaa Glu Lys
1               5

<210> SEQ ID NO 340
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Bip
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 340
```

```
Arg Ser Asp Thr Leu Xaa Xaa Glu Lys
1               5

<210> SEQ ID NO 341
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Bip
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 341

Arg Ser Asp Thr Leu Xaa Xaa Glu Lys
1               5

<210> SEQ ID NO 342
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Bip
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 342

Arg Ser Asp Thr Leu Xaa Xaa Glu Lys
1               5
```

```
<210> SEQ ID NO 343
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Bip
<220> FEATURE:
<221> NAME/KEY: MOD_RES
<222> LOCATION: (9)..(9)
<223> OTHER INFORMATION: N-Me-Lys
<220> FEATURE:
<223> OTHER INFORMATION: C-term NH2

<400> SEQUENCE: 343

Arg Ser Asp Thr Leu Xaa Xaa Glu Lys
1               5

<210> SEQ ID NO 344
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Bip
<220> FEATURE:
<221> NAME/KEY: MOD_RES
<222> LOCATION: (9)..(9)
<223> OTHER INFORMATION: D-N-Me-Lys
<220> FEATURE:
<223> OTHER INFORMATION: C-term NH2

<400> SEQUENCE: 344

Arg Ser Asp Thr Leu Xaa Xaa Glu Lys
1               5

<210> SEQ ID NO 345
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
``` the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Bip
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: N-Me-Lys
<220> FEATURE:
<223> OTHER INFORMATION: C-term NH2

<400> SEQUENCE: 345

Arg Ser Asp Thr Leu Xaa Xaa Glu Lys
1               5

<210> SEQ ID NO 346
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Bip
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-N-Me-Lys
<220> FEATURE:
<223> OTHER INFORMATION: C-term NH2

<400> SEQUENCE: 346

Arg Ser Asp Thr Leu Xaa Xaa Glu Lys
1               5

<210> SEQ ID NO 347
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6

```
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(2,4-Cl)
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 347

Arg Ser Asp Thr Leu Xaa Phe Glu Lys
1               5

<210> SEQ ID NO 348
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(2-carbamoyl)
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 348

Arg Ser Asp Thr Leu Xaa Phe Glu Lys
1               5

<210> SEQ ID NO 349
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
```

<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(3,4-Cl)
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 349

Arg Ser Asp Thr Leu Xaa Phe Glu Lys
1               5

<210> SEQ ID NO 350
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(3-carbamoyl)
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 350

Arg Ser Asp Thr Leu Xaa Phe Glu Lys
1               5

<210> SEQ ID NO 351
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES

```
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4CF3)
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 351

Arg Ser Asp Thr Leu Xaa Phe Glu Lys
1               5

<210> SEQ ID NO 352
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-COOH)
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 352

Arg Ser Asp Thr Leu Xaa Phe Glu Lys
1               5

<210> SEQ ID NO 353
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
```

<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-COOH)
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 353

Arg Ser Asp Thr Leu Xaa Phe Glu Lys
1               5

<210> SEQ ID NO 354
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-COOH)
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 354

Arg Ser Asp Thr Leu Xaa Phe Glu Lys
1               5

<210> SEQ ID NO 355
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-COOH)

```
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 355

Arg Ser Asp Thr Leu Xaa Phe Glu Lys
1               5

<210> SEQ ID NO 356
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-COOH)
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 356

Arg Ser Asp Thr Leu Xaa Phe Glu Lys
1               5

<210> SEQ ID NO 357
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-COOH)
<220> FEATURE:
<221> NAME/KEY: MOD_RES
<222> LOCATION: (8)..(8)
<223> OTHER INFORMATION: Beta-Homo-Glu
<220> FEATURE:
```

```
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 357

Arg Ser Asp Thr Leu Xaa Phe Glu Lys
1               5

<210> SEQ ID NO 358
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-COOH)
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 358

Arg Ser Asp Thr Leu Xaa Phe Glu Lys
1               5

<210> SEQ ID NO 359
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-F)
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
```

```
<222> LOCATION: (9)..(9)
<223> OTHER INFORMATION: D-Lys
<220> FEATURE:
<223> OTHER INFORMATION: C-term NH2

<400> SEQUENCE: 359

Arg Ser Asp Thr Leu Xaa Phe Glu Lys
1               5

<210> SEQ ID NO 360
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-OMe)
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 360

Arg Ser Asp Thr Leu Xaa Phe Glu Lys
1               5

<210> SEQ ID NO 361
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
```

<223> OTHER INFORMATION: D-Lys
<220> FEATURE:
<223> OTHER INFORMATION: C-term NH2

<400> SEQUENCE: 361

Arg Ser Asp Thr Leu Xaa Phe Glu Lys
1               5

<210> SEQ ID NO 362
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
<221> NAME/KEY: MOD_RES
<222> LOCATION: (9)..(9)
<223> OTHER INFORMATION: N-Me-Lys
<220> FEATURE:
<223> OTHER INFORMATION: C-term NH2

<400> SEQUENCE: 362

Arg Ser Asp Thr Leu Xaa Phe Glu Lys
1               5

<210> SEQ ID NO 363
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 363

```
Arg Ser Asp Thr Leu Xaa Phe Glu Lys
1               5

<210> SEQ ID NO 364
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
<221> NAME/KEY: MOD_RES
<222> LOCATION: (9)..(9)
<223> OTHER INFORMATION: N-Me-Lys
<220> FEATURE:
<223> OTHER INFORMATION: C-term NH2

<400> SEQUENCE: 364

Arg Ser Asp Thr Leu Xaa Phe Glu Lys
1               5

<210> SEQ ID NO 365
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
<221> NAME/KEY: MOD_RES
<222> LOCATION: (9)..(9)
<223> OTHER INFORMATION: D-N-Me-Lys
<220> FEATURE:
<223> OTHER INFORMATION: C-term NH2

<400> SEQUENCE: 365

Arg Ser Asp Thr Leu Xaa Phe Glu Lys
1               5

<210> SEQ ID NO 366
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: N-Me-Lys
<220> FEATURE:
<223> OTHER INFORMATION: C-term NH2

<400> SEQUENCE: 366

Arg Ser Asp Thr Leu Xaa Phe Glu Lys
1               5

<210> SEQ ID NO 367
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (7)..(7)
<223> OTHER INFORMATION: Phe(4-tBu)
<220> FEATURE:
<221> NAME/KEY: MOD_RES
<222> LOCATION: (8)..(8)
<223> OTHER INFORMATION: Beta-Homo-Glu
<220> FEATURE:
<221> NAME/KEY: MOD_RES
<222> LOCATION: (9)..(9)
<223> OTHER INFORMATION: D-N-Me-Lys
<220> FEATURE:
<223> OTHER INFORMATION: C-term NH2

<400> SEQUENCE: 367

Arg Ser Asp Thr Leu Xaa Phe Xaa Lys
1               5

<210> SEQ ID NO 368
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 368

Arg Ser Asp Thr Leu Xaa His Glu Lys
1               5

<210> SEQ ID NO 369
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 369

Arg Ser Asp Thr Leu Cys Xaa Glu Lys
1               5

<210> SEQ ID NO 370
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg

```
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 370

Arg Ser Asp Thr Leu Cys Xaa Glu Lys
1               5

<210> SEQ ID NO 371
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: Dab
<220> FEATURE:
<223> OTHER INFORMATION: C-term NH2

<400> SEQUENCE: 371

Arg Ser Asp Thr Leu Xaa Trp Glu Xaa
1               5

<210> SEQ ID NO 372
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Phe
<220> FEATURE:
<221> NAME/KEY: MOD_RES
<222> LOCATION: (9)..(9)
<223> OTHER INFORMATION: D-Lys
<220> FEATURE:
```

```
<223> OTHER INFORMATION: C-term NH2

<400> SEQUENCE: 372

Arg Ser Asp Thr Leu Xaa Trp Phe Lys
1               5

<210> SEQ ID NO 373
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Tyr
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 373

Arg Ser Asp Thr Leu Xaa Trp Tyr Lys
1               5

<210> SEQ ID NO 374
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 374

Arg Ser Asp Thr Leu Xaa Trp Pro Lys
1               5

<210> SEQ ID NO 375
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<223> OTHER INFORMATION: C-term NH2

<400> SEQUENCE: 375

Arg Ser Asp Thr Leu Xaa Trp Pro Lys
1               5

<210> SEQ ID NO 376
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Pro
<220> FEATURE:
<223> OTHER INFORMATION: C-term NH2

<400> SEQUENCE: 376

Arg Ser Asp Thr Leu Xaa Trp Pro Lys
1               5

<210> SEQ ID NO 377
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-His
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 377

Arg Ser Asp Thr Leu Xaa Trp His Lys
1               5

<210> SEQ ID NO 378
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: Phe(4-COOH)
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 378

Arg Ser Asp Thr Leu Xaa Trp Phe Lys
1               5

<210> SEQ ID NO 379
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: Tic
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 379

Arg Ser Asp Thr Leu Xaa Trp Xaa Lys
1               5

```
<210> SEQ ID NO 380
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Trp
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 380

Arg Ser Asp Thr Leu Xaa Trp Trp Lys
1               5

<210> SEQ ID NO 381
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term NH2

<400> SEQUENCE: 381

Arg Ser Asp Thr Leu Xaa Trp Lys
1               5

<210> SEQ ID NO 382
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Propionyl with a thioether bond between
      the N-term and the residue at position 6
<220> FEATURE:
<221> NAME/KEY: MOD_RES
<222> LOCATION: (1)..(1)
```

```
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term NH2

<400> SEQUENCE: 382

Arg Ser Asp Thr Leu Xaa Trp Lys
1               5

<210> SEQ ID NO 383
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Propionyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: homo-Cys
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term NH2

<400> SEQUENCE: 383

Arg Ser Asp Thr Leu Cys Trp Lys
1               5

<210> SEQ ID NO 384
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Benzyl with a thioether bond between
      the N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<223> OTHER INFORMATION: C-term NH2

<400> SEQUENCE: 384
```

```
Arg Ser Asp Thr Leu Xaa Tyr Glu Lys
1               5
```

<210> SEQ ID NO 385
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 385

```
Cys Arg Ser Asp Thr Leu Cys Gly Glu
1               5
```

<210> SEQ ID NO 386
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 386

```
Cys Arg Ser Asp Thr Leu Cys
1               5
```

<210> SEQ ID NO 387
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-Me-Benzoyl with a thioether bond
      between the N-term and the residue at position 6
<220> FEATURE:
<221> NAME/KEY: MOD_RES
<222> LOCATION: (1)..(1)
<223> OTHER INFORMATION: N(alpha)-Me-Arg, Arg, HArg, Dap, Dab, Arg-Me-
      sym, Arg-Me-asym, 4-Guan, Cit, Cav or suitable isostere
      replacements
<220> FEATURE:
<221> NAME/KEY: MOD_RES
<222> LOCATION: (2)..(2)
<223> OTHER INFORMATION: Ser, Gly or suitable isostere replacements
<220> FEATURE:
<221> NAME/KEY: MOD_RES
<222> LOCATION: (3)..(3)
<223> OTHER INFORMATION: Asp, N-Me-Asp, Asp(OMe), D-Asp or a suitable
      isostere replacements
<220> FEATURE:
<221> NAME/KEY: MOD_RES
<222> LOCATION: (4)..(4)
<223> OTHER INFORMATION: Thr, Gln, Ser, Asp, Pro, Gly, His, Ala, Ile,
      Phe, Lys, Arg, Asn, Glu, Val, Tyr, Trp, Leu, Met or N-Methyl
      amino acids including N-Me-Thr or suitable isostere replacements
<220> FEATURE:
<221> NAME/KEY: MOD_RES
<222> LOCATION: (5)..(5)
<223> OTHER INFORMATION: Gln, Asn, Asp, Pro, Gly, Ala, Phe, Leu, Glu,
      Ile, Val, HLeu, n-Butyl Ala, n-Pentyl Ala, n-Hexyl Ala, Nle,
      cyclobutyl-Ala, N-Me-Leu or suitable isostere replacements
<220> FEATURE:

```
<221> NAME/KEY: MOD_RES
<222> LOCATION: (6)..(6)
<223> OTHER INFORMATION: Cys, N-Me-Cys, D-Cys, HCys, Pen or D-Pen
<220> FEATURE:
<221> NAME/KEY: MOD_RES
<222> LOCATION: (7)..(7)
<223> OTHER INFORMATION: Absent, Gly, Gln, Asn, Asp, Ala, Ile, Leu,
      Val, Met, Thr, Lys, Trp, Tyr, His, Glu, Ser, Arg, Pro, Phe, Sar,
      1-Nal, 2-Nal, HPhe, Phe(4-F), O-Me-Tyr, dihydro-Trp, Dap, Dab,
      Dab(Ac), Orn, D-Orn, N-Me-Orn, N-Me-Dap, D-Dap, D-Dab, Bip,
<220> FEATURE:
<221> NAME/KEY: MOD_RES
<222> LOCATION: (7)..(7)
<223> OTHER INFORMATION: continued from above; Ala(3,3diphenyl),
      Biphenyl-Ala, aromatic ring substituted Phe, aromatic ring
      substituted Trp, aromatic ring substituted His, hetero aromatic
      amino acids, N-Me-Lys, N-Me-Lys(Ac), Bpa, Phe(3-Me), Phe(2-Me),
      Phe(2-CF3), beta-Me-Phe,
<220> FEATURE:
<221> NAME/KEY: MOD_RES
<222> LOCATION: (7)..(7)
<223> OTHER INFORMATION: continued from above; 4-Me-Phe or
      corresponding D-amino acids and suitable isostere replacements
<220> FEATURE:
<221> NAME/KEY: MOD_RES
<222> LOCATION: (8)..(8)
<223> OTHER INFORMATION: Absent, Glu, Lys, Gln, Pro, Gly, His, Ala, Ile,
      Phe, Lys, Arg, Leu, Val, Tyr, Trp, Met, Gla, Ser, Asn, D-Glu,
      beta-Homo-Glu, 2-Nal, 1-Nal, D-Asp, Bip, beta-Homo-Phe, beta-Glu,
      D-Tyr, D-Lys, Dap, Dab, Orn, D-Orn, N-Me-Orn, N-Me-Dap, N-Me-Dab,
<220> FEATURE:
<221> NAME/KEY: MOD_RES
<222> LOCATION: (8)..(8)
<223> OTHER INFORMATION: continued from above; N-Me-Lys, D-Dap, D-Dab,
      Glu, N-Me-Asp, alpha-H-Glu, suitable isosteres or corresponding D-
      amino acids
<220> FEATURE:
<221> NAME/KEY: MOD_RES
<222> LOCATION: (9)..(9)
<223> OTHER INFORMATION: Absent, Gln, Pro, Gly, His, Ala, Ile, Phe, Lys,
      Arg, Leu, Val, Tyr, Trp, Met, Glu, Ser, Asn, Gla, Dap, Dab, Orn,
      D-Orn, D-Lys, N-Me-Orn, N-Me-Dap, N-Me-Dab, N-Me-Lys, D-Dap, D-
      Dab, suitable isosteres or corresponding D-amino acids
<220> FEATURE:
<221> NAME/KEY: MOD_RES
<222> LOCATION: (10)..(10)
<223> OTHER INFORMATION: Absent, Gln, Pro, Gly, His, Ala, Ile, Phe, Lys,
      Arg, Leu, Val, Tyr, Trp, Met, Glu, Ser, Asn, Gla, Dap, Dab, Orn,
      D-Orn, D-Lys, N-Me-Orn, N-Me-Dap, N-Me-Dab, N-Me-Lys, D-Dap, D-
      Dab, suitable isosteres or corresponding D-amino acids

<400> SEQUENCE: 387

Xaa Xaa Xaa Xaa Xaa Xaa Xaa Xaa Xaa Xaa
1               5                   10

<210> SEQ ID NO 388
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Absent, or any naturally occurring amino acid,
      a suitable isostere or corresponding D-amino acids
<220> FEATURE:
<221> NAME/KEY: MOD_RES
<222> LOCATION: (4)..(4)
<223> OTHER INFORMATION: Any amino acid residue having a side chain with
      one or two carbons capable of forming a thioether bond
<220> FEATURE:
<221> NAME/KEY: misc_feature
<222> LOCATION: (4)..(10)
<223> OTHER INFORMATION: Thioether bond between position 4 and Xaa at
      position 10
```

```
<220> FEATURE:
<221> NAME/KEY: MOD_RES
<222> LOCATION: (5)..(5)
<223> OTHER INFORMATION: N(alpha)-Me-Arg, Arg, HArg, Dap, Dab, Arg-Me-
      sym, Arg-Me-asym, 4-Guan, Cit, Cav or suitable isostere
      replacements
<220> FEATURE:
<221> NAME/KEY: MOD_RES
<222> LOCATION: (6)..(6)
<223> OTHER INFORMATION: Ser, Gly or suitable isostere replacements
<220> FEATURE:
<221> NAME/KEY: MOD_RES
<222> LOCATION: (7)..(7)
<223> OTHER INFORMATION: Asp, N-Me-Asp, Asp(OMe), D-Asp or a suitable
      isostere replacements
<220> FEATURE:
<221> NAME/KEY: MOD_RES
<222> LOCATION: (8)..(8)
<223> OTHER INFORMATION: Thr, Gln, Ser, Asp, Pro, Gly, His, Ala, Ile,
      Phe, Lys, Arg, Asn, Glu, Val, Tyr, Trp, Leu, Met or N-Methyl amino
      acids including N-Me-Thr
<220> FEATURE:
<221> NAME/KEY: MOD_RES
<222> LOCATION: (9)..(9)
<223> OTHER INFORMATION: Gln, Asn, Asp, Pro, Gly, Ala, Phe, Leu, Glu,
      Ile, Val, HLeu, n-Butyl Ala, n-Pentyl Ala, n-Hexyl Ala, Nle,
      cyclobutyl-Ala, N-Me-Leu or suitable isostere replacements
<220> FEATURE:
<221> NAME/KEY: MOD_RES
<222> LOCATION: (10)..(10)
<223> OTHER INFORMATION: Cys, N-Me-Cys, D-Cys, HCys, Pen or D-Pen
<220> FEATURE:
<221> NAME/KEY: MOD_RES
<222> LOCATION: (11)..(11)
<223> OTHER INFORMATION: Gly, Gln, Asn, Asp, Ala, Ile, Leu, Val, Met,
      Thr, Lys, Trp, Tyr, His, Glu, Ser, Arg, Pro, Phe, Sar, 1-Nal, 2-
      Nal, D-1-Nal, D-2-Nal, HPhe, D-Phe, D-Tyr, Phe(4-F), O-Me-Tyr,
      dihydro-Trp, Dap, Dab, Dab(Ac), Orn, D-Orn, N-Me-Orn, N-Me-Dap, D-
      Dap, D-Dab,
<220> FEATURE:
<221> NAME/KEY: MOD_RES
<222> LOCATION: (11)..(11)
<223> OTHER INFORMATION: continued from above; Bip, Ala(3,3diphenyl),
      Biphenyl-Ala, aromatic ring substituted Phe, aromatic ring
      substituted Trp, aromatic ring substituted His, hetero aromatic
      amino acids, N-Me-Lys, N-Me-Lys(Ac), 4-Me-Phe or corresponding D-
      amino acids
<220> FEATURE:
<221> NAME/KEY: MOD_RES
<222> LOCATION: (11)..(11)
<223> OTHER INFORMATION: continued from above; and suitable isostere
      replacements
<220> FEATURE:
<221> NAME/KEY: MOD_RES
<222> LOCATION: (12)..(12)
<223> OTHER INFORMATION: Absent or Glu, Lys, Gln, Pro, Gly, His, Ala,
      Ile, Phe, Arg, Leu, Val, Tyr, Trp, Met, Gla, Ser, Asn, D-Glu,
      beta-HGlu, 2-Nal, 1-Nal, D-Asp, Bip, beta-Homo-Phe, beta-Glu, D-
      Tyr, D-Phe, D-Lys, Dap, Dab, Orn, D-Orn, N-Me-Orn, N-Me-Dap, N-Me-
      Dab, N-Me-Lys,
<220> FEATURE:
<221> NAME/KEY: MOD_RES
<222> LOCATION: (12)..(12)
<223> OTHER INFORMATION: continued from above; D-Dap, D-Dab, suitable
      isosteres or corresponding D-amino acids
<220> FEATURE:
<221> NAME/KEY: MOD_RES
<222> LOCATION: (13)..(13)
<223> OTHER INFORMATION: Absent, Gln, Pro, Gly, His, Ala, Ile, Phe, Lys,
      Arg, Leu, Val, Tyr, Trp, Met, Glu, Ser, Asn, Gla, Dap, Dab, Orn,
      D-Orn, D-Lys, N-Me-Orn, N-Me-Dap, N-Me-Dab, N-Me-Lys, D-N-Me-Lys,
      D-Dap, D-Dab, suitable isosteres or corresponding D-amino acids
<220> FEATURE:
<221> NAME/KEY: MOD_RES
<222> LOCATION: (14)..(14)
<223> OTHER INFORMATION: Absent, Gln, Pro, Gly, His, Ala, Ile, Phe, Lys,
      Arg, Leu, Val, Tyr, Trp, Met, Glu, Ser, Asn, Gla, Dap, Dab, Orn,
      D-Orn, D-Lys, N-Me-Orn, N-Me-Dap, N-Me-Dab, N-Me-Lys, D-N-Me-Lys,
      D-Dap, D-Dab suitable isosteres,
```

```
<220> FEATURE:
<221> NAME/KEY: MOD_RES
<222> LOCATION: (14)..(14)
<223> OTHER INFORMATION: continued from above; corresponding D-amino
      acids or corresponding N-Methyl amino acids

<400> SEQUENCE: 388

Xaa Xaa Xaa Xaa Xaa Xaa Xaa Xaa Xaa Xaa Xaa Xaa Xaa Xaa
1               5                   10

<210> SEQ ID NO 389
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Absent or is any amino acid
<220> FEATURE:
<221> NAME/KEY: MOD_RES
<222> LOCATION: (4)..(4)
<223> OTHER INFORMATION: Any amino acid, aliphatic amino acid, alicyclic
      amino acid or modified 2-methyl aromatic acid having side chain
      with one or two carbons capable of forming a thioether bond
<220> FEATURE:
<221> NAME/KEY: misc_feature
<222> LOCATION: (4)..(10)
<223> OTHER INFORMATION: Thioether bond between position 4 and Xaa at
      position 10
<220> FEATURE:
<221> NAME/KEY: MOD_RES
<222> LOCATION: (5)..(5)
<223> OTHER INFORMATION: N(alpha)-Me-Arg, Arg, HomoArg, Dap, Dab, Arg-
      Me-sym, Arg-Me-asym, 4-Guan, Cit, Cav, N-Me-Lys, Phe(4-quanidino),
      Phe(4-carbamoyl amino), Phe(4-NH2), N-Me-HomoArg, Tyr, His or
      suitable isostere replacements
<220> FEATURE:
<221> NAME/KEY: MOD_RES
<222> LOCATION: (6)..(6)
<223> OTHER INFORMATION: Ser, Gly, Thr, Ile or suitable isostere
      replacements
<220> FEATURE:
<221> NAME/KEY: MOD_RES
<222> LOCATION: (7)..(7)
<223> OTHER INFORMATION: Asp, N-Me-Asp, Asp(OMe), D-Asp or suitable
      isostere replacements
<220> FEATURE:
<221> NAME/KEY: MOD_RES
<222> LOCATION: (8)..(8)
<223> OTHER INFORMATION: Thr, Gln, Ser, Asp, Pro, Gly, His, Ala, Ile,
      Phe, Lys, Arg, Asn, Glu, Val, Tyr, Trp, Leu, Met, HomoLeu, Nle or
      N-Methyl amino acids including N-Me-Thr
<220> FEATURE:
<221> NAME/KEY: MOD_RES
<222> LOCATION: (9)..(9)
<223> OTHER INFORMATION: Gln, Asn, Asp, Pro, Gly, Ala, Phe, Leu, Glu,
      Ile, Val, HLeu, n-Butyl Ala, n-Pentyl Ala, n-Hexyl Ala, Nle,
      cyclobutyl-Ala, Cpa, Aoc, N-Me-Leu or suitable isostere
      replacements
<220> FEATURE:
<221> NAME/KEY: MOD_RES
<222> LOCATION: (10)..(10)
<223> OTHER INFORMATION: Cys, N-Me-Cys, D-Cys, HCys, Pen, D-Pen or Pen
      (=O)
<220> FEATURE:
<221> NAME/KEY: MOD_RES
<222> LOCATION: (11)..(11)
<223> OTHER INFORMATION: Absent, Trp, Phe, 2-Nal, 1-Nal, Tyr, His, Phe
      (4-F), Phe(4-CF3), Phe(4-CH3), Phe (4-tBu), Bip, Phe(4-COOH), Gly,
      3,3-DiPhenylGly, 3,3 diPhenyl-Ala, Tic, b-homo-Trp, D-1-Nal, D-2-
      Nal, Phe(2,4-diCl), Phe(3,4-diCl), Phe(4-carbomyl), Phe(3-
      Carbomyl),
<220> FEATURE:
<221> NAME/KEY: MOD_RES
```

```
<222> LOCATION: (11)..(11)
<223> OTHER INFORMATION: continued from above; Phe(2-carbomyl), Tyr(Me),
      HomoPhe, N-Me-Phe, N-Me-Tyr, Ser, Sar, Dihydro Trp, Ile, Leu, Arg,
      Thr, aromatic amino acids , substituted aromatic amino acids, Gly,
      Gln, Asn, Asp, Ala, Ile, Leu, Val,
<220> FEATURE:
<221> NAME/KEY: MOD_RES
<222> LOCATION: (11)..(11)
<223> OTHER INFORMATION: Met, Thr, Lys, Trp, Tyr, His, Glu, Ser, Arg,
      Pro, Phe, Sar, 1-Nal, 2-Nal, D-1-Nal, D-2-Nal, HPhe, D-Phe, D-Tyr,
      Phe(4-F), O-Me-Tyr, dihydro-Trp, Dap, Dab, Dab(Ac), Orn, D-Orn, N-
      Me-Orn, N-Me-Dap, D-Dap, D-Dab, Bip, Ala(3,3diphenyl), Biphenyl-
      Ala,
<220> FEATURE:
<221> NAME/KEY: MOD_RES
<222> LOCATION: (11)..(11)
<223> OTHER INFORMATION: continued from above; aromatic ring substituted
      Phe, aromatic ring substituted Trp, aromatic ring substituted His,
      hetero aromatic amino acids, N-Me-Lys, N-Me-Lys(Ac), 4-Me-Phe,
      Phe(4tBu), Phe(4-OMe), Phe(4-COOH), Phe(2-carbomyl),
<220> FEATURE:
<221> NAME/KEY: MOD_RES
<222> LOCATION: (11)..(11)
<223> OTHER INFORMATION: continued from above; Phe(3-carbomyl), Phe
      (CF3), Phe(2,4-diCl), Phe(3,4-diCl), Aic, N-Me-Tyr, N-Me-Phe, Tic,
      Phe(4CF3) or corresponding D-amino acids and suitable isostere
      replacements
<220> FEATURE:
<221> NAME/KEY: MOD_RES
<222> LOCATION: (12)..(12)
<223> OTHER INFORMATION: Absent, any aromatic amino acid, any
      substituted aromatic amino acid, Glu, D-Glu, HomoGlu, Beta-Homo-
      Glu, Asp, D-HomoGlu, Lys, Gln, Pro, Gly, His, Ala, Ile, Phe, Arg,
      Leu, Val, Tyr, Trp, Met, Gla, Ser, Asn, D-Glu, beta-Homo-Glu, 2-
      Nal, 1-Nal, D-Asp, Bip,
<220> FEATURE:
<221> NAME/KEY: MOD_RES
<222> LOCATION: (12)..(12)
<223> OTHER INFORMATION: continued from above; beta-HPhe, beta-Glu, D-
      Tyr, D-Phe, D-Lys, Dap, Dab, Orn, D-Orn, N-Me-Orn, N-Me-Dap, N-Me-
      Dab, N-Me-Lys, D-Dap, D-Dab, D-His, Phe(4-COOH), Tic, D-Trp, D-
      Leu, D-Arg, D-Thr, suitable isosteres or corresponding D-amino
      acids
<220> FEATURE:
<221> NAME/KEY: MOD_RES
<222> LOCATION: (13)..(14)
<223> OTHER INFORMATION: Absent or any amino acid
<220> FEATURE:
<221> NAME/KEY: MOD_RES
<222> LOCATION: (14)..(14)
<223> OTHER INFORMATION: Absent or any amino acid, any amino acid with
      an amine side chain, Lys, D-Lys, N-Me-Lys, D-N-Me-Lys, Orn, N-Me-
      Orn, Dab, N-Me-Dab, Dap, N-Me-Dap, Homo-Lys, D-Dap, D-Dab, D-Orn,
      Gln, Pro, Gly, His, Ala, Ile, Phe, Lys, Arg, Leu, Val, Tyr, Trp,
      Met, Glu, Ser, Asn,
<220> FEATURE:
<221> NAME/KEY: MOD_RES
<222> LOCATION: (14)..(14)
<223> OTHER INFORMATION: continued from above; Gla, Cys, HomoCys,
      suitable isosteres, corresponding D-amino acids, and
      corresponding N-Methyl amino acids

<400> SEQUENCE: 389

Xaa Xaa Xaa Xaa Xaa Xaa Xaa Xaa Xaa Xaa Xaa Xaa Xaa Xaa
1               5                   10

<210> SEQ ID NO 390
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 2-methyl benzoyl with a thioether bond
      between the N-term and the residue at position 6
<220> FEATURE:
```

```
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Pen, Cys, D-Cys or HomoCys

<400> SEQUENCE: 390

Arg Ser Glu Thr Leu Xaa
1               5

<210> SEQ ID NO 391
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl with a thioether bond between the
      N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term NH2

<400> SEQUENCE: 391

Arg Ser Asp Thr Leu Cys Trp Lys
1               5

<210> SEQ ID NO 392
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl with a thioether bond between the
      N-term and the residue at position 6
<220> FEATURE:
<221> NAME/KEY: MOD_RES
<222> LOCATION: (1)..(1)
<223> OTHER INFORMATION: N-Me-Arg
<220> FEATURE:
<221> NAME/KEY: MOD_RES
<222> LOCATION: (6)..(6)
<223> OTHER INFORMATION: Homo-Cys
<220> FEATURE:
<221> NAME/KEY: MOD_RES
<222> LOCATION: (8)..(8)
<223> OTHER INFORMATION: D-Lys
<220> FEATURE:
<223> OTHER INFORMATION: C-term NH2

<400> SEQUENCE: 392

Arg Ser Asp Thr Leu Cys Trp Lys
1               5

<210> SEQ ID NO 393
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(4)
<223> OTHER INFORMATION: Absent or any amino acid
<220> FEATURE:
<221> NAME/KEY: misc_feature
<222> LOCATION: (4)..(10)
<223> OTHER INFORMATION: Thioether bond between position 4 and Xaa at
      position 10
<220> FEATURE:
<221> NAME/KEY: MOD_RES
<222> LOCATION: (5)..(5)
<223> OTHER INFORMATION: N(alpha)-Me-Arg, Arg, HomoArg, Dap, Dab, Arg-
      Me-sym, Arg-Me-asym, 4-Guan, Cit, Cav, N-Me-Lys, Phe(4-quanidino),
      Phe(4-carbamoyl amino), Phe(4-NH2), N-Me-HomoArg, Tyr, His or
      suitable isostere replacements
<220> FEATURE:
<221> NAME/KEY: MOD_RES
<222> LOCATION: (6)..(6)
<223> OTHER INFORMATION: Ser, Gly, Thr, Ile or suitable isostere
      replacements
<220> FEATURE:
<221> NAME/KEY: MOD_RES
<222> LOCATION: (7)..(7)
<223> OTHER INFORMATION: Asp, N-Me-Asp, Asp(OMe), D-Asp or suitable
      isostere replacements
<220> FEATURE:
<221> NAME/KEY: MOD_RES
<222> LOCATION: (8)..(8)
<223> OTHER INFORMATION: Thr, Gln, Ser, Asp, Pro, Gly, His, Ala, Ile,
      Phe, Lys, Arg, Asn, Glu, Val, Tyr, Trp, Leu, Met, HomoLeu, Nle or
      N-Methyl amino acids including N-Me-Thr
<220> FEATURE:
<221> NAME/KEY: MOD_RES
<222> LOCATION: (9)..(9)
<223> OTHER INFORMATION: Gln, Asn, Asp, Pro, Gly, Ala, Phe, Leu, Glu,
      Ile, Val, HLeu, n-Butyl-Ala, n-Pentyl-Ala, n-Hexyl-Ala, Nle,
      cyclobutyl-Ala, Cpa, Aoc, N-Me-Leu or suitable isostere
      replacements
<220> FEATURE:
<221> NAME/KEY: MOD_RES
<222> LOCATION: (10)..(10)
<223> OTHER INFORMATION: Cys, N-Me-Cys, D-Cys, HCys, Pen, D-Pen or Pen
      (=O)
<220> FEATURE:
<221> NAME/KEY: MOD_RES
<222> LOCATION: (11)..(11)
<223> OTHER INFORMATION: Absent or Trp, Phe, 2-Nal, 1-Nal, Tyr, His, Phe
      (4-F), Phe(4-CF3), Phe(4-CH3), Phe(4-tBu), Bip, Phe(4-COOH), Gly,
      3,3-DiPhenylGly, 3,3 diPhenyl-Ala, Tic, beta-homo-Trp, D-1-Nal,
      D-2-Nal, Phe(2,4-diCl), Phe(3,4-diCl), Phe(4-carbomyl), Phe(3-
      Carbomyl),
<220> FEATURE:
<221> NAME/KEY: MOD_RES
<222> LOCATION: (11)..(11)
<223> OTHER INFORMATION: continued from above; Phe(2-carbomyl), Tyr(Me),
      HomoPhe, N-Me-Phe, N-Me-Tyr, Ser, Sar, Dihydro Trp, Ile, Leu, Arg,
      Thr, aromatic amino acids, substituted aromatic amino acids, Gly,
      Gln, Asn, Asp, Ala, Ile, Leu, Val, Met, Thr, Lys, Trp, Tyr, His,
      Glu,
<220> FEATURE:
<221> NAME/KEY: MOD_RES
<222> LOCATION: (11)..(11)
<223> OTHER INFORMATION: continued from above; Ser, Arg, Pro, Phe, Sar,
      1-Nal, 2-Nal, D-1-Nal, D-2-Nal, HPhe, D-Phe, D-Tyr, Phe(4-F), O-
      Me-Tyr, dihydro-Trp, Dap, Dab, Dab(Ac), Orn, D-Orn, N-Me-Orn, N-
      Me-Dap, D-Dap, D-Dab, Bip, Ala(3,3diphenyl), Biphenyl-Ala,
      aromatic
<220> FEATURE:
<221> NAME/KEY: MOD_RES
<222> LOCATION: (11)..(11)
<223> OTHER INFORMATION: continued from above; ring substituted Phe,
      aromatic ring substituted Trp, aromatic ring substituted His,
      hetero aromatic amino acids, N-Me-Lys, N-Me-Lys(Ac), 4-Me-Phe,
      Phe(4tBu), Phe(4-OMe), Phe(4-COOH), Phe(2-carbomyl),
<220> FEATURE:
<221> NAME/KEY: MOD_RES
<222> LOCATION: (11)..(11)
<223> OTHER INFORMATION: continued from above; Phe(3-carbomyl), Phe
```

```
        (CF3), Phe(2,4-diCl), Phe(3,4-diCl), Aic, N-Me-Tyr, N-Me-Phe, Tic,
        Phe(4CF3), Bpa, Phe(3-Me), Phe(2-Me), Phe(2-CF3), beta-Me-Phe or
        corresponding D-amino acids or suitable isostere replacements
<220> FEATURE:
<221> NAME/KEY: MOD_RES
<222> LOCATION: (12)..(12)
<223> OTHER INFORMATION: Absent or any aromatic amino acid, substituted
        aromatic amino acid, Glu, D-Glu, HomoGlu, Beta-Homo-Glu, Asp, D-
        HomoGlu, Lys, Gln, Pro, Gly, His, Ala, Ile, Phe, Arg, Leu, Val,
        Tyr, Trp, Met, Gla, Ser, Asn, D-Glu, Beta-Homo-Glu, 2-Nal, 1-Nal,
        D-Asp,
<220> FEATURE:
<221> NAME/KEY: MOD_RES
<222> LOCATION: (12)..(12)
<223> OTHER INFORMATION: continued from above; Bip, Beta-HPhe, Beta-Glu,
        D-Tyr, D-Phe, D-Lys, Dap, Dab, Orn, D-Orn, N-Me-Orn, N-Me-Dap, N-
        Me-Dab, N-Me-Lys, D-Dap, D-Dab, D-His, Phe(4-COOH), Tic, D-Trp,
        D-Leu, D-Arg, D-Thr, N-Me-Glu, N-Me-Asp, alpha-H-Glu,
<220> FEATURE:
<221> NAME/KEY: MOD_RES
<222> LOCATION: (12)..(12)
<223> OTHER INFORMATION: continued from above; isoteres or corresponding
        D-amino acids
<220> FEATURE:
<221> NAME/KEY: MOD_RES
<222> LOCATION: (13)..(14)
<223> OTHER INFORMATION: Absent or any amino acid

<400> SEQUENCE: 393

Xaa Xaa Xaa Xaa Xaa Xaa Xaa Xaa Xaa Xaa Xaa Xaa Xaa Xaa
1               5                   10

<210> SEQ ID NO 394
<211> LENGTH: 8
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<223> OTHER INFORMATION: N-term Aromatic acid group, 2-methylbenzoyl,
        propionyl, isobutyryl, acetyl or butyryl forming a thioether bond
        with Xaa at position 6
<220> FEATURE:
<221> NAME/KEY: misc_feature
<222> LOCATION: (1)..(1)
<223> OTHER INFORMATION: Optional N(alpha)methylation
<220> FEATURE:
<221> NAME/KEY: MOD_RES
<222> LOCATION: (6)..(6)
<223> OTHER INFORMATION: Cys, Pen, HCys, D-Cys
<220> FEATURE:
<221> NAME/KEY: MOD_RES
<222> LOCATION: (8)..(8)
<223> OTHER INFORMATION: Glu, D-Glu, D-Lys

<400> SEQUENCE: 394

Arg Ser Asp Thr Leu Xaa Trp Xaa
1               5
```

A4B7 INTEGRIN THIOETHER PEPTIDE ANTAGONISTS

CROSS REFERENCE TO RELATED APPLICATIONS

This application claims priority to U.S. Provisional Application No. 61/994,699, filed on May 16, 2014, U.S. Provisional Application No. 61/994,717, filed on May 16, 2014, U.S. Provisional Application No. 62/058,499, filed on Oct. 1, 2014, and U.S. Provisional Application No. 62/058,501, filed on Oct. 1, 2014, all of which are incorporated by reference herein in their entireties.

SEQUENCE LISTING

The Sequence Listing associated with this application is provided in text format in lieu of a paper copy, and is hereby incorporated by reference into the specification. The name of the text file containing the Sequence Listing is PRTH_010_02US_ST25.txt. The text file is 275 KB, was created on Oct. 8, 2015, and is being submitted electronically via EFS-Web.

FIELD OF THE INVENTION

The present invention relates to the field of engineered peptides, and to the field of peptides that bind to integrins. In particular, the present invention relates to thioether peptides (e.g. thioether peptide monomers and dimers) that inhibit binding of α4β7 to the mucosal addressin cell adhesion molecule (MAdCAM) in vitro, and show high selectivity against α4β1 binding.

BACKGROUND OF THE INVENTION

Integrins are noncovalently associated α/β heterodimeric cell surface receptors involved in numerous cellular processes ranging from cell adhesion and migration to gene regulation (Dubree, et al., Selective α4β7 Integrin Antagonist and Their Potential as Anti-inflammatory Agents, *J. Med. Chem.* 2002, 45, 3451-3457). Differential expression of integrins can regulate a cell's adhesive properties, allowing different leukocyte populations to be recruited to specific organs in response to different inflammatory signals. If left unchecked, the integrin-mediated adhesion process can lead to chronic inflammation and autoimmune disease.

The α4 integrins, α4β1 and α4β7, play essential roles in lymphocyte migration throughout the gastrointestinal tract. They are expressed on most leukocytes, including B and T lymphocytes, where they mediate cell adhesion via binding to their respective primary ligands, vascular cell adhesion molecule (VCAM), and mucosal addressin cell adhesion molecule (MAdCAM), respectively. The proteins differ in binding specificity in that VCAM binds both α4β1 and to a lesser extent α4β7, while MAdCAM is highly specific for α4β7. In addition to pairing with the α4 subunit, the β7 subunit also forms a heterodimeric complex with αE subunit to form αEβ7, which is primarily expressed on intraepithelial lymphocytes (IEL) in the intestine, lung and genitourinary tract. αEβ7 is also expressed on dendritic cells in the gut. The αEβ7 heterodimer binds to E-cadherin on the epithelial cells. The IEL cells are thought to provide a mechanism for immune surveillance within the epithelial compartment. Therefore, blocking αEβ7 and α4β7 together may be a useful method for treating inflammatory conditions of the intestine.

Inhibitors of specific integrins-ligand interactions have been shown effective as anti-inflammatory agents for the treatment of various autoimmune diseases. For example, monoclonal antibodies displaying high binding affinity for α4β7 have displayed therapeutic benefits for gastrointestinal auto-inflammatory/autoimmune diseases, such as Crohn's disease, and ulcerative colitis (Id). However, these therapies interfered with α4β1 integrin-ligand interactions thereby resulting in dangerous side effects to the patient. Therapies utilizing small molecule antagonists have shown similar side effects in animal models, thereby preventing further development of these techniques.

Accordingly, there is a need in the art for integrin antagonist molecules having high affinity for the α4β7 integrin and high selectivity against the α4β1 integrin, as a therapy for various gastrointestinal autoimmune diseases.

Such integrin antagonist molecules are disclosed herein.

SUMMARY OF THE INVENTION

The present invention has been developed in response to the present state of the art, and in particular, in response to the problems and needs in the art that have not yet been fully solved by currently available integrin antagonists that are selective for α4β7. Thus, in certain aspects, the present invention provides α4β7 antagonist thioether peptide monomers and dimers for use as anti-inflammatory and/or immunosuppressive agents. Further, the present invention provides α4β7 antagonist thioether peptides (e.g. monomers and dimers for use in treating a condition that is associated with a biological function of α4β7 or on cells or tissues expressing MAdCAM.

Aspects of the invention relate to a novel class of cyclized, thioether peptidic compounds exhibiting integrin antagonist activity, namely, exhibiting high specificity for α4β7 integrin. In certain embodiments, each peptide of the present invention comprises a downstream natural or unnatural amino acid and an upstream modified amino acid or aromatic group that are capable of bridging to form a cyclized structure through a thioether bond. Peptides of the present invention demonstrate increased stability when administered orally as a therapeutic agent. The peptides of the present invention further provide increased specificity and potency as compared to analogs that are cyclized through a bond other than a thioether bond, e.g., a disulfide bond.

In certain embodiments, cyclized, thioether peptidic compounds exhibiting integrin antagonist activity are monomer peptides. In particular embodiments, the compounds of the present invention comprise dimerized peptides, each subunit of the dimer forming a cyclized structure through a thioether bond. The thioether cyclization feature provides the peptides of the present invention increased stability, specificity, and potency as compared to analogs that are cyclized through a bond other than a thioether bond, e.g., a disulfide bond. In some embodiments, dimerization of thioether peptide monomers further provides for increased specificity and potency as compared monomer analogs.

In one embodiment, the invention provides a peptide molecule comprising a structure of Formula (V):

(Formula (V))
(SEQ ID NO: 49)
$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$ or a pharmaceutically acceptable salt thereof, wherein the peptide comprises a thioether bond between Xaa⁴ and Xaa¹⁰, and wherein:

Xaa¹ is absent, or Xaa¹ is any amino acid;
Xaa² is absent, or Xaa² is any amino acid;
Xaa³ is absent, or Xaa³ is any amino acid;
Xaa⁴ is an amino acid, aliphatic acid, alicyclic acid, or modified 2-methyl aromatic acid having a side chain with one or two carbons, and capable of forming a thioether bond with Xaa¹⁰;
Xaa⁵ is selected from the group consisting of N(alpha)-Me-Arg, Arg, HomoArg, Dap, Dab, Arg-Me-sym, Arg-Me-asym, 4-Guan, Cit, Cav, N-Me-Lys, Phe(4-quanidino), Phe (4-carbamoyl amino), Phe(4-NH₂), N-Me-HomoArg, Tyr, His, and suitable isostere replacements;
Xaa⁶ is selected from the group consisting of Ser, Gly, Thr, Ile, and suitable isostere replacements;
Xaa⁷ is selected from the group consisting of Asp, N-Me-Asp, Asp(OMe), D-Asp, and suitable isostere replacements;
Xaa⁸ is selected from the group consisting of Thr, Gln, Ser, Asp, Pro, Gly, His, Ala, Ile, Phe, Lys, Arg, Asn, Glu, Val, Tyr, Trp, Leu, Met, HomoLeu, Nle, and N-Methyl amino acids including N-Me-Thr;
Xaa⁹ is selected from the group consisting of Gln, Asn, Asp, Pro, Gly, Ala, Phe, Leu, Glu, Ile, Val, HLeu, n-Butyl Ala, n-Pentyl Ala, n-Hexyl Ala, Nle, cyclobutyl-Ala, Cpa, Aoc, N-Me-Leu, and suitable isostere replacements;
Xaa¹⁰ is selected from the group consisting of Cys, N-Me-Cys, D-Cys, HCys, Pen, D-Pen, and Pen(=O);
Xaa¹¹ is absent or is selected from the group consisting of: Trp, Phe, 2-Nal, 1-Nal, Tyr, His, Phe(4-F), Phe(4-CF3), Phe (4-CH3), Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe(4-carbomyl), Phe(3-Carbomyl), Phe (2-carbomyl), Tyr(Me), HomoPhe, N-Me-Phe, N-Me-Tyr, Ser, Sar, Dihydro Trp, Ile, Leu, Ser, Arg, Thr, Sar, and Ser, aromatic amino acids, substituted aromatic amino acids, Gly, Gln, Asn, Asp, Ala, Ile, Leu, Val, Met, Thr, Lys, Trp, Tyr, His, Glu, Ser, Arg, Pro, Phe, Sar, 1-Nal, 2-Nal, D-1-Nal, D-2-Nal, HPhe, D-Phe, D-Tyr, Phe(4-F), O-Me-Tyr, dihydro-Trp, Dap, Dab, Dab(Ac), Orn, D-Orn, N-Me-Orn, N-Me-Dap, D-Dap, D-Dab, Bip, Ala(3,3diphenyl), Biphenyl-Ala, aromatic ring substituted Phe, aromatic ring substituted Trp, aromatic ring substituted His, hetero aromatic amino acids, N-Me-Lys, N-Me-Lys(Ac), 4-Me-Phe, Phe(4tBu), Phe(4-OMe), Phe(4-COOH), Phe(2-carbomyl), Phe(3-carbomyl), Phe(CF3), Phe(2,4-diCl), Phe(3,4-diCl), Aic, N-Me-Tyr, N-Me-Phe, Tic, Phe(4CF3), Bpa, Phe(3-Me), Phe(2-Me), Phe(2-CF3), β-Me-Phe, and corresponding D-amino acids and suitable isostere replacements;
Xaa¹² is absent or selected from the group consisting of aromatic amino acids, substituted aromatic amino acids, Glu, D-Glu, HomoGlu, Beta-Homo-Glu, Asp, D-HomoGlu, Amide, Lys, COOH, CONH₂, Gln, Pro, Gly, His, Ala, Ile, Phe, Arg, Leu, Val, Tyr, Trp, Met, Gla, Ser, Asn, D-Glu, β-HGlu, 2-Nal, 1-Nal, D-Asp, Bip, β-HPhe, β-Glu, D-Tyr, D-Phe, D-Lys, Dap, Dab, Orn, D-Orn, N-Me-Orn, N-Me-Dap, N-Me-Dab, N-Me Lys, D-Dap, D-Dab, D-His, F(4-COOH), Tic, D-Trp, D-Leu, D-Arg, D-Thr, N-Me-Glu, N-Me-Asp, alpha-H-Glu, suitable isosteres, and corresponding D-amino acids;
Xaa¹³ is absent or any amino acid; and
Xaa¹⁴ is absent or any amino acid;
wherein if the peptide molecule is a peptide dimer or subunit thereof, then Xaa¹⁴ is absent or selected from the group consisting of: any amino acid with an amine side chain, Lys, D-Lys, N-Me-Lys, D-N-Me-Lys, Orn, N-Me-Orn, Dab, N-Me-Dab, Dap, N-Me-Dap, Homo-Lys, D-Dap, D-Dab, D-Orn, Gln, Pro, Gly, His, Ala, Ile, Phe, Lys, Arg, Leu, Val, Tyr, Trp, Met, Glu, Ser, Asn, Gla, Cys, HomoCys, COOH, CONH₂, suitable isosteres, corresponding D-amino acids, and corresponding N-Methyl amino acids, and wherein the peptide molecule comprises a thioether bond between Xaa⁴ and Xaa¹⁰.

In particular embodiments, Xaa¹, Xaa² and Xaa³ are absent. In certain embodiments, Xaa⁴ is a 2-methylbenzoyl moiety. In certain embodiments, Xaa⁵ is 2-Me-Arg. In particular embodiments, Xaa⁸ is selected from the group consisting of Thr, Gln, Ser, Asp, Gly, His, Ala, Ile, Phe, Lys, Arg, Asn, Glu, Val, Tyr, Trp, Leu, Met, HomoLeu, Nle, and N-Methyl amino acids including N-Me-Thr. In particular embodiments, Xaa⁹ is selected from the group consisting of Gln, Asn, Asp, Gly, Ala, Phe, Leu, Glu, Ile, Val, HLeu, n-Butyl Ala, n-Pentyl Ala, n-Hexyl Ala, Nle, cyclobutyl-Ala, Cpa, Aoc, N-Me-Leu, and suitable isostere replacements. In certain embodiments, Xaa¹⁴ is selected from the group consisting of: Lys, D-Lys, N-Me-Lys, D-N-Me-Lys, Orn, Dab, Dap, Homo-Lys, D-Dap, D-Dab, Cys, HomoCys, Pen, or D-Orn. In particular embodiments, Xaa¹⁴ is selected from the group consisting of: D-Lys, N-Me-Lys, and D-N-Me-Lys. In certain embodiments, the peptide molecule comprises N(alpha)methylation of at least one position selected from the group consisting of Xaa³, Xaa⁵, Xaa⁷-Xaa⁹, and Xaa¹¹-Xaa¹³. In certain embodiments, the peptide molecule comprises acylation for at least one position selected from the group consisting of Xaa¹-Xaa³ and Xaa¹¹-Xaa¹⁴.

In a related embodiment, the invention includes a peptide molecule comprising a structure of Formula (VI) (SEQ ID NO: 387):

(Formula VI)
Xaa¹-Xaa²-Xaa³-Xaa⁴-Xaa⁵-Xaa⁶-Xaa⁷-Xaa⁸-Xaa⁹-Xaa¹⁰-Xaa¹¹ or a pharmaceutically acceptable salt thereof, wherein
Xaa¹ is a 2-Me-benzoyl group capable of forming a thioether bond with Xaa⁷;
Xaa² is selected from the group consisting of N(alpha)-Me-Arg, Arg, HArg, Dap, Dab, Arg-Me-sym, Arg-Me-asym, 4-Guan, Cit, Cav, and suitable isostere replacements;
Xaa³ is selected from the group consisting of Ser, Gly, and suitable isostere replacements;
Xaa⁴ is selected from the group consisting of Asp, N-Me-Asp, Asp(OMe), D-Asp, and a suitable isostere replacements;
Xaa⁵ is selected from the group consisting of Thr, Gln, Ser, Asp, Pro, Gly, His, Ala, Ile, Phe, Lys, Arg, Asn, Glu, Val, Tyr, Trp, Leu, Met, and N-Methyl amino acids including N-Me-Thr, and suitable isostere replacements;
Xaa⁶ is selected from the group consisting of Gln, Asn, Asp, Pro, Gly, Ala, Phe, Leu, Glu, Ile, Val, HLeu, n-Butyl Ala, n-Pentyl Ala, n-Hexyl Ala, Nle, cyclobutyl-Ala, N-Me-Leu, and suitable isostere replacements;
Xaa⁷ is selected from the group consisting of Cys, N-Me-Cys, D-Cys, HCys, Pen, and D-Pen;
Xaa⁸ is selected from the group consisting of absent, Gly, Gln, Asn, Asp, Ala, Ile, Leu, Val, Met, Thr, Lys, Trp, Tyr, His, Glu, Ser, Arg, Pro, Phe, Sar, 1-Nal, 2-Nal, HPhe, Phe(4-F), O-Me-Tyr, dihydro-Trp, Dap, Dab, Dab(Ac), Orn, D-Orn, N-Me-Orn, N-Me-Dap, D-Dap, D-Dab, Bip, Ala(3, 3diphenyl), Biphenyl-Ala, aromatic ring substituted Phe, aromatic ring substituted Trp, aromatic ring substituted His, hetero aromatic amino acids, N-Me-Lys, N-Me-Lys(Ac), Bpa, Phe(3-Me), Phe(2-Me), Phe(2-CF3), β-Me-Phe, 4-Me-Phe, and corresponding D-amino acids and suitable isostere replacements;

$Xaa^9$ is selected from the group consisting of absent, Glu, Amide, Lys, COOH, $CONH_2$, Gln, Pro, Gly, His, Ala, Ile, Phe, Lys, Arg, Leu, Val, Tyr, Trp, Met, Gla, Ser, Asn, D-Glu, β-HGlu, 2-Nal, 1-Nal, D-Asp, Bip, β-HPhe, β-Glu, D-Tyr, D-Lys, Dap, Dab, Orn, D-Orn, N-Me-Orn, N-Me-Dap, N-Me-Dab, N-Me Lys, D-Dap, D-Dab, Glu, N-Me-Asp, alpha-H-Glu, suitable isosteres, and corresponding D-amino acids;

$Xaa^{10}$ is selected from the group consisting of absent, Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, N-Me-Lys, D-Dap, D-Dab, COOH, $CONH_2$, suitable isosteres, and corresponding D-amino acids; and $Xaa^{11}$ is selected from the group consisting of absent, Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, N-Me-Lys, D-Dap, D-Dab, COOH, $CONH_2$, suitable isosteres, and corresponding D-amino acids, wherein the peptide further comprises a thioether bond between $Xaa^1$ and $Xaa^7$, wherein the peptide further comprises a thioether bond between $Xaa^1$ and $Xaa^7$.

In particular embodiments, $Xaa^5$ is selected from the group consisting of Thr, Gln, Ser, Asp, Gly, His, Ala, Ile, Phe, Lys, Arg, Asn, Glu, Val, Tyr, Trp, Leu, Met, and N-Methyl amino acids including N-Me-Thr, and suitable isostere replacements. In particular embodiments, $Xaa^6$ is selected from the group consisting of Gln, Asn, Asp, Gly, Ala, Phe, Leu, Glu, Ile, Val, HLeu, n-Butyl Ala, n-Pentyl Ala, n-Hexyl Ala, Nle, cyclobutyl-Ala, N-Me-Leu, and suitable isostere replacements. In particular embodiments, any of the peptide molecules of the present invention, further comprise a terminal modifying group selected from the group consisting of DIG, PEG4, PEG13, PEG25, PEG1K, PEG2K, PEG4K, PEG5K, Polyethylene glycol having molecular weight from 400 Da to 40,000 Da, IDA, Ac-IDA, ADA, Glutaric acid, Isophthalic acid, 1,3-phenylenediacetic acid, 1,4-phenylenediacetic acid, 1,2-phenylenediacetic acid, AADA, suitable aliphatic acids, suitable aromatic acids, and heteroaromatic acids. In certain embodiments, the C-terminus of the peptide molecule further comprises a modifying group.

In certain embodiments, the peptide molecules are monomers.

In certain embodiments, the peptide molecules are dimers. In certain embodiments, a dimer comprises two peptide molecules of the present invention dimerized by a linker. In particular embodiments, the linker is selected from the group consisting of: DIG, PEG4, PEG4-biotin, PEG13, PEG25, PEG1K, PEG2K, PEG3.4K, PEG4K, PEG5K, IDA, ADA, Boc-IDA, Glutaric acid, Isophthalic acid, 1,3-phenylenediacetic acid, 1,4-phenylenediacetic acid, 1,2-phenylenediacetic acid, Triazine, Boc-Triazine, IDA-biotin, PEG4-Biotin, AADA, suitable aliphatics, aromatics, heteroaromatics, and polyethylene glycol based linkers having a molecular weight from approximately 400 Da to approximately 40,000 Da. In certain embodiments, the two peptide molecules are dimerized via their C-termini.

In another embodiment, the present invention includes a pharmaceutical composition comprising a peptide molecule of the invention and a pharmaceutically acceptable carrier, diluent or excipient. In particular embodiments, the pharmaceutical composition is formulated for oral delivery. In certain embodiments, it further comprises an enteric coating. In certain embodiments, the enteric coating releases the pharmaceutical composition within a subject's lower gastrointestinal system.

In a further related embodiment, the present invention provides a method for treating or preventing a disease or condition that is associated with a biological function of integrin α4β7, the method comprising providing to a subject in need thereof an effective amount of a peptide molecule of the invention or a pharmaceutical composition of the invention. In certain embodiments, the disease or condition is an inflammatory bowel disease. In particular embodiments, the inflammatory bowel disease is ulcerative colitis or Crohn's disease. In particular embodiments, the peptide molecule inhibits binding of α4β7 to MAdCAM. In certain embodiments, the peptide molecule or the pharmaceutical composition is provided to the subject in need thereof at an interval sufficient to ameliorate the condition. In certain embodiments, the interval is selected from the group consisting of around the clock, hourly, every four hours, once daily, twice daily, three times daily, four times daily, every other day, weekly, bi-weekly, and monthly. In particular embodiments, the peptide molecule or pharmaceutical composition is provided as an initial does followed by one or more subsequent doses, and the minimum interval between any two doses is a period of less than 1 day, and wherein each of the doses comprises an effective amount of the peptide molecule. In particular embodiments, the effective amount of the peptide molecule or the pharmaceutical composition is sufficient to achieve at least one of the following: a) about 50% or greater saturation of MAdCAM binding sites on α4β7 integrin molecules; b) about 50% or greater inhibition of α4β7 integrin expression on the cell surface; and c) about 50% or greater saturation of MAdCAM binding sites on α4β7 molecules and about 50% or greater inhibition of α4β7 integrin expression on the cell surface, wherein i) the saturation is maintained for a period consistent with a dosing frequency of no more than twice daily; ii) the inhibition is maintained for a period consistent with a dosing frequency of no more than twice daily; or iii) the saturation and the inhibition are each maintained for a period consistent with a dosing frequency of no more than twice daily. In certain embodiments, the peptide molecule is administered orally, parenterally, or topically.

BRIEF DESCRIPTION OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 5 shows a pair of integrin antagonist monomer subunits wherein the subunits are aligned and linked at their respective C-termini by a linker that connects two sulfur-containing amino-acids to form a peptide dimer linking sulfhydryl-to-sulfhydryl crosslinking of the present invention, wherein $X_1$ and $X_2$ are H or Me; and the linker (Y) is defined as shown. In particular embodiments, the linker (Y) can comprise homobifunctional maleimide crosslinkers, di-halide, 1,2-Bis(bromomomethyl)benzene, 1,2-Bis(chloromomethyl)benzene, 1,3-Bis(bromomomethyl)benzene, 1,3-Bis(chloromomethyl)benzene, 1,4-Bis(bromomomethyl)benzene, 1,4-Bis(chloromomethyl)benzene, 3,3'-Bis-bromomethyl-biphenyl, or 2,2'-Bis-bromomethyl-biphenyl. Certain haloacetyl crosslinkers contain an iodoacetyl or a bromoacetyl groups. In certain embodiments, these homobifunctional linkers may contain spacers, e.g., comprising a PEG or an aliphatic chain.

FIG. 6 is a chart demonstrating potency and stability data in simulated intestinal fluids (SIF) for various thioether peptide dimer compounds according to SEQ ID NO: 23 and Formula (II) in accordance with various non-limiting representative embodiment of the present invention. Lower case letters indicate D-amino acids.

FIG. 7 is a chart demonstrating potency data of various peptide monomer compounds according to Formula II in accordance with various non-limiting representative embodiments of the present invention.

FIG. 8 is a chart demonstrating stability data in simulated intestinal fluids (SIF) for various peptide monomer compounds according to Formula (II) in accordance with various non-limiting representative embodiment of the present invention.

SEQUENCE IDENTIFIERS

Figure 1:
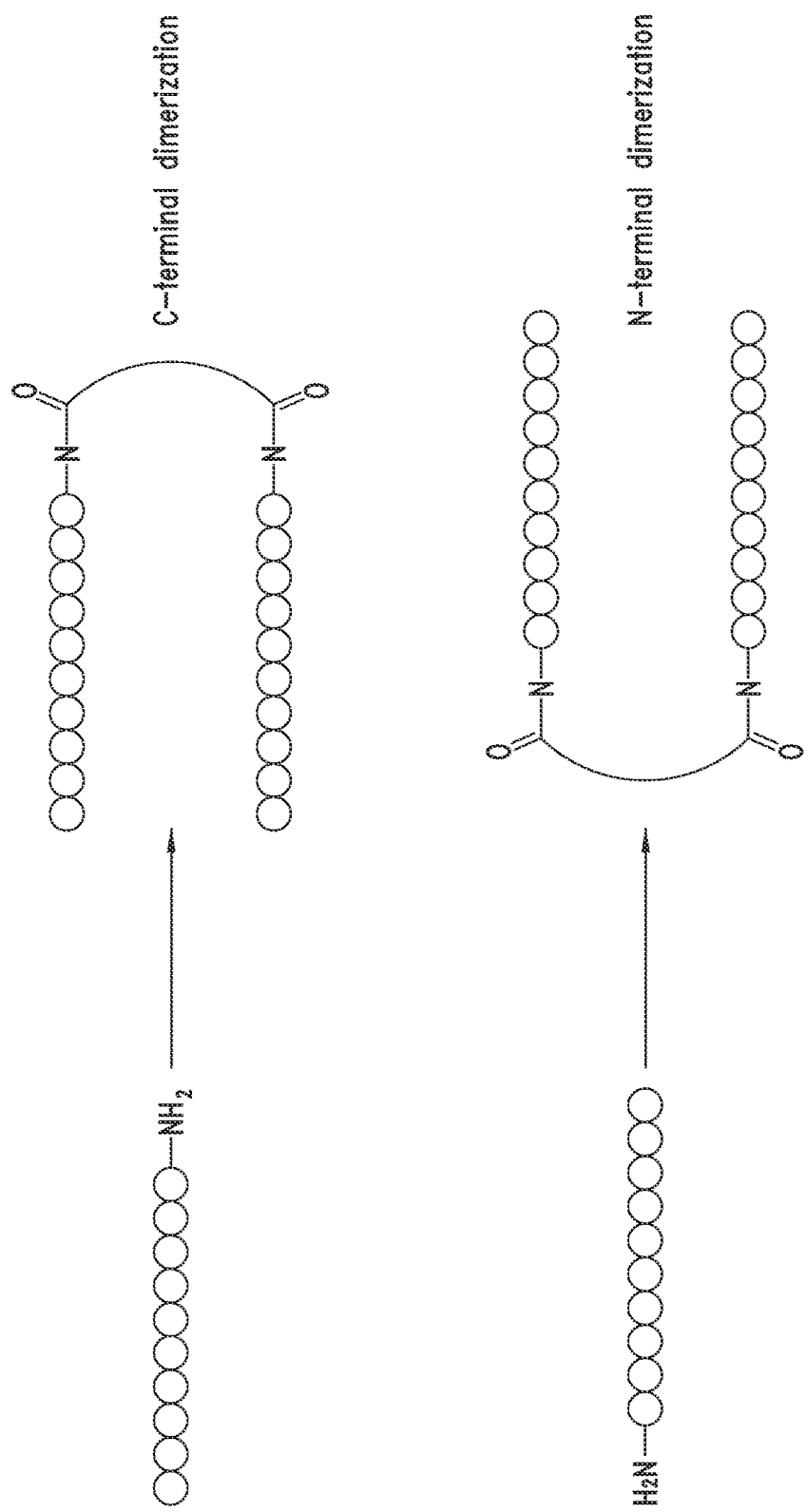
FIG. 1 is a schematic showing C- and N-terminal dimerization via linker molecules according to certain representative embodiments of peptide dimers of the present invention. For example, in C-terminal dimerization, the $NH_2$ group may be a side chain of the C-terminal amino acid, and in N-terminal dimerization, the $NH_2$ group may be an N-terminal free amine group.

The amino acid sequences listed in the accompanying sequence listing are shown using three letter code for amino acids, as defined in 37 C.F.R. 1.822. Sequences of monomer peptide molecules or the monomer subunits of dimer molecules are shown.

In the accompanying sequence listing:

SEQ ID NO: 1 shows a monomer peptide molecule or a peptide subunit of a dimer molecule representing various thioether peptides or peptide subunits of Formula (I).

SEQ ID NO: 2 shows a monomer peptide molecule or a peptide subunit of a dimer molecule representing various thioether peptides or peptide subunits of Formula (II).

SEQ ID NOs: 1-32 show amino acid sequences of illustrative thioether monomer peptides or thioether peptide subunits that are dimerized to form various thioether dimer compounds in accordance with the present invention, wherein these sequences have been substituted with an N(alpha)-Me-Arg.

SEQ ID NO: 33 shows a monomer peptide molecule or a peptide subunit of a dimer molecule representing various thioether peptides or peptide subunits of Formula (I-1).

SEQ ID NO: 34 shows a monomer peptide molecule or a peptide subunit of a dimer molecule representing various thioether peptides or peptide subunits of Formula (I-2).

SEQ ID NO: 35 shows a monomer peptide molecule or a peptide subunit of a dimer molecule representing various thioether peptides or peptide subunits of Formula (I-3).

SEQ ID NO: 36 shows a monomer peptide molecule or a peptide subunit of a dimer molecule representing various thioether peptides or peptide subunits of Formula (I-A).

SEQ ID NO: 37 shows a monomer peptide molecule or a peptide subunit of a dimer molecule representing various thioether peptides or peptide subunits of Formula (I-B).

SEQ ID NO: 38 shows a monomer peptide molecule or a peptide subunit of a dimer molecule representing various thioether peptides or peptide subunits of Formula (I-C).

SEQ ID NO: 39 shows a monomer peptide molecule or a peptide subunit of a dimer molecule representing various thioether peptides or peptide subunits of Formula (I-D).

SEQ ID NO: 40 shows a monomer peptide molecule or a peptide subunit of a dimer molecule representing various thioether peptides or peptide subunits of Formula (I-E).

SEQ ID NO: 41 shows a monomer peptide molecule or a peptide subunit of a dimer molecule representing various thioether peptides or peptide subunits of Formula (I-F).

SEQ ID NO: 42 shows a monomer peptide molecule or a peptide subunit of a dimer molecule representing various thioether peptides or peptide subunits of Formula (I-G).

SEQ ID NO: 43 shows a monomer peptide molecule or a peptide subunit of a dimer molecule representing various thioether peptides or peptide subunits of Formula (I-H).

SEQ ID NO: 44 shows a monomer peptide molecule or a peptide subunit of a dimer molecule representing various thioether peptides or peptide subunits of Formula (I-I).

SEQ ID NO: 45 shows a monomer peptide molecule or a peptide subunit of a dimer molecule representing various thioether peptides or peptide subunits of Formula (II-A).

SEQ ID NO: 46 shows a monomer peptide molecule or a peptide subunit of a dimer molecule representing various thioether peptides or peptide subunits of Formula (III).

SEQ ID NO: 47 shows a monomer peptide molecule or a peptide subunit of a dimer molecule representing various thioether peptides or peptide subunits of Formula (IV).

SEQ ID NO: 48 shows a monomer peptide molecule or a peptide subunit of a dimer molecule representing various thioether peptides or peptide subunits of Formula (A).

SEQ ID NO:49 shows a monomeric peptide molecule or a peptide subunit of a dimer molecule representing various thioether peptides or peptide subunits of Formula (V)

SEQ ID NO:50 shows a monomeric peptide molecule or a peptide subunit of a dimer molecule representing various thioether peptides or peptide subunits of Formula (VI).

SEQ ID NOs: 1, 2, 5, 6, 9-21 and 25-32 show various amino acid sequences of illustrative thioether peptides that may be acylated at their N-terminus using one of the acylating organic compounds and methods disclosed herein, including but not limited to cyclopropylacetic acid, 4-Fluorobenzoic acid, 4-fluorophenylacetic acid, 3-Phenylpropionic acid, Succinic acid, Glutaric acid, Cyclopentane carboxylic acid, 3,3,3-trifluoropropeonic acid, and 3-Fluoromethylbutyric acid.

SEQ ID NOs: 1-21 and 25-32 show amino acid sequences of illustrative monomer subunits that may be dimerized at either their N- or C-terminuses to form various thioether dimer compounds in accordance with the present invention.

SEQ ID NOs: 22-24 show amino acid sequences of monomer subunits that may be dimerized at their C-terminuses to form various thioether dimer compounds in accordance with the present invention.

DETAILED DESCRIPTION OF THE INVENTION

As discussed above, integrins are heterodimers that function as cell adhesion molecules. The α4 integrins, α4β1 and α4β7, play essential roles in lymphocyte migration throughout the gastrointestinal tract. They are expressed on most leukocytes, including B and T lymphocytes, monocytes, and dendritic cells, where they mediate cell adhesion via binding to their respective primary ligands, namely vascular cell adhesion molecule (VCAM) and mucosal addressin cell adhesion molecule (MAdCAM). VCAM and MAdCAM differ in binding specificity, in that VCAM binds both α4β1 and α4β7, while MAdCAM is highly specific for α4β7.

The present invention relates generally to thioether peptides (e.g. peptide monomers and dimers) that have been shown to have integrin antagonist activity. In particular, the present invention relates to various peptides that form cyclized structures through thioether bonds. In certain embodiments, the thioether bonds are cyclized via covalent bonds formed between an upstream amino acid or aromatic acid group, and a downstream sulfur containing amino acid or isostere thereof. Surprisingly, thioether bonds formed when the upstream amino acid or aromatic acid group is 2-methylbenzoyl show superior potency. In some embodiments, thioether peptides comprising 2-methylbenzoyl possess superior potency as compared to thioether peptides not comprising 2-methylbenzoyl. Some aspects of the present invention contemplate that thioether peptide integrin inhibitors comprising 2-methybenzoyl show superior potency compared to non-cyclized integrin peptide inhibitors. In some embodiments, thioether peptide integrin inhibitors comprising 2-methylbenzoyl show superior potency compared to other integrin peptide inhibitors that do not include this moiety. As used herein, "superior potency" will be understood by those of skill in the art to mean a greater, higher, better, or improved potency.

Differences in the expression profiles of VCAM and MAdCAM provide the most convincing evidence of their role in inflammatory diseases. Both are constitutively expressed in the gut; however, VCAM expression extends into peripheral organs, while MAdCAM expression is confined to organs of the gastrointestinal tract. In addition, elevated MAdCAM expression in the gut has now been correlated with several gut-associated inflammatory diseases, including Crohn's disease, ulcerative colitis, and hepatitis C.

The thioether peptide monomer and dimer molecules of the invention may be used in combination with other compositions and procedures for the treatment of disease. Additionally, the monomer or dimer molecules of the present invention may be combined with pharmaceutically acceptable excipients, and optionally sustained-release matrices, such as biodegradable polymers, to form therapeutic compositions.

Definitions

As used herein, the singular forms "a," "and" and "the" include plural references unless the context clearly dictates otherwise.

When the term "comprising" is used herein, it is understood that the present invention also includes the same embodiments wherein the term "comprising" is substituted with "consisting essentially of" or "consisting of."

As used in the present specification the following terms have the meanings indicated:

The term "peptide," as used herein, refers broadly to a structure comprising a sequence of two or more amino acids joined together by peptide bonds. In particular embodiments, it refers to a sequence of two or more amino acids joined together by peptide bonds. It should be understood that this term does not connote a specific length of a polymer of amino acids, nor is it intended to imply or distinguish whether the polypeptide is produced using recombinant techniques, chemical or enzymatic synthesis, or is naturally occurring. The term "peptide", as used generically herein, includes both peptide monomers and peptide dimers.

The term "monomer" as used herein may also be referred to as "peptide monomer," "peptide monomer molecule," or "monomer peptide." The term "monomer" indicates a single sequence of two or more amino acids joined together by peptide bonds.

The term "dimer," as used herein, refers broadly to a peptide comprising two monomer peptide subunits (e.g., thioether monomer peptides) that are linked at their respective C- or N-terminuses. Dimers of the present invention may include homodimers or heterodimers that function as integrin antagonists. The term "dimer" may also be referred to herein to as a "peptide dimer," "peptide dimer molecule," "dimer peptide," or "dimer compound." The term "monomer peptide subunit" may also be referred to herein as "monomer subunit," "peptide monomer subunit," "peptide subunit," "peptide dimer subunit," "dimer subunit," "monomeric subunit," or "subunit of a peptide dimer."

The term "thioether," as used herein, refers to a cyclized, covalent bond formed between an upstream amino acid or aromatic acid group, and a downstream sulfur-containing amino acid, or isostere thereof, i.e., a C—S bond.

The term "linker," as used herein, refers broadly to a chemical structure that is capable of linking together two thioether monomer subunits to form a dimer.

The term "L-amino acid," as used herein, refers to the "L" isomeric form of a peptide, and conversely the term "D-amino acid" refers to the "D" isomeric form of a peptide. The amino acid residues described herein are preferred to be in the "L" isomeric form, however, residues in the "D" isomeric form can be substituted for any L-amino acid residue, as long as the desired functional is retained by the peptide.

Unless otherwise indicated, the term "NH$_2$," as used herein, refers to the free amino group present at the amino terminus of a polypeptide. The term "OH," as used herein, refers to the free carboxy group present at the carboxy terminus of a peptide. Further, the term "Ac," as used herein, refers to Acetyl protection through acylation of the N-terminus of a polypeptide. Where indicated, "NH$_2$" refers to a free amino group side chain of an amino acid. Where indicated, the term "Ac," as used herein refers to acylation of an amino acid with $NH_2$ group.

The term "carboxy," as used herein, refers to $-CO_2H$.

The term "isotere" or "isostere replacement," as used herein, refers to any amino acid or other analog moiety having chemical and/or structural properties similar to a specified amino acid. In particular embodiments, an "isostere" or "suitable isostere" of an amino acid is another amino acid of the same class, wherein amino acids belong to the following classes based on the propensity of the side chain to be in contact with polar solvent like water: hydrophobic (low propensity to be in contact with water), polar or charged (energetically favorable contact with water). The charged amino acid residues include lysine (+), arginine (+), aspartate (−) and glutamate (−). Polar amino acids include serine, threonine, asparagine, glutamine, histidine and tyrosine. The hydrophobic amino acids include alanine, valine, leucine, isoleucine, proline, phenylalanine, tryptophane, cysteine and methionine. The amino acid glycine does not have a side chain and is hard to assign to one of the above classes. However, glycine is often found at the surface of proteins, often within loops, providing high flexibility to these regions, and an isostere may have a similar feature. Proline has the opposite effect, providing rigidity to the protein structure by imposing certain torsion angles on the segment of the polypeptide chain.

The term "cyclized," as used herein, refers to a reaction in which one part of a polypeptide molecule becomes linked to another part of the polypeptide molecule to form a closed ring, such as by forming a thioether bond. In particular embodiments, peptide monomers and monomer subunits of peptide dimers of the present invention are cyclized via an intramolecular thioether bond.

The term "receptor," as used herein, refers to chemical groups of molecules on the cell surface or in the cell interior that have an affinity for a specific chemical group or molecule. Binding between peptide molecules and targeted integrins can provide useful diagnostic tools.

The term "integrin-related diseases," as used herein, refer to indications that manifest as a result of integrin binding, and which may be treated through the administration of an integrin antagonist.

The term "pharmaceutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

The term "N(alpha)Methylation", as used herein, describes the methylation of the alpha amine of an amino acid, also generally termed as an N-methylation.

The term "sym methylation" or "Arg-Me-sym", as used herein, describes the symmetrical methylation of the two nitrogens of the guanidine group of arginine. Further, the term "asym methylation" or "Arg-Me-asym" describes the methylation of a single nitrogen of the guanidine group of arginine.

The term "acylating organic compounds," as used herein refers to various compounds with carboxylic acid functionality, which may be used to acylate the C- and/or N-termini of a peptide molecule. Non-limiting examples of acylating organic compounds include cyclopropylacetic acid, 4-Fluorobenzoic acid, 4-fluorophenylacetic acid, 3-Phenylpropionic acid, Succinic acid, Glutaric acid, Cyclopentane carboxylic acid, glutaric acid, succinic acid, 3,3,3-trifluoropropeonic acid, 3-Fluoromethylbutyric acid.

All peptide sequences are written according to the generally accepted convention whereby the α-N-terminal amino acid residue is on the left and the α-C-terminal is on the right. As used herein, the term "α-N-terminal" refers to the free α-amino group of an amino acid in a peptide, and the term "α-C-terminal" refers to the free α-carboxylic acid terminus of an amino acid in a peptide.

The term "amino acid" or "any amino acid" as used here refers to any and all amino acids, including naturally occurring amino acids (e.g., α-amino acids), unnatural amino acids, modified amino acids, and non-natural amino acids. It includes both D- and L-amino acids. Natural amino acids include those found in nature, such as, e.g., the 23 amino acids that combine into peptide chains to form the building-blocks of a vast array of proteins. These are primarily L stereoisomers, although a few D-amino acids occur in bacterial envelopes and some antibiotics. The "non-standard," natural amino acids are pyrrolysine (found in methanogenic organisms and other eukaryotes), selenocysteine (present in many noneukaryotes as well as most eukaryotes), and N-formylmethionine (encoded by the start codon AUG in bacteria, mitochondria and chloroplasts). "Unnatural" or "non-natural" amino acids are non-proteinogenic amino acids (i.e., those not naturally encoded or found in the genetic code) that either occur naturally or are chemically synthesized. Over 140 natural amino acids are known and thousands of more combinations are possible. Examples of "unnatural" amino acids include β-amino acids ($β^3$ and $ρ^2$), homo-amino acids, proline and pyruvic acid derivatives, 3-substituted alanine derivatives, glycine derivatives, ring-substituted phenylalanine and tyrosine derivatives, linear core amino acids, diamino acids, D-amino acids, alpha-methyl amino acids and N-methyl amino acids. Unnatural or non-natural amino acids also include modified amino acids. "Modified" amino acids include amino acids (e.g., natural amino acids) that have been chemically modified to include a group, groups, or chemical moiety not naturally present on the amino acid.

Generally, the names of naturally occurring and non-naturally occurring aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)" Biochemistry, 14(2), (1975). To the extent that the names and abbreviations of amino acids and aminoacyl residues employed in this specification and appended claims differ from those suggestions, they will be made clear to the reader. Some abbreviations useful in describing the invention are defined below in the following Table 1.

TABLE 1

Abbreviations

| Abbreviation | Definition |
| --- | --- |
| DIG | DIGlycolic acid (Linker) |
| Dap | Diaminopropionic acid |
| Dab | Diaminobutyric acid |
| Pen | Penicillamine |
| Sar | Sarcosine |
| Cit | Citroline |
| Cav | Cavanine |
| 4-Guan | 4-Guanidine-Phenylalanine |
| N—Me-Arg; N(alpha)Methylation | N-Methyl-Arginine |
| Ac— | Acetyl |
| 2-Nal | 2-Napthylalanine |
| 1-Nal | 1-Napthylalanine |
| Bip | Biphenylalanine |
| O—Me-Tyr | Tyrosine (O-Methyl) |
| N—Me-Lys | N-Methyl-Lysine |
| N—Me-Lys (Ac) | N—Me-Acetyl (ε) Lysine |
| Ala (3,3 diphenyle) | 3,3 diphenyl alanine |
| $NH_2$ | Free Amine |
| $CONH_2$ | Amide |
| COOH | Acid |
| Phe (4-F) | 4-Fluoro-Phenylanine |
| PEG13 | Bifunctional PEG linker with 13 PolyEthylene Glycol units |
| PEG25 | Bifunctional PEG linker with 25 PolyEthylene Glycol units |
| PEG1K | Bifunctional PEG linker with PolyEthylene Glycol Mol wt of 1000 Da |
| PEG2K | Bifunctional PEG linker with PolyEthylene Glycol Mol wt of 2000 Da |
| PEG3.4K | Bifunctional PEG linker with PolyEthylene Glycol Mol wt of 3400 Da |
| PEG5K | Bifunctional PEG linker with PolyEthylene Glycol Mol wt of 5000 Da |
| IDA | β-Ala-Iminodiacetic acid (Linker) |
| IDA-Palm | β-Ala (Palmityl)-Iminodiacetic acid |
| HPhe | Homo Phenylalanine |
| Ahx | Aminohexanoic acid |
| DIG-OH | Glycolic monoacid |
| Triazine | Amino propyl Triazine di-acid |
| Boc-Triazine | Boc-Triazine di-acid |
| Trifluorobutyric acid | Acylated with 4,4,4-Trifluorobutyric acid |
| 2-Methly-trifluorobutyric acid | acylated with 2-methy-4,4,4-Butyric acid |
| Trifluorpentanoic acid | Acylated with 5,5,5-Trifluoropentnoic acid |
| 1,4-Phenylenediacetic acid | para-Phenylenediacetic acid (Linker) |
| 1,3-Phenylenediacetic acid | meta-Phenylenediacetic acid (Linker) |
| DTT | Dithiothreotol |
| Nle | Norleucine |
| β-HTrp | β-homoTrypophane |
| β-HPhe | β-homophenylalanine |
| Phe(4-CF$_3$) | 4-Trifluoromethyl Phenylalanine |
| β-Glu | β-Glutamic acid (structure shown) |
| β-HGlu beta-Homo-Glu | β-homoglutamic acid (structure shown) |
| 2-2-Indane | 2-Aminoindane-2-carboxylic acid |
| 1-1-Indane | 1-Aminoindane-1-carboxylic acid |
| Cpa | Cyclopentyl alanine |
| Orn | Ornithine |
| Aoc | 2-Amono octonoic acid |
| Cba | Cyclibutyl alanine |
| HCha | homocyclohexyl Alanine |
| Cyclobutyl | Cyclobutylalanine |
| β-HPhe, B-H-K | β-homophenylalanine |
| HLeu, homo-Leu, hK, | Homoleucine |
| Gla | Gama-Carboxy-Glutamic acid |
| Tic | (3S−)-1,2,3,4-tetrahydroisoquinoline-3-carboxylic acid (structure shown) |
| Phe(4CF3) | L-Phe(4-CF$_3$)—OH Phe(4-trifluoromethyl 3-(4-trifluoromethyl-phenyl)propionic acid |
| Phe(2,4-diCl) | (S)-2-amino-3-(2,4-dichlorophenyl) propionic acid |
| Phe(3,4-diCl) | (S)-2-amino-3-(3,4-dichlorophenyl) propionic acid |
| Pen(=O) | Penicillamine sulfoxide |
| Aic | aminoindan-2-carboxylic acid |
| Phe(2-carbomyl) | L-2-carbamoylphenylalanine |
| Phe(3-carbomyl) | L-3-carbamoylphenylalanine |
| Phe(4-COOH) | (4-carboxy-tert-butyl)-L-phenylalanine |
| Phe(4-Ome) | (S)-4-methoxyphenylalanine |
| Phe(4tBu) | (S)-2-amino-3-(4-tert-butyl-phenyl) propionic acid |
| Phe(4-F) | 4-fluoro-L-phenylalanine |
| Glu(OMe) | L-glutamic acid g-methyl ester |
| alpha-bromobutyryl | (structure shown) |
| alpha-bromopropenyl; Propionyl | (structure shown) |
| alpha-bromoisobutyryl | (structure shown) |

TABLE 1-continued

| Abbreviation | Definition |
|---|---|
| alpha-H-E; alpha-hGlu | Homo Glutamic acid |
| F(2-Me) | 2-Methyl Phenylalanine |
| 4-Benzyl | *(structure)* |
| 2-Benzyl | *(structure)* |
| 3-Benzyl | *(structure)* |
| erythro-b-F-S | Erythreo-β-Phenylserine |
| Threo-b-F-S | Threo-β-Phenylserine |
| F(2-CF3) | 2-Trifluoromethyl-Phenylalanine |
| F(CF3) | 4-Trifluoromethyl-Phenylalinine |
| F(4-Me); 4-Me—F | 4-Methyl Phenylalanine |
| F(3-Me) | 3-Methyl Phenylalanine |
| Alpha-hGlu | HomoGlutamic acid |
| ATC | D-L-2-aminotetralin-2-carboxylic acid |
| BPA | *(structure)* |
| b-Me—F | *(structure)* |
| β-dimethyl-F | *(structure)* |
| 2-Chloro Benzoyl | *(structure)* |
| N—Me-E | N-Methyl Glutamic acid |
| k(Ac) | Nε-Acety-D-Lysine |
| k(PEG8) | PEG8 conjugated (Nε)-D-Lys |
| N—Me-k(Ac) | N-methyl Nε-Acetyl -D-Lysine |
| N—Me-K(Ac) | N-methyl Nε-Acetyl-Lysine |
| F(4-tBu); F(4tBu) | 4-tButyl-Phenylalanine |
| C(thioether propane) | S—CH2—CH2—CH2—S |
| l(D-L) | D-leucine |

Thioether Peptide Monomers and Thioether Peptide Dimers

Figure 3:
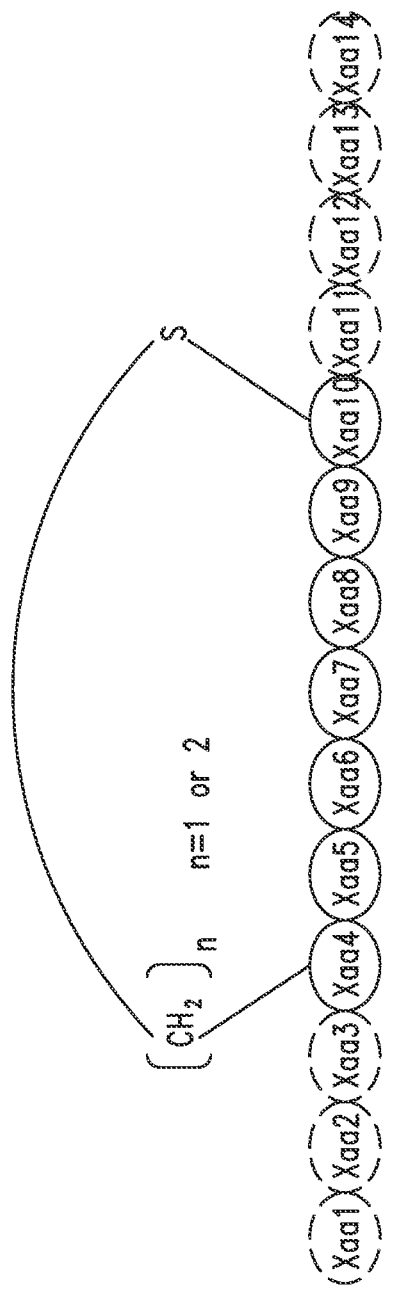
FIG. 3 is a schematic showing a cyclized, thioether peptide monomer or monomer subunit of a dimer molecule according to SEQ ID NO: 1 (Formula (I)), wherein a thioether bond is formed between Xaa$^4$ and Xaa$^{10}$ in accordance with a representative embodiment of the present invention.

The present invention relates generally to thioether peptides that have been shown to have integrin antagonist activity. In particular, the present invention relates to various peptides that form cyclized structures through thioether bonds, e.g., intramolecular thioether bonds. Certain embodiments relate to thioether peptide monomers with integrin antagonist activity. Some embodiments relate to thioether peptide dimers with integrin antagonist activity comprising hetero- or homo-monomer thioether peptide subunits, wherein the thioether peptide subunits are linked at either their C- or N-terminuses, e.g., as shown in FIG. 1. The cyclized structure of the peptide monomers or peptide subunits have been shown to increase the potency, selectivity, and stability of the peptide molecules, as discussed below. A non-limiting, representative illustration of the cyclized structure of Formula (I) is shown in FIG. 3. In some embodiments, dimerizing the peptide monomer increases potency, selectivity, and/or stability compared to a non-dimerized peptide.

In some instances, the monomer peptides further comprise C- and/or N-termini that comprise free amine (or both C- and N-termini that comprise free amine). Similarly, a peptide dimer may comprise one or more C- or N-termini that comprise a free amine. Thus, a user may modify either terminal end to include a modifying group such as a PEGylation, e.g., a small PEGylation (e.g. PEG4-PEG13). A user may further modify either terminal end through acylation. For example, in some instances at least one of the N- and C-terminus of a peptide molecule is acylated with an acylating organic compound selected from the group consisting of 2-Me-Trifluorobutyl, Trifluoropentyl, Acetyl, Octonyl, Butyl, Pentyl, Hexyl, Palmityl, Trifluoromethyl butyric, cyclopentane carboxylic, cyclopropylacetic, 4-fluorobenzoic, 4-fluorophenyl acetic, 3-Phenylpropionic acid. In some instances, peptide molecules of the instant invention comprise both a free carboxy terminal and a free amino terminal, whereby a user may selectively modify the peptide to achieve a desired modification. It is further understood that the C-terminal residues of the thioether peptides, e.g., thioether monomers, disclosed herein are amides or acids, unless otherwise indicated. One having skill in the art will therefore appreciate that the thioether peptides of the instant invention may be selectively modified, as desired.

Figure 2:
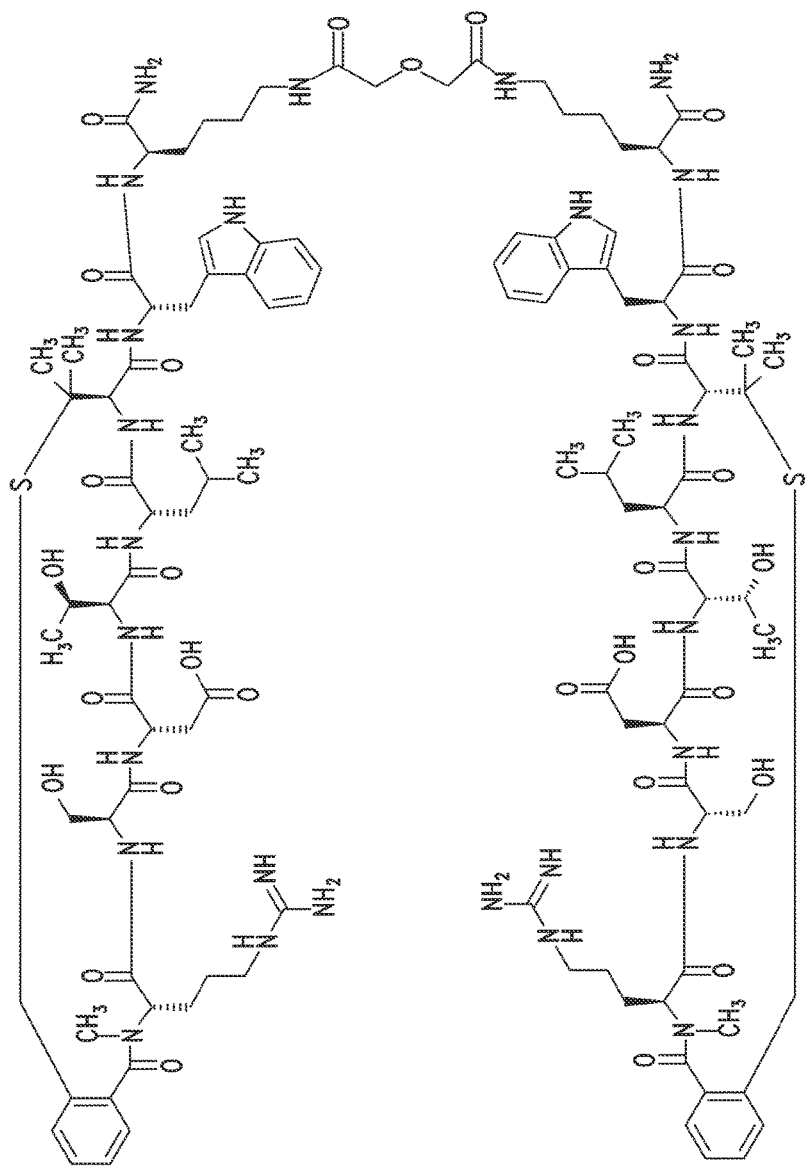
FIG. 2 is a schematic showing an integrin antagonist peptide dimer, comprising two thioether monomer subunits according to SEQ ID NO: 22, wherein the subunits are aligned and linked at their respective C-termini by a DIG linker moiety in accordance with a representative embodiment of the present invention. Lowercase k indicates D-Lysine.

With respect to peptide dimers, it is understood that monomer subunits are dimerized to form thioether peptide dimer molecules in accordance with the present teaching and as shown generally in FIGS. 1 and 2. The monomer subunits are joined or dimerized by a suitable linker moiety, as defined herein. Some of the monomer subunits are shown having C- and N-termini that both comprise free amine. Thus, a user may modify either terminal end of the monomer subunit to eliminate either the C- or N-terminal free amine, thereby permitting dimerization at the remaining free amine. Thus, some of the monomer subunits comprise both a free carboxy or amide at C-terminal and a free amino terminal, whereby a user may selectively modify the subunit to achieve dimerization at a desired terminus. One having skill in the art will therefore appreciate that the monomer subunits of the instant invention may be selectively modified to achieve a single, specific amine for a desired dimerization.

It is further understood that the C-terminal residues of the monomer subunits disclosed herein are amides, unless otherwise indicated. Further, it is understood that dimerization at the C-terminal is facilitated by using a suitable amino acid with a side chain having amine functionality, as is generally understood in the art. In particular embodiments, a linker binds to functional amine groups in the C-terminal amino acid of each of the peptide monomer subunits to form a dimer. Regarding the N-terminal residues, it is generally understood that dimerization may be achieved through the free amine of the terminal residue, or may be achieved by using a suitable amino acid side chain having a free amine, as is generally understood in the art.

Figure 5:
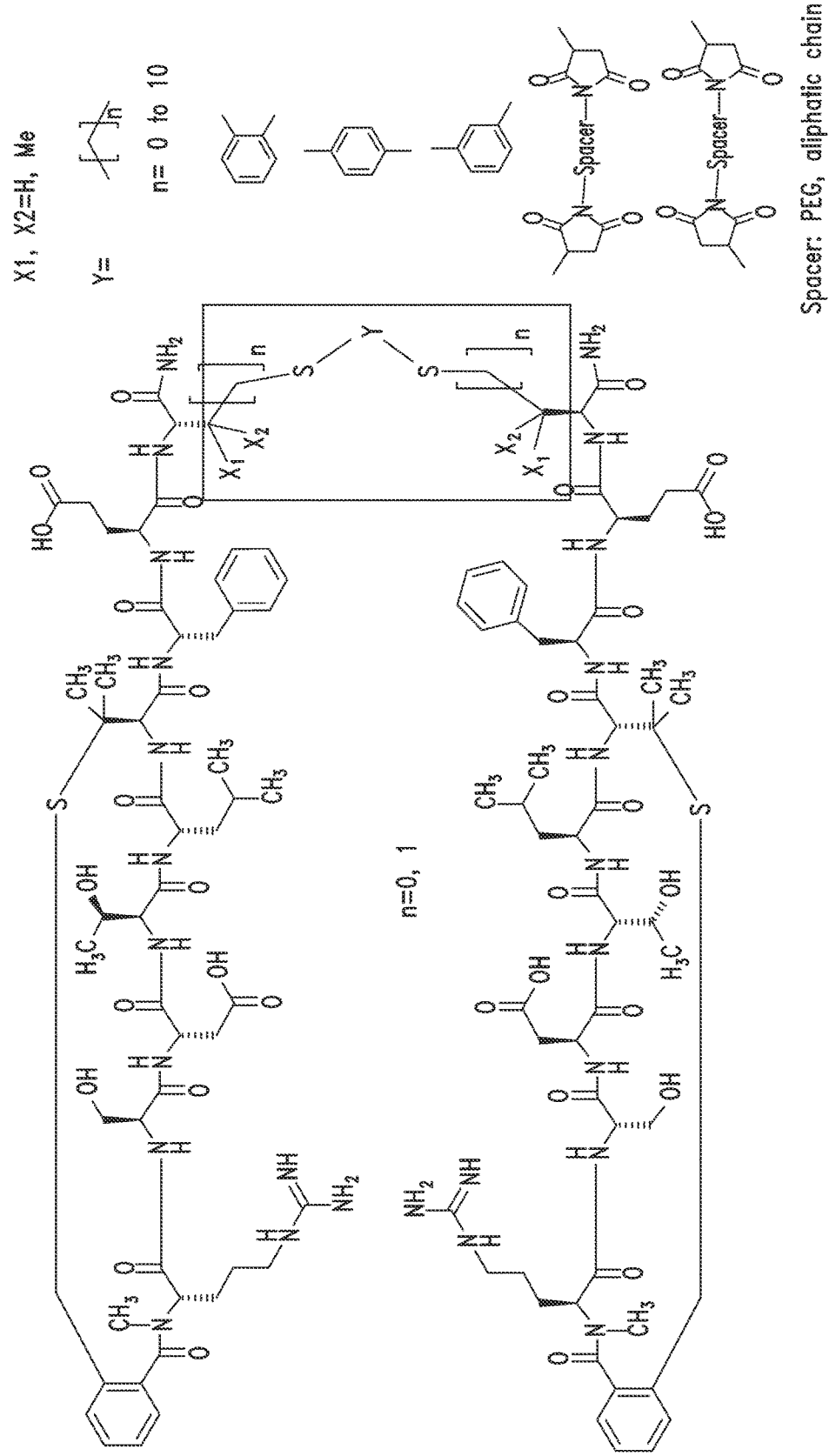
FIG. 5 is a diagram of an illustrative linker system that may be used to dimerize monomer subunits of dimer molecules of the present invention, e.g., dimerization through a sulfhydryl group.

In particular embodiments, dimers are dimerized through a sulfhydryl group, e.g., via the C-terminus of each monomer subunit of the dimer. FIG. 5 shows a pair of integrin antagonist monomer subunits wherein the subunits are aligned and linked at their respective C-termini by a linker that connects two sulfur-containing amino-acids to form a peptide dimer linking sulfhydryl-to-sulfhydryl crosslinking of the present invention, wherein $X_1$ and $X_2$ are H or Me; and the linker (Y) is defined as shown. In particular embodiments, the linker (Y) can comprise homobifunctional maleimide crosslinkers, di-halide, 1,2-Bis(bromomomethyl)benzene, 1,2-Bis(chloromomethyl)benzene, 1,3-Bis(bromomomethyl)benzene, 1,3-Bis(chloromomethyl)benzene, 1,4-Bis(bromomomethyl)benzene, 1,4-Bis(chloromomethyl)benzene, 3,3'-Bis-bromomethyl-biphenyl, or 2,2'-Bis-bromomethyl-biphenyl. Certain haloacetyl crosslinkers contain an iodoacetyl or a bromoacetyl groups. In certain embodiments, these homobifunctional linkers may contain spacers, e.g., comprising a PEG or an aliphatic chain.

In some instances, N-terminal dimerization is proceeded by acylating the C-terminus using one of the acylating organic compounds and methods disclosed herein, including but not limited to Acetyl, cyclopropylacetic acid, 4-Fluorobenzoic acid, 4-fluorophenylacetic acid, 3-Phenylpropionic acid, Succinic acid, Glutaric acid, Cyclopentane carboxylic acid, 3,3,3-trifluoropropeonic acid, and 3-Fluoromethylbutyric acid. For example, where a C-terminal dimerization is desired, the N-terminuses of the respective monomer subunits will generally acylated prior to the C-terminuses being joined by a suitable linking moiety to provide a thioether dimer compound. Conversely, where an N-terminal dimerization is desired, the C-terminuses of the respective monomer subunits may be acylated when the C-terminus comprises a free amine, the N-terminuses being joined by a suitable linking moiety to provide a thioether dimer compound.

The peptide monomers and dimers of the instant invention, or peptide subunits thereof, may further comprise one or more terminal modifying groups. In at least one embodiment, a terminal end of a peptide is modified to include a terminal modifying group selected from the non-limiting group consisting of DIG, PEG4, PEG13, PEG25, PEG K, PEG2K, PEG4K, PEG5K, Polyethylene glycol having molecular weight from 400 Da to 40,000 Da, PEG having a molecular weight of 40,000 Da to 80,000 Da, IDA, ADA, Glutaric acid, Succinic acid, Isophthalic acid, 1,3-phenylenediacetic acid, 1,4-phenylenediacetic acid, 1,2-phenylenediacetic acid, AADA, and suitable aliphatics, aromatics, and heteroaromatics.

In certain embodiments the N- or C-terminus of the peptide monomer or peptide dimer subunit is linked to a modifying group. In certain embodiments, the N-terminus of a peptide is modified by one to three suitable groups, e.g., as represented by $Xaa^1$, $Xaa^2$, and $Xaa^3$, e.g., of Formula (I) or (I-A). Similarly, in certain embodiments, the C-terminus of a peptide is modified by a suitable group. For example, the C-terminus may be acylated. In some instances, the C-terminus further comprises a suitable linker moiety, as disclosed herein. In certain embodiments, the C-terminus comprises $NH_2$ or OH.

For some embodiments of peptide dimers or peptide monomers described herein, any of $Xaa^1$-$Xaa^5$, $Xaa^7$-$Xaa^9$, and $Xaa^{11}$-$Xaa^{12}$ are N(alpha)Methylated. $Xaa^5$ may further be Arg-Me-sym or Arg-Me-asym, and $Xaa^{11}$ may be O-Me-Tyr, N-Me-Lys(Ac), or 4-Me-Phe. The N-terminus may further be acylated. In some instances, any of $Xaa^1$-$Xaa^4$, and $Xaa^{11}$-$Xaa^{14}$ are acylated. For example, in some instances one or more residues at positions $Xaa^8$-$Xaa^{11}$ are acylated with an acylating organic compound selected from the group consisting of 2-Me-Trifluorobutyl, Trifluoropentyl, Acetyl, Octonyl, Butyl, Pentyl, Hexyl, Palmityl, Trifluoromethyl butyric, cyclopentane carboxylic, cyclopropylacetic, 4-fluorobenzoic, 4-fluorophenyl acetic, and 3-Phenylpropionic acid. In some instances one or more residues at positions $Xaa^1$-$Xaa^4$, and $Xaa^{11}$-$Xaa^{14}$ are acylated with an acylating organic compound selected from the group consisting of 2-me-Trifluorobutyl, Trifluoropentyl, Acetyl, Octonyl, Butyl, Pentyl, Hexyl, Palmityl, Lauryl, Oleoyl, and Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, small PEG (e.g., PEG4-PEG13) is used as spacer before acylations.

In some embodiments of the peptide dimers, peptide dimer subunits or peptide monomers described herein, the N-terminus further comprises a suitable linker moiety or other modifying group. In some embodiments of peptide monomers described herein, the N-terminus may further be acylated.

Non-limiting examples of terminal modifying groups are provided in Table 2.

TABLE 2

| Abbreviation | Description | Structure |
|---|---|---|
| DIG | DIGlycolic acid, | |
| PEG4 | Bifunctional PEG linker with 4 PolyEthylene Glycol units | 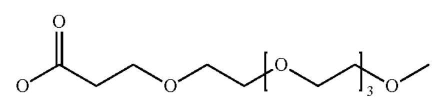 |
| PEG13 | PEG with 13 PolyEthylene Glycol units | 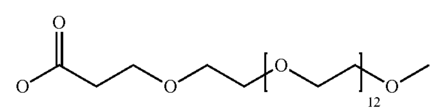 |
| PEG25 | PEG with 25 PolyEthylene Glycol units | 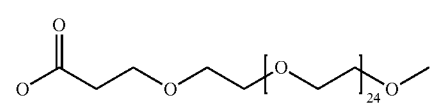 |
| PEG1K | PolyEthylene Glycol Mol wt of 1000 Da | |
| PEG2K | PolyEthylene Glycol Mol wt of 2000 Da | |
| PEG3.4K | PolyEthylene Glycol Mol wt of 3400 Da | |
| PEG5K | PolyEthylene Glycol Mol wt of 5000 Da | |
| DIG | DIGlycolic acid, | |
| IDA | β-Ala-Iminodiacetic acid | 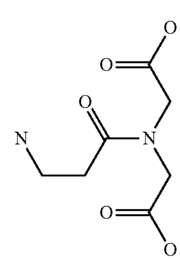 [SMILES: NCCC(=O)N(CC(=O)O)CC(=O)O] |

*Illustrative Terminal Modifying Groups*

TABLE 2-continued

Illustrative Terminal Modifying Groups

| Abbreviation | Description | Structure |
|---|---|---|
| Boc-IDA | Boc-β-Ala-Iminodiacetic acid | 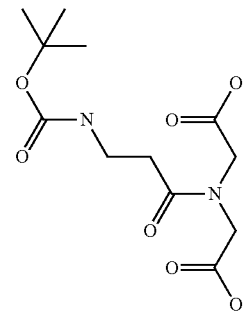 [SMILES: CC(C)(C)OC(=O)NCCC(=O)N(CC(=O)O)CC(=O)O] |
| Ac-IDA | Acetyl-β-Ala-Iminodiacetic acid | 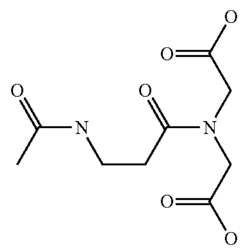 [SMILES: CC(=O)NCCC(=O)N(CC(=O)O)CC(=O)O] |
| GTA | Glutaric acid | 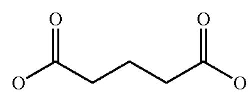 |
| PMA | Pemilic acid | 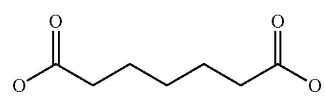 [SMILES: O=C(O)CCCCCC(=O)O] |
| AZA | Azelaic acid | 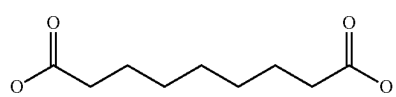 [SMILES: O=C(O)CCCCCCCC(=O)O] |
| DDA | Dodecanedioic acid | 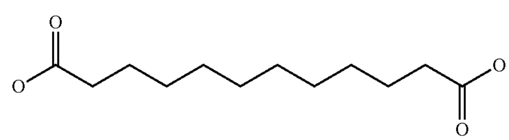 [SMILES: O=C(O)CCCCCCCCCCC(=O)O] |
| ADA | Amino diacetic acid | 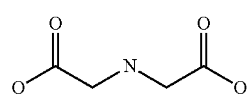 |
| AADA | n-Acetyl amino acetic acid | 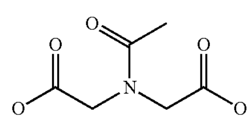 |
| PEG4-Biotin | PEG4-Biotin (Product number 10199, QuantaBioDesign) | 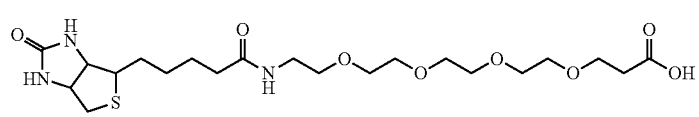 [SMILES: O=C(O)CCOCCOCCOCCOCCNC(=O)CCCCC1SCC2NC(=O)NC21] |

The linker moieties of the instant invention may include any structure, length, and/or size that is compatible with the teachings herein. In at least one embodiment, a linker moiety is selected from the non-limiting group consisting of DIG, PEG4, PEG4-biotin, PEG13, PEG25, PEG1K, PEG2K, PEG3.4K, PEG4K, PEG5K, IDA, ADA, Boc-IDA, Glutaric acid, Isophthalic acid, 1,3-phenylenediacetic acid, 1,4-phenylenediacetic acid, 1,2-phenylenediacetic acid, Triazine, Boc-Triazine, IDA-biotin, PEG4-Biotin, AADA, suitable aliphatics, aromatics, heteroaromatics, and polyethylene glycol based linkers having a molecular weight from approximately 400 Da to approximately 40,000 Da or approximately 40,000 Da to approximately 80,000 Da.

When the linker is IDA, ADA or any linker with free amine it can be acylated with acylating organic compound selected from the group consisting of 2-me-Trifluorobutyl, Trifluoropentyl, Acetyl, Octonyl, Butyl, Pentyl, Hexyl, Palmityl, Lauryl, Oleoyl, Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid, straight chain aliphatic acids with 10 to 20 carbon units, cholic acid and other bile acids. In some instances small PEG (PEG4-PEG13), Glu, or Asp is used as spacer before acylations.

In certain embodiments, the linker connects two monomeric subunits by connecting two sulfur containing C- or N-terminal amino acids. In some embodiments, the two sulfur containing amino acids are connected by a linker comprising a di-halide, an aliphatic chain, or a PEG. In certain embodiments, the linker connects two monomeric subunits by connecting sulfur containing C-terminal amino acids at the C-terminus of each monomer subunit. In some embodiments, the two sulfur containing amino acids are connected by a linker comprising homobifunctional maleimide crosslinkers, di-halide, 1,2-Bis(bromomomethyl)benzene, 1,2-Bis(chloromomethyl)benzene, 1,3-Bis(bromomomethyl)benzene, 1,3-Bis(chloromomethyl)benzene, 1,4-Bis(bromomomethyl)benzene, 1,4-Bis(chloromomethyl)benzene, 3,3'-bis-bromomethyl-biphenyl, or 2,2'-bis-bromomethyl-biphenyl. Particular haloacetyl crosslinkers contain an iodoacetyl or a bromoacetyl group. These homobifunctional linkers may contain spacers comprising PEG or an aliphatic chain.

Non-limiting examples of suitable linker moieties are provided in Table 3.

TABLE 3

Illustrative Linker Moieties

| Abbrivation | Discription | Structure |
|---|---|---|
| DIG | DIGlycolic acid, | |
| PEG4 | Bifunctional PEG linker with 4 PolyEthylene Glycol units | 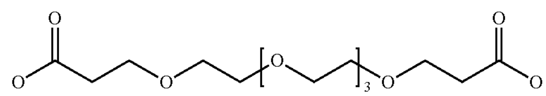 |
| PEG13 | Bifunctional PEG linker with 13 PolyEthylene Glycol units | 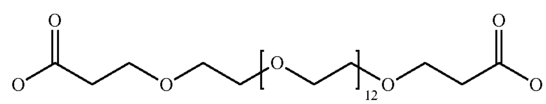 |
| PEG25 | Bifunctional PEG linker with 25 PolyEthylene Glycol units | 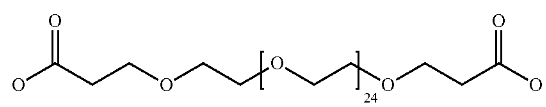 |
| PEG1K | Bifunctional PEG linker with PolyEthylene Glycol Mol wt of 1000 DA | |
| PEG2K | Bifunctional PEG linker with PolyEthylene Glycol Mol wt of 2000 DA | |
| PEG3.4K | Bifunctional PEG linker with PolyEthylene Glycol Mol wt of 3400 DA | |
| PEG5K | Bifunctional PEG linker with PolyEthylene Glycol Mol wt of 5000 DA | |
| DIG | DIGlycolic acid, | |
| IDA | β-Ala-Iminodiacetic acid | 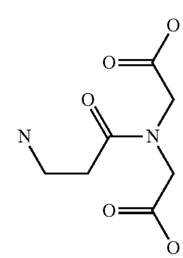 [SMILES: NCCC(=O)N(CC(=O)O)CC(=O)O] |

TABLE 3-continued

Illustrative Linker Moieties

| Abbrivation | Discription | Structure |
|---|---|---|
| Boc-IDA | Boc-β-Ala-Iminodiacetic acid | 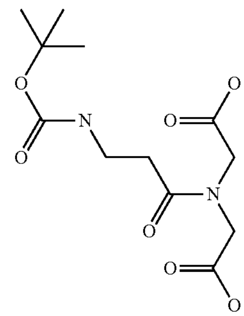 [SMILES: CC(C)(C)OC(=O)NCCC(=O)N(CC(=O)O)CC(=O)O] |
| Ac-IDA | Ac-β-Ala-Iminodiacetic acid | 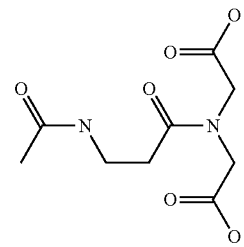 [SMILES: CC(=O)NCCC(=O)N(CC(=O)O)CC(=O)O] |
| IDA-Palm | Palmityl-β-Ala-Iminodiacetic acid | 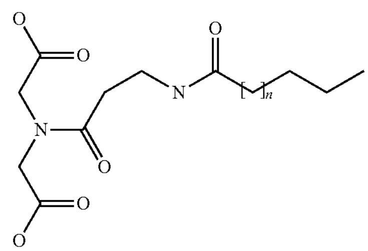 |
| GTA | Glutaric acid | 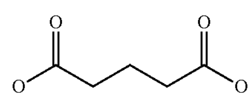 |
| PMA | Pemilic acid | 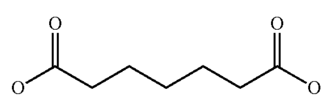 [SMILES: O=C(O)CCCCCC(=O)O] |
| AZA | Azelaic acid | 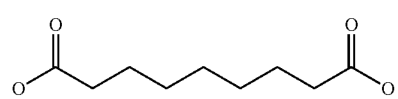 [SMILES: O=C(O)CCCCCCCC(=O)O] |
| DDA | Dodecanedioic acid | 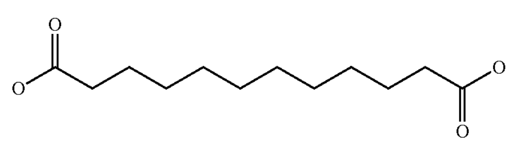 [SMILES: O=C(O)CCCCCCCCCCC(=O)O] |
| IPA | Isopthalic acid | 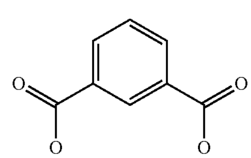 [SMILES: O=C(O)c1cccc(C(=O)O)c1] |

TABLE 3-continued

Illustrative Linker Moieties

| Abbriviation | Discription | Structure |
|---|---|---|
| 1,3-PDA | 1,3-Phenylenediacetic acid | 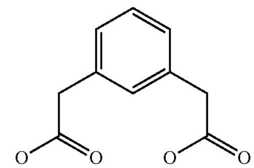 [SMILES: O=C(O)Cc1cccc(CC(=O)O)c1] |
| 1,4-PDA | 1,4-Phenylenediacetic acid | 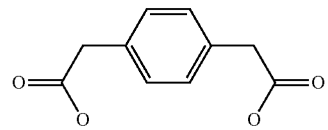 [SMILES: O=C(O)Cc1ccc(CC(=O)O)cc1] |
| 1,2-PDA | 1,2-Phenylenediacetic acid | 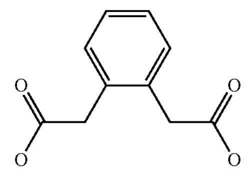 [SMILES: O=C(O)Cc1ccccc1CC(=O)O] |
| Triazine | Amino propyl Triazine di-acid | 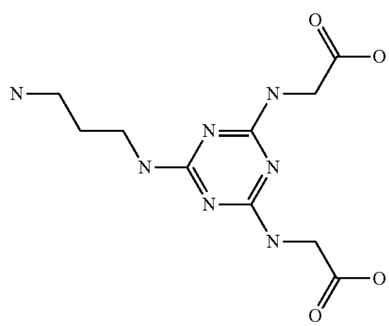 [SMILES: NCCCNc1nc(NCC(=O)O)nc(NCC(=O)O)n1] |
| Boc-Triazine | Boc-Triazine di-acid | 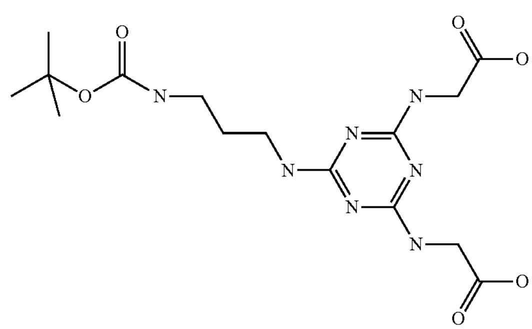 [SMILES: CC(C)(C)OC(=O)NCCCNc1nc(NCC(=O)O)nc(NCC(=O)O)n1] |
| ADA | Amino diacetic acid | 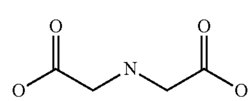 |
| AADA | n-Acetyl amino acetic acid | 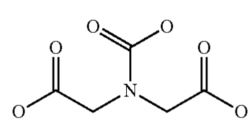 [SMILES: O=C(O)CN(CC(=O)O)C(=O)O] |
| PEG4-Biotin | PEG4-Biotin (Product number 10199, QuantaBioDesign) | 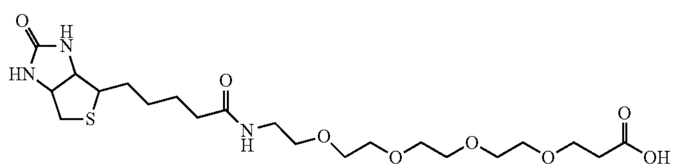 [SMILES: O=C(O)CCOCCOCCOCCOCCNC(=O)CCCCC1SCC2NC(=O)NC21] |

TABLE 3-continued
Illustrative Linker Moieties
| Abbriviation | Discription | Structure |
|---|---|---|
| 1,4 BMB | 1,4-Bis(halo-momethyl)benzene | 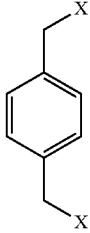<br>X = Cl, Br |
| 1,2 BMB | 1,2-Bis(halo-momethyl)benzene | 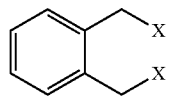<br>X-Cl, Br |
| 1,3 BMB | 1,3-Bis(halo-momethyl)benzene, | 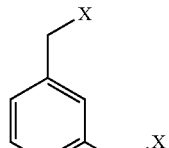<br>X = Cl, Br |
| 1,3 BMBip | 3,3'-Bis-Halomethyl-Biphenyl | 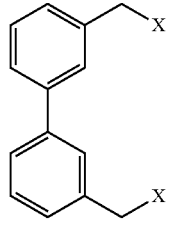<br>X = Cl, Br |
| IDA-Biotin | N-Biotin-β-Ala-Iminodiacetic acid | 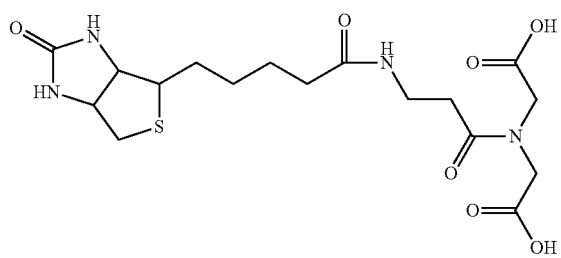 [SMILES: O=C(O)CN(CC(=O)O)C(=O)CCNC(=O)CCCCC1SCC2NC(=O)NC21] |
| 2,2 BMBip | 2,2'-Bis-Halomethyl-Biphenyl | 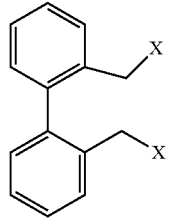<br>X = Cl, Br |

TABLE 3-continued

Illustrative Linker Moieties

| Abbrivation | Discription | Structure |
|---|---|---|
| BMAl | Bis-MaI-dPEG | 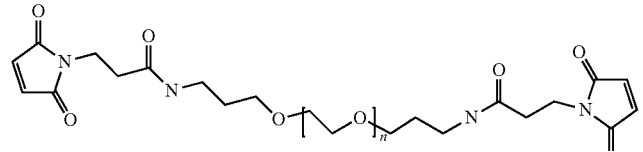<br>n = 1 to 20 |

The present invention further includes various thioether peptide monomers or thioether peptide dimers (and subunits thereof) that have been substituted with various modified amino acids, including but not limited to any of those shown in Table 1 or described herein. For example, some peptides include Dab, Dap, Pen, Sar, Cit, Cav, HLeu, 2-Nal, D-1-Nal, D-2-Nal, Bip, O-Me-Tyr, β-HTrp, β-HPhe, Phe (4-CF3), 2-2-Indane, 1-1-Indane, Cyclobutyl, β-HPhe, HLeu, Gla, HPhe, 1-Nal, Nle, homo amino acids, D-amino acids, 3-3-diPhe, cyclobutyl-Ala, HCha, Phe(4-NH2), Bip, β-HPhe, β-Glu, 4-guan, and various N-methylated amino acids. One having skill in the art will appreciate that additional substitutions may be made to achieve similar desired results, and that such substitutions are within the teaching and spirit of the present invention. In certain embodiments, any of the peptides, e.g. peptide dimers and peptide monomer or subunits thereof, described herein or shown in the sequence listing or accompanying figures further comprises one or more amino acid substitutions, e.g., in certain embodiments, one or more amino acid residues is substituted with Dab, Dap, Pen, Sar, Cit, Cav, HLeu, 2-Nal, D-1-Nal, D-2-Nal, Bip, O-Me-Tyr, β-HTrp, β-HPhe, Phe (4-CF3), 2-2-Indane, 1-1-Indane, Cyclobutyl, 3-HPhe, HLeu, Gla, HPhe, 1-Nal, Nle, homo amino acids, D-amino acids, 3-3-diPhe, cyclobutyl-Ala, HCha, Phe(4-NH2), Bip, β-HPhe, β-Glu, 4-guan, or an N-methylated amino acid, such as, e.g., N-methyl-Arg.

As used herein, "Xaa" can stand for one or more of any naturally occurring amino acids, unnatural amino acids, modified amino acids, and/or non-naturally occurring amino acids, including D- and L-amino acids, aminoacyl residues or any chemical moiety capable of substituting and amino acid position. In some embodiments, Xaa designates that more than one amino acid, aminoacyl residue, or chemical residency may occupy a given position in the peptide. In particular embodiments, Xaa designates that a single non-naturally occurring, unnatural, or modified amino acid, or an aminoacyl residue or a chemical moiety (e.g., a 2-methyl-benzoyl moiety) occupies a given position in the polypeptide.

One aspect of the present invention relates to a thioether peptide monomer, a thioether peptide dimer, or a thioether subunit of a dimer molecule comprising the structure according to Formula (I):

(Formula (I));

SEQ ID NO: 388
$Xaa^1-Xaa^2-Xaa^3-Xaa^4-Xaa^5-Xaa^6-Xaa^7-Xaa^8-Xaa^9-Xaa^{10}-Xaa^{11}-Xaa^{12}-Xaa^{13}-Xaa^{14}$;

FIG. 1), or a pharmaceutically acceptable salt thereof, wherein the peptide monomer or one or both subunits of the thioether peptide dimer comprises a thioether bond between $Xaa^4$ and $Xaa^{10}$ to provide a cyclized structure, and wherein:

$Xaa^1$ is absent, or selected from the group consisting of any naturally occurring amino acid, a suitable isostere, and corresponding D-amino acids;

$Xaa^2$ is absent, or $Xaa^2$ is selected from the group consisting of any naturally occurring amino acid, a suitable isostere, and corresponding D-amino acids;

$Xaa^3$ is absent, or $Xaa^3$ is selected from the group consisting of any naturally occurring amino acid, a suitable isostere, and corresponding D-amino acids;

$Xaa^4$ is an amino acid residue having a side chain with one or two carbons, and forming a thioether bond with $Xaa^{10}$;

$Xaa^5$ is selected from the group consisting of N(alpha)-Me-Arg, Arg, HArg, Dap, Dab, Arg-Me-sym, Arg-Me-asym, 4-Guan, Cit, Cav, and suitable isostere replacements;

$Xaa^6$ is selected from the group consisting of Ser, Gly, and suitable isostere replacements;

$Xaa^7$ is selected from the group consisting of Asp, N-Me-Asp, Asp(OMe), D-Asp, and a suitable isostere replacements;

$Xaa^8$ is selected from the group consisting of Thr, Gln, Ser, Asp, Pro, Gly, His, Ala, Ile, Phe, Lys, Arg, Asn, Glu, Val, Tyr, Trp, Leu, Met, and N-Methyl amino acids including N-Me-Thr;

$Xaa^9$ is selected from the group consisting of Gln, Asn, Asp, Pro, Gly, Ala, Phe, Leu, Glu, Ile, Val, HLeu, n-Butyl Ala, n-Pentyl Ala, n-Hexyl Ala, Nle, cyclobutyl-Ala, N-Me-Leu, and suitable isostere replacements;

$Xaa^{10}$ is selected from the group consisting of Cys, N-Me-Cys, D-Cys, HCys, Pen, and D-Pen;

$Xaa^{11}$ is absent, or selected from the group consisting of Gly, Gln, Asn, Asp, Ala, Ile, Leu, Val, Met, Thr, Lys, Trp, Tyr, His, Glu, Ser, Arg, Pro, Phe, Sar, 1-Nal, 2-Nal, D-1-Nal, D-2-Nal, HPhe, D-Phe, D-Tyr, Phe(4-F), O-Me-Tyr, dihydro-Trp, Dap, Dab, Dab(Ac), Orn, D-Orn, N-Me-Orn, N-Me-Dap, D-Dap, D-Dab, Bip, Ala(3,3diphenyl), Biphenyl-Ala, aromatic ring substituted Phe, aromatic ring substituted Trp, aromatic ring substituted His, hetero aromatic amino acids, N-Me-Lys, N-Me-Lys(Ac), 4-Me-Phe, and corresponding D-amino acids and suitable isostere replacements;

$Xaa^{12}$ is absent, or $Xaa^{12}$ is selected from the group consisting of Glu, Amide, Lys, COOH, Gln, Pro, Gly, His, Ala, Ile, Phe, Arg, Leu, Val, Tyr, Trp, Met, Gla, Ser, Asn, D-Glu, β-HGlu, 2-Nal, 1-Nal, D-Asp, Bip, β-HPhe, β-Glu, D-Tyr, D-Phe, D-Lys, Dap, Dab, Orn, D-Orn, N-Me-Orn, N-Me-Dap, N-Me-Dab, N-Me Lys, D-Dap, D-Dab, suitable isosteres, and corresponding D-amino acids;

$Xaa^{13}$ may be absent, or $Xaa^{13}$ is selected from the group consisting of Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, N-Me-Lys, D-N-Me-Lys, D-Dap, D-Dab, COOH, CONH$_2$, suitable isosteres, and corresponding D-amino acids;

Xaa$^4$ is absent, or Xaa$^4$ is selected from the group consisting of Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, N-Me-Lys, D-N-Me-Lys, D-Dap, D-Dab, COOH, CONH$_2$, suitable isosteres, corresponding D-amino acids, and corresponding N-Methyl amino acids.

In some embodiments of Formula (I), Xaa$^4$ is selected from the group consisting of modified Ser, modified HSer, a suitable isostere, and corresponding D-amino acids and capable of forming a thioether bond with Xaa$^{10}$. In other instances, Xaa$^4$ is an aliphatic acid having from one to four carbons and capable of forming a thioether bond with Xaa$^{10}$. In some instances, Xaa$^4$ is a five- or six-membered alicyclic acid having a modified 2-methyl group that forms a thioether bond with Xaa$^{10}$. In some embodiments, Xaa$^4$ is acetyl, propionyl, alpha-bromoispbutyryl, or 2-methylbenzoyl. In particular embodiments, Xaa$^4$ is a 2-methylbenzoyl moiety that forms a thioether bond with Xaa$^{10}$.

The present invention also includes peptides comprising the same structure as shown in Formula (I) or any of the other formulas or tables described herein, but where the thioether bond is in the reverse orientation. In such embodiments of the invention, it may generally be considered that the amino acid residues or other chemical moieties shown at Xaa$^4$ are instead present at Xaa$^{10}$, and the amino acid residues shown at Xaa$^{10}$ are instead present at Xaa$^4$, i.e., the amino acid residue comprising the sulfur of the resulting thioether bond is located at Xaa$^4$ instead of Xaa$^{10}$, and the amino acid residue or other moiety having a carbon side chain capable of forming a thioether bond with Xaa$^4$ is located at Xaa$^{10}$. In this reverse orientation, however, the amino acid or chemical moiety at position Xaa$^{10}$ is one that comprises a free amine. For example, in particular embodiments, the amino acid at Xaa$^{10}$ is a protected homoserine, such as, e.g., homoserine (OTBDMS). Thus, in particular reverse orientation embodiments of Formula (I), Xaa$^{10}$ is an amino acid residue having a side chain with one or two carbons, and forming a thioether bond with Xaa$^4$, and Xaa$^4$ is selected from the group consisting of Cys, N-Me-Cys, D-Cys, HCys, Pen, and D-Pen. Specific examples of amino acid residues and other chemical moieties present at corresponding positions of other formulas and tables are described herein.

In certain embodiments, a thioether peptide dimer comprises two peptide monomer subunit of Formula (I), wherein these subunits are linked via a linker moiety through their C- or N-termini. In one embodiment, they are linked via both their C-termini.

In another aspect, the present invention includes a thioether peptide molecule (e.g. a peptide monomer, peptide dimer, or a peptide dimer subunit) comprising the structure according to Formula (I-1) (SEQ ID NO: 389):

(Formula (I-1))
Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$, or a pharmaceutically acceptable salt thereof, wherein the peptide comprises a thioether bond between Xaa$^4$ and Xaa$^{10}$, and wherein:

Xaa$^1$ is absent, or Xaa$^1$ is any amino acid;
Xaa$^2$ is absent, or Xaa$^2$ is any amino acid;
Xaa$^3$ is absent, or Xaa$^3$ is any amino acid;
Xaa$^4$ is an amino acid, aliphatic acid, alicyclic acid, or modified 2-methyl aromatic acid having a side chain with one or two carbons, and capable of forming a thioether bond with Xaa$^{10}$;
Xaa$^5$ is selected from the group consisting of N(alpha)-Me-Arg, Arg, HomoArg, Dap, Dab, Arg-Me-sym, Arg-Me-asym, 4-Guan, Cit, Cav, N-Me-Lys, Phe(4-quanidino), Phe (4-carbamoyl amino), Phe(4-NH$_2$), N-Me-HomoArg, Tyr, His, and suitable isostere replacements;
Xaa$^6$ is selected from the group consisting of Ser, Gly, Thr, Ile, and suitable isostere replacements; wherein if Formula (I-1) is directed to a dimer peptide subunit, then in some embodiments, Xaa$^6$ is selected from the group consisting of Ser, Gly, Thr, and suitable isostere replacements;
Xaa$^7$ is selected from the group consisting of Asp, N-Me-Asp, Asp(OMe), D-Asp, and suitable isostere replacements;
Xaa$^8$ is selected from the group consisting of Thr, Gln, Ser, Asp, Pro, Gly, His, Ala, Ile, Phe, Lys, Arg, Asn, Glu, Val, Tyr, Trp, Leu, Met, HomoLeu, Nle, and N-Methyl amino acids including N-Me-Thr,
Xaa$^9$ is selected from the group consisting of Gln, Asn, Asp, Pro, Gly, Ala, Phe, Leu, Glu, Ile, Val, HLeu, n-Butyl Ala, n-Pentyl Ala, n-Hexyl Ala, Nle, cyclobutyl-Ala, Cpa, Aoc, N-Me-Leu, and suitable isostere replacements;
Xaa$^{10}$ is selected from the group consisting of Cys, N-Me-Cys, D-Cys, HCys, Pen, D-Pen, and Pen(=O);
Xaa$^{11}$ is absent, or Xaa$^{11}$ is selected from the group consisting of: Trp, Phe, 2-Nal, 1-Nal, Tyr, His, Phe(4-F), Phe(4-CF3), Phe (4-CH3), Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe(4-carbomyl), Phe(3-Carbomyl), Phe (2-carbomyl), Tyr(Me), HomoPhe, N-Me-Phe, N-Me-Tyr, Ser, Sar, Dihydro Trp, Ile, Leu, Ser, Arg, Thr, Sar, and Ser, aromatic amino acids, substituted aromatic amino acids, Gly, Gln, Asn, Asp, Ala, Ile, Leu, Val, Met, Thr, Lys, Trp, Tyr, His, Glu, Ser, Arg, Pro, Phe, Sar, 1-Nal, 2-Nal, D-1-Nal, D-2-Nal, HPhe, D-Phe, D-Tyr, Phe(4-F), O-Me-Tyr, dihydro-Trp, Dap, Dab, Dab (Ac), Orn, D-Orn, N-Me-Orn, N-Me-Dap, D-Dap, D-Dab, Bip, Ala(3,3diphenyl), Biphenyl-Ala, aromatic ring substituted Phe, aromatic ring substituted Trp, aromatic ring substituted His, hetero aromatic amino acids, N-Me-Lys, N-Me-Lys(Ac), 4-Me-Phe, Phe(4tBu), Phe(4-OMe), Phe(4-COOH), Phe(2-carbomyl), Phe(3-carbomyl), Phe(CF3), Phe (2,4-diCl), Phe(3,4-diCl), Aic, N-Me-Tyr, N-Me-Phe, Tic, Phe(4CF3), and corresponding D-amino acids and suitable isostere replacements;
Xaa$^{12}$ is absent, or Xaa$^{12}$ is selected from the group consisting of aromatic amino acids, substituted aromatic amino acids, Glu, D-Glu, HomoGlu, Beta-Homo-Glu, Asp, D-HomoGlu, Amide, Lys, COOH, CONH$_2$, Gln, Pro, Gly, His, Ala, Ile, Phe, Arg, Leu, Val, Tyr, Trp, Met, Gla, Ser, Asn, D-Glu, 13-HGlu, 2-Nal, 1-Nal, D-Asp, Bip, 13-HPhe, 13-Glu, D-Tyr, D-Phe, D-Lys, Dap, Dab, Orn, D-Orn, N-Me-Orn, N-Me-Dap, N-Me-Dab, N-Me Lys, D-Dap, D-Dab, D-His, F(4-COOH), Tic, D-Trp, D-Leu, D-Arg, D-Thr, suitable isosteres, and corresponding D-amino acids;
Xaa$^{13}$ is absent, or Xaa$^{13}$ is any amino acid; and
Xaa$^{14}$ is absent or any amino acid; wherein in certain embodiments, if Formula (I-1) is directed to a peptide dimer or subunit thereof, then Xaa$^{14}$ is absent or selected from the group consisting of: any amino acid with an amine side chain, Lys, D-Lys, N-Me-Lys, D-N-Me-Lys, Orn, N-Me-Orn, Dab, N-Me-Dab, Dap, N-Me-Dap, Homo-Lys, D-Dap, D-Dab, D-Orn, Gln, Pro, Gly, His, Ala, Ile, Phe, Lys, Arg, Leu, Val, Tyr, Trp, Met, Glu, Ser, Asn, Gla, Cys, HomoCys, COOH, CONH2, suitable isosteres, corresponding D-amino acids, and corresponding N-Methyl amino acids.

In some embodiments, $Xaa^4$ is acetyl, propionyl, alpha-bromoispbutyryl, or 2-methylbenzoyl. In particular embodiments, $Xaa^4$ is 2-methylbenzoyl. In particular embodiments, $Xaa^4$ is 2-methylbenzoyl.

In certain embodiments, a thioether peptide dimer comprises two peptide monomer subunit of Formula (I-1), wherein these subunits are linked via a linker moiety through their C- or N-termini. In one embodiment, they are linked via both their C-termini.

In particular embodiments, Formula (I-1) is directed to a peptide monomer or a peptide dimer (or subunit thereof), and $Xaa^7$ is selected from the group consisting of Asp, N-Me-Asp, and D-Asp.

In certain embodiments, $Xaa^{13}$ is present and selected from the group consisting of Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, N-Me-Lys, D-N-Me-Lys, D-Dap, D-Dab, COOH, $CONH_2$, suitable isosteres, and corresponding D-amino acids.

In certain embodiments, $Xaa^{14}$ is present. In certain embodiments, $Xaa^{14}$ is selected from the group consisting of Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, N-Me-Lys, D-N-Me-Lys, D-Dap, D-Dab, COOH, $CONH_2$, suitable isosteres, corresponding D-amino acids, and corresponding N-Methyl amino acids. In certain embodiments, $Xaa^{14}$ is D-Lys, N-Me-Lys, Dap, or Dab. In particular embodiments, Formula (I-1) is directed to a dimer peptide or subunit thereof and $Xaa^{14}$ is Cys, HomoCys or Pen. In certain embodiments, $Xaa^{12}$ and $Xaa^{13}$ are absent, and $Xaa^{14}$ is D-Lys, N-Me-Lys, Dap, or Dab. In certain embodiments, $Xaa^{13}$ is absent, and $Xaa^4$ is D-Lys, N-Me-Lys, Dap, or Dab.

In some embodiments, $Xaa^{12}$, $Xaa^{13}$ and $Xaa^{14}$ are absent.

In certain embodiments, the amino acid immediately carboxyl to $Xaa^{10}$ is an aromatic amino acid.

In particular embodiments, Formula I-1 is directed to a peptide monomer, dimer, or subunit thereof, and any one or more of $Xaa^1$, $Xaa^2$ or $Xaa^3$ is selected from the group consisting of any naturally occurring amino acid, a suitable isostere, and corresponding D-amino acids In particular embodiments, $Xaa^4$ is an amino acid residue having a side chain with one or two carbons.

In particular instances, a peptide monomer, dimer, or subunit thereof of any of the Formula and peptides described herein comprises $Xaa^4$, where $Xaa^4$ is selected from the group consisting of modified Ser, modified HomoSer (e.g., Homo-Ser-Cl), a suitable isostere, and corresponding D-amino acids. In other instances, $Xaa^4$ is an aliphatic acid having from one to four carbons and forming a thioether bond with $Xaa^{10}$. In some instances, $Xaa^4$ is a five- or six-membered alicyclic acid having a modified 2-methyl group that forms a thioether bond with $Xaa^{10}$. In some embodiments, $Xaa^4$ is a 2-methylbenzoyl moiety.

For some embodiments, at least one of $Xaa^1$, $Xaa^2$, $Xaa^3$, $Xaa^5$, $Xaa^7$, $Xaa^8$, $Xaa^9$, $Xaa^{11}$, $Xaa^{12}$, $Xaa^{13}$ and $Xaa^{14}$ is N(alpha)Methylated. In some instances, at least one of $Xaa^1$, $Xaa^2$, $Xaa^3$, $Xaa^4$, $Xaa^{11}$, $Xaa^{12}$, $Xaa^{13}$ and $Xaa^{14}$ are acylated. For example, in some instances one or more residues at positions $Xaa^1$-$Xaa^4$, and $Xaa^{11}$-$Xaa^{14}$ are acylated with an acylating organic cisestyl, Hexyl, Palmityl, Lauryl, Oleoyl, and Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, small PEG (e.g., PEG4-PEG13) is used as spacer before acylations. The present invention also includes reverse order thioether bond embodiments of Formula (I-1), wherein $Xaa^{10}$ is an amino acid, aliphatic acid, alicyclic acid, or modified 2-methyl aromatic acid having a side chain with one or two carbons, and capable of forming a thioether bond with $Xaa^4$; and $Xaa^4$ is selected from the group consisting of Cys, N-Me-Cys, D-Cys, HCys, Pen, D-Pen, and Pen(=O). In this reverse orientation, the amino acid or chemical moiety at position $Xaa^{10}$ is one that comprises a free amine. One example of an amino acid or chemical moiety that provides a free amine is homoserine or a protected homoserine, e.g., homserine (OTBDMS).

In one aspect, the present invention provides a peptide (e.g. a peptide monomer, a peptide dimer, or a peptide dimer subunit) comprising the structure according to Formula (I-2)(SEQ ID NO: 34):

(Formula I-2)
$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$, or a pharmaceutically acceptable salt thereof, wherein the peptide molecule comprises a thioether bond between $Xaa^4$ and $Xaa^{10}$, and wherein $Xaa^1$ is absent, or $Xaa^1$ is selected from the group consisting of any naturally occurring amino acid, a suitable isostere, and corresponding D-amino acids;

$Xaa^2$ is absent, or $Xaa^2$ is selected from the group consisting of any naturally occurring amino acid, a suitable isostere, and corresponding D-amino acids;

$Xaa^3$ is absent, or $Xaa^3$ is selected from the group consisting of any naturally occurring amino acid, a suitable isostere, and corresponding D-amino acids;

$Xaa^4$ is an amino acid, aliphatic acid, alicyclic acid, or modified 2-methyl aromatic acid having a side chain with one or two carbons, and capable of forming a thioether bond with $Xaa^{10}$;

$Xaa^5$ is selected from the group consisting of N(alpha)-Me-Arg, Arg, HomoArg, Dap, Dab, Arg-Me-sym, Arg-Me-asym, 4-Guan, Cit, Cav, N-Me-Lys, Phe (4-quanidino), Phe (4-carbomyl amino), Phe(4-NH2), N-Me-Homo-Arg, Tyr and His, and suitable isostere replacements;

$Xaa^6$ is selected from the group consisting of Ser, Gly, Thr, Ile, and suitable isostere replacements;

$Xaa^7$ is selected from the group consisting of Asp, N-Me-Asp, Asp(OMe), D-Asp, and a suitable isostere replacement; wherein in certain embodiments, if Formula (I-2) is directed to a peptide dimer subunit then $Xaa^7$ is selected from the group consisting of Asp, N-Me-Asp, D-Asp, and a suitable isostere replacement;

$Xaa^8$ is selected from the group consisting of Thr, Gln, Ser, Asp, Pro, Gly, His, Ala, Ile, Phe, Lys, Arg, Asn, Glu, Val, Tyr, Trp, Leu, Met, hLeu, Nle and N-Methyl amino acids including N-Me-Thr, $Xaa^9$ is selected from the group consisting of Gln, Asn, Asp, Pro, Gly, Ala, Phe, Leu, Glu, Ile, Val, HomoLeu, n-Butyl Ala, n-Pentyl Ala, n-Hexyl Ala, Nle, cyclobutyl-Ala, N-Me-Leu, Cpa, Aoc and suitable isostere replacements; and $Xaa^{10}$ is selected from the group consisting of Cys, N-Me-Cys, D-Cys, HomoCys, Pen, D-Pen, modified Homo-Ser and modified Ser; wherein in certain embodiments, if Formula (I-2) is directed to a peptide dimer subunit, then $Xaa^{10}$ is selected from the group consisting of Cys, N-Me-Cys, D-Cys, HomoCys, Pen, and D-Pen;

Xaa$^{11}$ is absent, or Xaa$^{11}$ is selected from the group consisting of or selected from the group consisting of: aromatic amino acids, substituted aromatic amino acids, Tic, and corresponding D-amino acids and suitable isostere replacements;

Xaa$^{12}$ is absent, or Xaa$^{12}$ is selected from the group consisting of: aromatic amino acids, substituted aromatic amino acids, Glu, D-Glu, homoGlu, Asp, D-Asp, D-homo-Glu, Gla, beta-Homo-Glu, Tic, and corresponding D-amino acids and suitable isosteres;

Xaa$^3$ is absent, or Xaa$^3$ is selected from the group consisting of Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, N-Me-Lys, D-N-Me-Lys, D-Dap, D-Dab, COOH, CONH$_2$, suitable isosteres, and corresponding D-amino acids; and wherein some embodiments, if Formula (I-2) is directed to a peptide monomer, then Xaa$^{14}$ is any amino acid; and in other embodiments, if Formula (I-2) is directed to a peptide dimer subunit, then Xaa$^{14}$ is selected from the group consisting of: any amino acid with an amine side chain, Lys, D-Lys, N-Me-Lys, D-N-Me-Lys, Orn, N-Me-Orn, Dab, N-Me-Dab, Dap, N-Me-Dap, Homo-Lys, D-Dap, D-Dab, D-Orn, Gln, Pro, Gly, His, Ala, Ile, Phe, Lys, Arg, Leu, Val, Tyr, Trp, Met, Glu, Ser, Asn, Gla, Cys, HomoCys, Pen, COOH, CONH2, suitable isosteres, corresponding D-amino acids, and corresponding N-Methyl amino acids.

The present invention also contemplates reverse order thioether bond embodiments of Formula (I-2), wherein Xaa$^{10}$ is an amino acid, aliphatic acid, alicyclic acid, or modified 2-methylbenzoyl moiety acid having a free NH$_2$ group, and capable of forming a thioether bond with Xaa$^4$; and Xaa$^4$ is selected from the group consisting of Cys, N-Me-Cys, D-Cys, HomoCys, Pen, D-Pen; wherein in certain embodiments, Xaa$^4$ is selected from the group consisting of Cys, N-Me-Cys, D-Cys, HomoCys, and Pen.

In one aspect, the present invention provides a peptide (e.g. a peptide monomer, a peptide dimer, or a peptide dimer subunit) comprising the structure according to Formula (I-3)(SEQ ID NO: 35):

```
Formula (I-3))
Xaa¹-Xaa²-Xaa³-Xaa⁴-Xaa⁵-Xaa⁶-Xaa⁷-Xaa⁸-Xaa⁹-Xaa¹⁰-
Xaa¹¹-Xaa¹²-Xaa¹³-Xaa¹⁴,
``` or a pharmaceutically acceptable salt thereof, wherein:

Xaa$^2$ is absent, Ac, or any amino acid;

Xaa$^3$ is absent, Ac, or any amino acid;

Xaa$^4$ is selected from the group consisting of Cys, Homo-Cys, Pen, Homo-Ser-Cl, Homo-Ser, and a 2-methylbenzoyl moiety;

Xaa$^5$ is selected from the group consisting of: N-Me-Arg, Arg, N-Me-Lys, Phe (4-quanidino), Phe(4-carbonylamino), Cit, Phe(4-NH2), N-Me-Homo-Arg, Homo-Arg, Tyr and His;

Xaa$^6$ is Ser, Gly, Ile or Thr; wherein in some embodiments, if Formula I-3 is directed to a peptide monomer then Xaa$^6$ is Ser;

Xaa$^7$ is Asp or D-Asp;

Xaa$^8$ is selected from the group consisting of: Thr, Val, Ile, Leu, hLeu and Nle;

Xaa$^9$ is selected from the group consisting of: Leu, Nle, Cpa, Cba, HomoLeu, Aoc, and N-Me-Leu;

Xaa$^{10}$ is selected from the group consisting of: Cys, D-Cys, HomoCys, Pen, modified HomoSer and modified Ser, wherein in some embodiments, if Formula I-3 is directed to a peptide monomer, then Xaa$^{10}$ is selected from the group consisting of: Cys, D-Cys, HomoCys, and Pen;

Xaa$^{11}$ is absent or selected from the group consisting of: aromatic amino acids, and substituted aromatic amino acids;

Xaa$^{12}$ is absent or selected from the group consisting of: aromatic amino acids, substituted aromatic amino acids, Glu, D-Glu, homoGlu, Asp, D-Asp, D-homoGlu, Gla, beta-Homo-Glu, and corresponding D-amino acids and suitable isosteres;

Xaa$^{13}$ is absent or any amino acid, wherein in particular embodiments, Xaa$^3$ is absent or Pro; and wherein in some embodiments, if Formula I-3 is directed to a peptide monomer, then Xaa$^{14}$ is any amino acid; and wherein other embodiments, if Formula I-3 is directed to a peptide dimer subunit, then Xaa$^4$ is absent or selected from the group consisting of: any amino acid with an amine side chain, Lys, D-Lys, N-Me-Lys, D-N-Me-Lys, Orn, N-Me-Orn, Dab, N-Me-Dab, Dap, N-Me-Dap, Homo-Lys, D-Dap, D-Dab, D-Orn, Gln, Pro, Gly, His, Ala, Ile, Phe, Lys, Arg, Leu, Val, Tyr, Trp, Met, Glu, Ser, Asn, Gla, Cys, HomoCys, Pen, COOH, CONH$_2$, suitable isosteres, corresponding D-amino acids, and corresponding N-Methyl amino acids.

The present invention also includes reverse orientation thioether bond embodiments of Formula (I-3), wherein Xaa$^{10}$ is selected from the group consisting of Homo-Ser-Cl, Homo-Ser, modified Homo-Ser (e.g., Homo Ser(OTB-DMS)) and a 2-methylbenzoyl moiety with free NH$_2$ group; and Xaa$^4$ is selected from the group consisting of: Cys, D-Cys, HomoCys, Pen; wherein in some embodiments, Xaa$^{10}$ is selected from the group consisting of: Homo-Ser, modified Homo-Ser and a 2-methylbenzoyl moiety.

In some embodiments of any of the peptides described herein, including but not limited to those of Formula (I), (V), (I-1), (I-2), and (I-3), Xaa$^4$ is selected from Cys, HomoCys, Pen, and a 2-methylbenzoyl moiety. In certain embodiments, Xaa$^4$ is selected from the group consisting of a modified Ser, a modified HomoSer, a suitable isostere, and corresponding D-amino acids. In one embodiment, Xaa$^4$ is a Homo-Ser-Cl (before the thioether bond is formed with Xaa$^{10}$ whereby the Cl is removed) or a HomoSer precursor (e.g., HomoSer(O-TBDMS). In other instances, Xaa$^4$ is an aliphatic acid having from one to four carbons and forming a thioether bond with Xaa$^{10}$. In some instances, Xaa$^4$ is a five- or six-membered alicyclic acid having a modified 2-methyl group that forms a thioether bond with Xaa$^{10}$. In some instances, Xaa$^4$ is a 2-methylbenzoyl moiety. In some embodiments, the amino acid directly carboxyl to Xaa$^{10}$ is an aromatic amino acid. In some embodiments, Xaa$^7$ is Asp.

One of skill in the art will appreciate that certain amino acids and other chemical moieties are modified when bound to another molecule. For example, an amino acid side chain may be modified when it forms an intramolecular bridge with another amino acid side chain. In addition, when Homo-Ser-Cl binds to an amino acid such as Cys or Pen via a thioether bond, the Cl moiety is released. Accordingly, as used herein, reference to an amino acid or modified amino acid, such as Homo-Ser-Cl, present in a peptide dimer of the present invention (e.g., at position Xaa$^4$ or position Xaa$^1$) is meant to include the form of such amino acid or modified amino acid present in the peptide both before and after forming the intramolecular bond.

In some embodiments of any of the peptides described herein, including but not limited to those of Formula (I), (V), (I-1), (I-2), and (I-3), Xaa$^{11}$ is selected from the group consisting of: Gly, Gln, Asn, Asp, Ala, Ile, Leu, Val, Met, Thr, Lys, Trp, Tyr, His, Glu, Ser, Arg, Pro, Phe, Sar, 1-Nal, 2-Nal, D-1-Nal, D-2-Nal, HPhe, D-Phe, D-Tyr, Phe(4-F), O-Me-Tyr, dihydro-Trp, Dap, Dab, Dab(Ac), Orn, D-Orn, N-Me-Orn, N-Me-Dap, D-Dap, D-Dab, Bip, Ala(3,3diphenyl), Biphenyl-Ala, aromatic ring substituted Phe, aromatic ring substituted Trp, aromatic ring substituted His, hetero aromatic amino acids, N-Me-Lys, N-Me-Lys(Ac), 4-Me-Phe, and corresponding D-amino acids and suitable isostere replacements. In particular embodiments of any of the monomer peptides described herein, $Xaa^{11}$ is an aromatic amino acid or a substituted aromatic amino acid. In certain embodiments, $Xaa^{11}$ is Phe (4tBu), D-Lys, N-Me-Lys, or D-N-Me-Lys.

In some embodiments of any of the peptides described herein, including but not limited to those of Formula (I), (V), (I-1), (I-2), and (I-3), $Xaa^{12}$ is selected from the group consisting of Glu, Amide, Lys, COOH, Gln, Pro, Gly, His, Ala, Ile, Phe, Arg, Leu, Val, Tyr, Trp, Met, Gla, Ser, Asn, D-Glu, β-HGlu, 2-Nal, 1-Nal, D-Asp, Bip, β-HPhe, β-Glu, D-Tyr, D-Phe, D-Lys, Dap, Dab, Orn, D-Orn, N-Me-Orn, N-Me-Dap, N-Me-Dab, N-Me Lys, D-Dap, D-Dab, suitable isosteres, and corresponding D-amino acids.

In particular embodiments of any of the compounds and genuses described herein, $Xaa^5$ is selected from the group consisting of Cit, Phe(4-carbomyl amino), and N-Me-Homo-Arg; $Xaa^8$ is selected from the group consisting of Leu, HomoLeu, Nle and Val; $Xaa^9$ is selected from the group consisting of: Cba, HomoLeu, and Cpa; $Xaa^{11}$ is selected from the group consisting of Tic, Phe(2-carbomyl), Phe(3-carbomyl), Phe (4-COOH), Phe(4-OMe), and Phe(4tBu); $Xaa^{12}$ is selected from the group consisting of Aic, Gln, Cit, Glu(OMe), D-His, Tic, Phe(3-COOH), D-Arg, Bip, D-Trp, Phe, D-Phe, D-Val, D-Thr, D-1-Nal, D-2-Nal, Thr, Val; or $Xaa^{13}$ is Pro.

In particular embodiments of any of the peptide described herein, including those of Formula (I), (V), (I-1), (I-2), and (I-3), $Xaa^8$ is not Pro. In particular embodiments of any of the peptide described herein, including those of Formula (I), (V), (I-1), (I-2), and (I-3), $Xaa^9$ is not Pro.

In certain embodiments of any of the peptides (e.g. peptide momomers, peptide dimers or peptide dimer subunits) described herein, including but not limited to those of Formula (I), (V), (I-1), (I-2), and (I-3), $Xaa^{14}$ is selected from the group consisting of Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, N-Me-Lys, D-N-Me-Lys, D-Dap, D-Dab, COOH, CONH₂, suitable isosteres, corresponding D-amino acids, and corresponding N-Methyl amino acids. In certain embodiments, $Xaa^4$ is D-Lys, N-Me-Lys, Dap, or Dab. In some embodiments of any of the peptide dimer subunits, $Xaa^{14}$ (or the C-terminal amino acid) is Cys, HomoCys or Pen.

In some embodiments of any of the peptides (e.g. peptide momomers, peptide dimers or peptide dimer subunits) described herein, including but not limited to those of Formula (I), (V), (I-1), (I-2), and (I-3), $Xaa^{14}$ is selected from the group consisting of any amino acid with an amine side chain, Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, N-Me-Lys, D-N-Me-Lys, D-Dap, D-Dab, COOH, CONH₂, suitable isosteres, corresponding D-amino acids, and corresponding N-Methyl amino acids In some embodiments of any of the peptides described herein, including but not limited to those of Formula (I), (V), (I-1), (I-2), and (I-3), $Xaa^{14}$ is selected from the group consisting of: any amino acid with a free amine side chain, Lys, D-Lys, N-Me-Lys, D-N-Me-Lys, Orn, Dab, Dap, Homo-Lys, D-Dap, D-Dab, or D-Orn.

In some embodiments of any of the peptides (e.g. peptide momomers, peptide dimers or peptide dimer subunits) described herein, including but not limited to those of Formula (I), (V), (I-1), (I-2), and (I-3), the amino acid residue directly C-terminal to $Xaa^{10}$ is an aromatic amino acid. In certain embodiments, the amino acid directly C-terminal to $Xaa^{10}$ is selected from aromatic amino acids, substituted aromatic amino acids, and Tic. In certain embodiments, the amino acid directly C-terminal to $Xaa^{10}$ is an aromatic amino acid.

In one embodiment of Formula (I-1), herein referred to as Formula (I-A) (SEQ ID NO: 36);

$Xaa^1$ is absent or any amino acid;

$Xaa^2$ is absent or any amino acid;

$Xaa^3$ is absent or any amino acid;

$Xaa^4$ is a 2-methyl-benzoyl moiety or a modified Homo-Ser, optionally Homo-Ser-Cl;

$Xaa^5$ is selected from the group consisting of: N-Me-Arg, Arg, N-Me-Lys, Phe (4-quanidino), Phe(4-carbonylamino), Cit, Phe(4-NH2), N-Me-Homo-Arg, Homo-Arg, Tyr and His;

$Xaa^6$ is Ser, Gly, Thr or Ile; wherein in some embodiments, if Formula (I-A) is directed to a peptide dimer subunit, then $Xaa^6$ is Ser;

$Xaa^7$ is Asp or D-Asp;

$Xaa^8$ is selected from the group consisting of: Thr, Val, Ile, Leu, hLeu, Nle, and Val;

$Xaa^9$ is selected from the group consisting of: Leu, Nle, Cpa, Cba, HomoLeu, Aoc, and N-Me-Leu; wherein in some embodiments, if Formula I-A is directed to a monomer peptide, then $Xaa^9$ is selected from the group consisting of: Leu, Nle, Cpa, HomoLeu, Aoc, and N-Me-Leu;

$Xaa^{10}$ is Pen, Cys, D-Cys or HomoCys; and $Xaa^{11}$ is absent or selected from the group consisting of: Trp, Phe, 2-Nal, 1-Nal, Tyr, His, Phe(4-F), Phe(4-CF3), Phe (4-CH3), Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe(4-carbomyl), Phe(3-Carbomyl), Phe (2-carbomyl), Tyr(Me), HomoPhe, N-Me-Phe, N-Me-Tyr, Ser, Sar, Dihydro Trp, Ile, Leu, Arg, Thr, Sar, and Ser, wherein in some embodiments, if Formula (I-A) is directed to a dimer peptide subunit, then $Xaa^{11}$ is absent or selected from the group consisting of: Trp, Phe, 2-Nal, 1-Nal, Tyr, His, Phe(4-F), Phe(4-CF3), Phe (4-CH3), Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe(4-carbomyl), Phe(3-Carbomyl), Phe (2-carbomyl), Tyr(Me), HomoPhe, N-Me-Phe, N-Me-Tyr, Ser, Sar, Dihydro Trp, Ile, Leu, Arg, and Thr; and $Xaa^{12}$ is absent or selected from the group consisting of: any aromatic amino acid, Glu, D-Glu, homoGlu, Asp, D-Asp, D-homoGlu, D-Asp, Gla, beta-homo-Glu, corresponding D-amino acid, and isosteres; wherein in some embodiments, if Formula (I-A) is directed to a peptide monomer, then $Xaa^{12}$ is absent or selected from the group consisting of: any aromatic amino acid, Glu, D-Glu, homo-Glu, Asp, D-Asp, D-homoGlu, Gla, beta-homo-Glu, corresponding D-amino acid, and isosteres;

wherein in some embodiments, if Formula (I-A) is directed to a peptide monomer, then $Xaa^{13}$ is absent or any amino acid; and wherein in other embodiments, if Formula (I-A) is directed to a peptide dimer subunit, then $Xaa^{13}$ is absent;

wherein in some embodiments, if Formula (I-A) is directed to a peptide monomer, then Xaa⁴ is any amino acid; and wherein other embodiments, if Formula (I-A) is directed to a peptide dimer subunit, then Xaa¹⁴ is selected from the group consisting of: any amino acid with a free amino group on a side chain, Lys, D-Lys, N-Me-Lys, D-N-Me-Lys, Orn, Dab, Dap, Homo-Lys, D-Dap, D-Dab, Cys, HomoCys, Pen, or D-Orn.

In certain embodiments, Formula (I-A) is directed to a peptide monomer and Xaa¹³ is absent.

In one embodiment of Formula (I-1), herein referred to as Formula (I-B) (SEQ ID NO: 37),
Xaa¹ is absent or any amino acid;
Xaa² is absent or any amino acid;
Xaa³ is absent or any amino acid;
Xaa⁴ is a 2-methylbenzoyl moiety or a modified Homo-Ser, optionally Homo-Ser-Cl;
Xaa⁵ is N-Me-Arg;
Xaa⁶ is Ser, Gly, Thr, or Ile; wherein in some embodiments, if Formula (I-B) is directed to a peptide dimer subunit then Xaa⁶ is Ser;
Xaa⁷ is Asp or D-Asp;
Xaa⁸ is selected from the group consisting of: Thr, Val, Ile, Leu, hLeu and Nle;
Xaa⁹ is selected from the group consisting of: Leu, Nle, Cpa, Cba, HomoLeu, Aoc, and N-Me-Leu;
Xaa¹⁰ is Pen, Cys, D-Cys or HomoCys;
Xaa¹¹ is selected from the group consisting of: Trp, Phe, 2-Nal, 1-Nal, Tyr, His, Phe(4-F), Phe(4-CF3), Phe (4-CH3), Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe(4-carbomyl), Phe(3-Carbomyl), Tyr(Me), HomoPhe, N-Me-Phe, N-Me-Tyr, Ser, Sar, Dihydro Trp, Ile, Leu, Ser, Arg, Thr, Sar, Ser and any substituted aromatic amino acid and corresponding D-amino acids; wherein in some embodiments, if Formula (I-B) is directed to a peptide dimer subunit, then Xaa¹¹ is selected from the group consisting of: Trp, Phe, 2-Nal, 1-Nal, Tyr, His, Phe(4-F), Phe(4-CF3), Phe (4-CH3), Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe(4-carbomyl), Phe(3-Carbomyl), Tyr(Me), HomoPhe, N-Me-Phe, N-Me-Tyr, Dihydro Trp, Ile, Leu, Ser, Arg, Thr, Sar, and Ser;
Xaa¹² is selected from the group consisting of: any aromatic amino acid, Glu, D-Glu, homoGlu, Asp, D-Asp, D-homoGlu, Gla, beta-homo-Glu, corresponding D-amino acid and isosteres;
Xaa³ is absent;
wherein some embodiments, if Formula (I-B) is directed to a peptide monomer, then Xaa¹⁴ is any amino acid; and
in other embodiments, if Formula (I-B) is directed to a peptide dimer subunit, then Xaa¹⁴ is selected from the group consisting of: Lys, D-Lys, N-Me-Lys, D-N-Me-Lys, Orn, Dab, Dap, Homo-Lys, D-Dap, D-Dab, Cys, HomoCys, Pen, or D-Orn.

In one embodiment of Formula (I-1), herein referred to as Formula (I-C) (SEQ ID NO: 38),
Xaa¹ is absent or any amino acid;
Xaa² is absent or any amino acid;
Xaa³ is absent or any amino acid;
Xaa⁴ is a 2-methylbenzoyl moiety or a modified Homo-Ser, optionally Homo-Ser-Cl;
Xaa⁵ is N-Me-Arg;

Xaa⁶ is Ser, Gly, Thr, or Ile; wherein in some embodiments, if Formula (I-C) is directed to a peptide dimer subunit, then Xaa⁶ is Ser;
Xaa⁷ is Asp or D-Asp;
Xaa⁸ is selected from the group consisting of: Thr, Val, Ile, Leu, hLeu and Nle;
Xaa⁹ is selected from the group consisting of: Leu, Nle, Cpa, Cba, HomoLeu, Aoc, and N-Me-Leu;
Xaa¹⁰ is Pen, Cys, D-Cys or HomoCys;
Xaa¹¹ is selected from the group consisting of: Trp, Phe, 2-Nal, 1-Nal, Tyr, His, Phe(4-F), Phe(4-CF3), Phe (4-CH3), Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe(4-carbomyl), Phe(3-Carbomyl), Tyr(Me), HomoPhe, N-Me-Phe, N-Me-Tyr, Sar, Dihydro Trp, Ile, Leu, Ser, Arg, Thr, Sar, and Ser; or
Xaa¹² is selected from the group consisting of: any aromatic amino acid, Glu, D-Glu, homoGlu, Asp, D-Asp, D-homoGlu, Gla, beta-homo-Glu, corresponding D-amino acid and isosteres;
Xaa¹³ is absent or any amino acid; wherein in other embodiments, if Formula (I-C) is directed to a peptide dimer subunit, then Xaa¹³ is absent; and
wherein in some embodiments, if Formula (I-C) is directed to a peptide monomer subunit then Xaa⁴ is any amino acid; and
wherein in other embodiments, if Formula (I-C) is directed to a peptide dimer subunit then Xaa¹⁴ is selected from the group consisting of: Lys, D-Lys, N-Me-Lys, D-N-Me-Lys, Orn, Dab, Dap, Homo-Lys, D-Dap, D-Dab, Cys, HomoCys, Pen, or D-Orn.

In certain embodiments, Formula (I-C) is directed to a peptide monomer and Xaa¹³ is absent.

In one embodiment of Formula (I-1), herein referred to as Formula (I-D) (SEQ ID NO: 39),
Xaa¹ is absent or any amino acid;
Xaa² is absent or any amino acid;
Xaa³ is absent or any amino acid;
Xaa⁴ is a 2-methylbenzoyl moiety or a modified Homo-Ser, optionally Homo-Ser-Cl;
Xaa⁵ is N-Me-Arg;
Xaa⁶ is Ser;
Xaa⁷ is Asp or D-Asp;
Xaa⁸ is Thr or Val;
Xaa⁹ is selected from the group consisting of: Leu, Nle, Cpa, Cba, HomoLeu, Aoc, and N-Me-Leu;
Xaa¹⁰ is Pen, Cys, D-Cys or HomoCys;
Xaa¹¹ is selected from the group consisting of: Trp, Phe, 2-Nal, 1-Nal, Tyr, His, Phe(4-F), Phe(4-CF3), Phe (4-CH3), Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe(4-carbomyl), Phe(3-Carbomyl), Tyr(Me), HomoPhe, N-Me-Phe, N-Me-Tyr, Ser, Sar, Dihydro Trp, Ile, Leu, Ser, Arg, Thr, Sar, and Ser,
Xaa¹² is absent or selected from the group consisting of: any aromatic amino acid, Glu, D-Glu, homoGlu, Asp, D-Asp, D-homoGlu, Gla, beta-homo-Glu, corresponding D-amino acid and isosteres;
Xaa³ is absent; and
wherein in some embodiments, if Formula (I-D) is directed to a peptide monomer then Xaa¹⁴ is any amino acid; and wherein in other embodiments, if Formula (I-D) is directed to a peptide dimer subunit, then Xaa⁴ is selected from the group consisting of: Lys, D-Lys, N-Me-Lys, D-N-Me-Lys, Orn, Dab, Dap, Homo-Lys, D-Dap, D-Dab, Cys, HomoCys, Pen, or D-Orn.

In one embodiment of Formula (I-1), herein referred to as Formula (I-E) (SEQ ID NO: 40),
Xaa$^1$ is absent or any amino acid;
Xaa$^2$ is absent or any amino acid;
Xaa$^3$ is absent or any amino acid;
Xaa$^4$ is a 2-methylbenzoyl moiety or a modified Homo-Ser, optionally Homo-Ser-Cl;
Xaa$^5$ is N-Me-Arg;
Xaa$^6$ is Ser;
Xaa$^7$ is Asp or D-Asp;
Xaa$^8$ is Thr or Val;
Xaa$^9$ is selected from the group consisting of: Leu, Nle, Cpa, Cba, HomoLeu, Aoc, and N-Me-Leu;
Xaa$^{10}$ is Pen, Cys, D-Cys or HomoCys;
Xaa$^{11}$ is selected from the group consisting of: Trp, Phe, 2-Nal, 1-Nal, Tyr, His, Phe(4-F), Phe(4-CF3), Phe (4-CH3). Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe(4-carbomyl), Phe(3-Carbomyl), Tyr(Me), HomoPhe, N-Me-Phe, N-Me-Tyr, Ser, Sar, Dihydro Trp, Ile, Leu, Ser, Arg, Thr, Sar, and Ser,
Xaa$^{12}$ is absent or selected from the group consisting of: any aromatic amino acid, Glu, D-Glu, and beta-homo-Glu;
Xaa$^3$ is absent; and,
wherein in some embodiments, if Formula (I-E) is directed to a peptide monomer, then Xaa$^{14}$ is any amino acid; and in other embodiments, if Formula (I-E) is directed to a peptide dimer subunit, then Xaa$^{14}$ is selected from the group consisting of: Lys, D-Lys, N-Me-Lys, D-N-Me-Lys, Orn, Dab, Dap, Homo-Lys, D-Dap, D-Dab, Cys, HomoCys, Pen, or D-Orn.

In one embodiment of Formula (I-1), herein referred to as Formula (I-F) (SEQ ID NO: 41),
Xaa$^1$ is absent or any amino acid;
Xaa$^2$ is absent or any amino acid;
Xaa$^3$ is absent or any amino acid;
Xaa$^4$ is a 2-methylbenzoyl moiety or a modified Homo-Ser, optionally Homo-Ser-Cl;
Xaa$^5$ is N-Me-Arg;
Xaa$^6$ is Ser;
Xaa$^7$ is Asp or D-Asp;
Xaa$^8$ is Thr or Val;
Xaa$^9$ is Leu;
Xaa$^{10}$ is Pen, Cys, D-Cys or HomoCys;
Xaa$^{11}$ is selected from the group consisting of: Trp, Phe, 2-Nal, 1-Nal, Tyr, His, Phe(4-F), Phe(4-CF3), Phe (4-CH3). Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe(4-carbomyl), Phe(3-Carbomyl), Tyr(Me), HomoPhe, N-Me-Phe, N-Me-Tyr, Ser, Sar, Dihydro Trp, Ile, Leu, Ser, Arg, Thr, Sar, and Ser,
Xaa$^{12}$ is selected from the group consisting of: any aromatic amino acid, Glu, D-Glu, beta-homo-Glu, corresponding D-amino acid and isosteres;
Xaa$^3$ is absent; and
wherein in some embodiments, if Formula (I-F) is directed to a peptide monomer, then Xaa$^{14}$ is any amino acid; and wherein in some embodiments, if Formula (I-F) is directed to a peptide dimer subunit, then Xaa$^4$ is selected from the group consisting of: Lys, D-Lys, N-Me-Lys, D-N-Me-Lys, Orn, Dab, Dap, Homo-Lys, D-Dap, D-Dab, Cys, HomoCys, Pen, or D-Orn.

In certain embodiments, Xaa$^{14}$ is selected from the group consisting of: Lys, D-Lys, N-Me-Lys, D-N-Me-Lys.

In one embodiment of Formula (I-1), herein referred to as Formula (I-G) (SEQ ID NO: 42),
Xaa$^1$ is absent or any amino acid;
Xaa$^2$ is absent or any amino acid;
Xaa$^3$ is absent or any amino acid;
Xaa$^4$ is a 2-methylbenzoyl moiety or a modified Homo-Ser, optionally Homo-Ser-Cl;
Xaa$^5$ is N-Me-Arg;
Xaa$^6$ is Ser;
Xaa$^7$ is Asp or D-Asp;
Xaa$^8$ is Thr or Val;
Xaa$^9$ is Leu;
Xaa$^{10}$ is Pen, Cys, D-Cys or HomoCys;
Xaa$^{11}$ is selected from the group consisting of: Trp, Phe, 2-Nal, 1-Nal, Tyr, His, Phe(4-F), Phe(4-CF3), Phe (4-CH3). Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe(4-carbomyl), Phe(3-Carbomyl), Tyr(Me), HomoPhe, N-Me-Phe, N-Me-Tyr, Ser, Sar, Dihydro Trp, Ile, Leu, Ser, Arg, Thr, Sar, and Ser,
Xaa$^{12}$ is selected from the group consisting of: any aromatic amino acid, Glu, D-Glu, and beta-homo-Glu;
Xaa$^{13}$ is absent; and
wherein in some embodiments, if Formula I-G is directed to a peptide monomer, then Xaa$^{14}$ is any amino acid; and wherein in other embodiments, if Formula I-G is directed to a peptide dimer subunit, then Xaa$^{14}$ is selected from the group consisting of: Lys, D-Lys, N-Me-Lys, D-N-Me-Lys, Orn, Dab, Dap, Homo-Lys, D-Dap, D-Dab, Cys, HomoCys, Pen, or D-Orn.

In certain embodiments, Xaa$^4$ is selected from the group consisting of: D-Lys, N-Me-Lys, and D-N-Me-Lys.

In one embodiment of Formula (I-1), herein referred to as Formula (I-H) (SEQ ID NO: 43),
Xaa$^1$ is absent or any amino acid;
Xaa$^2$ is absent or any amino acid;
Xaa$^3$ is absent or any amino acid;
Xaa$^4$ is a 2-methylbenzoyl moiety or a modified Homo-Ser, optionally Homo-Ser-Cl;
Xaa$^5$ is N-Me-Arg;
Xaa$^6$ is Ser;
Xaa$^7$ is Asp;
Xaa$^8$ is Thr or Val;
Xaa$^9$ is Leu;
Xaa$^{10}$ is Pen, Cys, D-Cys or HomoCys;
Xaa$^{11}$ is selected from the group consisting of: Trp, Phe, 2-Nal, 1-Nal, Tyr, His, Phe(4-F), Phe(4-CF3), Phe (4-CH3). Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe(4-carbomyl), Phe(3-Carbomyl), Tyr(Me), HomoPhe, N-Me-Phe, N-Me-Tyr, Ser, Sar, Dihydro Trp, Ile, Leu, Ser, Arg, Thr, Sar, and Ser,
Xaa$^{12}$ is selected from the group consisting of: any aromatic amino acid, Glu, D-Glu, and beta-homo-Glu;
Xaa$^3$ is absent; and
wherein in some embodiments, if Formula I-H is directed to a peptide monomer, then Xaa$^4$ is any amino acid; and wherein in some embodiments, if Formula I-H is directed to a peptide dimer subunit, then Xaa$^4$ is selected from the group consisting of: D-Lys, N-Me-Lys, and D-N-Me-Lys.

In one embodiment of Formula (I-1), herein referred to as Formula (I-I) (SEQ ID NO: 44),
Xaa$^1$ is absent or any amino acid;
Xaa$^2$ is absent or any amino acid;
Xaa$^3$ is absent or any amino acid;
Xaa$^4$ is a 2-methylbenzoyl moiety or a modified Homo-Ser, optionally Homo-Ser-Cl;
Xaa$^5$ is N-Me-Arg;
Xaa$^6$ is Ser;
Xaa$^7$ is Asp or D-Asp;

Xaa⁸ is Thr or Val;

Xaa⁹ is Leu;

Xaa¹⁰ is Pen, Cys, D-Cys or HomoCys;

Xaa¹¹ selected from the group consisting of: Trp, Phe, 2-Nal, 1-Nal, Tyr, His, Phe(4-F), Phe(4-CF3), Phe (4-CH3), Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe(4-carbomyl), Phe(3-Carbomyl), Tyr(Me), and HomoPhe;

Xaa¹² is selected from the group consisting of: any aromatic amino acid, Glu, D-Glu, and beta-homo-Glu;

Xaa¹³ is absent; and wherein in some embodiments, if Formula I-I is directed to a peptide monomer then Xaa¹⁴ is any amino acid; and wherein in other embodiments, if Formula I-I is directed to a peptide dimer subunit, then Xaa¹⁴ is selected from the group consisting of: D-Lys, N-Me-Lys, and D-N-Me-Lys.

In certain embodiments of Formulas (I), (V), (I-1), (I-2), (I-3), (V), or any of (I-A), (I-B), I-C), (I-D), (I-E), (I-F), (I-G), (I-H), and (I-I), Xaa¹¹ may also be Bpa, Phe(3-Me), Phe(2-Me), Phe(2-CF3), or 13-Me-Phe.

In certain embodiments of Formulas (I), (V), (I-1), (I-2), (I-3), (V) or any of (I-A), (I-B), I-C), (I-D), (I-E), (I-F), (I-G), (I-H), and (I-I), Xaa¹² may also be N-Me-Glu, N-Me-Asp, or alpha-H-Glu.

In particular embodiments of Formulas (I), (V), (I-1), (I-2), (I-3), (V), or any of (I-A), (I-B), I-C), (I-D), (I-E), (I-F), (I-G), (I-H), and (I-I), e.g., when the peptide is a dimer, Xaa¹⁴ is selected from the group consisting of: Lys, D-Lys, N-Me-Lys, D-N-Me-Lys, Orn, Dab, Dap, Homo-Lys, D-Dap, D-Dab, Cys, HomoCys, Pen, or D-Orn, while in other embodiments, Xaa¹⁴ is selected from D-Lys, N-Me-Lys, and D-N-Me-Lys.

In one embodiment of Formula (I-1), Xaa¹ is absent, or Xaa¹ is any amino acid;

Xaa² is absent, or Xaa² is any amino acid;

Xaa³ is absent, or Xaa³ is any amino acid;

Xaa⁴ is an amino acid, aliphatic acid, alicyclic acid, or modified 2-methyl aromatic acid having a side chain with one or two carbons, and capable of forming a thioether bond with Xaa¹⁰;

Xaa⁵ is selected from the group consisting of N(alpha)-Me-Arg, Arg, HomoArg, Dap, Dab, Arg-Me-sym, Arg-Me-asym, 4-Guan, Cit, Cav, N-Me-Lys, Phe(4-quanidino), Phe (4-carbamoyl amino), Phe(4-NH₂), N-Me-HomoArg, Tyr, His, and suitable isostere replacements;

Xaa⁶ is selected from the group consisting of Ser, Gly, Thr, Ile, and suitable isostere replacements;

Xaa⁷ is selected from the group consisting of Asp, N-Me-Asp, Asp(OMe), D-Asp, and suitable isostere replacements;

Xaa⁸ is selected from the group consisting of Thr, Gln, Ser, Asp, Pro, Gly, His, Ala, Ile, Phe, Lys, Arg, Asn, Glu, Val, Tyr, Trp, Leu, Met, HomoLeu, Nle, and N-Methyl amino acids including N-Me-Thr, Xaa⁹ is selected from the group consisting of Gln, Asn, Asp, Pro, Gly, Ala, Phe, Leu, Glu, Ile, Val, HLeu, n-Butyl Ala, n-Pentyl Ala, n-Hexyl Ala, Nle, cyclobutyl-Ala, Cpa, Aoc, N-Me-Leu, and suitable isostere replacements;

Xaa¹⁰ is selected from the group consisting of Cys, N-Me-Cys, D-Cys, HCys, Pen, D-Pen, and Pen(═O);

Xaa¹¹ is absent or is selected from the group consisting of: Trp, Phe, 2-Nal, 1-Nal, Tyr, His, Phe(4-F), Phe(4-CF3), Phe (4-CH3), Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe(4-carbomyl), Phe(3-Carbomyl), Phe (2-carbomyl), Tyr(Me), HomoPhe, N-Me-Phe, N-Me-Tyr, Ser, Sar, Dihydro Trp, Ile, Leu, Ser, Arg, Thr, Sar, and Ser, aromatic amino acids, substituted aromatic amino acids, Gly, Gln, Asn, Asp, Ala, Ile, Leu, Val, Met, Thr, Lys, Trp, Tyr, His, Glu, Ser, Arg, Pro, Phe, Sar, 1-Nal, 2-Nal, D-1-Nal, D-2-Nal, HPhe, D-Phe, D-Tyr, Phe(4-F), O-Me-Tyr, dihydro-Trp, Dap, Dab, Dab(Ac), Orn, D-Orn, N-Me-Orn, N-Me-Dap, D-Dap, D-Dab, Bip, Ala(3,3diphenyl), Biphenyl-Ala, aromatic ring substituted Phe, aromatic ring substituted Trp, aromatic ring substituted His, hetero aromatic amino acids, N-Me-Lys, N-Me-Lys(Ac), 4-Me-Phe, Phe(4tBu), Phe(4-OMe), Phe(4-COOH), Phe(2-carbomyl), Phe(3-carbomyl), Phe(CF3), Phe(2,4-diCl), Phe(3,4-diCl), Aic, N-Me-Tyr, N-Me-Phe, Tic, Phe(4CF3), Bpa, Phe(3-Me), Phe(2-Me), Phe(2-CF3), 3-Me-Phe, and corresponding D-amino acids and suitable isostere replacements;

Xaa¹² is absent or selected from the group consisting of aromatic amino acids, substituted aromatic amino acids, Glu, D-Glu, HomoGlu, Beta-Homo-Glu, Asp, D-HomoGlu, Amide, Lys, COOH, CONH₂, Gln, Pro, Gly, His, Ala, Ile, Phe, Arg, Leu, Val, Tyr, Trp, Met, Gla, Ser, Asn, D-Glu, 13-HGlu, 2-Nal, 1-Nal, D-Asp, Bip, 13-HPhe, 3-Glu, D-Tyr, D-Phe, D-Lys, Dap, Dab, Orn, D-Orn, N-Me-Orn, N-Me-Dap, N-Me-Dab, N-Me Lys, D-Dap, D-Dab, D-His, F(4-COOH), Tic, D-Trp, D-Leu, D-Arg, D-Thr, N-Me-Glu, N-Me-Asp, alpha-H-Glu, suitable isosteres, and corresponding D-amino acids;

Xaa³ is absent or any amino acid; and

Xaa¹⁴ is absent or any amino acid.

In other embodiments, Xaa¹ is absent or any amino acid;

Xaa² is absent or any amino acid;

Xaa³ is absent or any amino acid;

Xaa⁴ is a 2-methyl-benzoyl moiety or a modified Homo-Ser, optionally Homo-Ser-Cl;

Xaa⁵ is selected from the group consisting of: N-Me-Arg, Arg, N-Me-Lys, Phe (4-quanidino), Phe(4-carbonylamino), Cit, Phe(4-NH2), N-Me-Homo-Arg, Homo-Arg, Tyr and His;

Xaa⁶ is Ser, Gly, Thr or Ile;

Xaa⁷ is Asp or D-Asp;

Xaa⁸ is selected from the group consisting of: Thr, Val, Ile, Leu, hLeu, Nle, and Val;

Xaa⁹ is selected from the group consisting of: Leu, Nle, Cpa, Cba, HomoLeu, Aoc, and N-Me-Leu;

Xaa¹⁰ is Pen, Cys, D-Cys or HomoCys; and

Xaa¹¹ is absent or selected from the group consisting of: Trp, Phe, 2-Nal, 1-Nal, Tyr, His, Phe(4-F), Phe(4-CF3), Phe (4-CH3), Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe(4-carbomyl), Phe(3-Carbomyl), Phe (2-carbomyl), Tyr(Me), HomoPhe, N-Me-Phe, N-Me-Tyr, Ser, Sar, Dihydro Trp, Ile, Leu, Arg, Thr, Sar, Bpa, Phe(3-Me), Phe(2-Me), Phe(2-CF3), 13-Me-Phe, and Ser;

Xaa¹² is absent or selected from the group consisting of: any aromatic amino acid, Glu, D-Glu, homoGlu, Asp, D-Asp, D-homoGlu, D-Asp, Gla, beta-homo-Glu, N-Me-Glu, N-Me-Asp, alpha-H-Glu, corresponding D-amino acid, and isosteres;

Xaa³ is absent or any amino acid; and

Xaa¹⁴ is any amino acid.

In other embodiments,

Xaa¹ is absent or any amino acid;

Xaa² is absent or any amino acid;

Xaa³ is absent or any amino acid;

Xaa⁴ is a 2-methylbenzoyl moiety or a modified Homo-Ser, optionally Homo-Ser-Cl;

Xaa⁵ is N-Me-Arg;

Xaa⁶ is Ser, Gly, Thr, or Ile;

Xaa⁷ is Asp or D-Asp;
Xaa⁸ is selected from the group consisting of: Thr, Val, Ile, Leu, hLeu and Nle;
Xaa⁹ is selected from the group consisting of: Leu, Nle, Cpa, Cba, HomoLeu, Aoc, and N-Me-Leu;
Xaa¹⁰ is Pen, Cys, D-Cys or HomoCys;
Xaa¹¹ is selected from the group consisting of: Trp, Phe, 2-Nal, 1-Nal, Tyr, His, Phe(4-F), Phe(4-CF3), Phe (4-CH3), Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe(4-carbomyl), Phe(3-Carbomyl), Tyr(Me), HomoPhe, N-Me-Phe, N-Me-Tyr, Ser, Sar, Dihydro Trp, Ile, Leu, Ser, Arg, Thr, Sar, Bpa, Phe(3-Me), Phe(2-Me), Phe(2-CF3), β-Me-Phe, Ser and any substituted aromatic amino acid and corresponding D-amino acids;
Xaa¹² is selected from the group consisting of: any aromatic amino acid, Glu, D-Glu, homoGlu, Asp, D-Asp, D-homoGlu, Gla, beta-homo-Glu, N-Me-Glu, N-Me-Asp, alpha-H-Glu, corresponding D-amino acid and isosteres;
Xaa³ is absent; and
Xaa¹⁴ is any amino acid.
In other embodiments,
Xaa¹ is absent or any amino acid;
Xaa² is absent or any amino acid;
Xaa³ is absent or any amino acid;
Xaa⁴ is a 2-methylbenzoyl moiety or a modified Homo-Ser, optionally Homo-Ser-Cl;
Xaa⁵ is N-Me-Arg;
Xaa⁶ is Ser, Gly, Thr, or Ile;
Xaa⁷ is Asp or D-Asp;
Xaa⁸ is selected from the group consisting of: Thr, Val, Ile, Leu, hLeu and Nle;
Xaa⁹ is selected from the group consisting of: Leu, Nle, Cpa, Cba, HomoLeu, Aoc, and N-Me-Leu;
Xaa¹⁰ is Pen, Cys, D-Cys or HomoCys;
Xaa¹ is selected from the group consisting of: Trp, Phe, 2-Nal, 1-Nal, Tyr, His, Phe(4-F), Phe(4-CF3), Phe (4-CH3). Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe(4-carbomyl), Phe(3-Carbomyl), Tyr(Me), HomoPhe, N-Me-Phe, N-Me-Tyr, Sar, Dihydro Trp, Ile, Leu, Ser, Arg, Thr, Sar, Bpa, Phe(3-Me), Phe(2-Me), Phe(2-CF3), β-Me-Phe, and Ser;
Xaa¹² is selected from the group consisting of: any aromatic amino acid, Glu, D-Glu, homoGlu, Asp, D-Asp, D-homoGlu, Gla, beta-homo-Glu, N-Me-Glu, N-Me-Asp, alpha-H-Glu, corresponding D-amino acid and isosteres;
Xaa¹³ is absent or any amino acid; and
Xaa¹⁴ is any amino acid.
In other embodiments:
Xaa¹ is absent or any amino acid;
Xaa² is absent or any amino acid;
Xaa³ is absent or any amino acid;
Xaa⁴ is a 2-methylbenzoyl moiety or a modified Homo-Ser, optionally Homo-Ser-Cl;
Xaa⁵ is N-Me-Arg;
Xaa⁶ is Ser;
Xaa⁷ is Asp or D-Asp;
Xaa⁸ is Thr or Val;
Xaa⁹ is selected from the group consisting of: Leu, Nle, Cpa, Cba, HomoLeu, Aoc, and N-Me-Leu;
Xaa¹⁰ is Pen, Cys, D-Cys or HomoCys;
Xaa¹¹ is selected from the group consisting of: Trp, Phe, 2-Nal, 1-Nal, Tyr, His, Phe(4-F), Phe(4-CF3), Phe (4-CH3), Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe(4-carbomyl), Phe(3-Carbomyl), Tyr(Me), HomoPhe, N-Me-Phe, N-Me-Tyr, Ser, Sar, Dihydro Trp, Ile, Leu, Ser, Arg, Thr, Sar, Bpa, Phe(3-Me), Phe(2-Me), Phe(2-CF3), β-Me-Phe, and Ser;
Xaa¹² is absent or selected from the group consisting of: any aromatic amino acid, Glu, D-Glu, homoGlu, Asp, D-Asp, D-homoGlu, Gla, beta-homo-Glu, N-Me-Glu, N-Me-Asp, alpha-H-Glu, corresponding D-amino acid and isosteres;
Xaa¹³ is absent; and
Xaa¹⁴ is any amino acid.
In other embodiments:
Xaa¹ is absent or any amino acid;
Xaa² is absent or any amino acid;
Xaa³ is absent or any amino acid;
Xaa⁴ is a 2-methylbenzoyl moiety or a modified Homo-Ser, optionally Homo-Ser-Cl;
Xaa⁵ is N-Me-Arg;
Xaa⁶ is Ser;
Xaa⁷ is Asp or D-Asp;
Xaa⁸ is Thr or Val;
Xaa⁹ is selected from the group consisting of: Leu, Nle, Cpa, Cba, HomoLeu, Aoc, and N-Me-Leu;
Xaa¹⁰ is Pen, Cys, D-Cys or HomoCys;
Xaa¹¹ is selected from the group consisting of: Trp, Phe, 2-Nal, 1-Nal, Tyr, His, Phe(4-F), Phe(4-CF3), Phe (4-CH3). Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe(4-carbomyl), Phe(3-Carbomyl), Tyr(Me), HomoPhe, N-Me-Phe, N-Me-Tyr, Ser, Sar, Dihydro Trp, Ile, Leu, Ser, Arg, Thr, Sar, Bpa, Phe(3-Me), Phe(2-Me), Phe(2-CF3), β-Me-Phe, and Ser;
Xaa¹² is absent or selected from the group consisting of: any aromatic amino acid, Glu, D-Glu, beta-homo-Glu, N-Me-Glu, N-Me-Asp, alpha-H-Glu;
Xaa¹³ is absent; and
Xaa¹⁴ is any amino acid.
In other embodiments:
Xaa¹ is absent or any amino acid;
Xaa² is absent or any amino acid;
Xaa³ is absent or any amino acid;
Xaa⁴ is a 2-methylbenzoyl moiety or a modified Homo-Ser, optionally Homo-Ser-Cl;
Xaa⁵ is N-Me-Arg;
Xaa⁶ is Ser;
Xaa⁷ is Asp or D-Asp;
Xaa⁸ is Thr or Val;
Xaa⁹ is Leu;
Xaa¹⁰ is Pen, Cys, D-Cys or HomoCys;
Xaa¹¹ is selected from the group consisting of: Trp, Phe, 2-Nal, 1-Nal, Tyr, His, Phe(4-F), Phe(4-CF3), Phe (4-CH3). Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe(4-carbomyl), Phe(3-Carbomyl), Tyr(Me), HomoPhe, N-Me-Phe, N-Me-Tyr, Ser, Sar, Dihydro Trp, Ile, Leu, Ser, Arg, Thr, Sar, Bpa, Phe(3-Me), Phe(2-Me), Phe(2-CF3), β-Me-Phe, and Ser;
Xaa¹² is selected from the group consisting of: any aromatic amino acid, Glu, D-Glu, beta-homo-Glu, N-Me-Glu, N-Me-Asp, alpha-H-Glu, corresponding D-amino acid and isosteres;
Xaa³ is absent; and
Xaa¹⁴ is any amino acid.
In other embodiments:
Xaa¹ is absent or any amino acid;
Xaa² is absent or any amino acid;
Xaa³ is absent or any amino acid;

Xaa⁴ is a 2-methylbenzoyl moiety or a modified Homo-Ser, optionally Homo-Ser-Cl;
Xaa⁵ is N-Me-Arg;
Xaa⁶ is Ser;
Xaa⁷ is Asp or D-Asp;
Xaa⁸ is Thr or Val;
Xaa⁹ is Leu;
Xaa¹⁰ is Pen, Cys, D-Cys or HomoCys;
Xaa¹¹ is selected from the group consisting of: Trp, Phe, 2-Nal, 1-Nal, Tyr, His, Phe(4-F), Phe(4-CF3), Phe (4-CH3). Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe(4-carbomyl), Phe(3-Carbomyl), Tyr(Me), HomoPhe, N-Me-Phe, N-Me-Tyr, Ser, Sar, Dihydro Trp, Ile, Leu, Ser, Arg, Thr, Sar, Bpa, Phe(3-Me), Phe(2-Me), Phe(2-CF3), β-Me-Phe, and Ser;
Xaa¹² is selected from the group consisting of: any aromatic amino acid, Glu, D-Glu, N-Me-Glu, N-Me-Asp, alpha-H-Glu, and beta-homo-Glu;
Xaa¹³ is absent; and
Xaa¹⁴ is any amino acid.

In other embodiments:
Xaa¹ is absent or any amino acid;
Xaa² is absent or any amino acid;
Xaa³ is absent or any amino acid;
Xaa⁴ is a 2-methylbenzoyl moiety or a modified Homo-Ser, optionally Homo-Ser-Cl;
Xaa⁵ is N-Me-Arg;
Xaa⁶ is Ser;
Xaa⁷ is Asp;
Xaa⁸ is Thr or Val;
Xaa⁹ is Leu;
Xaa¹⁰ is Pen, Cys, D-Cys or HomoCys;
Xaa¹¹ is selected from the group consisting of: Trp, Phe, 2-Nal, 1-Nal, Tyr, His, Phe(4-F), Phe(4-CF3), Phe (4-CH3). Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe(4-carbomyl), Phe(3-Carbomyl), Tyr(Me), HomoPhe, N-Me-Phe, N-Me-Tyr, Ser, Sar, Dihydro Trp, Ile, Leu, Ser, Arg, Thr, Sar, Bpa, Phe(3-Me), Phe(2-Me), Phe(2-CF3), β-Me-Phe, and Ser;
Xaa¹² is selected from the group consisting of: any aromatic amino acid, Glu, D-Glu, N-Me-Glu, N-Me-Asp, alpha-H-Glu, and beta-homo-Glu;
Xaa³ is absent; and
Xaa¹⁴ is any amino acid.

In other embodiments:
Xaa¹ is absent or any amino acid;
Xaa² is absent or any amino acid;
Xaa³ is absent or any amino acid;
Xaa⁴ is a 2-methylbenzoyl moiety or a modified Homo-Ser, optionally Homo-Ser-Cl;
Xaa⁵ is N-Me-Arg;
Xaa⁶ is Ser;
Xaa⁷ is Asp or D-Asp;
Xaa⁸ is Thr or Val;
Xaa⁹ is Leu;
Xaa¹⁰ is Pen, Cys, D-Cys or HomoCys;
Xaa¹¹ is selected from the group consisting of: Trp, Phe, 2-Nal, 1-Nal, Tyr, His, Phe(4-F), Phe(4-CF3), Phe (4-CH3). Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe(4-carbomyl), Phe(3-Carbomyl), Tyr(Me), Bpa, Phe(3-Me), Phe(2-Me), Phe(2-CF3), 3-Me-Phe, and HomoPhe;

Xaa¹² is selected from the group consisting of: any aromatic amino acid, Glu, D-Glu, N-Me-Glu, N-Me-Asp, alpha-H-Glu, and beta-homo-Glu;
Xaa¹³ is absent; and
Xaa¹⁴ is any amino acid.

In some embodiments of any of the peptides (e.g. peptide monomers, or peptide dimers or subunits thereof) described herein, including but not limited to those of Formula (I) (including (I-A)-(I-I), (I-1), (I-2) and (I-3)) or Formula (V), Xaa⁷ is Asp.

In some embodiments of any of the peptides (e.g. peptide monomers, or peptide dimers or subunits thereof) described herein, including but not limited to those of Formula (I) (including (I-A)-(I-I), (I-1), (I-2) and (I-3) or Formula (V)), the N-terminus of the peptide is acylated.

In some embodiments of any of the peptides (e.g. peptide monomers or peptide dimers or subunits thereof) described herein, including but not limited to those of Formula (I) (including (I-A)-(I-I), (I-1), (I-2) and (I-3) or Formula (V)), Xaa¹⁴ or the C-terminal amino acid does not comprise a free amine.

In some embodiments of any of the peptides (e.g. peptide monomers or peptide dimers or subunits thereof) described herein, including but not limited to those of Formula (I) (including (I-A)-(I-I), (I-1), (I-2) and (I-3) or Formula (V)), Xaa¹⁴ or the C-terminus comprises an NH₂ or an OH. In particular embodiments, Xaa¹³ is D-Lys Xaa¹⁴ or the C-terminus is an OH.

In some embodiments of any of the peptide (e.g. peptide monomers or peptide dimers or subunits thereof) described herein, including but not limited to those of Formula (I) (including (I-A)-(I-I), (I-1), (I-2) and (I-3) or Formula (V)), a free amine in the C-terminal amino acid of the peptide monomer is capped, e.g., with an acetyl group.

In some embodiments of any of the peptides (e.g. peptide monomers or peptide dimers or subunits thereof) described herein, including but not limited to those of Formula (I) (including (I-A), (I-I), (I-1), (I-2) and (I-3)) or Formula (V), the peptide monomer or dimer subunit comprises an intramolecular thioether bond between Xaa⁴ and Xaa¹⁰. In certain embodiments, Xaa⁴ is a 2-methylbenzoyl moiety, and Xaa¹⁰ is Pen. In certain embodiments, Xaa⁴ is Homo-Ser-Cl, and Xaa¹⁰ is Cys, D-Cys, or HomoCys.

In some embodiments of any of the peptides (e.g. peptide monomers or peptide dimers or subunits thereof) described herein, including but not limited to those of Formula (I) (including (I-A)-(I-I), (I-1), (I-2) and (I-3)) or Formula (V), at least one of Xaa¹, Xaa², Xaa³, Xaa⁵, Xaa⁷, Xaa⁸, Xaa⁹, Xaa¹¹, Xaa¹², Xaa¹³ and Xaa¹⁴ is N(alpha)Methylated.

In some instances of any of the peptides (e.g. peptide monomers or peptide dimers or subunits thereof) described herein, any of Xaa¹-Xaa⁴, and Xaa¹¹-Xaa¹⁴ are acylated. For example, in some instances one or more residues at positions Xaa¹-Xaa⁴, and Xaa¹¹-Xaa¹⁴ are acylated with an acylating organic compound selected from the group consisting of 2-me-Trifluorobutyl, Trifluoropentyl, Acetyl, Octonyl, Butyl, Pentyl, Hexyl, Palmityl, Lauryl, Oleoyl, and Lauryl, Trifluoromethyl butyric, cyclopentane carboxylic, cyclopropylacetic, 4-fluorobenzoic, 4-fluorophenyl acetic, 3-Phenyl-propionic, tetrahedro-2H-pyran-4carboxylic, succinic acid, and glutaric acid. In some instances, small PEG (e.g., PEG4-PEG13) is used as spacer before acylations.

In certain embodiments, the N-terminus of a peptide monomer or peptide dimer subunit represented by Formula (I) (including (I-A)-(I-I), (I-1), (I-2) and (I-3)), or Formula (II) or Formula (V) or Formula (VI), or any other peptide described herein, can be modified by one to three suitable groups, as represented by $Xaa^1$, $Xaa^2$, and $Xaa^3$ in Formula (I), (I-A), (I-B) and (I-C) or Formula (V). The N-terminus may further be acylated e.g., as described herein with respect to peptide monomers or peptide dimer subunits of Formula (I), Formula (V), Formula (II), and Formula (VI). In some instances, the N-terminus further comprises a suitable linker moiety or other modifying group.

Similarly, in certain embodiments, the C-terminus of a peptide monomer or dimer subunit represented by Formula (I) (including (I-A)-(I-I)), (I-1), (I-2) and (I-3), or Formula (V), or a peptide monomer or peptide dimer subunit of Formula (II), or any other peptide described herein, can be modified by a suitable group. For example, the C-terminus may be acylated. In some instances, the C-terminus further comprises a suitable linker moiety or modifying group, as disclosed herein. In certain embodiments, the C-terminus comprises $NH_2$ or OH.

In some embodiments, $Xaa^1$, $Xaa^2$, and $Xaa^3$ of Formula (I) (including (I-1)-(I-I)), (I-1), (I-2) and (I-3) or Formula (V) are absent. In particular embodiments $Xaa^1$, $Xaa^2$, and $Xaa^3$ of any peptide dimer subunit described herein are absent. In other embodiments, $Xaa^1$ is absent, and $Xaa^2$ and $Xaa^3$ represent suitable groups for modifying the N-terminus of the peptide monomer or peptide dimer subunit. Further, in some embodiments $Xaa^1$ and $Xaa^2$ are absent, and $Xaa^3$ represents a single suitable group for modifying the N-terminus of the peptide monomer or peptide dimer subunit.

With continued reference to the peptide monomers and peptide of the general formula of Formula (I), (I-1), (I-2) and (I-3) or Formula (V), $Xaa^{1-3}$ may comprise any naturally occurring amino acid, a suitable isostere, or corresponding D-amino acid. In some embodiments, at least one of $Xaa^{1-3}$ is absent. For example, in some instances $Xaa^1$ is absent, whereby $Xaa^2$ is the N-terminus. In other instances $Xaa^1$ and $Xaa^2$ are absent, whereby $Xaa^3$ is the N-terminus. Further still, in some instances $Xaa^{1-3}$ are absent, whereby $Xaa^4$ is the N-terminus. In some embodiments, the N-terminal residue is acylated or comprises a free amine. In some embodiments, the N-terminal residue of the peptide monomer or peptide dimer subunit is a 2-methyl benzoyl moiety (abbreviated herein as 2-benzyl).

In certain embodiments, peptide monomers, or peptide dimers having subunits of Formula (I) (including (I-A)-(I-I)), (I-1), (I-2) and (I-3) or Formula (V), or any other peptide described herein, the amino acid residue directly C-terminal to $Xaa^{10}$ is an aromatic amino acid.

In other embodiments, the N-terminal residue of peptide monomers or peptide dimer subunits of Formula (I) (including (I-A)-(I-I), (I-1), (I-2) and (I-3)), or any other peptide described herein, further comprises a suitable linker moiety, e.g., a linker moiety, or modifying group selected from the group consisting of DIG, PEG4, PEG13, PEG25, PEG K, PEG2K, PEG4K, PEG5K, Polyethylene glycol having molecular weight from 400 Da to 40,000 Da, PEG having a molecular weight of 40,000 Da to 80,000 Da, IDA, Ac-IDA, ADA, Glutaric acid, AADA, suitable aliphatic acids, suitable aromatic acids, and heteroaromatic acids.

In various embodiments of any of the peptides (e.g. peptide monomers, peptide dimers, or subunits thereof) described herein, one or more of the amino acids represented by $Xaa^{1-3}$ may be either absent or selected from the group consisting of any naturally occurring amino acid, a suitable isostere, and corresponding D-amino acids. When $Xaa^1$ and $Xaa^2$ are absent, $Xaa^3$ is the N-terminus. When $Xaa^{1-3}$ are absent, $Xaa^4$ is the N-terminus.

In some embodiments, $Xaa^4$ is an amino acid residue having a side chain with one or two carbons, and forming a thioether bond with $Xaa^{1-3}$. In some instances, $Xaa^4$ is selected from the group consisting of modified Ser, modified HSer, a suitable isostere, and corresponding D-amino acids. In other instances, $Xaa^4$ is an aliphatic acid having from one to four carbons and forming a thioether bond with $Xaa^{1-3}$. In some instances, $Xaa^4$ is a five- or six-membered alicyclic acid having a modified 2-methyl group that forms a thioether bond with $Xaa^{1-3}$. In some embodiments, $Xaa^4$ is a 2-methyl-benzoyl moiety or a modified form thereof. In certain embodiments, $Xaa^4$ Cys, Pen, homocys, D-Pen, D-Cys or D-homocys. In certain embodiments, $Xaa^4$ is 2-chloromethylbenzoic acid, 2-chloro-acetic acid, 3-chloro-propanoic acid, 4-chloro-butyric acid, 3-chloro-isobutyric acid, Ser(Cl); $Xaa^{1-3}$ is Cys, Pen, D-Cys, HomoCys; and the intramolecular bond is a thioether bond. One of skill in the art will appreciate that upon bonding with another amino acid, e.g., $Xaa^{1-3}$, the Cl of hSer(Cl) will be removed.

For each embodiment of the peptide monomers or peptide dimer subunits of Formula (I) and (I-A) or Formula (V), and any of the peptide monomers or peptide dimers described herein, a thioether bond exists between $Xaa^4$ and $Xaa^{10}$ in the monomer peptides or in one or both of the peptide dimer subunits. Thus, the thioether peptide monomers or peptide dimer subunits of the present invention are cyclized through a thioether bond.

In some embodiments of any of the peptides described herein, $Xaa^5$ is selected from the group consisting of N(alpha)-Me-Arg, Arg, HArg, Dap, Dab, Arg-Me-sym, Arg-Me-asym, 4-Guan, Cit, Cav, and suitable isostere replacements. In some embodiments, $Xaa^5$ is N(alpha)Methylated. Preferably, $Xaa^5$ is N-Me-Arg. In other embodiments, preferably $Xaa^5$ is Arg.

In some embodiments of any of the peptides (e.g. peptide monomers, peptide dimers, or subunits thereof), described herein, $Xaa^6$ is selected from the group consisting of Ser, Gly, Thr, Ile, and suitable isostere replacements. Preferably, $Xaa^6$ is Ser. In some embodiments of any of the peptide dimer subunits described herein, $Xaa^6$ is selected from the group consisting of Ser, Gly, Thr, Ile, and suitable isostere replacements. In some embodiments of any of the peptide monomers described herein, $Xaa^6$ is selected from the group consisting of Ser, Gly, and suitable isostere replacements.

In some embodiments of any of the peptide monomers or dimers described herein, $Xaa^7$ is selected from the group consisting of Asp, N-Me-Asp, D-Asp, Asp(OMe), and a suitable isostere replacements. In some embodiments of any of the peptide dimers described herein, $Xaa^7$ is selected from the group consisting of Asp, N-Me-Asp, D-Asp, and a suitable isostere replacements. In some embodiments, $Xaa^7$ is N(alpha)Methylated. Preferably, $Xaa^7$ is Asp.

In some embodiments of any of the peptides described herein, $Xaa^8$ is selected from the group consisting of Thr, Gln, Ser, Asp, Pro, Gly, His, Ala, Ile, Phe, Lys, Arg, Asn, Glu, Val, Tyr, Trp, Leu, Met, and N-Methyl amino acids including N-Me-Thr, and suitable isostere replacements. In some embodiments, $Xaa^8$ is N(alpha)Methylated. Preferably, $Xaa^8$ is Thr.

In some embodiments of any of the peptides described herein, $Xaa^9$ is selected from the group consisting of Gln, Asn, Asp, Pro, Gly, Ala, Phe, Leu, Glu, Ile, Val, HLeu, n-Butyl Ala, n-Pentyl Ala, n-Hexyl Ala, Nle, cyclobutyl-Ala, N-Me-Leu, and suitable isostere replacements. In some embodiments, $Xaa^9$ is N(alpha)Methylated. In certain embodiments, $Xaa^9$ is Leu.

In some embodiments of any of the peptide monomers or peptide dimer subunits described herein, $Xaa^{10}$ is selected from the group consisting of Cys, N-Me-Cys, D-Cys, HCys, Pen, and D-Pen. In some embodiments, $Xaa^{10}$ is selected from the group consisting of Cys, N-Me-Cys, D-Cys, HCys, and Pen. In one embodiment, $Xaa^{10}$ is Pen. In another embodiment, $Xaa^{10}$ is preferably Cys.

In some embodiments of any of the peptides described herein, $Xaa^{11}$ is absent, or $Xaa^{11}$ is selected from the group consisting of Gly, Gln, Asn, Asp, Ala, Ile, Leu, Val, Met, Thr, Lys, Trp, Tyr, His, Glu, Ser, Arg, Pro, Phe, Sar, 1-Nal, 2-Nal, D-1-Nal, D-2-Nal, HPhe, Phe(4-F), O-Me-Tyr, dihydro-Trp, D-Phe, D-Tyr, Dap, Dab, Dab(Ac), Orn, D-Orn, N-Me-Orn, N-Me-Dap, D-Dap, D-Dab, Bip, Ala(3,3diphenyl), Biphenyl-Ala, aromatic ring substituted Phe, aromatic ring substituted Trp, aromatic ring substituted His, hetero aromatic amino acids, N-Me-Lys, N-Me-Lys(Ac), 4-Me-Phe, and corresponding D-amino acids and suitable isostere replacements. In some embodiments, $Xaa^{11}$ is preferably Trp. In some other embodiments, $Xaa^{11}$ is Phe. In some embodiments, $Xaa^{11}$ is F(4tBu), F(4-COOH), Bip, 1-Nal or 2-Nal. In particular embodiments of peptide monomers described herein, $Xaa^{11}$ is N(alpha)Methylated. In certain embodiments of peptide monomers or peptide dimer subunits described herein, $Xaa^{11}$ is Phe. In some embodiments, $Xaa^{11}$ is N(alpha)Methylated. Further, in some embodiments $Xaa^{11}$ is acylated.

In at least one embodiment of peptide monomers or peptide dimer subunits described herein, $Xaa^{11}$ is absent and $Xaa^{10}$ is the C-terminus. When $Xaa^{12-14}$ are absent, $Xaa^{11}$ is the C-terminus of the subunit. When $Xaa^{11}$ is the C-terminus of the subunit, $Xaa^{11}$ may be modified to include a suitable linker moiety in accordance with the present invention.

In some embodiments of peptide monomers or peptide dimers described herein, $Xaa^{12}$ is absent, or $Xaa^{12}$ is selected from the group consisting of Glu, Lys, COOH, CONH$_2$, Gln, Pro, Gly, His, Ala, Ile, Phe, Lys, Arg, Leu, Val, Tyr, Trp, Met, Gla, Ser, Asn, D-Glu, β-HGlu, 2-Nal, 1-Nal, D-Asp, Bip, β-HPhe, β-Glu, D-Tyr, D-Phe, D-Lys, Dap, Dab, Orn, D-Orn, N-Me-Orn, N-Me-Dap, N-Me-Dab, N-Me Lys, D-Dap, D-Dab, suitable isosteres, and corresponding D-amino acids. In some embodiments of peptide dimers described herein, $Xaa^{12}$ is absent, or $Xaa^{12}$ is selected from the group consisting of Glu, Lys, Gln, Pro, Gly, His, Ala, Ile, Phe, Lys, Arg, Leu, Val, Tyr, Trp, Met, Gla, Ser, Asn, D-Glu, β-HGlu, 2-Nal, 1-Nal, D-Asp, Bip, β-HPhe, β-Glu, D-Tyr, D-Phe, D-Lys, Dap, Dab, Orn, D-Orn, N-Me-Orn, N-Me-Dap, N-Me-Dab, N-Me Lys, D-Dap, D-Dab, suitable isosteres, and corresponding D-amino acids. In certain embodiments, $Xaa^{12}$ is Glu, D-Glu, β-HGlu, or Asp. In some embodiments, $Xaa^{12}$ is β-Hglu.

In some embodiments of the peptide monomer or peptide dimers described herein, $Xaa^{13}$ and $Xaa^{4}$ are absent, and $Xaa^{12}$ is the C-terminus of the subunit. In some embodiments of the peptide dimers described herein, when $Xaa^{12}$ is the C-terminus of the subunit, $Xaa^{12}$ may be modified to include a suitable linker moiety in accordance with the present invention.

In some embodiments of any of the peptides (e.g. peptide monomers, peptide dimers, or subunits thereof) described herein, $Xaa^{13}$ is absent, or $Xaa^{13}$ is selected from the group consisting of Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, N-Me-Lys, D-N-Me-Lys, D-Dap, D-Dab, suitable isosteres, and corresponding D-amino acids. In some embodiments of peptide monomers described herein, $Xaa^{13}$ is absent, or $Xaa^{13}$ is selected from COOH and CONH$_2$. In at least one embodiment, $Xaa^{13}$ is Lys. Further still in some embodiments $Xaa^{13}$ is D-Lys. In some embodiments of the peptide dimer subunits described herein, when $Xaa^{14}$ is absent, $Xaa^{13}$ is the C-terminus; and when $Xaa^{13}$ is the C-terminus of the subunit, $Xaa^{13}$ may be modified to include a suitable linker moiety in accordance with the present invention.

Further, in some embodiments of the peptide monomers or dimer subunits described herein, $Xaa^{14}$ is absent, or $Xaa^{4}$ is selected from the group consisting of Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, COOH, CONH$_2$, N-Me-Lys, D-N-Me-Lys, D-Dap, D-Dab, suitable isosteres, corresponding D-amino acids, and corresponding N-Methyl amino acids. Further, in some embodiments of the peptide dimer subunits described herein, $Xaa^{14}$ is absent, or $Xaa^{14}$ is selected from the group consisting of Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, N-Me-Lys, D-N-Me-Lys, D-Dap, D-Dab, suitable isosteres, corresponding D-amino acids, and corresponding N-Methyl amino acids. In at least one embodiment of the peptide monomers and dimer subunits described herein, $Xaa^{4}$ is Lys, D-Lys, or N-Me-Lys. In some embodiments of the peptide monomer or peptide dimer subunits of the present invention, $Xaa^{4}$ is Cys, HomoCys or Pen. In some embodiments of the peptide monomer or peptide dimer subunits of the present invention, $Xaa^{4}$ is Cys, D-Cys, HomoCys, Pen, or D-Pen.

In some embodiments of any of the peptide monomers or dimer subunits described herein, $Xaa^{12}$ is present, $Xaa^{13}$ is absent, and $Xaa^{14}$ is present. In particular embodiments, $Xaa^{11}$ is Phe(4tBu), Phe(4-COOH), Bip, 2-Nal or 1-Nal; $Xaa^{12}$ is Glu or β-homoGlu, $Xaa^{13}$ is absent, and $Xaa^{4}$ is D-Lys or N-Me-Lys.

In at least one embodiment of the dimer subunits described herein, $Xaa^{4}$ is the C-terminus, and when $Xaa^{4}$ is the C-terminus of the subunit, $Xaa^{4}$ may be modified to include a linker moiety in accordance with the present invention.

In at least one embodiment of peptide monomers and peptide dimer subunits, including peptide monomers and dimers of Formula (I), described herein, $Xaa^{14}$ are absent, whereby $Xaa^{10}$ is the C-terminus. When $Xaa^{12-14}$ are absent, $Xaa^{11}$ is the C-terminus. Similarly, when $Xaa^{13}$ and $Xaa^{14}$ are absent, $Xaa^{12}$ is the C-terminus. Further, when $Xaa^{14}$ is absent, $Xaa^{13}$ is the C-terminus. In some embodiments, the C-terminus of the thioether peptide monomer or dimer subunit is modified to include a suitable linker moiety (e.g. a linker moiety) or modifying group in accordance with the present invention.

Figure 4:
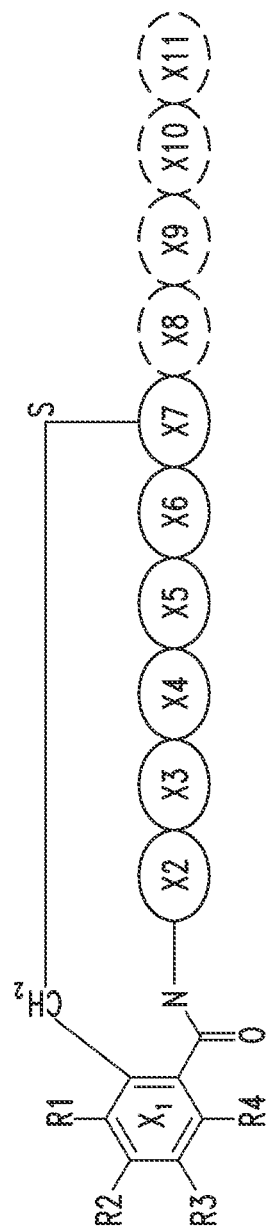
FIG. 4 is a schematic showing a cyclized, thioether peptide monomer or monomer subunit of a dimer molecule according to SEQ ID NO: 2 (Formula (II)), wherein Xaa$^1$ is a 2-methylbenzoyl moiety forming a thioether bond with Xaa$^7$ in accordance with a representative embodiment of the present invention. Non-limiting examples of suitable chemical moieties for substitution at R1-R4 are provided and discussed below.

In certain embodiments of any of the peptide monomers or dimer subunits (e.g. the peptide monomers and dimers of Formula (I)) described herein, $Xaa^{1}$, $Xaa^{2}$ and $Xaa^{3}$ are absent, and the N-terminus of the peptide comprises an aromatic group that is capable of forming a thioether bond with $Xaa^{10}$. In some embodiments, $Xaa^{4}$ comprises a 2-methylbenzoyl moiety forming an amide bond with $Xaa^{5}$, and further comprising a methyl group forming a thioether bond with $Xaa^{10}$. The 2-methylbenzoyl moiety further comprises substituent R-groups represented by R1-R4, e.g., as shown in FIG. 4.

In some instances of peptide monomers or dimers described herein, at least one substituent R-group of $Xaa^{1}$ is a free amine, whereby the N-terminus of the thioether monomer or dimer peptide of, e.g., Formula (I) or Formula (I-1), may be extended. In other instances, one or more substituent groups represented by R1-R4 is selected from the group consisting of hydrogen, a methyl group, a fluorocarbon group, a hydrocarbon, Cl, CF3, OMe, OEt, CONH$_2$, an aromatic group, a small pegylation group, a terminal modifying group, an acylation, a free amine, and an acid. In some embodiments, one or more substituent groups represented by R1-R4 is selected from the group consisting of hydrogen, a methyl group, a fluorocarbon group, a hydrocarbon, Cl, CF3, OMe, OEt, $CONH_2$, CH3, CH2CH3, an aromatic group, a small pegylation group, a terminal modifying group, an acylation, a free amine, and an acid.

In particular embodiments of any of the peptides herein, including those comprising a structure of any one of Formulas (I), (I-1), (I-2), (I-3), (V) or (I-A)-(I-I) or Formula (V), the thioether bond is in the reverse order, such that the amino acid residues and chemical moieties shown in $Xaa^4$ are instead present in $Xaa^{10}$, and the amino acid resides shown at $Xaa^{10}$ are instead present at $Xaa^4$. In this reverse orientation, the amino acid or chemical moiety at position $Xaa^{10}$ is one that comprises a free amine.

In some embodiments of the peptide monomers and dimer subunits described herein, the C-terminal residue of Formula (I) or Formula (V) or any peptide monomer or peptide dimer described herein further comprises a modifying group or a suitable linker moiety, e.g., a modifying group or linker selected from the group consisting of DIG, PEG4, PEG13, PEG25, PEG1K, PEG2K, PEG4K, PEG5K, Polyethylene glycol having molecular weight from 400 Da to 40,000 Da, PEG having a molecular weight of 40,000 Da to 80,000 Da, IDA, Ac-IDA, ADA, Glutaric acid, Succinic acid, Isophthalic acid, 1,3-phenylenediacetic acid, 1,4-phenylenediacetic acid, 1,2-phenylenediacetic acid, AADA, suitable aliphatic acids, suitable aromatic acids, heteroaromatic acids. Examples of other linkers are described herein and include but are not limited to those linkers shown in Table 2.

Referring now to FIG. 4, one aspect of the present invention relates to a thioether peptide monomer or dimer (or subunit of a peptide dimer molecule) comprising the structure according to Formula (II):

$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$, (SEQ ID NO: 2)

or a pharmaceutically acceptable salt thereof, wherein the peptide monomer or each subunit of the thioether peptide dimer comprises a thioether bond between $Xaa^1$ and $Xaa^7$.

The N-terminus of a peptide monomer or dimer subunit represented by Formula (II) comprises an aromatic group that is capable of forming a thioether bond with $Xaa^7$. In some embodiments, $Xaa^1$ comprises a 2-methylbenzoyl moiety forming an amide bond with $Xaa^2$, and further comprising a methyl group forming a thioether bond with $Xaa^7$. The 2-methylbenzoyl moiety may further comprise substituent R-groups represented by R1-R4, e.g., as shown in FIG. 4, including those described herein.

In some instances, at least one substituent R-group of $Xaa^1$ is a free amine, whereby the N-terminus of the thioether peptide of Formula (II) may be extended. In other instances, one or more substituent groups represented by R1-R4 is selected from the group consisting of hydrogen, a methyl group, a fluorocarbon group, a hydrocarbon, Cl, CF3, OMe, OEt, $CONH_2$, an aromatic group, a small pegylation group, a terminal modifying group, an acylation, a free amine, and an acid.

For each embodiment of Formula (II) or Formula (VI), a thioether bond exists between $Xaa^1$ and $Xaa^7$. Thus, the thioether peptide monomers and dimer subunits of the present invention are cyclized through a thioether bond. In one embodiment, $Xaa^7$ is Cys. In another embodiment, preferably $Xaa^7$ is Pen. In other embodiments, $Xaa^7$ is D-Cys or homo-Cys.

In some embodiments of peptides (e.g. peptide monomers, dimers, or dimer subunits) described herein, $Xaa^1$ comprises an R group that is capable of being acylated via an acylating organic compound. In other instances, $Xaa^1$ of a peptide dimer subunit comprises an R group that is capable of being modified with a suitable linker moiety, whereby the N-terminuses of two peptide dimer subunits according to Formula (I) may be dimerized. In certain embodiments, $Xaa^1$ is a 2-methyl benzoyl moiety.

In particular embodiments of the Formula (II) or Formula (VI) peptides (e.g. peptide monomers or peptide dimers or subunits thereof) of the present invention, $Xaa^1$ is a modified HomoSer or a modified Ser group that is capable of forming a thioether bond with $Xaa^7$, and $Xaa^7$ is Cys, Pen, D-Cys, Homo Cys. The N-terminal residue further comprises a modifying group or suitable linker moiety, e.g., a modifying group or linker selected from the group consisting of DIG, PEG4, PEG13, PEG25, PEG1K, PEG2K, PEG4K, PEG5K, Polyethylene glycol having molecular weight from 400 Da to 40,000 Da, PEG having a molecular weight of 40,000 Da to 80,000 Da, IDA, Ac-IDA, ADA, Glutaric acid, Succinic acid, Isophthalic acid, 1,3-phenylenediacetic acid, 1,4-phenylenediacetic acid, 1,2-phenylenediacetic acid, AADA, suitable aliphatic acids, suitable aromatic acids, heteroaromatic acids. Examples of other linkers are described herein and include but are not limited to those shown in Table 3.

For each embodiment of Formula (II), $Xaa^2$ is selected from the group consisting of N(alpha)-Me-Arg, Arg, HArg, Dap, Dab, Arg-Me-sym, Arg-Me-asym, 4-Guan, Cit, Cav, and suitable isostere replacements. In some embodiments, $Xaa^2$ is N(alpha)Methylated. Preferably, $Xaa^2$ is N-Me-Arg. In other embodiments, preferably $Xaa^2$ is Arg.

For each embodiment of Formula (II), $Xaa^3$ is selected from the group consisting of Ser, Gly, and suitable isostere replacements. Preferably, $Xaa^3$ is Ser.

For each embodiment of Formula (II), $Xaa^4$ is selected from the group consisting of Asp, N-Me-Asp, Asp(OMe), D-Asp, and a suitable isostere replacements. In some embodiments, $Xaa^4$ is N(alpha)Methylated. In some embodiments, $Xaa^4$ is Asp or N-Me-Asp. In some embodiments, $Xaa^4$ is Asp.

For each embodiment of Formula (II), $Xaa^5$ is selected from the group consisting of Thr, Gln, Ser, Asp, Pro, Gly, His, Ala, Ile, Phe, Lys, Arg, Asn, Glu, Val, Tyr, Trp, Leu, Met, and N-Methyl amino acids including N-Me-Thr, and suitable isostere replacements. In some embodiments, $Xaa^5$ is N(alpha)Methylated. In some embodiments, $Xaa^5$ is selected from the group consisting of Thr, Gln, Ser, Asp, Gly, His, Ala, Ile, Phe, Lys, Arg, Asn, Glu, Val, Tyr, Trp, Leu, Met, and N-Methyl amino acids including N-Me-Thr, and suitable isostere replacements. Preferably, $Xaa^5$ is Thr.

For each embodiment of Formula (II), $Xaa^6$ is selected from the group consisting of Gln, Asn, Asp, Pro, Gly, Ala, Phe, Leu, Glu, Ile, Val, HLeu, n-Butyl Ala, n-Pentyl Ala, n-Hexyl Ala, Nle, cyclobutyl-Ala, N-Me-Leu, and suitable isostere replacements. In some embodiments, $Xaa^6$ is selected from the group consisting of Gln, Asn, Asp, Pro, Gly, Ala, Phe, Leu, Glu, Ile, Val, HLeu, n-Butyl Ala, n-Pentyl Ala, n-Hexyl Ala, Nle, cyclobutyl-Ala, N-Me-Leu, and suitable isostere replacements. In some embodiments, $Xaa^6$ is N(alpha)Methylated. Preferably, $Xaa^6$ is Leu.

For each embodiment of Formula (II), $Xaa^7$ is selected from the group consisting of Cys, N-Me-Cys, D-Cys, HCys, Pen, and D-Pen. Preferably, in one embodiment Xaa$^7$ is Pen. In another embodiment, Xaa$^7$ is preferably Cys.

For each embodiment of Formula (II), Xaa$^8$ is selected from the group consisting of Gly, Gln, Asn, Asp, Ala, Ile, Leu, Val, Met, Thr, Lys, Trp, Tyr, His, Glu, Ser, Arg, Pro, Phe, Sar, 1-Nal, 2-Nal, D-1-Nal, D-2-Nal, D-Phe, D-Tyr, HPhe, Phe(4-F), O-Me-Tyr, dihydro-Trp, Dap, Dab, Dab (Ac), Orn, D-Orn, N-Me-Orn, N-Me-Dap, D-N-Me-Lys, D-Dap, D-Dab, Bip, Ala(3,3diphenyl), Biphenyl-Ala, aromatic ring substituted Phe, aromatic ring substituted Trp, aromatic ring substituted His, hetero aromatic amino acids, N-Me-Lys, N-Me-Lys(Ac), 4-Me-Phe, and corresponding D-amino acids and suitable isostere replacements. In other embodiments, Xaa$^8$ is N(alpha)Methylated. Further, in some embodiments Xaa$^8$ is acylated. In some embodiments of peptide monomers or peptide dimers described herein, Xaa$^8$ is absent.

In particular embodiments of peptide dimer subunits of Formula (II) or Formula (VI), Xaa$^{9-11}$ are absent, and Xaa$^8$ is the C-terminus of the subunit. When Xaa$^8$ is the C-terminus of the subunit, Xaa$^8$ may be modified to include a suitable linker moiety in accordance with the present invention.

In some embodiments of the peptide monomers and dimer subunits of Formula (II) or Formula (VI), Xaa$^9$ is absent, or Xaa$^9$ is selected from the group consisting of Glu, Amide, Lys, Gln, Pro, Gly, His, Ala, Ile, Phe, Lys, COOH, Arg, Leu, Val, Tyr, Trp, Met, Gla, Ser, Asn, D-Glu, β-HGlu, 2-Nal, 1-Nal, D-1-Nal, D-2-Nal, D-Phe, D-Tyr, D-Asp, Bip, β-HPhe, β-Glu, D-Tyr, D-Lys, Dap, Dab, Orn, D-Orn, N-Me-Orn, N-Me-Dap, N-Me-Dab, N-Me Lys, D-N-Me-Lys D-Dap, D-Dab, suitable isosteres, and corresponding D-amino acids. In particular embodiments of peptide monomer or dimer subunits described herein, Xaa$^9$ is absent or COOH. In certain embodiments, Xaa$^9$ is Glu, D-Glu, β-HGlu, or Asp.

In some embodiments of peptide dimer subunits, when Xaa$^{10}$ and Xaa$^{11}$ are absent, Xaa$^9$ is the C-terminus of the subunit. When Xaa$^9$ is the C-terminus of the subunit, Xaa$^9$ may be modified to include a suitable linker moiety in accordance with the present invention.

For each embodiment of Formula (II) or Formula (VI), Xaa$^{10}$ may be absent, or Xaa$^{10}$ is selected from the group consisting of Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, D-N-Me-Lys N-Me-Lys, D-Dap, D-Dab, suitable isosteres, and corresponding D-amino acids. In at least one embodiment, Xaa$^{10}$ is Lys. Further still in some embodiments Xaa$^{10}$ is D-Lys. In particular embodiments of peptide monomers or peptide dimers described herein, Xaa$^{10}$ is COOH or CONH$_2$.

In certain embodiments of peptide monomers or peptide dimer subunits comprising Formula (II) or Formula (VI), when Xaa$^{11}$ is absent, Xaa$^{10}$ is the C-terminus. When Xaa$^{10}$ is the C-terminus of the subunit, Xaa$^{10}$ may be modified to include a suitable linker moiety in accordance with the present invention. Further, in some embodiments, Xaa$^{11}$ is absent, or selected from the group consisting of Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, D-N-Me-Lys N-Me-Lys, D-Dap, D-Dab, suitable isosteres, and corresponding D-amino acids. In at least one embodiment, Xaa$^{10}$ is Lys. Further still in some embodiments Xaa$^{10}$ is D-Lys. In some embodiments of peptide monomers, Xaa$^{10}$ is COOH or CONH$_2$.

In certain embodiments of peptide monomers or peptide dimer subunits, Xaa$^{11}$ is the C-terminus. When Xaa$^{11}$ is the C-terminus of the subunit, Xaa$^{11}$ may be modified to include a linker moiety in accordance with the present invention.

In at least one embodiment of peptide monomers of the present invention, Xaa$^{8-11}$ are absent, whereby Xaa$^7$ is the C-terminus.

In particular embodiments of peptide monomer and dimer subunits comprising Formula (II), when Xaa$^{9-11}$ are absent, Xaa$^8$ is the C-terminus. Similarly, in certain embodiments, when Xaa$^{10}$ and Xaa$^{11}$ are absent, Xaa$^9$ is the C-terminus. Further, when Xaa$^{11}$ is absent, Xaa$^{10}$ is the C-terminus. In some embodiments, the C-terminus of the thioether peptide is modified to include a modifying group in accordance with the present invention. In some embodiments, the C-terminus of the thioether peptide monomer or dimer subunit comprises NH$_2$ or OH.

In particular embodiments of any of the peptides herein, including those comprising a structure of any one of Formulas (II), (II-A), (A), (III), or (IV) or Formula (VI), the thioether bond is in the reverse order, such that the amino acid residues and chemical moieties shown in Xaa$^1$ are instead present in Xaa$^7$, and the amino acid resides shown at Xaa$^7$ are instead present at Xaa$^1$. In this reverse orientation, the amino acid or chemical moiety at position Xaa$^7$ is one that comprises a free amine.

In certain embodiments peptides comprising Formula (II) or Formula (VI):

Xaa$^1$ is a 2-Me-benzoyl group capable of forming a thioether bond with Xaa$^7$;

Xaa$^2$ is selected from the group consisting of N(alpha)-Me-Arg, Arg, HArg, Dap, Dab, Arg-Me-sym, Arg-Me-asym, 4-Guan, Cit, Cav, and suitable isostere replacements;

Xaa$^3$ is selected from the group consisting of Ser, Gly, and suitable isostere replacements;

Xaa$^4$ is selected from the group consisting of Asp, N-Me-Asp, Asp(OMe), D-Asp, and a suitable isostere replacements;

Xaa$^5$ is selected from the group consisting of Thr, Gln, Ser, Asp, Pro, Gly, His, Ala, Ile, Phe, Lys, Arg, Asn, Glu, Val, Tyr, Trp, Leu, Met, and N-Methyl amino acids including N-Me-Thr, and suitable isostere replacements;

Xaa$^6$ is selected from the group consisting of Gln, Asn, Asp, Pro, Gly, Ala, Phe, Leu, Glu, Ile, Val, HLeu, n-Butyl Ala, n-Pentyl Ala, n-Hexyl Ala, Nle, cyclobutyl-Ala, N-Me-Leu, and suitable isostere replacements;

Xaa$^7$ is selected from the group consisting of Cys, N-Me-Cys, D-Cys, HCys, Pen, and D-Pen;

Xaa$^8$ is selected from the group consisting of absent, Gly, Gln, Asn, Asp, Ala, Ile, Leu, Val, Met, Thr, Lys, Trp, Tyr, His, Glu, Ser, Arg, Pro, Phe, Sar, 1-Nal, 2-Nal, HPhe, Phe(4-F), O-Me-Tyr, dihydro-Trp, Dap, Dab, Dab(Ac), Orn, D-Orn, N-Me-Orn, N-Me-Dap, D-Dap, D-Dab, Bip, Ala(3, 3diphenyl), Biphenyl-Ala, aromatic ring substituted Phe, aromatic ring substituted Trp, aromatic ring substituted His, hetero aromatic amino acids, N-Me-Lys, N-Me-Lys(Ac), 4-Me-Phe, and corresponding D-amino acids and suitable isostere replacements;

Xaa$^9$ is selected from the group consisting of absent, Glu, Amide, Lys, COOH, CONH$_2$, Gln, Pro, Gly, His, Ala, Ile, Phe, Lys, Arg, Leu, Val, Tyr, Trp, Met, Gla, Ser, Asn, D-Glu, β-HGlu, 2-Nal, 1-Nal, D-Asp, Bip, β-HPhe, β-Glu, D-Tyr, D-Lys, Dap, Dab, Orn, D-Orn, N-Me-Orn, N-Me-Dap, N-Me-Dab, N-Me Lys, D-Dap, D-Dab, suitable isosteres, and corresponding D-amino acids;

Xaa$^{10}$ is selected from the group consisting of absent, Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, N-Me-Lys, D-Dap, D-Dab, COOH, CONH$_2$, suitable isosteres, and corresponding D-amino acids; and $Xaa^{11}$ is selected from the group consisting of absent, Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, N-Me-Lys, D-Dap, D-Dab, COOH, CONH$_2$, suitable isosteres, and corresponding D-amino acids, wherein the peptide further comprises a thioether bond between $Xaa^1$ and $Xaa^7$.

Another aspect of the present invention relates to a thioether peptide monomer or each subunit of a dimer compound comprising the structure according to Formula (II-A) (SEQ ID NO: 45), (Formula II-A))
$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$, or a pharmaceutically acceptable salt thereof, wherein the peptide comprises a thioether bond between $Xaa^1$ and $Xaa^7$, wherein $Xaa^1$ (or the N-terminus) of the peptide represented by Formula (II-A) comprises a group, e.g., optionally an aromatic group, that is capable of forming a thioether bond with $Xaa^7$. In some embodiments, $Xaa^1$ comprises a 2-methylbenzoyl moiety forming an amide bond with $Xaa^2$, and further comprising a methyl group forming a thioether bond with $Xaa^7$. The 2-methylbenzoyl moiety further comprises substituent R-groups represented by R1-R4; in some instances, at least one substituent R-group of $Xaa^1$ is a free amine, whereby the N-terminus of the thioether peptide of Formula (II-A) may be extended; in other instances, one or more substituent groups represented by R1-R4 is selected from the group consisting of hydrogen, a methyl group, a fluorocarbon group, a hydrocarbon, Cl, CF3, OMe, OEt, CONH$_2$, an aromatic group, a small pegylation group, a terminal modifying group, an acylation, a free amine, and an acid. In particular embodiments, Formula (II-A) is directed to a peptide monomer or peptide dimer subunit and $Xaa^1$ is a modified Ser or a modified Homo-Ser, e.g., Homo-Ser-Cl. In some embodiments, Formula (II-A) is directed to a peptide dimer subunit and $Xaa^4$ is modified Homo-Ser, and $Xaa^{10}$ is Cys, D-Cys, or HomoCys.

For each embodiment of Formula (II-A), $Xaa^2$ is selected from the group consisting of N(alpha)-Me-Arg, Arg, HArg, Dap, Dab, Arg-Me-sym, Arg-Me-asym, 4-Guan, Cit, Cav, and suitable isostere replacements. In some embodiments, $Xaa^2$ is N(alpha)Methylated. Preferably, $Xaa^2$ is N-Me-Arg. In other embodiments, preferably $Xaa^2$ is Arg.

For each embodiment of Formula (II-A), $Xaa^3$ is selected from the group consisting of Ser, Gly, Thr, Ile and suitable isostere replacements. Preferably, $Xaa^3$ is Ser.

For embodiments of Formula (II-A) directed to peptide monomers, $Xaa^4$ is selected from the group consisting of Asp, N-Me-Asp, Asp(OMe), D-Asp, and a suitable isostere replacements. For embodiments of Formula (II-A), $Xaa^4$ is selected from the group consisting of Asp, N-Me-Asp, D-Asp, and a suitable isostere replacements. In some embodiments of peptide monomers and dimer subunits, $Xaa^4$ is N(alpha)Methylated. Preferably, $Xaa^4$ is Asp.

For each embodiment of Formula (II-A), $Xaa^5$ is selected from the group consisting of Thr, Gln, Ser, Asp, Pro, Gly, His, Ala, Ile, Phe, Lys, Arg, Asn, Glu, Val, Tyr, Trp, Leu, Met, and N-Methyl amino acids including N-Me-Thr, and suitable isostere replacements. In some embodiments, $Xaa^5$ is N(alpha)Methylated. Preferably, $Xaa^5$ is Thr.

For each embodiment of Formula (II-A), $Xaa^6$ is selected from the group consisting of Gln, Asn, Asp, Pro, Gly, Ala, Phe, Leu, Glu, Ile, Val, HLeu, n-Butyl Ala, n-Pentyl Ala, n-Hexyl Ala, Nle, cyclobutyl-Ala, N-Me-Leu, and suitable isostere replacements. In some embodiments, $Xaa^6$ is N(alpha)Methylated. In some embodiments, $Xaa^6$ is Leu.

For each embodiment of Formula (II-A), $Xaa^7$ is selected from the group consisting of Cys, N-Me-Cys, D-Cys, HCys, Pen, D-Pen and Pen(=O). Preferably, in one embodiment $Xaa^7$ is Pen. In another embodiment, $Xaa^7$ is preferably Cys. In particular embodiments of peptides (e.g. peptide momomers, dimers or subunits thereof) of Formula (II-A), $Xaa^7$ is capable of forming a thioether bond with $Xaa^1$. In some embodiments of peptides (e.g. peptide momomers, dimers or subunits thereof) of Formula (II-A), $Xaa^7$ is Cys, D-Cys or HomoCys.

For each embodiment of Formula (II-A), $Xaa^8$ is absent, or $Xaa^8$ is selected from the group consisting of Gly, Gln, Asn, Asp, Ala, Ile, Leu, Val, Met, Thr, Lys, Trp, Tyr, His, Glu, Ser, Arg, Pro, Phe, Sar, 1-Nal, 2-Nal, D-1-Nal, D-2-Nal, D-Phe, D-Tyr, HPhe, Phe(4-F), O-Me-Tyr, dihydro-Trp, Dap, Dab, Dab(Ac), Orn, D-Orn, N-Me-Orn, N-Me-Dap, D-N-Me-Lys, D-Dap, D-Dab, Bip, Ala(3,3diphenyl), Biphenyl-Ala, Phe(4tBu), Phe(4-OMe), Phe(4-COOH), Phe(2-carbomyl), Phe(3-carbomyl), Phe(CF3), Phe(2,4-diCl), Phe(3,4-diCl), Aic, N-Me-Tyr, N-Me-Phe, Tic, Phe(4CF3), aromatic ring substituted Phe, aromatic ring substituted Trp, aromatic ring substituted His, hetero aromatic amino acids, N-Me-Lys, N-Me-Lys(Ac), 4-Me-Phe, and corresponding D-amino acids and suitable isostere replacements. In other embodiments, $Xaa^8$ is N(alpha)Methylated. Further, in some embodiments $Xaa^8$ is acylated.

In some embodiments of Formula (II-A), $Xaa^9$ is absent, or $Xaa^9$ is selected from the group consisting of Glu, Amide, Lys, COOH, Gln, Pro, Gly, His, Ala, Ile, Phe, Lys, Arg, Leu, Val, Tyr, Trp, Met, Gla, Ser, Asn, D-Glu, β-HGlu, 2-Nal, 1-Nal, D-1-Nal, D-2-Nal, D-Phe, D-Tyr, D-Asp, Bip, β-HPhe, β-Glu, D-Tyr, D-Lys, Dap, Dab, Orn, D-Orn, N-Me-Orn, N-Me-Dap, N-Me-Dab, N-Me Lys, D-N-Me-Lys D-Dap, D-Dab, O-Me-Glu, suitable isosteres, and corresponding D-amino acids. Preferably, $Xaa^9$ is Glu, D-Glu, 1-HGlu, Asp, D-His, F(4-COOH), Tic, D-Trp, D-Leu, D-Arg, D-Thr.

For particular embodiments of Formula (II-A), $Xaa^{10}$ may be absent or any amino acid. For certain embodiments, $Xaa^{10}$ may be absent or $Xaa^{10}$ is selected from the group consisting of Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, D-N-Me-Lys N-Me-Lys, D-Dap, D-Dab, COOH, CONH2, suitable isosteres, and corresponding D-amino acids. In at least one embodiment, $Xaa^{10}$ is Lys. Further still in some embodiments $Xaa^{10}$ is D-Lys.

Further, in particular embodiments of Formula (II-A) directed to peptide monomers, $Xaa^{11}$ is absent or any amino acid. In certain embodiments directed to peptide monomers, $Xaa^{11}$ is selected from the group consisting of Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Omr, N-Me-Dap, N-Me-Dab, D-N-Me-Lys, N-Me-Lys, D-Dap, D-Dab, COOH, CONH2, suitable isosteres, and corresponding D-amino acids. In at least one embodiment, $Xaa^{11}$ is Lys. Further still in some embodiments $Xaa^{11}$ is D-Lys.

In particular embodiments of Formula (II-A) directed to peptide dimer subunits, $Xaa^{11}$ is absent or selected from the group consisting of Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, D-N-Me-Lys, N-Me-Lys, D-Dap, D-Dab, Cys, HomoSys, Pen, suitable isosteres, and corresponding D-amino acids, and amino acids comprising a free amine group. In at least one embodiment, $Xaa^{11}$ is Lys. Further still in some embodiments $Xaa^{11}$ is D-Lys. In at least one embodiment, $Xaa^{11}$ is the C-terminus. When $Xaa^{11}$ is the C-terminus of the subunit, $Xaa^{11}$ may be modified to include a linker moiety in accordance with the present invention.

In particular embodiments of Formula (II-A), $Xaa^9$ is not O-Me-Glu, and it absent or selected from the group consisting of Glu, Amide, Lys, COOH, Gin, Pro, Gly, His, Ala, Ile, Phe, Lys, Arg, Leu, Val, Tyr, Trp, Met, Gla, Ser, Asn, D-Glu, β-HGlu, 2-Nal, 1-Nal, D-1-Nal, D-2-Nal, D-Phe, D-Tyr, D-Asp, Bip, β-HPhe, β-Glu, D-Tyr, D-Lys, Dap, Dab, Orn, D-Orn, N-Me-Orn, N-Me-Dap, N-Me-Dab, N-Me Lys, D-N-Me-Lys D-Dap, D-Dab, O-Me-Glu, suitable isosteres, and corresponding D-amino acids.

In particular embodiments of peptide monomers and dimer subunits, e,g,m those of Formula (II) or (VI), $Xaa^{8-11}$ are absent, whereby $Xaa^7$ is the C-terminus. When $Xaa^{9-11}$ are absent, $Xaa^8$ is the C-terminus. Similarly, when $Xaa^{10}$ and $Xaa^{11}$ are absent, $Xaa^9$ is the C-terminus. Further, when $Xaa^{11}$ is absent, $Xaa^{10}$ is the C-terminus. In certain embodiments, $Xaa^{8-10}$ are absent, and $Xaa^{11}$ is the C-terminus. In certain embodiments, $Xaa^8$ is present, $Xaa^{9-10}$ are absent and $Xaa^{11}$ is the C-terminus. In certain embodiments, $Xaa^8$ and $Xaa^9$ are present, $Xaa^{10}$ is absent and $Xaa^{11}$ is the C-terminus. In some embodiments of peptide monomers or dimers, the C-terminus of the thioether peptide is modified to include a modifying group or linker in accordance with the present invention.

For certain embodiments of Formula (II-A), a thioether bond exists between $Xaa^1$ and $Xaa^7$. Thus, the thioether peptides of the present invention may be cyclized through a thioether bond. In one embodiment, $Xaa^7$ is Cys. In another embodiment, preferably $Xaa^7$ is Pen. In other embodiments, $Xaa^7$ is D-Cys or homo-Cys. In certain embodiments, $Xaa^1$ is Homo-Ser-Cl, and $Xaa^7$ is Cys, D-Cys or HomoCys.

In some embodiments of peptide monomer, the C-terminal residue of Formula (II) or (II-A) further comprises a modifying group selected from the group consisting of DIG, PEG4, PEG13, PEG25, PEG1K, PEG2K, PEG4K, PEG5K, Polyethylene glycol having molecular weight from 400 Da to 40,000 Da, PEG having a molecular weight of 40,000 Da to 80,000 Da, IDA, Ac-IDA, ADA, Glutaric acid, Isophthalic acid, 1,3-phenylenediacetic acid, 1,4-phenylenediacetic acid, 1,2-phenylenediacetic acid, AADA, suitable aliphatic acids, suitable aromatic acids, heteroaromatic acids. In some embodiments, the C-terminus of the thioether peptide comprises $NH_2$ or OH.

Some embodiments of the peptide monomers of the present invention comprise a peptide molecule comprising an N(alpha)-Me-Arg residue, as represented by at least one of SEQ ID NOs: 1-32.

In one embodiment, a thioether peptide of the present invention comprises one or two peptide dimer subunits or a peptide monomer of Formula (A) (SEQ ID NO: 48):

(Formula (A))
$Xaa^1-Xaa^2-Xaa^3-Xaa^4-Xaa^5-Xaa^6-Xaa^7-Xaa^8-Xaa^9-Xaa^{10}$, or a pharmaceutically acceptable salt thereof, wherein $Xaa^1$ comprises an aromatic group capable of forming a thioether bond with Xaa7, such as a 2-methylbenzoyl moiety;

$Xaa^2$ is N-methyl-Arg;

$Xaa^3$ is Ser, Gly, Thr, or Ile; and wherein in some embodiments if Formula (A) is directed to a peptide monomer then $Xaa^3$ is Ser, Gly, Thr, or Ile; and wherein in other embodiments if Formula (A) is directed to a peptide dimer subunit then $Xaa^3$ is Ser, and $Xaa^4$ is Asp;

$Xaa^5$ is Thr;

$Xaa^6$ is Leu or Nle;

$Xaa^7$ is Cys, D-Cys, Hcys, or Pen;

$Xaa^8$ is Trp, Tic, Bip, 1-Nal, 2-Nal, Phe(4tBu), or Phe(4-COOH);

$Xaa^9$ is Glu, β-homo-Glu, or D-Glu;

Formula (A) is directed to a peptide monomer and $Xaa^{10}$ is any amino acid; or Formula (A) is directed to a peptide dimer subunit, and $Xaa^{10}$ is Lys, D-Lys, N-Me-Lys or D-N-Me-Lys; and wherein the peptide molecule comprises a thioether bond between $Xaa^1$ and $Xaa^7$.

In particular embodiments of Formula (A), $Xaa^{10}$ is D-Lys or N-Me-Lys.

In certain embodiments, $Xaa^{10}$ or the C-terminus of the peptide comprises an $NH_2$ or an OH.

In certain embodiments of peptide monomers, a free amine in the C-terminal amino acid is capped, e.g., with an acetyl group.

Illustrative thioether peptide dimers (and subunits thereof) and peptide monomers of the present invention are shown in the accompanying figures and sequence listing.

In certain embodiments, a thioether peptide monomer, dimer or peptide subunit of a dimer, optionally a homodimer, of the present invention comprises Formula (III) (SEQ ID NO: 46):

(Formula (III)
$Xaa^1-Xaa^2-Xaa^3-Xaa^4-Xaa^5-Xaa^6-Xaa^7-Xaa^8-Xaa^9-Xaa^{10}$ or a pharmaceutically acceptable salt thereof, wherein the thioether peptide comprises a thioether bond between $Xaa^1$ and $Xaa^7$ in the peptide monomer or in one or both peptide monomer subunits, wherein the two subunits of Formula (III) of a peptide dimer are dimerized at their C-termini via a linker, e.g., DIG, and wherein $Xaa^1$ is 2-methylbenzoyl;

$Xaa^2$ is N-Me-Arg;

$Xaa^3$ is Ser, Gly, Thr, or Ile; or $Xaa^4$ is Asp;

$Xaa^5$ is Thr; and $Xaa^6$ is Leu or Nle; or $Xaa^7$ is Pen, Cys or d-Cys; or $Xaa^8$ is Phe, D-Phe, Tyr, Bip, Tic, 1-Nal, 2-Nal, or Trp;

$Xaa^9$ is D-Glu, Glu, Tyr, b-homo-Glu, or 2-Nal; and $Xaa^{10}$ is D-Lys, N-Me-D-Lys, Dap, Phe, D-Phe or absent.

In certain embodiments, Formula (III) is directed to a peptide monomer wherein:

$Xaa^1$ is 2-methylbenzoyl;

$Xaa^2$ is N-Me-Arg;

$Xaa^3$ is Ser, Gly, Thr, or Ile;

$Xaa^4$ is Asp;

$Xaa^5$ is Thr;

$Xaa^6$ is Leu or Nle;

$Xaa^7$ is Pen, Cys or d-Cys;

$Xaa^8$ is Phe, D-Phe, Tyr, 1-Nal, 2-Nal, or Trp;

Xaa⁹ is D-Glu, Glu, Tyr, b-homo-Glu, or 2-Nal; and
Xaa¹⁰ is D-Lys, N-Me-D-Lys, Dap, Phe, D-Phe or absent.

In certain embodiments, Formula (III) is directed to a peptide dimer subunit wherein:
Xaa¹ is 2-methylbenzoyl;
Xaa² is N-Me-Arg;
Xaa³ is Ser;
Xaa⁴ is Asp;
Xaa⁵ is Thr;
Xaa⁶ is Leu;
Xaa⁷ is Pen or, Cys;
Xaa⁸ is Phe, Tyr, Bip, Tic, 2-Nal, or Trp;
Xaa⁹ is D-Glu; and
Xaa¹⁰ is D-Lys.

In certain embodiments of peptide monomers, Xaa¹⁰ is acetylated or comprises a modifying group, e.g., PEG8.

In certain embodiments, the C-terminus of a peptide monomer or subunit of a peptide dimer comprises an NH₂ or an OH. In particular embodiments, the C-terminus of a peptide dimer subunit comprises an NH₂ or an OH either before or after dimerization.

In certain embodiments, a thioether peptide, e.g. a peptide monomer or peptide dimer, optionally a homodimer, of the present invention comprises Formula (IV) (SEQ ID NO: 47):

(Formula (IV))
Xaa¹-Xaa²-Xaa³-Xaa⁴-Xaa⁵-Xaa⁶-Xaa⁷-Xaa⁸-Xaa⁹-Xaa¹⁰ or a pharmaceutically acceptable salt thereof, wherein the thioether peptide comprises a thioether bond between Xaa¹ and Xaa⁷ in the peptide monomer or in one or both peptide subunits of a peptide dimer, wherein the two subunits of Formula (IV) are dimerized at their C-termini via a linker, e.g., DIG, and wherein
Xaa¹ is 2-methylbenzoyl;
Xaa² is N-Me-Arg;
Xaa³ is Ser;
Xaa⁴ is Asp;
Xaa⁵ is Thr;
Xaa⁶ is Leu or Nle;
Xaa⁷ is Pen, Cys, homoCys, Pen(=O), or D-Cys; wherein in certain embodiments, if Formula (IV) is directed to a peptide monomer, then Xaa⁷ is Pen, Cys, homoCys, or D-Cys;
Xaa⁸ is Phe, D-Phe, Tyr, D-Tyr, His, Bip, Tic, 1-Nal, 2-Nal, F(CH3), F(2,4-diCl), F(3,4-diCl), Aic, N-Me-Tyr, N-Me-Phe, F(2-carbomyl), F(3-carbomyl), F(4-COOH), F(4OMe), F(4tBu), F-(4-F), F(4CF3), or Trp; and
Xaa⁹ is absent, Glu, β-homo-Glu, Bip, O-Me-Glu, D-Lys, D-Phe, Tyr, 2-Nal, D-Tyr, Pro, Tic, D-Glu, D-Thr, D-Arg, D-Leu, D-Trp, F(4-COOH), D-His, Pro, D-Pro, or E(OMe); wherein in some embodiments, if Formula (IV) is directed to a peptide dimer subunit, then Xaa⁹ is Glu, β-homo-Glu, Bip, O-Me-Glu, D-Lys, D-Phe, Tyr, 2-Nal, D-Tyr, Pro, Tic, D-Glu, D-Thr, D-Arg, D-Leu, D-Trp, F(4-COOH), D-His, Pro, D-Pro, or E(OMe);
wherein in some embodiments, if Formula (IV) is directed to a peptide monomer, then Xaa¹⁰ is absent or any amino acid residue; and
wherein in other embodiments, if Formula (IV) is directed to a peptide dimer subunit, then Xaa¹⁰ is D-Lys, N-Me-Lys, N-Me-D-Lys, Lys, Dap, Dab, D-Dab, D-Dap, Orn N-Me-Orn, D-Orn.

In certain embodiments of the peptide monomer or peptide dimer, Xaa¹⁰ or the C-terminal amino acid does not comprise a free amine. In particular embodiments of the peptide monomer or peptide dimer, Xaa¹⁰ is D-Lys, N-Me-Lys, N-Me-D-Lys, Dap, Phe, Ser, Glu, or absent.

In certain embodiments of Formulas (II), (II-A), (A), (III), (IV), (VI) or Formula (VI), Xaa⁸ may also be Bpa, Phe(3-Me), Phe(2-Me), Phe(2-CF3), or β-Me-Phe.

In certain embodiments of Formulas (II), (II-A), (A), (III), (IV), (VI) or Formula (VI), Xaa⁹ may also be N-Me-Glu, N-Me-Asp, or alpha-H-Glu.

In certain embodiments of Formulas (II), (II-A), (A), (III), (IV), (VI) or Formula (VI), e.g., when the peptide is a dimer, Xaa¹⁰ is selected from the group consisting of: Lys, D-Lys, N-Me-Lys, D-N-Me-Lys, Orn, Dab, Dap, Homo-Lys, D-Dap, D-Dab, Cys, HomoCys, Pen, or D-Orn, while in other embodiments, Xaa¹⁰ is selected from D-Lys, N-Me-Lys, and D-N-Me-Lys.

In certain embodiments of the peptide monomers or peptide dimers described herein, the N-terminus of the peptide is acylated.

In certain embodiments of the peptide monomers and dimer subunits, Xaa¹⁰ or the C-terminus of each peptide or peptide subunit comprises an NH₂ or an OH. In certain embodiments of the peptide dimer subunits, the C-terminus of comprises an NH₂ or an OH either before or after dimerization.

In certain embodiments of peptide monomers described herein, a free amine in the C-terminal amino acid is capped, e.g., with an acetyl group.

Particular aspects of the present invention relate to peptide inhibitors of α4β7 comprising the following core consensus sequence (shown left to right from N-term to C-term):

(SEQ ID NO: 390)
Y-(N-Me-Arg)-Ser-Glu-Thr-Leu-X wherein Y is a 2-methyl benzoyl moiety capable of forming a thioether bond with X, and wherein X is an amino acid residue selected from Pen, Cys, D-Cys and HomoCys. In particular embodiments, X is Pen. In particular embodiments, the core sequence comprises an intramoleculer thioether bond between X and Y. In particular embodiments, the peptide inhibitor is a monomer. In particular embodiments, the peptide inhibitor is a dimer comprising two peptide monomer subunits, each comprising this core sequence. In particular embodiments, the monomer peptide inhibitor comprises 7-15 amino acid residues. In particular embodiments, each monomer subunit of the dimer peptide inhibitor comprises 7-15 amino acid residues. In certain embodiments, the two monomer subunits are linker via their respective N- or C-termini. In particular embodiments, they are linker by each of their C-termini. In certain embodiments, the peptide inhibitor further comprises an aromatic amino acid immediately downstream of X. In particular embodiments, any of the peptides described herein may comprise this core sequence.

In some embodiments, the N- or C-terminal residue of Formula (I), Formula (II), Formula (III), Formula (IV), Formula (V), Formula (VI) Formula (I-A), Formula (II-A), Formula (A), or any of the other peptide monomers or peptide subunits of dimer molecules described herein, further comprises a modifying group or suitable linker moiety selected from the group consisting of: DIG, PEG4, PEG13, PEG25, PEG1K, PEG2K, PEG4K, PEG5K, Polyethylene glycol having molecular weight from 400 Da to 40,000 Da, PEG having a molecular weight of 40,000 Da to 80,000 Da, IDA, Ac-IDA, ADA, Glutaric acid, Isophthalic acid, 1,3-phenylenediacetic acid, 1,4-phenylenediacetic acid, 1,2-phenylenediacetic acid, AADA, suitable aliphatic acids, suitable aromatic acids, heteroaromatic acids.

Particular embodiments of the present invention relate to a peptide dimer comprising a linker. When the linker is IDA, ADA or any linker with free amine, it can be acylated with acylating organic compound selected from the group consisting of 2-me-Trifluorobutyl, Trifluoropentyl, Acetyl, Octonyl, Butyl, Pentyl, Hexyl, Palmityl, Lauryl, Oleoyl, Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid, straight chain aliphatic acids with 10 to 20 carbon units, cholic acid and other bile acids. In some instances small PEG (PEG4-PEG13), Glu, Asp, is used as spacer before acylations.

Some embodiments of the present invention comprise a peptide monomer or dimer molecule comprising an N(alpha)-Me-Arg residue, as represented by at least one of SEQ ID NOs: 1-23.

In certain embodiments, a peptide monomer or at least one subunit of a peptide dimer molecule of the present invention comprises, consists essentially of, or consists of an amino acid sequence or structure described herein, including any of the amino acid sequences shown in the accompanying sequence listing or figures, with or without any indicated N- or C-terminal modifications, linkers or modifying group. In certain embodiments, a peptide dimer molecule of the present invention comprises two peptide monomer subunits, each having an amino acid sequence or structure described herein, including any of the amino acid sequences shown in the accompanying sequence listing or figures, with or without any indicated N- or C-terminal modifications, linkers or modifying group. In particular embodiments, a peptide monomer or one or both of the peptide monomer subunits present in a peptide dimer molecule includes a thioether intramolecular linkage, e.g., a thioether bond between two amino acids within the peptide or subunit. In particular embodiments, the peptide subunits of a peptide dimer molecule are dimerized via their N- or C-termini, e.g., using a suitable linker such as DIG.

In certain embodiments of the peptide dimer molecules, the present invention includes a peptide subunit comprising, consisting essentially of, or consisting of an amino acid sequence or structure described herein, including any of the amino acid sequences shown in the accompanying sequence listing or figures, with or without any indicated N- or C-terminal modifications, linkers or modifying group. In certain embodiments, the peptide subunit includes a thioether intramolecular linkage, e.g., a thioether bond between two amino acids within the peptide subunit. In particular embodiments, the peptide monomer subunit comprises a linker moiety, e.g., DIG, at it N- or C-termini.

In certain embodiments of any of the peptide monomers or dimer peptide subunits described herein, including those of Formula (I)-(VI) and Tables 4 and 5, or of the figures herein, the peptide monomer or subunit comprises a thioether bond. In certain embodiments, with respect to Formula (I) or (V), the thioether bond exists between $Xaa^4$ and $Xaa^{10}$, wherein with respect to Formulas (II)-(IV) and (VI), the thioether bond exists between $Xaa^1$ and $Xaa^7$. In certain embodiments, the thioether is formed between a 2-methyl benzoyl moiety (e.g., at $Xaa^4$ in Formula (I) or $Xaa^1$ in Formula (II)) and either Pen or Cys (e.g., at $Xaa^{10}$ in Formula (I) or $Xaa^7$ in Formula (II)). In particular embodiments, the 2-methyl benzoyl moiety forms an amide bond with an adjacent amino acid residue and comprises a methyl group forming a thioether bond with the Pen or Cys residue.

In particular embodiments of any of the various Formulas described herein, peptides having the same structure or sequence as disclosed in any one or more of PCT/US2013/064439, PCT/US2014/032391 or PCT/US2014/032392 are excluded. In other embodiments of the present invention, the peptides comprise a sequence or structure set forth in any of PCT/US2013/064439, PCT/US2014/032391 or PCT/US2014/032392.

Peptide Molecule Structure and Biological Activity

The present invention provides various novel antagonist peptide monomers and peptide dimers, including peptide monomers and dimer molecule subunits which are cyclized through a thioether bond. These peptide molecules have been tested to more clearly characterize the increased affinity for α4β7 binding, increased selectivity against α4β1, and increased stability in simulated intestinal fluid (SIF) as well as in gastric environment under reduced conditions. These novel antagonist molecules demonstrate high binding affinity with α4β7, thereby preventing binding between α4β7 and the MAdCAM ligand. Accordingly, these peptide molecules have shown to be effective in eliminating and/or reducing the inflammation process in various experiments.

The present invention thus provides various thioether peptide monomer and dimer molecules which bind or associate with the α4β7 integrin, e.g., in serum, SIF, or SGF, to disrupt or block binding between α4β7 and the MAdCAM ligand. Some peptide monomer or peptide subunits of the invention may be constructed solely of natural amino acids. Alternatively, the peptide monomer and dimer molecules may include non-natural amino acids including, but not limited to, modified amino acids and suitable aromatic acid groups, namely a 2-methylbenzoyl moiety. Modified amino acids include natural amino acids which have been chemically modified to include a group, groups, or chemical moiety not naturally present on the amino acid. The thioether peptide momoner and dimer molecules of the present invention may additionally include D-amino acids.

In certain embodiments, peptide dimer and monomer molecules of the present invention inhibit or reduce binding between α4β7 and the MAdCAM ligand. In certain embodiments, a peptide of the present invention reduces binding of α4β7 and the MAdCAM ligand by at least 20%, at least 30%, at least 40%, at least 50%, at least 60%, at least 70%, at least 80%, or at least 90% as compared to a negative control peptide. Methods of determining binding are known in the art and described herein, and include ELISA assays, for example.

In certain embodiments, a peptide monomer or dimer molecule of the present invention has an IC50 of <500 nM, <250 nM, <100 nM, <50 nM, <25 nM, or <10 nM.

Methods of determining activity are known in the art and include any of those described in the accompanying Examples.

Some antagonist thioether cyclized peptide monomer and dimer molecules have been shown to be gastrointestinal stable and provide high levels of specificity and affinity for the α4β7 integrin. Some implementations of the present invention provide a peptide monomer or dimer molecule comprising a half-life of greater than 180 minutes when exposed to simulated intestinal fluids (SIF). Some implementations further provide a thioether peptide monomer or dimer molecule comprising a half-life from approximately 1 minute to approximately 180 minutes. Similarly these peptides are stable to gastric environment under reduced conditions with half-life >120 min when tested in DTT (Dithiothreitol) assay.

In certain embodiments, a peptide monomer or dimer molecule of the present invention has increased stability, increased gastrointestinal stability, or increased stability in stimulated intestinal fluid (SIF), as compared to a control peptide. In particular embodiments, a control peptide is a peptide having the identical or a highly related amino acid sequence (e.g., >90% sequence identity) as the peptide monomer or dimer molecule, but which does not form a cyclized structure through a thioether bond. In some embodiments relating to dimer molecules, the control peptide is not dimerized. In particular embodiments, the only difference between the peptide monomer or dimer molecule and the control peptide is that the peptide comprises one or more amino acid substitutions that introduce one or more amino acid residues into the peptide, wherein the introduced residue(s) forms a thioether bond with another residue in the peptide.

Methods of determining the stability of a peptide are known in the art. In certain embodiments, the stability of a peptide (e.g. a peptide monomer or dimer as described herein) is determined using an SIF assay, e.g., as described in the accompanying Examples.

In particular embodiments, a peptide monomer or dimer molecule of the present invention has a half-life under a given set of conditions (e.g., temperature) of greater than 1 minute, greater than 10 minutes, greater than 20 minutes, greater than 30 minutes, greater than 60 minutes, greater than 90 minutes, greater than 120 minutes, greater than 3 hours, or greater than four hours when exposed to SIF. In certain embodiments, the temperature is about 25° C., about 4° C., or about 37° C., and the pH is a physiological pH, or a pH about 7.4.

In some embodiments, the half-life is measured in vitro using any suitable method known in the art, e.g., in some embodiments, the stability of a peptide monomer or dimer molecule of the present invention is determined by incubating the peptide with pre-warmed human serum (Sigma) at 37° C. Samples are taken at various time points, typically up to 24 hours, and the stability of the sample is analyzed by separating the peptide monomer or dimer from the serum proteins and then analyzing for the presence of the peptide monomer or dimer of interest using LC-MS.

In some embodiments, a peptide monomer or dimer molecule of the present invention exhibits improved solubility or improved aggregation characteristics as compared to a control peptide. Solubility may be determined via any suitable method known in the art.

In some embodiments, suitable methods known in the art for determining solubility include incubating peptides in various buffers (Acetate pH4.0, Acetate pH5.0, Phos/Citrate pH5.0, Phos Citrate pH6.0, Phos pH 6.0, Phos pH 7.0, Phos pH7.5, Strong PBS pH 7.5, Tris pH7.5, Tris pH 8.0, Glycine pH 9.0, Water, Acetic acid (pH 5.0 and other known in the art) and testing for aggregation or solubility using standard techniques. These include, but are not limited to, visual precipitation, dynamic light scattering, Circular Dichroism and fluorescent dyes to measure surface hydrophobicity, and detect aggregation or fibrillation, for example.

In some embodiments, improved solubility means the peptide monomer or dimer is more soluble in a given liquid than is a control peptide.

In some embodiments, the peptide monomer and dimer molecules of the present invention have less degradation (i.e., more degradation stability), e.g., greater than or about 10% less, greater than or about 20% less, greater than or about 30% less, greater than or about 40 less, or greater than or about 50% less degradation than a control peptide. In some embodiments, degradation stability is determined via any suitable method known in the art. In some embodiments, suitable methods known in the art for determining degradation stability include the method described in Hawe et al J Pharm Sci, VOL. 101, NO. 3, 2012, p 895-913, incorporated herein in its entirety. Such methods are in some embodiments used to select potent peptide monomer or dimer molecules with enhanced shelf lives.

In some embodiments, peptide dimer or monomer molecules of the present invention have increased redox stability as compared to a control peptide. Methods of determining redox stability are described herein.

In certain embodiments, peptide dimer or monomer molecules of the present invention inhibit or reduce α4β7-mediated inflammation. In related embodiments, peptide monomers or dimers of the present invention inhibit or reduce α4β7-mediated secretion of one or more cytokines. Methods of determining inhibition of cytokine secretion and inhibition of signaling molecules are known in the art.

In certain embodiments, peptide monomer or dimer molecules of the present invention demonstrate increased binding selectivity. In certain instances, peptide monomers or dimers of the present invention binds to α4β7 with at least a two-fold, three-fold, five-fold, or ten-fold greater affinity than the monomers or dimers bind to α4β1.

The peptide monomer or dimer molecules of the present invention demonstrate increased potency as a result of substituting various natural amino acyl residues with N-methylated analog residues. In particular embodiments, potency is measured as IC50 of binding to α4β7, e.g., determined as described herein, while in some embodiments, potency indicates functional activity, e.g., according to a cell adhesion assay as described herein or a PBMC assay described herein. For example, SEQ ID NOs.: 1-32 represent peptide monomer or subunit sequences that are substituted with N(alpha)methylated arginine.

In particular embodiments, any of these superior characteristics of the peptides of the present invention are measured as compared to a control peptide, e.g., a peptide shown in Table 8.

Referring now to FIG. 6 and Tables 5 and 7, charts are provided which include various data illustrating increased potency and/or stability for various non-limiting sample thioether peptide dimer molecules in accordance with the instant invention.

Simulated Intestinal Fluid (SIF) Stability assays were performed for the majority of the dimer molecules. A selective sampling of these results is provided in FIG. 6. Indicated thioether peptides in FIG. 6 represent a non-limiting, representative group of dimer peptides with stability of greater than 180 minutes (half-life) in SIF. These thioether dimer compounds further represent IC50 values of less than 25 nM in ELISA as well as cell adhesion assays, further demonstrating their high selectivity for α4β7. For other peptides in FIG. 6, it is expected that they will have an IC50<50 nM in α4β7 ELISA or cell adhersion assays.

Referring now to FIGS. 7 and 8 and Tables 4 and 6, charts are provided which includes various data illustrating increased potency for various non-limiting illustrative thioether peptide monomers in accordance with the instant invention. Potency assays were performed for all peptide molecules represented by SEQ ID NOs: 22 and 23 and additional peptides as shown. Selectivity assays (for α4β1) were performed for certain thioether peptides. A selective sampling of these results is provided in FIGS. 7 and 8. Improvements in potency for α4β7 were tested in both ELISA and cell adhesion assays.

According to the protocols discussed herein, applicant successfully synthesized and purified all of the integrin antagonist thioether peptides (e.g. peptide monomers and peptide dimers) represented by SEQ ID NOs: 22 to 24 and additional peptides shown in Tables 4-7 and FIGS. 6-8. The majority of these molecules were subjected to an α4β7-MAdCAM Competition ELISA assay, an α4β1-VCAM Competition ELISA assay, and an α4β7-MadCAM cell adhesion assay. Results are provided in Tables 6-7 and FIGS. 6-8.

The thioether peptides shown in FIG. 7 represent a non-limiting, representative group of peptides with IC50 values less than 50 nM in ELISA assays. The peptides further represent IC50 values of less than 300 nM in cell adhesion assays. For other peptides with data not shown, it is expected that they will have an IC50<50 nM in α4β7 ELISA or cell adhersion assays.

When Arg is replaced with N-Me-Arg, a significant improvement in potency for α4β7 was shown in both ELISA and cell adhesion assays. N(alpha)methylation further demonstrated increased molecular stability. One having skill in the art will appreciate that methylated isosteres of arginine may further demonstrate similar increases in potency and/or stability.

Referring now to FIGS. 6 and 8 charts are provided which include data illustrating increased stability for various non-limiting sample thioether peptide molecules in accordance with the instant invention. Simulated Intestinal Fluid (SIF) Stability assays were performed for the majority of the peptide molecules. A selective sampling of these results is provided in FIGS. 6 and 8. The thioether peptides in FIGS. 6 and 8 represent a non-limiting, representative group of peptides with stability of greater than 180 minutes (half-life) in SIF.

Methods of Manufacture and Enhancing Peptide Stability

The peptides (e.g. peptide monomers or peptide dimers) of the present invention may be synthesized by techniques that are known to those skilled in the art. Such techniques include the use of commercially available robotic protein synthesizers (e.g. Symphony multiplex peptide synthesizer from Protein Technologies). In some embodiments, novel peptide monomers or dimer subunits are synthesized and purified using techniques described herein.

Certain aspects of the present invention contemplate peptides comprising thioether bonds. Thioether bonds are cyclized covalent bonds formed between an upstream amino acid or aromatic acid group and a downstream sulfur-containing amino acid or isotere thereof. Thioether bonds of the present invention may be generated using standard techniques in the art, including those described herein. Particular aspects contemplate that the generation of a thioether bond increases gastrointestinal stability of a peptide molecule. Thus, in particular embodiments, gastrointestinal stability of a peptide can be increased by cyclizing the peptide via a thioether bond.

In some embodiments, monomeric subunits of the present invention may be dimerized to form homomeric or heteromeric dimer peptides through known techniques in the art. In certain embodiments, peptide subunits described herein are joined by linker moieties (e.g. linkers shown in Table 3) conjugated at the N or C-termini. A linker may be conjugated to peptide subunit at a C- or N-terminal free amine through techniques known in the art, including but not limited to techniques described herein. Some embodiments contemplate that dimerization of the peptide molecule increases stability, potency, and/or specificity as compared to non-dimerized monomeric subunits of the peptide.

Certain aspects of the present invention contemplate amino acid substitutions that increase stability of a peptide monomer or peptide dimer in different contexts. Accordingly, in certain embodiments, the present invention includes modifying a peptide molecule, e.g., a peptide molecule described herein or Substitutions may be performed by standard techniques known to those of skill in the art. In some embodiments, stability of a peptide (e.g. a peptide monomer or dimer described herein or in Dubree, et al., Selective α4β7 Integrin Antagonist and Their Potential as Anti-inflammatory Agents, *J. Med. Chem.* 2002, 45, 3451-3457) in simulated intestinal fluids (SIF) is increased by substituting N-Me-Arg for one or more unmethylated arginine residues. In particular embodiments, SIF or gastrointestinal stability of a peptide is increased by substituting Pen for one or more cysteine residues. Certain aspects of the present invention contemplate amino acid substitutions that increase redox stability (i.e. increasing the resistance of a peptide to a change in its oxidation state) of a peptide monomer or peptide dimer described herein. In particular embodiments, redox stability is determined by an assay described herein. In particular embodiments, redox stability is increased by at least 20%, at least 50%, at least 2-fold, at least 3-fold, at least 4-fold, at least 5-fold, or at least 10-fold as compared to a control peptide. Substitutions may be performed by standard techniques known to those of skill in the art. In some embodiments, redox or gastrointestinal stability of a peptide (e.g. peptide monomer or dimer described herein) is increased by substituting N-Me-Arg for one or more unmethylated arginine residues.

In particular embodiments, the invention provides a method for stabilizing a peptide molecule, e.g., a peptide molecule described herein, comprising cyclizing the peptide molecule by forming a thioether bond between $Xaa^4$ and $Xaa^{10}$.

In certain embodiments, the invention includes a method for stabilizing a peptide molecule, e.g., of Formula (II), comprising: substituting $Xaa^1$ with an aromatic acid group capable of forming a thioether bond with $Xaa^7$; substituting $Xaa^7$ with an amino acid residue that is capable of forming a thioether bond with $Xaa^1$; and forming a thioether bond between $Xaa^1$ and $Xaa^7$ to provide a cyclized peptide. In certain embodiments, $Xaa^7$ is selected from the group consisting of Cys, N-Me-Cys, D-Cys, HCys, Pen, and D-Pen. In certain embodiments, $Xaa^1$ is a 2-methylbenzoyl moiety. The same method applies to peptide molecules, e.g., of Formula (I), where Xaa4 and Xaa10 are substituted and cyclized instead of Xaa1 and Xaa7, respectively.

Methods of Treatment and Pharmaceutical Compositions

In some embodiments, the present invention provides a method for treating an individual or subject afflicted with a condition or indication characterized by integrin binding, wherein the method comprises providing or administering to the individual or subject an integrin antagonist thioether peptide molecule described herein, e.g., as represented by SEQ ID NOs: 1-384 or shown in Tables 5-7. In particular embodiments, the individual or subject is provided with or administered with a pharmaceutical composition comprising the peptide monomer or peptide dimer of the invention. In particular embodiments, subjects or individuals are mammals, e.g., humans or non-human mammals, such as a dog, cat or horse.

In one embodiment, a method is provided for treating an individual or subject afflicted with a condition or indication characterized by inappropriate trafficking of cells expressing α4β7 to tissues comprising cells expressing MAdCAM, comprising administering to the individual or subject an α4β7-antagonist peptide molecule described herein, e.g., SEQ ID NOs: 1-384 or Tables 4 and 5, in an amount sufficient to inhibit (partially or fully) the trafficking of cells expressing α4β7 to tissues comprising cells expressing MAdCAM.

In a further related embodiments, the present invention includes a method for treating a condition in a subject or individual in need thereof, wherein the condition is treatable by reducing the activity (partially or fully) of α4β7 in the subject, comprising providing or administering an α4β7-antagonist peptide molecule described herein to the subject. In particular embodiments, the condition is an inflammatory condition of the gastrointestinal system.

In a further related embodiments, the present invention includes a method for treating a subject, e.g., a mammal or human, afflicted with a condition that is associated with a biological function α4β7, comprising providing or administering to the subject a thioether peptide molecule described herein, e.g., a peptide monomer or peptide dimer having a structure of Formula (I) or (II), in an amount sufficient to inhibit (partially or fully) the biological function of α4β7 to tissues expressing MAdCAM. In particular embodiments, the subject is provided with an effective amount of the peptide monomer or peptide dimer sufficient to at least partially inhibit the biological function of α4β7 to tissues expressing MAdCAM. In certain embodiments, the condition is inflammatory bowel disease. In additional embodiments, the invention includes a method of treating or preventing a disease or condition in a subject in need thereof, comprising providing or administering to the subject, e.g., a mammal, an effective amount of a peptide dimer or peptide monomer described herein, wherein the disease or condition is selected from the group consisting of Inflammatory Bowel Disease (IBD) (including adult IBD, pediatric IBD and adolescent IBD), ulcerative colitis, Crohn's disease, Celiac disease (nontropical Sprue), enteropathy associated with seronegative arthropathies, microscopic colitis, collagenous colitis, eosinophilic gastroenteritis, radiotherapy, chemotherapy, pouchitis resulting after proctocolectomy and ileoanal anastomosis, gastrointestinal cancer, pancreatitis, insulin-dependent diabetes mellitus, mastitis, cholecystitis, cholangitis, pericholangitis, chronic bronchitis, chronic sinusitis, asthma, primary sclerosing cholangitis, human immunodeficiency virus (HIV) infection in the GI tract, eosinophilic asthma, eosinophilic esophagitis, gastritis, colitis, microscopic colitis and graft versus host disease (GVDH) (including intestinal GVDH). In particular embodiments of any of the methods of treatment described herein, the subject has been diagnosed with or is considered to be at risk of developing one of these diseases or conditions.

In particular embodiments of any of the methods of treatment described herein, the peptide molecule (or pharmaceutical composition comprising the peptide molecule) is administered to the individual by a form of administration selected from the group consisting of oral, intravenous, peritoneal, intradermal, subcutaneous, intramuscular, intrathecal, inhalation, vaporization, nebulization, sublingual, buccal, parenteral, rectal, vaginal, and topical.

In certain embodiments, the α4β7 integrin antagonist peptide molecule comprises an increased half-life as compared to other peptides. In particular embodiments, the increased half-life is at least one day in vitro or in vivo. In certain embodiments wherein the increased half-life is equal to or greater than a period consistent with no more frequent than twice daily dosing in vivo, the α4β7 integrin antagonist peptide molecule is provided in a pharmaceutical preparation that is administered orally. In certain embodiments wherein the increased half-life is from approximately 12 hours to greater than 24 in vivo, the α4β7 integrin antagonist peptide molecule is provided in a pharmaceutical preparation that is administered parenterally. In certain embodiments when the increased half-life is from approximately 12 hours to greater than 24 hours in vivo, the α4β7 integrin antagonist peptide molecule is provided in a pharmaceutical preparation that is administered topically.

In some embodiments, the present invention provides a method whereby a pharmaceutical composition comprising an integrin antagonist thioether peptide molecule described herein, e.g., SEQ ID NOs: 1-384 or Tables 4 or 5, is administered to a subject or patient as a first treatment. In another embodiment, the method further comprises administering to the subject a second treatment, i.e., a second active agent. In another embodiment, the second treatment or active agent is administered to the subject before and/or simultaneously with and/or after the pharmaceutical composition is administered to the subject. In other embodiment, the second treatment or active agent comprises an anti-inflammatory agent. In another embodiment, the second treatment or active agent (which may be present in a pharmaceutical composition) comprises an agent selected from the group consisting of non-steroidal anti-inflammatory drugs, steroids, and immune modulating agents. In another embodiment, the method comprises administering to the subject a third treatment.

The thioether peptide monomer and dimer molecules of the invention, including but not limited to those specified in the examples, possess integrin-antagonist activity. In certain embodiments, peptide integrin inhibitors (e.g. thioether peptide monomers and dimers described herein) are administered to a subject in need of treatment for Inflammatory Bowel Disease (IBD), ulcerative colitis, Crohn's disease, Celiac disease (nontropical Sprue), enteropathy associated with seronegative arthropathies, microscopic or collagenous colitis, eosinophilic gastroenteritis, radio- and chemotherapy, or pouchitis resulting after proctocolectomy and ileoanal anastomosis and various forms of gastrointestinal cancer, osteoporosis, arthritis, multiple sclerosis, chronic pain, weight gain, and/or depression.

In another embodiment, peptide integrin inhibitors of the present invention are administered to a subject in need of treatment for pancreatitis, insulin-dependent diabetes mellitus, mastitis, cholecystitis, cholangitis, pericholangitis, chronic bronchitis, chronic sinusitis, asthma and/or graft versus host disease. In addition, these peptide monomer and dimer molecules may be useful in the prevention or reversal of these diseases when used in combination with currently available therapies, medical procedures, and therapeutic agents.

In one embodiment, a method is provided for treating an individual or subject afflicted with a condition or indication characterized by α4β7 integrin binding, wherein the method comprises administering to the individual or subject an effective amount of an α4β7 integrin antagonist peptide molecule described herein, e.g., SEQ ID NOs: 1-384 or Tables 4 or 5. In some instances, an α4β7 integrin antagonist peptide molecule described herein, e.g., corresponding to SEQ ID NOs: 1-384 or Tables 4 or 5, and having high specificity for α4β7 is administered to an individual as part of a therapeutic treatment for a condition or indication characterized by α4β7 integrin binding.

In particular embodiments, the peptide molecules of the present invention are present in a pharmaceutical composition further comprising one or more pharmaceutically acceptable diluents, carriers, or excipients. In particular embodiments, they are formulated as a liquid or solid. In particular embodiments, they are formulated as a tablet or capsule, or as a liquid suspension. Some embodiments of the present invention further provide a method for treating an individual with an α4β7 integrin antagonist peptide molecule of the present invention that is suspended in a sustained-release matrix. A sustained-release matrix, as used herein, is a matrix made of materials, usually polymers, which are degradable by enzymatic or acid-base hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. On particular biodegradable matrix is a matrix of one of either polylactide, polyglycolide, or polylactide co-glycolide (copolymers of lactic acid and glycolic acid).

In some aspects, the invention provides a pharmaceutical composition for oral delivery. The various embodiments and thioether peptide molecule compositions of the instant invention may be prepared for oral administration according to any of the methods, techniques, and/or delivery vehicles described herein. Further, one having skill in the art will appreciate that the peptide molecule compositions of the instant invention may be modified or integrated into a system or delivery vehicle that is not disclosed herein, yet is well known in the art and compatible for use in oral delivery of small peptide molecules.

Oral dosage forms or unit doses compatible for use with the peptides of the present invention may include a mixture of peptide active drug components, and nondrug components or excipients, as well as other non-reusable materials that may be considered either as an ingredient or packaging. Oral compositions may include at least one of a liquid, a solid, and a semi-solid dosage forms. In some embodiments, an oral dosage form is provided comprising an effective amount of a thioether peptide molecule described herein, e.g., corresponding to any of SEQ ID NOs: 1-384 or Tables 4 or 5, wherein the dosage form comprises at least one of a pill, a tablet, a capsule, a gel, a paste, a drink, and a syrup. In some instances, an oral dosage form is provided that is designed and configured to achieve delayed release of the thioether peptide molecule in the small intestine of the subject.

In one embodiment, an oral pharmaceutical composition comprising a thioether peptide of the present invention comprises an enteric coating that is designed to delay release of the peptide molecule in the small intestine. In at least some embodiments, a pharmaceutical composition is provided which comprises a peptide molecule described herein, e.g., corresponding to any of SEQ ID NOs: 1-384, or Tables 4 or 5, and a protease inhibitor, such as aprotinin, in a delayed release pharmaceutical formulation. In some instances it is preferred that a pharmaceutical composition of the instant invention comprise an enteric coat that is soluble in gastric juice at a pH of about 5.0 or higher. In at least one embodiment, a pharmaceutical composition is provided comprising an enteric coating comprising a polymer having dissociable carboxylic groups, such as derivatives of cellulose, including hydroxypropylmethyl cellulose phthalate, cellulose acetate phthalate and cellulose acetate trimellitate and similar derivatives of cellulose and other carbohydrate polymers.

In one embodiment, a pharmaceutical composition comprising a thioether peptide molecule described herein, e.g., corresponding to any of SEQ ID NOs: 1-384 or Tables 4 and 5, is provided in an enteric coating, the enteric coating being designed to protect and release the pharmaceutical composition in a controlled manner within the lower gastrointestinal system of a subject, and to avoid systemic side effects. In addition to enteric coatings, the peptide molecules of the instant invention may be encapsulated, coated, engaged or otherwise associated within any compatible oral drug delivery system or component. For example, in some embodiments a peptide molecule of the present invention is provided in a lipid carrier system comprising at least one of polymeric hydrogels, nanoparticles, microspheres, micelles, and other lipid systems.

To overcome peptide degradation in the small intestine, some implementations of the present invention comprise a hydrogel polymer carrier system in which a peptide molecule in accordance with the present invention is contained, whereby the hydrogel polymer protect the peptide from proteolysis in the small intestine. The peptide molecules of the present invention may further be formulated for compatible use with a carrier system that is designed to increase the dissolution kinetics and enhance intestinal absorption of the peptides. These methods include the use of liposomes, micelles and nanoparticles to increase GI tract permeation of peptides.

Various bioresponsive systems may also be combined with one or more thioether peptide molecules of the present invention to provide a pharmaceutical agent for oral delivery. In some embodiments, a peptide molecule of the instant invention is used in combination with a bioresponsive system, such as hydrogels and mucoadhesive polymers with hydrogen bonding groups (e.g., PEG, poly(methacrylic) acid [PMAA], cellulose, Eudragit, chitosan and alginate) to provide a therapeutic agent for oral administration. Other embodiments include a method for optimizing or prolonging drug residence time for a peptide molecule disclosed herein, wherein the surface of the peptide molecule is modified to comprise mucoadhesive properties through hydrogen bonds, polymers with linked mucins or/and hydrophobic interactions. These modified peptide molecules may demonstrate increase drug residence time within the subject, in accordance with a desired feature of the invention. Moreover, targeted mucoadhesive systems may specifically bind to receptors at the enterocytes and M-cell surfaces, thereby further increasing the uptake of particles containing the peptide molecules.

Other embodiments comprise a method for oral delivery of a thioether peptide molecule described herein, e.g., corresponding to any of SEQ ID NOs: 1-384 or Tables 4 or 5, wherein the peptide molecule is used in combination with permeation enhancers that promote the transport of the peptides across the intestinal mucosa by increasing paracellular or transcellular permeation. For example, in one embodiment a permeation enhancer is combined with a thioether peptide molecule described herein, e.g., corresponding to any of SEQ ID NOs: 1-384, or Tables 4 or 5, wherein the permeation enhancer comprises at least one of a long-chain fatty acid, a bile salt, an amphiphilic surfactant, and a chelating agent. In one embodiment, a permeation enhancer comprising sodium N-[(hydroxybenzoyl)amino] caprylate is used to form a weak noncovalent association with the peptide molecule of the instant invention, wherein the permeation enhancer favors membrane transport and further dissociation once reaching the blood circulation. In another embodiment, a peptide molecule of the present invention is conjugated to oligoarginine, thereby increasing cellular penetration of the peptide into various cell types. Further, in at least one embodiment a noncovalent bond is provided between a thioether peptide molecule described herein, e.g., SEQ ID NOs: 1-384 or Tables 4 or 5, and a permeation enhancer selected from the group consisting of a cyclodextrin (CD) and a dendrimers, wherein the permeation enhancer reduces peptide aggregation and increasing stability and solubility for the peptide molecule.

Other embodiments of the invention provide a method for treating an individual with an α4β7 integrin antagonist thioether peptide molecule having an increased half-life. In one aspect, the present invention provides an integrin antagonist thioether peptide molecule having a half-life of at least several hours to one day in vitro or in vivo (e.g., when administered to a human subject) sufficient for daily (q.d.) or twice daily (b.i.d.) dosing of a therapeutically effective amount. In another embodiment, the peptide molecule has a half-life of three days or longer sufficient for weekly (q.w.) dosing of a therapeutically effective amount. Further, in another embodiment the peptide molecule has a half-life of eight days or longer sufficient for bi-weekly (b.i.w.) or monthly dosing of a therapeutically effective amount. In another embodiment, the thioether peptide molecule is derivatized or modified such that is has a longer half-life as compared to an underivatized or unmodified peptide molecule. In another embodiment, the peptide molecule contains one or more chemical modifications to increase serum half-life.

When used in at least one of the treatments or delivery systems described herein, a therapeutically effective amount of one of the thioether peptide molecules of the present invention may be employed in pure form or, where such forms exist, in pharmaceutically acceptable salt form. As used herein, a "therapeutically effective amount" of the compound of the invention is meant to describe a sufficient amount of the thioether peptide molecule to treat an integrin-related disease, (for example, to reduce inflammation associated with IBD) at a desired benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including: a) the disorder being treated and the severity of the disorder; b) activity of the specific compound employed; c) the specific composition employed, the age, body weight, general health, sex and diet of the patient; d) the time of administration, route of administration, and rate of excretion of the specific compound employed; e) the duration of the treatment; f) drugs used in combination or coincidental with the specific compound employed, and like factors well known in the medical arts. For example, it is well within the skill of the art to start doses of the compound at levels lower than those required to achieve the desired therapeutic effect and to gradually increase the dosage until the desired effect is achieved.

Alternatively, a compound of the present invention may be administered as pharmaceutical compositions containing the thioether peptide molecule of interest in combination with one or more pharmaceutically acceptable excipients. A pharmaceutically acceptable carrier or excipient refers to a non-toxic solid, semi-solid or liquid filler, diluent, encapsulating material or formulation auxiliary of any type. The compositions may be administered parenterally, intracisternally, intravaginally, intraperitoneally, intrarectally, topically (as by powders, ointments, drops, suppository, or transdermal patch), rectally, or buccally. The term "parenteral" as used herein refers to modes of administration which include intravenous, intramuscular, intraperitoneal, intrasternal, subcutaneous, intradermal and intraarticular injection and infusion.

In particular embodiments, pharmaceutical compositions for parenteral injection comprise pharmaceutically acceptable sterile aqueous or nonaqueous solutions, dispersions, suspensions or emulsions, as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

Injectable depot forms are made by forming microencapsule matrices of the drug in biodegradable polymers such as polylactide-polyglycolide, poly(orthoesters), poly(anhydrides), and (poly)glycols, such as PEG. Depending upon the ratio of drug to polymer and the nature of the particular polymer employed, the rate of drug release can be controlled. Depot injectable formulations are also prepared by entrapping the drug in liposomes or microemulsions which are compatible with body tissues.

The injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Topical administration includes administration to the skin or mucosa, including surfaces of the lung and eye. Compositions for topical lung administration, including those for inhalation and intranasal, may involve solutions and suspensions in aqueous and non-aqueous formulations and can be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars such as lactose.

Alternatively, the composition may be pressurized and contain a compressed gas, such as nitrogen or a liquefied gas propellant. The liquefied propellant medium and indeed the total composition is preferably such that the active ingredient does not dissolve therein to any substantial extent. The pressurized composition may also contain a surface active agent, such as a liquid or solid non-ionic surface active agent or may be a solid anionic surface active agent. It is preferred to use the solid anionic surface active agent in the form of a sodium salt.

A further form of topical administration is to the eye. A compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material. Alternatively, the compounds of the invention may be injected directly into the vitreous and aqueous humour.

Compositions for rectal or vaginal administration are preferably suppositories which may be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art.

Total daily dose of the compositions of the invention to be administered to a human or other mammal host in single or divided doses may be in amounts, for example, from 0.0001 to 300 mg/kg body weight daily and more usually 1 to 300 mg/kg body weight.

Non-invasive Detection of Intestinal Inflammation

The thioether peptides of the invention may be used for detection, assessment and diagnosis of intestinal inflammation by microPET imaging using an orally stable thioether peptide monomer or dimer molecule selected from and corresponding to SEQ ID NOs: 1-32, or described herein or in the accompanying Figures, and that is further labeled with at least one of a chelating group and a detectable label as part of a non-invasive diagnostic procedure. In one embodiment, an integrin antagonist thioether peptide monomer or dimer molecule is conjugated with a bifunctional chelator to provide an orally stable peptide molecule. In another embodiment, an integrin antagonist peptide monomer or dimer molecule is radiolabeled to provide an orally stable peptide molecule. The orally stable, chelated or radiolabeled peptide molecule is then administered to a subject orally or rectally. In one embodiment, the orally stable peptide monomer or dimer molecule is included in drinking water. Following uptake of the peptide molecules, microPET imaging may be used to visualize inflammation throughout the subject's bowels and digestive track.

EXAMPLES

Example 1

Synthesis of Thioether Peptide Monomer and Dimer Molecules

The peptide monomers or peptide subunits of the present invention may be synthesized by many techniques that are known to those skilled in the art. Novel and unique thioether peptide molecules were synthesized and purified, and dimerized in the case of peptide dimer molecules, using the techniques provided herein.

Synthesis

The peptides of the present invention were synthesized using the Merrifield solid phase synthesis techniques on Protein Technology's Symphony multiple channel synthesizer. The peptides were assembled using HBTU (O-Benzotriazole-N,N,N',N'-tetramethyl-uronium-hexafluoro-phosphate), Diisopropylethylamine(DIEA) coupling conditions. Rink Amide MBHA resin (100-200 mesh, 0.57 mmol/g) was used for peptides with C-terminal amides and pre-loaded Wang Resin with N-a-Fmoc protected amino acid was used for peptides with C-terminal acids. The coupling reagents (HBTU and DIEA premixed) were prepared at 100 mmol concentration. Similarly amino acids solutions were prepared at 100 mmol concentration. The peptides were assembled using standard Symphony protocols.

Assembly

The peptide sequences were assembled as follows: Resin (250 mg. 0.14 mmol) in each reaction vial was washed twice with 4 ml of DMF followed by treatment with 2.5 ml of 20% 4-methyl piperidine (Fmoc de-protection) for 10 min. The resin was then filtered and washed two times with DMF (4 ml) and re-treated with N-methyl piperidine for additional 30 minute. The resin was again washed three times with DMF (4 ml) followed by addition 2.5 ml of amino acid and 2.5 ml of HBTU-DIEA mixture. After 45 min of frequent agitations, the resin was filtered and washed three timed with DMF (4 ml each). For a typical peptide of the present invention, double couplings were performed. For N-Me-Arg and 2-(Chloromethyl)benzoic acid coupling, double coupling of 2.0 eq 2-(Chloromethyl)benzoic acid, 2.0 eq PyAOP, and 4 eq DIEA in DMF for 1 hr. Reaction completion was monitored using the Chloranil test. After completing the coupling reaction, the resin was washed three times with DMF (4 ml each) before proceeding to the next amino acid coupling.

Cleavage

Following completion of the peptide assembly, the peptide was cleaved from the resin by treatment with cleavage reagent, TFA:water:TIPS (92.5v:5v:2.5v). The cleavage reagent was able to successfully cleave the peptide from the resin, as well as all remaining side chain protecting groups.

The cleavage reaction mixture was stirred for 2 h at room temperature. The spent resin was filtered off. The filtrate was then precipitated into cold ethyl ether and centrifuged to collect the peptide. The ethyl ether was decanted, and the solid precipitate was washed two times with cold ethyl ether. The crude peptide was dissolved in a solution of acetonitrile:water (7:3 with 1% TFA) and filtered. The quality of linear peptide was then verified using electrospray ionization mass spectrometry (ESI-MS) (Micromass/Waters ZQ) before being purified.

Thioether Bond Formation

The unpurified linear monomer (50 mg) was dissolved in 50:50 ACN:water (2.5 mg/ml) then diluted to about 1 mg/mL in 0.1M Tris-HCl pH8.5 buffer. The reaction was monitored using LCMS. When the reaction is completed (usually overnight), diluted the reaction mixture with water and purify by RP-HPLC.

Purification

Analytical reverse-phase, high performance liquid chromatography (HPLC) was performed on a Gemini C18 column (4.6 mm×250 mm) (Phenomenex). Semi-Preparative reverse phase HPLC was performed on a Gemini 10 μm C18 column (22 mm×250 mm) (Phenomenex) or Jupiter 10 μm, 300 AO C18 column (21.2 mm×250 mm) (Phenomenex). Separations were achieved using linear gradients of buffer B in A (Mobile phase A: water containing 0.15% TFA, mobile phase B: Acetonitrile (ACN) containing 0.1% TFA), at a flow rate of 1 mL/min (analytical) and 15 mL/min (preparative). Separations were achieved using linear gradients of buffer B in A (Mobile phase A: water containing 0.15% TFA, mobile phase B: Acetonitrile (ACN) containing 0.1% TFA), at a flow rate of 1 mL/min (analytical) and 15 mL/min (preparative).

Linker Activation and Dimerization

Small Scale DIG Linker Activation Procedure:

5 mL of NMP was added to a glass vial containing IDA diacid (304.2 mg, 1 mmol), N-hydroxysuccinimide (NHS, 253.2 mg, 2.2 eq. 2.2 mmol) and a stirring bar. The mixture was stirred at room temperature to completely dissolve the solid starting materials. N,N'-Dicyclohexylcarbodiimide (DCC, 453.9 mg, 2.2 eq., 2.2 mmol) was then added to the mixture. Precipitation appeared within 10 min and the reaction mixture was further stirred at room temperature overnight. The reaction mixture was then filtered to remove the precipitated dicyclohexylurea (DCU). The activated linker was kept in a closed vial prior to use for dimerization. The nominal concentration of the activated linker was approximately 0.20 M.

For dimerization using PEG linkers, there was no pre-activation step involved. Commercially available pre-activated bi-functional PEG linkers were used.

Dimerization Procedure:

2 mL of anhydrous DMF was added to a vial containing peptide monomer (0.1 mmol). The pH of the peptide was then adjusted to 8-9 with DIEA. Activated linker (IDA or PEG13, PEG 25) (0.48 eq relative to monomer, 0.048 mmol) was then added to the monomer solution. The reaction mixture was stirred at room temperature for one hour. Completion of the dimerization reaction was monitored using analytical HPLC. The time for completion of dimerization reaction varied depending upon the linker. After completion of reaction, the peptide was precipitated in cold ether and centrifuged. The supernatant ether layer was discarded. The precipitation step was repeated twice. The crude dimer was then purified using reverse phase HPLC (Luna C18 support, 10 u, 100 A, Mobile phase A: water containing 0.1% TFA, mobile phase B: Acetonitrile (ACN) containing 0.1% TFA, gradient of 15% B and change to 45% B over 60 min, flow rate 15 ml/min). Fractions containing pure product were then freeze-dried on a lyophilyzer.

The peptide monomers and peptide dimers shown in Tables 4 and 5 were synthesized and further characterized. Table 4 shows various monomer peptide compounds according to various non-limiting representative embodiments of the present invention. The amino acid residues are numbers $Xaa^{1-10}$, in accordance with Formula (II). However, these residues should be understood to also correspond to $Xaa^{4-13}$ in Formula (I). The amino acid sequence of the peptide is shown, wherein "2-benzyl" indicates 2-methylbenzoyl, and lower case letters indicate D-amino acids. Each peptide is cyclized via an intramolecular thioether bond between the amino acid residue or moiety shown at position 1 and the amino acid residue shown at position 7. Table 5 shows various peptide dimer compounds according to various non-limiting representative embodiments of the present invention. The amino acid sequence of the peptide is shown, wherein "2-benzyl" indicates 2-methylbenzoyl, and lower case letters indicate D-amino acids. The amino acid residues are numbers $Xaa^{1-10}$, in accordance with Formula (II). However, these residues should be understood to also correspond to $Xaa^{4-13}$ in Formula (I). Each monomer subunit of the peptide dimer is cyclized via an intramolecular thioether bond between the amino acid residue or moiety shown at position 1 and the amino acid residue shown at position 7. The peptide monomer subunits of the peptide dimers are dimerized at their C-termini by the indicated DIG, ADA, IDA, IDA-Palm, IDA-Lauryl, IDA-oleoyl, or IDA-PEG linker.

TABLE 4

Illustrative Thioether Monomers

| SEQ ID NO | Peptide sequence | 1 | 2 | 3 | 4 | 5 | 6 | 7 | 8 | 9 | 10 | |
|---|---|---|---|---|---|---|---|---|---|---|---|---|
| 391 | (thioether) | Acetyl | N—Me-R | S | D | T | L | C | W | k | NH2 | |
| 392 | (thioether) | Acetyl | N—Me-R | S | D | T | L | homoCys | W | k | NH2 | |
| 51 | (thioether) | Propionyl | N—Me-R | S | D | T | L | C | W | k | NH2 | |
| 52 | (thioether) | alpha-bromoispbutyryl | N—Me-R | S | D | T | L | C | W | k | NH2 | |
| 53 | (thioether) | Acetyl | N—Me-R | S | D | T | L | Pen | W | k | NH2 | |
| 54 | (thioether) | Propionyl | N—Me-R | S | D | T | L | Pen | W | k | NH2 | |
| 55 | (thioether) | 2-Benzyl | N—Me-R | S | D | T | L | C | W | E | k | NH2 |
| 56 | (thioether) | 2-Benzyl | N—Me-R | S | D | T | L | Pen | W | E | k | NH2 |
| 57 | (thioether) | Propionyl | N—Me-R | S | D | T | L | hC | W | k | NH2 | |
| 58 | ((thioether) | Butyryl | N—Me-R | S | D | T | L | C | W | k | NH2)2 | |
| 59 | (thioether) | 2-Benzyl | R | S | D | T | L | C | W | k | NH2 | |
| 60 | (thioether) | 2-Benzyl | N—Me-R | S | D | T | L | Pen | W | e | k | NH2 |
| 61 | (thioether) | 2-Benzyl | N—Me-R | S | D | T | L | Pen | W | b-H-E | k | NH2 |
| 62 | (thioether) | 2-Benzyl | N—Me-R | S | D | T | L | Pen | W | E | N—Me-k | NH2 |
| 63 | (thioether) | 2-Benzyl | N—Me-R | S | D | T | L | Pen | W | Y | N—Me—K | NH2 |
| 64 | (thioether) | 2-Benzyl | N—Me-R | S | D | T | Nle | Pen | W | E | k | NH2 |

TABLE 4-continued

Illustrative Thioether Monomers

| SEQ ID NO | Peptide sequence | 1 | 2 | 3 | 4 | 5 | 6 | 7 | 8 | 9 | 10 | |
|---|---|---|---|---|---|---|---|---|---|---|---|---|
| 65 | (thioether) | 2-Benzyl | N—Me-R | S | D | T | L | Pen | F | e | k | NH2 |
| 66 | (thioether) | 2-Benzyl | N—Me-R | S | D | T | L | c | W | b-H-E | k | NH2 |
| 67 | (thioether) | 2-Benzyl | N—Me-R | S | D | T | L | Hcys | W | E | k | NH2 |
| 68 | (thioether) | 2-Benzyl | N—Me-R | S | D | T | L | Pen | 1-Nal | e | k | NH2 |
| 69 | (thioether) | 2-Benzyl | N—Me-R | S | D | T | L | Pen | 1-Nal | e | N—Me—K | NH2 |
| 70 | (thioether) | 2-Benzyl | N—Me-R | S | D | T | L | Pen | 2-Nal | b-H-E | k | NH2 |
| 71 | (thioether) | 2-Benzyl | N—Me-R | S | D | T | L | Pen | f | 2-Nal | k | NH2 |
| 72 | (thioether) | 2-Benzyl | N—Me-R | S | D | T | L | Pen | f | E | k | NH2 |
| 73 | (thioether) | 2-Benzyl | N—Me-R | S | D | T | L | Pen | F | b-H-E | k | NH2 |
| 74 | (thioether) | 2-Benzyl | N—Me-R | S | D | T | L | Pen | Y | b-H-E | k | NH2 |
| 75 | (thioether) | 2-Benzyl | N—Me-R | S | D | T | L | Pen | 2-Nal | e | k | NH2 |
| 76 | (thioether) | 2-Benzyl | N—Me-R | S | D | T | L | Pen | F(CF3) | E | k | NH2 |
| 77 | (thioether) | 2-Benzyl | N—Me-R | S | D | T | L | Pen | 1Nal | E | k | NH2 |
| 78 | (thioether) | 2-Benzyl | N—Me-R | S | D | T | L | Pen | Y | E | k | NH2 |
| 79 | (thioether) | 2-Benzyl | N—Me-R | S | D | T | L | Pen | Y | e | k | NH2 |
| 80 | (thioether) | 2-Benzyl | N—Me-R | S | D | T | L | Pen | W | E | k(Ac) | NH2 |
| 81 | (thioether) | 2-Benzyl | N—Me-R | S | D | T | L | Pen | W | e | k(Ac) | NH2 |
| 82 | (thioether) | 2-Benzyl | N—Me-R | S | D | T | L | Pen | W | e | k(PEG8) | NH2 |
| 83 | (thioether) | 2-Benzyl | N—Me-R | S | D | T | L | Pen | W | b-H-E | k(Ac) | NH2 |
| 84 | (thioether) | 2-Benzyl | N—Me-R | S | D | T | L | Pen | W | E | N—Me-k(Ac) | NH2 |
| 85 | (thioether) | 2-Benzyl | N—Me-R | S | D | T | L | Pen | W | Y | N—Me—K(Ac) | NH2 |
| 86 | (thioether) | 2-Benzyl | N—Me-R | S | D | T | Nle | Pen | W | E | k(Ac) | NH2 |
| 87 | (thioether) | 2-Benzyl | N—Me-R | S | D | T | L | Pen | F | e | k(Ac) | NH2 |
| 88 | (thioether) | 2-Benzyl | N—Me-R | S | D | T | L | Pen | F(CF3) | E | k(Ac) | NH2 |
| 89 | (thioether) | 2-Benzyl | N—Me-R | S | D | T | L | Pen | 1Nal | E | k(Ac) | NH2 |
| 90 | (thioether) | 2-Benzyl | N—Me-R | S | D | T | L | Pen | Y | E | k(Ac) | NH2 |
| 91 | (thioether) | 2-Benzyl | N—Me-R | S | D | T | L | Pen | Y | e | k(Ac) | NH2 |
| 92 | ((thioether) | 2-Benzyl | N—Me-R | S | D | T | L | Pen | W | E | Dap | NH2 |
| 93 | ((thioether) | 2-Benzyl | N—Me-R | S | D | T | L | Pen | W | E | Dab | NH2 |
| 94 | ((thioether) | 2-Benzyl | N—Me-R | S | D | T | L | Pen | W | e | Dap | NH2 |
| 95 | ((thioether) | 2-Benzyl | N—Me-R | S | D | T | L | Pen | W | e | Dab | NH2 |
| 96 | ((thioether) | 2-Benzyl | N—Me-R | S | D | T | L | Pen | W | E | NH2 | |
| 97 | ((thioether) | 2-Benzyl | N—Me-R | S | D | T | L | Pen | W | e | NH2 | |
| 98 | ((thioether) | 2-Benzyl | N—Me-R | S | D | T | L | Pen | W | e | NH2 | |
| 99 | ((thioether) | 2-Benzyl | N—Me-R | S | D | T | L | Pen | W | e | L | NH2 |
| 100 | ((thioether) | 2-Benzyl | N—Me-R | S | D | T | L | Pen | W | e | S | NH2 |
| 101 | ((thioether) | 2-Benzyl | N—Me-R | S | D | T | L | Pen | W | e | F | NH2 |
| 102 | ((thioether) | 2-Benzyl | N—Me-R | S | D | T | L | Pen | W | e | H | NH2 |
| 103 | ((thioether) | 2-Benzyl | N—Me-R | S | D | T | L | Pen | W | e | Q | NH2 |
| 104 | ((thioether) | 2-Benzyl | N—Me-R | S | D | T | L | Pen | W | e | Y | NH2 |
| 105 | ((thioether) | 2-Benzyl | N—Me-R | S | D | T | L | Pen | W | e | l | NH2 |
| 106 | ((thioether) | 2-Benzyl | N—Me-R | S | D | T | L | Pen | W | e | s | NH2 |
| 107 | ((thioether) | 2-Benzyl | N—Me-R | S | D | T | L | Pen | W | e | f | NH2 |
| 108 | ((thioether) | 2-Benzyl | N—Me-R | S | D | T | L | Pen | W | e | e | NH2 |
| 109 | ((thioether) | 2-Benzyl | N—Me-R | S | D | T | L | Pen | W | e | h | NH2 |
| 110 | ((thioether) | 2-Benzyl | N—Me-R | S | D | T | L | Pen | W | e | y | NH2 |
| 111 | (thioether) | 3-Benzyl | N—Me-R | S | D | T | L | Pen | W | e | k | NH2 |
| 112 | (thioether) | 4-Benzyl | N—Me-R | S | D | T | L | Pen | W | e | k | NH2 |
| 113 | ((thioether) | 2-Benzyl | N—Me-R | S | D | T | L | Pen | W | e | E | NH2 |
| 114 | ((thioether) | 2-Benzyl | N—Me-R | S | D | T | L | Pen | 2-Nal | e | NH2 | |
| 115 | ((thioether) | 2-Benzyl | N—Me-R | S | D | T | L | Pen | W | E(OMe) | k | NH2 |
| 116 | ((thioether) | 2-Benzyl | N—Me-R | S | D | T | L | Pen | 2-Nal | NH2 | | |
| 117 | (thioether) | 2-Benzyl | N—Me-R | S | D | T | L | C | Tic | E | k | NH2 |
| 118 | (thioether) | 2-Benzyl | N—Me-R | S | D | T | L | C | Tic | k | OH | |
| 119 | (thioether) | 2-Benzyl | N—Me-R | S | D | T | L | Pen | Atc | bHE | NH2 | |
| 120 | ((thioether) | 2-Benzyl | N—Me-R | S | D | T | L | Pen | erythro-b-F—S | bHE | NH2 | |
| 121 | ((thioether) | 2-Benzyl | N—Me-R | S | D | T | L | Pen | erythro-b-F—S | bHE | NH2 | |
| 122 | ((thioether) | 2-Benzyl | N—Me-R | S | D | T | L | Pen | threo-b-F—S | bHE | NH2 | |
| 123 | ((thioether) | 2-Benzyl | N—Me-R | S | D | T | L | Pen | threo-b-F—S | bHE | NH2 | |
| 124 | ((thioether) | 2-Benzyl | N—Me-R | S | D | T | L | Pen | B pa | bHE | NH2 | |
| 125 | ((thioether) | 2-Benzyl | N—Me-R | S | D | T | L | Pen | F(3-Me) | bHE | NH2 | |
| 126 | ((thioether) | 2-Benzyl | N—Me-R | S | D | T | L | Pen | F(2-Me) | bHE | NH2 | |
| 127 | ((thioether) | 2-Benzyl | N—Me-R | S | D | T | L | Pen | F(2-CF3)) | bHE | NH2 | |
| 128 | ((thioether) | 2-Benzyl | N—Me-R | S | D | T | L | Pen | b-Me—F | bHE | NH2 | |
| 129 | ((thioether) | 2-Benzyl | N—Me-R | S | D | T | L | Pen | b-Me—F | bHE | NH2 | |
| 130 | ((thioether) | 2-Benzyl | N—Me-R | S | D | T | L | Pen | b-dimethyl-F | bHE | NH2 | |
| 131 | ((thioether) | 2-Benzyl | N—Me-R | S | D | T | L | Pen | b-dimethyl-F | bHE | NH2 | |
| 132 | ((thioether) | 2-Benzyl | N—Me-R | S | D | T | L | Pen | 4-Me—F | bHE | NH2 | |
| 133 | ((thioether) | 2-Benzyl | N—Me-R | S | D | T | L | Pen | Bip | bHE | NH2 | |
| 134 | ((thioether) | 2-Benzyl | N—Me-R | S | D | T | L | Pen | F(4-tBu) | b-H-E | NH2 | |
| 135 | ((thioether) | 2-Benzyl | N—Me-R | S | D | T | L | Pen | F(4tBu) | N—Me-E | NH2 | |
| 136 | ((thioether) | 2-Benzyl | N—Me-R | S | D | T | L | Pen | F(4tBu) | N—Me-D | NH2 | |
| 137 | ((thioether) | 2-Benzyl | N—Me-R | S | D | T | L | Pen | F(4tBu) | alpha-H-E | NH2 | |
| 138 | ((thioether) | 2-Benzyl | Cit | S | D | T | L | Pen | F(4-tBu) | b-H-E | NH2 | |
| 139 | ((thioether) | 2-Benzyl | N—Me-R | A | D | T | L | Pen | F(4-tBu) | b-H-E | NH2 | |

TABLE 4-continued

Illustrative Thioether Monomers

| SEQ ID NO | Peptide sequence | 1 | 2 | 3 | 4 | 5 | 6 | 7 | 8 | 9 | 10 |
|---|---|---|---|---|---|---|---|---|---|---|---|
| 140 | ((thioether)) | 2-Benzyl | N—Me-R | Abu | D | T | L | Pen | F(4-tBu) | b-H-E | NH2 |
| 141 | ((thioether)) | 2-Benzyl | N—Me-R | Tbu | D | T | L | Pen | F(4-tBu) | b-H-E | NH2 |
| 142 | ((thioether)) | 2-Benzyl | N—Me-R | S | D | T | L | Pen | F(4-tBu) | N—Me-E | OH |
| 224 | thioether | 2-Benzyl | N—Me-R | S | D | T | L | Pen | W | e | Dap | Ac |
| 225 | thioether | 2-Benzyl | N—Me-R | S | D | T | Nle | Pen | F | e | N—Me-k | NH2 |
| 226 | thioether | 2-Benzyl | N—Me-R | S | D | T | Nle | Pen | W | E | N—Me—K | NH2 |
| 227 | thioether | 2-Benzyl | N—Me-R | S | D | T | Nle | Pen | F | e | N—Me-k | NH2 |
| 228 | thioether | 2-Benzyl | N—Me-R | S | D | T | Nle | Pen | W | E | N—Me-k | NH2 |
| 229 | thioether | 2-Benzyl | N—Me-R | S | D | T | Nle | Pen | F | e | N—Me-k | NH2 |
| 230 | Ac | C(thioether propane) | N—Me-R | S | D | T | L | C(thioether propane) | W | E | k | NH2 |
| 231 | thioether | 2-Benzyl | N—Me-R | S | D | T | L | Pen | W | E | Dab | Ac |
| 232 | thioether | 2-Benzyl | N—Me-R | S | D | T | L | Pen | W | e | Dab | Ac |
| 233 | ((thioether)) | 2-Benzyl | N—Me-R | S | D | T | L | Pen | W | E | Dab | NH2 |
| 234 | thioether | 2-Benzyl | N—Me-R | S | D | T | L | Pen | W | E | Dap | Ac |
| 235 | ((thioether)) | 2-Benzyl | N—Me-R | S | D | T | L | C | Tic | e | k | NH2 |
| 236 | ((thioether)) | 2-Benzyl | N—Me-R | S | D | T | L | Pen | W | f | k | NH2 |
| 237 | ((thioether)) | 2-Benzyl | N—Me-R | S | D | T | L | Pen | W | y | k | NH2 |
| 238 | ((thioether)) | 2-Benzyl | N—Me-R | S | D | T | L | C | Tic | e | k | NH2 |
| 239 | ((thioether)) | 2-Benzyl | N—Me-R | S | D | T | L | Pen | W | P | k | NH2 |
| 240 | ((thioether)) | 2-Benzyl | N—Me-R | S | D | T | L | Pen | W | P | K | NH2 |
| 241 | ((thioether)) | 2-Benzyl | N—Me-R | S | D | T | L | Pen | W | P | K | NH2 |
| 242 | ((thioether)) | 2-Benzyl | N—Me-R | S | D | T | L | Pen | F(2-carbamoyl) | e | k | NH2 |
| 243 | ((thioether)) | 2-Benzyl | N—Me-R | S | D | T | L | Pen | F(3-carbamoyl) | e | k | NH2 |
| 244 | ((thioether)) | 2-Benzyl | N—Me-R | S | D | T | L | Pen | F(4-COOH) | e | k | NH2 |
| 245 | ((thioether)) | 2-Benzyl | N—Me-R | S | D | T | L | Pen | F(2,4-Cl) | e | k | NH2 |
| 246 | ((thioether)) | 2-Benzyl | N—Me-R | S | D | T | L | Pen | F(3,4-Cl) | e | k | NH2 |
| 247 | ((thioether)) | 2-Benzyl | N—Me-R | S | D | T | L | Pen | F(4-OMe) | e | k | NH2 |
| 248 | ((thioether)) | 2-Benzyl | N—Me-R | S | D | T | L | Pen | W | h | k | NH2 |
| 249 | ((thioether)) | 2-Benzyl | N—Me-R | S | D | T | L | Pen | W | F(4-COOH) | k | NH2 |
| 250 | ((thioether)) | 2-Benzyl | N—Me-R | S | D | T | L | Pen | F(4tBu) | e | k | NH2 |
| 251 | ((thioether)) | 2-Benzyl | N—Me-R | S | D | T | L | Pen | F(4-F) | e | k | NH2 |
| 252 | ((thioether)) | 2-Benzyl | N—Me-R | S | D | T | L | Pen | Bip | e | k | NH2 |
| 253 | ((thioether)) | 2-Benzyl | N—Me-R | S | D | T | L | Pen | W | Tic | k | NH2 |
| 254 | ((thioether)) | 2-Benzyl | N—Me-R | S | D | T | L | Pen | W | w | k | NH2 |
| 255 | ((thioether)) | 2-Benzyl | N—Me-R | S | D | T | L | Pen | 1-Nal | f | k | NH2 |
| 256 | ((thioether)) | 2-Benzyl | N—Me-R | S | D | T | L | Pen | 1-Nal | h | k | NH2 |
| 257 | ((thioether)) | 2-Benzyl | N—Me-R | S | D | T | L | Pen | 1-Nal | l | k | NH2 |
| 258 | ((thioether)) | 2-Benzyl | N—Me-R | S | D | T | L | Pen | 1-Nal | r | k | NH2 |
| 259 | ((thioether)) | 2-Benzyl | N—Me-R | S | D | T | L | Pen | 1-Nal | Tic | k | NH2 |
| 260 | ((thioether)) | 2-Benzyl | N—Me-R | S | D | T | L | Pen | 1-Nal | t | k | NH2 |
| 261 | ((thioether)) | 2-Benzyl | N—Me-R | S | D | T | L | Pen | 2-Nal | f | k | NH2 |
| 262 | ((thioether)) | 2-Benzyl | N—Me-R | S | D | T | L | Pen | 2-Nal | h | k | NH2 |
| 263 | ((thioether)) | 2-Benzyl | N—Me-R | S | D | T | L | Pen | 2-Nal | l | k | NH2 |
| 264 | ((thioether)) | 2-Benzyl | N—Me-R | S | D | T | L | Pen | 2-Nal | r | k | NH2 |
| 265 | ((thioether)) | 2-Benzyl | N—Me-R | S | D | T | L | Pen | 2-Nal | Tic | k | NH2 |
| 266 | ((thioether)) | 2-Benzyl | N—Me-R | S | D | T | L | Pen | F(4CF3) | e | k | NH2 |
| 267 | ((thioether)) | 2-Benzyl | N—Me-R | S | D | T | L | Pen | Y | e | k | NH2 |
| 268 | ((thioether)) | 2-Benzyl | N—Me-R | S | D | T | L | Pen | H | e | k | NH2 |
| 269 | ((thioether)) | 2-Benzyl | N—Me-R | S | D | T | L | Pen | F(4tBu) | E | k | NH2 |
| 270 | ((thioether)) | 2-Benzyl | N—Me-R | S | D | T | L | Pen | F(4tBu) | b-HomoGlu | k | NH2 |
| 271 | ((thioether)) | 2-Benzyl | N—Me-R | S | D | T | L | Pen | F(4-COOH) | E | k | NH2 |
| 272 | ((thioether)) | 2-Benzyl | N—Me-R | S | D | T | L | Pen | F(4-COOH) | E | k | NH2 |
| 273 | ((thioether)) | 2-Benzyl | N—Me-R | S | D | T | L | Pen | F(4-COOH) | E | k | NH2 |
| 274 | ((thioether)) | 2-Benzyl | N—Me-R | S | D | T | L | Pen | F(4-COOH) | b-HomoGlu | k | NH2 |
| 275 | ((thioether)) | 2-Benzyl | N—Me-R | S | D | T | L | Pen | F(4-COOH) | b-HomoGlu | k | NH2 |
| 276 | ((thioether)) | 2-Benzyl | N—Me-R | S | D | T | L | Pen | F(4-COOH) | b-HomoGlu | k | NH2 |
| 277 | ((thioether)) | 2-Benzyl | N—Me-R | S | D | T | L | Pen | Bip | E | k | NH2 |
| 278 | ((thioether)) | 2-Benzyl | N—Me-R | S | D | T | L | Pen | Bip | b-HomoGlu | k | NH2 |
| 279 | ((thioether)) | 2-Benzyl | N—Me-R | S | D | T | L | Pen | 2-Nal | E | k | NH2 |
| 280 | ((thioether)) | 2-Benzyl | N—Me-R | S | D | T | L | Pen | 2-Nal | b-HomoGlu | k | NH2 |
| 281 | ((thioether)) | 2-Benzyl | N—Me-R | S | D | T | L | Pen | 1-Nal | E | k | NH2 |
| 282 | ((thioether)) | 2-Benzyl | N—Me-R | S | D | T | L | Pen | 1-Nal | b-HomoGlu | k | NH2 |
| 283 | ((thioether)) | 2-Benzyl | N—Me-R | S | D | T | L | Pen | 2-Nal | k | NH2 | |
| 284 | ((thioether)) | 2-Benzyl | N—Me-R | S | D | T | L | Pen | 2-Nal | k | NH2 | |

TABLE 4-continued

Illustrative Thioether Monomers

| SEQ ID NO | Peptide sequence | 1 | 2 | 3 | 4 | 5 | 6 | 7 | 8 | 9 | 10 | |
|---|---|---|---|---|---|---|---|---|---|---|---|---|
| 285 | ((thioether) | 2-Benzyl | N—Me-R | S | D | T | L | Pen | F(4tBu) | E | N—Me—K | NH2 |
| 286 | ((thioether) | 2-Benzyl | N—Me-R | S | D | T | L | Pen | F(4tBu) | E | N—Me-k | NH2 |
| 287 | ((thioether) | 2-Benzyl | N—Me-R | S | D | T | L | Pen | F(4tBu) | b-Homo Glu | N—Me—K | NH2 |
| 288 | ((thioether) | 2-Benzyl | N—Me-R | S | D | T | L | Pen | F(4tBu) | b-Homo Glu | N—Me-k | NH2 |
| 289 | ((thioether) | 2-Benzyl | N—Me-R | S | D | T | L | Pen | Bip | E | N—Me—K | NH2 |
| 290 | ((thioether) | 2-Benzyl | N—Me-R | S | D | T | L | Pen | Bip | E | N—Me-k | NH2 |
| 291 | ((thioether) | 2-Benzyl | N—Me-R | S | D | T | L | Pen | Bip | b-Homo Glu | N—Me—K | NH2 |
| 292 | ((thioether) | 2-Benzyl | N—Me-R | S | D | T | L | Pen | Bip | b-Homo Glu | N—Me-k | NH2 |
| 293 | ((thioether) | 2-Benzyl | N—Me-R | S | D | T | L | Pen | 2-Nal | E | N—Me—K | NH2 |
| 294 | ((thioether) | 2-Benzyl | N—Me-R | S | D | T | L | Pen | 2-Nal | E | N—Me-k | NH2 |
| 295 | ((thioether) | 2-Benzyl | N—Me-R | S | D | T | L | Pen | 2-Nal | b-HomoGlu | N—Me—K | NH2 |
| 296 | ((thioether) | 2-Benzyl | N—Me-R | S | D | T | L | Pen | 2-Nal | b-Homo Glu | N—Me-k | NH2 |
| 297 | ((thioether) | 2-Benzyl | N—Me-R | S | D | T | L | Pen | 1-Nal | E | N—Me—K | NH2 |
| 298 | ((thioether) | 2-Benzyl | N—Me-R | S | D | T | L | Pen | 1-Nal | E | N—Me-k | NH2 |
| 299 | ((thioether) | 2-Benzyl | N—Me-R | S | D | T | L | Pen | 1-Nal | b-Homo Glu | N—Me—K | NH2 |
| 300 | ((thioether) | 2-Benzyl | N—Me-R | S | D | T | L | Pen | 1-Nal | b-Homo Glu | N—Me-k | NH2 |

TABLE 5

Illustrative Thioether Dimers

| SEQ ID NO | Peptide sequence | 1 | 2 | 3 | 4 | 5 | 6 | 7 | 8 | 9 | 10 | | Linker |
|---|---|---|---|---|---|---|---|---|---|---|---|---|---|
| 143 | [(thioether) | Acetyl | N—Me—R | S | D | T | L | C | W | k | NH2]2 | | DIG |
| 144 | [(thioether) | Propionyl | N—Me—R | S | D | T | L | C | W | k | NH2]2 | | DIG |
| 145 | [(thioether) | 2-Benzyl | N—Me—R | S | D | T | L | C | W | E | k | NH2]2 | DIG |
| 146 | [(thioether) | 2-Benzyl | N—Me—R | S | D | T | L | Pen | W | E | k | NH2]2 | DIG |
| 147 | ((thioether) | Acetyl | N—Me—R | S | D | T | L | Pen | W | k | NH2)2 | | DIG |
| 148 | ((thioether) | Propionyl | N—Me—R | S | D | T | L | Pen | W | k | NH2)2 | | DIG |
| 149 | [(thioether) | Propionyl | N—Me—R | S | D | T | L | hC | W | k | NH2]2 | | DIG |
| 150 | ((thioether) | 2-Benzyl | N—Me—R | S | D | T | L | Pen | W | e | k | NH2)2 | DIG |
| 151 | ((thioether) | 2-Benzyl | N—Me—R | S | D | T | L | Pen | W | b-H-E | k | NH2)2 | DIG |
| 152 | ((thioether) | 2-Benzyl | N—Me—R | S | D | T | L | Pen | W | E | N—Me-k | NH2)2 | DIG |
| 153 | ((thioether) | 2-Benzyl | N—Me—R | S | D | T | L | Pen | W | Y | N—Me—K | NH2)2 | DIG |
| 154 | ((thioether) | 2-Benzyl | N—Me—R | S | D | T | Nle | Pen | W | E | k | NH2)2 | DIG |
| 155 | ((thioether) | 2-Benzyl | N—Me—R | S | D | T | L | Pen | F | e | k | NH2)2 | DIG |
| 156 | (thioether) | 2-Benzyl | N—Me—R | S | D | T | L | c | W | b-H-E | k | NH2)2 | DIG |
| 157 | (thioether) | 2-Benzyl | N—Me—R | S | D | T | L | Hcys | W | E | k | NH2)2 | DIG |
| 158 | (thioether) | 2-Benzyl | N—Me—R | S | D | T | L | Pen | 1-Nal | e | k | NH2)2 | DIG |
| 159 | (thioether) | 2-Benzyl | N—Me—R | S | D | T | L | Pen | 2-Nal | e | k | NH2)2 | DIG |
| 160 | (thioether) | 2-Benzyl | N—Me—R | S | D | T | L | Pen | 1-Nal | e | N—Me—K | NH2)2 | DIG |
| 161 | (thioether) | 2-Benzyl | N—Me—R | S | D | T | L | Pen | 2-Nal | b-H-E | k | NH2)2 | DIG |
| 162 | (thioether) | 2-Benzyl | N—Me—R | S | D | T | L | Pen | f | 2-Nal | k | NH2)2 | DIG |
| 163 | (thioether) | 2-Benzyl | N—Me—R | S | D | T | L | Pen | f | E | k | NH2)2 | DIG |
| 164 | (thioether) | 2-Benzyl | N—Me—R | S | D | T | L | Pen | F | b-H-E | k | NH2)2 | DIG |
| 165 | (thioether) | 2-Benzyl | N—Me—R | S | D | T | L | Pen | Y | b-H-E | k | NH2)2 | DIG |
| 166 | ((thioether) | 2-Benzyl | N—Me—R | S | D | T | L | Pen | F(CF3) | E | k | NH2)2 | DIG |
| 167 | ((thioether) | 2-Benzyl | N—Me—R | S | D | T | L | Pen | 1Nal | E | k | NH2)2 | DIG |
| 168 | ((thioether) | 2-Benzyl | N—Me—R | S | D | T | L | Pen | Y | E | k | NH2)2 | DIG |
| 169 | ((thioether) | 2-Benzyl | N—Me—R | S | D | T | L | Pen | Y | e | k | NH2)2 | DIG |
| 170 | ((thioether) | 2-Benzyl | N—Me—R | S | D | T | L | Pen | W | e | k | NH2)2 | ADA |
| 171 | ((thioether) | 2-Benzyl | N—Me—R | S | D | T | L | Pen | W | e | k | NH2)2 | IDA |
| 172 | (thioether) | 2-Benzyl | N—Me—R | S | D | T | L | Pen(=O) | 2-Nal | e | k | NH2)2 | DIG |
| 173 | (thioether) | 2-Benzyl | N—Me—R | S | D | T | L | Pen(=O) | 2-Nal | e | k | NH2)2 | DIG |
| 174 | (thioether) | 2-Benzyl | N—Me—R | S | D | T | L | Pen | W | e | k | NH2)2 | IDA-Biotine |
| 175 | (thioether) | 2-Benzyl | N—Me—R | S | D | T | L | Pen | W | e | k | NH2)2 | IDA-PEG4-Biotin |
| 176 | (thioether) | 2-Benzyl | N—Me—R | S | D | T | L | Pen | F(2,4-diCl) | e | k | NH2)2 | DIG |
| 177 | (thioether) | 2-Benzyl | N—Me—R | S | D | T | L | Pen | F(3,4-diCl) | e | k | NH2)2 | DIG |
| 178 | (thioether) | 2-Benzyl | N—Me—R | S | D | T | L | Pen | Bip | e | k | NH2)2 | DIG |

TABLE 5-continued

Illustrative Thioether Dimers

| SEQ ID NO | Peptide sequence | 1 | 2 | 3 | 4 | 5 | 6 | 7 | 8 | 9 | 10 | | | Linker |
|---|---|---|---|---|---|---|---|---|---|---|---|---|---|---|
| 179 | ((thioether) | 2-Benzyl | N—Me—R | S | D | T | L | c | Aic | e | k | NH2)2 | | DIG |
| 180 | ((thioether) | 2-Benzyl | N—Me—R | S | D | T | L | C | Aic | e | k | NH2)2 | | DIG |
| 181 | ((thioether) | 2-Benzyl | N—Me—R | S | D | T | L | D-Pen | W | E | k | NH2)2 | | DIG |
| 182 | ((thioether) | 2-Benzyl | N—Me—R | S | D | T | L | C | N—Me—Y | E | k | NH2)2 | | DIG |
| 183 | ((thioether) | 2-Benzyl | N—Me—R | S | D | T | L | C | N—Me—F | E | k | NH2)2 | | DIG |
| 184 | ((thioether) | 2-Benzyl | N—Me—R | S | D | T | L | G | Tic | e | k | NH2)2 | | DIG |
| 185 | ((thioether) | 2-Benzyl | N—Me—R | S | D | T | L | c | Tic | e | k | NH2)2 | | DIG |
| 186 | ((thioether) | 2-Benzyl | N—Me—R | S | D | T | L | C | f | E | k | NH2)2 | | DIG |
| 187 | ((thioether) | 2-Benzyl | N—Me—R | S | D | T | L | C | f | e | k | NH2)2 | | DIG |
| 188 | ((thioether) | 2-Benzyl | N—Me—R | S | D | T | L | D-Pen | Y | e | k | NH2)2 | | DIG |
| 189 | ((thioether) | 2-Benzyl | N—Me—R | S | E | T | L | Pen | F | e | k | NH2)2 | | DIG |
| 190 | ((thioether) | 2-Benzyl | N—Me—R | S | D | T | L | Pen | W | e | L | k | NH2)2 | DIG |
| 191 | ((thioether) | 2-Benzyl | N—Me—R | S | D | T | L | Pen | W | e | S | k | NH2)2 | DIG |
| 192 | ((thioether) | 2-Benzyl | N—Me—R | S | D | T | L | Pen | W | e | F | k | NH2)2 | DIG |
| 193 | ((thioether) | 2-Benzyl | N—Me—R | S | D | T | L | Pen | W | e | H | k | NH2)2 | DIG |
| 194 | ((thioether) | 2-Benzyl | N—Me—R | S | D | T | L | Pen | W | e | E | k | NH2)2 | DIG |
| 195 | ((thioether) | 2-Benzyl | N—Me—R | S | D | T | L | Pen | W | e | Y | k | NH2)2 | DIG |
| 196 | ((thioether) | 2-Benzyl | N—Me—R | S | D | T | L | Pen | W | e | I (D-L) | k | NH2)2 | DIG |
| 197 | ((thioether) | 2-Benzyl | N—Me—R | S | D | T | L | Pen | W | e | s | k | NH2)2 | DIG |
| 198 | ((thioether) | 2-Benzyl | N—Me—R | S | D | T | L | Pen | W | e | f | k | NH2)2 | DIG |
| 199 | ((thioether) | 2-Benzyl | N—Me—R | S | D | T | L | Pen | W | e | h | k | NH2)2 | DIG |
| 200 | ((thioether) | 2-Benzyl | N—Me—R | S | D | T | L | Pen | W | e | e | k | NH2)2 | DIG |
| 201 | ((thioether) | 2-Benzyl | N—Me—R | S | D | T | L | Pen | W | e | y | k | NH2)2 | DIG |
| 202 | ((thioether) | 2-Benzyl | N—Me—R | S | D | T | L | Pen | W | Bip | k | NH2)2 | | DIG |
| 203 | ((thioether) | 2-Benzyl | N—Me—R | S | D | T | L | Pen | F | Bip | k | NH2)2 | | DIG |
| 204 | ((thioether) | 2-Benzyl | N—Me—R | S | D | T | L | Pen | F | e | Bip | k | OH)2 | DIG |
| 205 | ((thioether) | 2-Benzyl | N—Me—R | S | D | T | L | C | Tic | Bip | k | NH2)2 | | DIG |
| 206 | (thioether) | 2-Benzyl | N—Me—R | S | D | T | L | Pen | 2-Nal | Bip | k | NH2)2 | | DIG |
| 207 | ((thioether) | 2-Benzyl | N—Me—R | S | D | T | L | C | Tic | e | k | OH)2 | | DIG |
| 208 | ((thioether) | 2-Benzyl | N—Me—R | S | D | T | L | Pen | Bip | e | k | OH)2 | | DIG |
| 209 | ((thioether) | 2-Benzyl | N—Me—R | S | D | T | L | Pen | W | e | k | OH)2 | | DIG |
| 210 | ((thioether) | 2-Benzyl | N—Me—R | S | D | T | L | Pen | W | E(OMe) | k | NH2 | | DIG |
| 211 | ((thioether) | 2-Benzyl | N—Me—R | S | D | T | L | C | Tic | E(OMe) | k | NH2 | | DIG |
| 212 | ((thioether) | 2-Benzyl | N—Me—R | S | D | T | L | Pen | W | e | k | NH2)2 | | IDA-Palm |
| 213 | ((thioether) | 2-Benzyl | N—Me—R | S | D | T | L | Pen | W | e | k | NH2)2 | | IDA-Lauryl |
| 214 | ((thioether) | 2-Benzyl | N—Me—R | S | D | T | L | Pen | W | e | k | NH2)2 | | IDA-oleoyl |
| 215 | ((thioether) | 2-Benzyl | N—Me—R | S | D | T | L | Pen | W | e | k | NH2)2 | | IDA-PEG12-NH2 |
| 216 | ((thioether) | 2-Benzyl | N—Me—R | S | D | T | L | C | Tic | k | NH2)2 | | | DIG |
| 217 | ((thioether) | 2-Benzyl | N—Me—R | S | D | T | L | Pen | W | e | k | NH2)2 | | IDA-PEG12-NH-oleoyl |
| 218 | ((thioether) | 2-Benzyl | N—Me—R | S | D | T | L | Pen | W | e | k | NH2)2 | | IDA-PEG12-NH-Lauryl |
| 219 | ((thioether) | 2-Benzyl | N—Me—R | S | D | T | L | C | Tic | E | k | NH2)2 | | DIG |
| 220 | ((thioether) | 2-Benzyl | N—Me—R | S | D | T | L | C | Tic | E(OMe) | k | OH)2 | | DIG |
| 221 | ((thioether) | 2-Benzyl | N—Me—R | S | D | T | L | C | Tic | k | OH)2 | | | DIG |
| 222 | ((thioether) | 2-Benzyl | N—Me—R | S | D | T | L | Pen | F(4-tBu) | bHE | k | NH2)2 | | DIG |
| 223 | ((thioether) | 2-Benzyl | N—Me—R | S | D | T | L | Pen | F(4-tBu) | bHE | k | OH)2 | | DIG |
| 301 | (thioether | Butyryl | N—Me—R | S | D | T | L | C | W | k | NH2)2 | DIG | | |
| 302 | (thioether | 2-Benzyl | N—Me—R | S | D | T | L | c | W | b-H-E | k | NH2)2 | | DIG |
| 303 | (thioether | 2-Benzyl | N—Me—R | S | D | T | L | Hcys | W | E | k | NH2)2 | | DIG |
| 304 | thioether | 2-Benzyl | N—Me—R | S | D | T | L | Pen | W | E | Dap | Ac | | |
| 305 | thioether | 2-Benzyl | N—Me—R | S | D | T | L | Pen | W | E | Dab | Ac | | |
| 306 | thioether | 2-Benzyl | N—Me—R | S | D | T | L | Pen | W | e | Dap | Ac | | |
| 307 | thioether | 2-Benzyl | N—Me—R | S | D | T | L | Pen | W | e | Dab | Ac | | |
| 308 | (thioether | 2-Benzyl | N—Me—R | S | D | T | L | Pen | W | e | k | NH2)2 | | DIG |
| 309 | thioether | 2-Benzyl | N—Me—R | S | D | T | L | Pen | W | e | NH2 | | | |
| 310 | (thioether | 3-Benzyl | N—Me—R | S | D | T | L | Pen | W | e | k | NH2)2 | | DIG |
| 311 | (thioether | 4-Benzyl | N—Me—R | S | D | T | L | Pen | W | e | k | NH2)2 | | DIG |
| 312 | ((thioether) | 2-Benzyl | N—Me—R | S | D | T | L | Pen | W | e | k | NH2)2 | | IDA-PEG12-NH-Lauryl |
| 313 | (thioether) | 2-Benzyl | N—Me—R | S | D | T | L | C | Tic | k | OH | | | |
| 314 | ((thioether) | 2-Benzyl | N—Me—R | S | D | T | L | Pen | W | E(OMe) | k | NH2)2 | | DIG |
| 315 | ((thioether) | 2-Benzyl | N—Me—R | S | D | T | L | Pen | 1-Nal | f | k | NH2)2 | | DIG |

TABLE 5-continued

Illustrative Thioether Dimers

| SEQ ID NO | Peptide sequence | 1 | 2 | 3 | 4 | 5 | 6 | 7 | 8 | 9 | 10 | | Linker |
|---|---|---|---|---|---|---|---|---|---|---|---|---|---|
| 316 | ((thioether) | 2-Benzyl | N—Me—R | S | D | T | L | Pen | 1-Nal | h | k | NH2)2 | DIG |
| 317 | ((thioether) | 2-Benzyl | N—Me—R | S | D | T | L | Pen | 1-Nal | l | k | NH2)2 | DIG |
| 318 | ((thioether) | 2-Benzyl | N—Me—R | S | D | T | L | Pen | 1-Nal | r | k | NH2)2 | DIG |
| 319 | ((thioether) | 2-Benzyl | N—Me—R | S | D | T | L | Pen | 1-Nal | Tic | k | NH2)2 | DIG |
| 320 | ((thioether) | 2-Benzyl | N—Me—R | S | D | T | L | Pen | 1-Nal | t | k | NH2)2 | DIG |
| 321 | ((thioether) | 2-Benzyl | N—Me—R | S | D | T | L | Pen | 1-Nal | E | k | NH2)2 | DIG |
| 322 | ((thioether) | 2-Benzyl | N—Me—R | S | D | T | L | Pen | 1-Nal | b-HomoGlu | k | NH2)2 | DIG |
| 323 | ((thioether) | 2-Benzyl | N—Me—R | S | D | T | L | Pen | 1-Nal | E | N—Me—K | NH2)2 | DIG |
| 324 | ((thioether) | 2-Benzyl | N—Me—R | S | D | T | L | Pen | 1-Nal | E | N—Me—k | NH2)2 | DIG |
| 325 | ((thioether) | 2-Benzyl | N—Me—R | S | D | T | L | Pen | 1-Nal | b-HomoGlu | N—Me—K | NH2)2 | DIG |
| 326 | ((thioether) | 2-Benzyl | N—Me—R | S | D | T | L | Pen | 1-Nal | b-HomoGlu | N—Me—k | NH2)2 | DIG |
| 327 | ((thioether) | 2-Benzyl | N—Me—R | S | D | T | L | Pen | 2-Nal | f | k | NH2)2 | DIG |
| 328 | ((thioether) | 2-Benzyl | N—Me—R | S | D | T | L | Pen | 2-Nal | h | k | NH2)2 | DIG |
| 329 | ((thioether) | 2-Benzyl | N—Me—R | S | D | T | L | Pen | 2-Nal | l | k | NH2)2 | DIG |
| 330 | ((thioether) | 2-Benzyl | N—Me—R | S | D | T | L | Pen | 2-Nal | r | k | NH2)2 | DIG |
| 331 | ((thioether) | 2-Benzyl | N—Me—R | S | D | T | L | Pen | 2-Nal | Tic | k | NH2)2 | DIG |
| 332 | ((thioether) | 2-Benzyl | N—Me—R | S | D | T | L | Pen | 2-Nal | E | k | NH2)2 | DIG |
| 333 | ((thioether) | 2-Benzyl | N—Me—R | S | D | T | L | Pen | 2-Nal | b-HomoGlu | k | NH2)2 | DIG |
| 334 | ((thioether) | 2-Benzyl | N—Me—R | S | D | T | L | Pen | 2-Nal | k | NH2 | | DIG |
| 335 | ((thioether) | 2-Benzyl | N—Me—R | S | D | T | L | Pen | 2-Nal | k | NH2 | | DIG |
| 336 | ((thioether) | 2-Benzyl | N—Me—R | S | D | T | L | Pen | 2-Nal | E | N—Me—K | NH2)2 | DIG |
| 337 | ((thioether) | 2-Benzyl | N—Me—R | S | D | T | L | Pen | 2-Nal | E | N—Me—k | NH2)2 | DIG |
| 338 | ((thioether) | 2-Benzyl | N—Me—R | S | D | T | L | Pen | 2-Nal | b-HomoGlu | N—Me—K | NH2)2 | DIG |
| 339 | ((thioether) | 2-Benzyl | N—Me—R | S | D | T | L | Pen | 2-Nal | b-HomoGlu | N—Me—k | NH2)2 | DIG |
| 340 | ((thioether) | 2-Benzyl | N—Me—R | S | D | T | L | Pen | Bip | e | k | NH2)2 | DIG |
| 341 | ((thioether) | 2-Benzyl | N—Me—R | S | D | T | L | Pen | Bip | E | k | NH2)2 | DIG |
| 342 | ((thioether) | 2-Benzyl | N—Me—R | S | D | T | L | Pen | Bip | b-HomoGlu | k | NH2)2 | DIG |
| 343 | ((thioether) | 2-Benzyl | N—Me—R | S | D | T | L | Pen | Bip | E | N—Me—K | NH2)2 | DIG |
| 344 | ((thioether) | 2-Benzyl | N—Me—R | S | D | T | L | Pen | Bip | E | N—Me—k | NH2)2 | DIG |
| 345 | ((thioether) | 2-Benzyl | N—Me—R | S | D | T | L | Pen | Bip | b-HomoGlu | N—Me—K | NH2)2 | DIG |
| 346 | ((thioether) | 2-Benzyl | N—Me—R | S | D | T | L | Pen | Bip | b-HomoGlu | N—Me—k | NH2)2 | DIG |
| 347 | ((thioether) | 2-Benzyl | N—Me—R | S | D | T | L | Pen | F(2,4-Cl) | e | k | NH2)2 | DIG |
| 348 | ((thioether) | 2-Benzyl | N—Me—R | S | D | T | L | Pen | F(2-carbamoyl) | e | k | NH2)2 | DIG |
| 349 | ((thioether) | 2-Benzyl | N—Me—R | S | D | T | L | Pen | F(3,4-Cl) | e | k | NH2)2 | DIG |
| 350 | ((thioether) | 2-Benzyl | N—Me—R | S | D | T | L | Pen | F(3-carbamoyl) | e | k | NH2)2 | DIG |
| 351 | ((thioether) | 2-Benzyl | N—Me—R | S | D | T | L | Pen | F(4CF3) | e | k | NH2)2 | DIG |
| 352 | ((thioether) | 2-Benzyl | N—Me—R | S | D | T | L | Pen | F(4-COOH) | e | k | NH2)2 | DIG |
| 353 | ((thioether) | 2-Benzyl | N—Me—R | S | D | T | L | Pen | F(4-COOH) | E | k | NH2)2 | DIG |
| 354 | ((thioether) | 2-Benzyl | N—Me—R | S | D | T | L | Pen | F(4-COOH) | E | k | NH2)2 | DIG |
| 355 | ((thioether) | 2-Benzyl | N—Me—R | S | D | T | L | Pen | F(4-COOH) | E | k | NH2)2 | DIG |
| 356 | ((thioether) | 2-Benzyl | N—Me—R | S | D | T | L | Pen | F(4-COOH) | b-HomoGlu | k | NH2)2 | DIG |
| 357 | ((thioether) | 2-Benzyl | N—Me—R | S | D | T | L | Pen | F(4-COOH) | b-HomoGlu | k | NH2)2 | DIG |
| 358 | ((thioether) | 2-Benzyl | N—Me—R | S | D | T | L | Pen | F(4-COOH) | b-HomoGlu | k | NH2)2 | DIG |
| 359 | ((thioether) | 2-Benzyl | N—Me—R | S | D | T | L | Pen | F(4-F) | e | k | NH2)2 | DIG |
| 360 | ((thioether) | 2-Benzyl | N—Me—R | S | D | T | L | Pen | F(4-OMe) | e | k | NH2)2 | DIG |
| 361 | ((thioether) | 2-Benzyl | N—Me—R | S | D | T | L | Pen | F(4tBu) | e | k | NH2)2 | DIG |
| 362 | ((thioether) | 2-Benzyl | N—Me—R | S | D | T | L | Pen | F(4tBu) | E | k | NH2)2 | DIG |
| 363 | ((thioether) | 2-Benzyl | N—Me—R | S | D | T | L | Pen | F(4tBu) | b-HomoGlu | k | NH2)2 | DIG |
| 364 | ((thioether) | 2-Benzyl | N—Me—R | S | D | T | L | Pen | F(4tBu) | E | N—Me—k | NH2)2 | DIG |
| 365 | ((thioether) | 2-Benzyl | N—Me—R | S | D | T | L | Pen | F(4tBu) | E | N—Me—k | NH2)2 | DIG |
| 366 | ((thioether) | 2-Benzyl | N—Me—R | S | D | T | L | Pen | F(4tBu) | b-HomoGlu | N—Me—k | NH2)2 | DIG |
| 367 | ((thioether) | 2-Benzyl | N—Me—R | S | D | T | L | Pen | F(4tBu) | b-HomoGlu | N—Me—k | NH2)2 | DIG |
| 368 | ((thioether) | 2-Benzyl | N—Me—R | S | D | T | L | Pen | H | e | k | NH2)2 | DIG |
| 369 | ((thioether) | 2-Benzyl | N—Me—R | S | D | T | L | C | Tic | e | k | NH2 | DIG |
| 370 | ((thioether) | 2-Benzyl | N—Me—R | S | D | T | L | C | Tic | e | k | NH2)2 | DIG |
| 371 | ((thioether) | 2-Benzyl | N—Me—R | S | D | T | L | Pen | W | E | Dab | NH2)2 | DIG |
| 372 | ((thioether) | 2-Benzyl | N—Me—R | S | D | T | L | Pen | W | f | k | NH2)2 | DIG |

TABLE 5-continued

Illustrative Thioether Dimers

| SEQ ID NO | Peptide sequence | 1 | 2 | 3 | 4 | 5 | 6 | 7 | 8 | 9 | 10 | | Linker |
|---|---|---|---|---|---|---|---|---|---|---|---|---|---|
| 373 | ((thioether) | 2-Benzyl | N—Me—R | S | D | T | L | Pen | W | y | k | NH2)2 | DIG |
| 374 | ((thioether) | 2-Benzyl | N—Me—R | S | D | T | L | Pen | W | P | k | NH2)2 | DIG |
| 375 | ((thioether) | 2-Benzyl | N—Me—R | S | D | T | L | Pen | W | P | K | NH2)2 | DIG |
| 376 | ((thioether) | 2-Benzyl | N—Me—R | S | D | T | L | Pen | W | p | K | NH2)2 | DIG |
| 377 | ((thioether) | 2-Benzyl | N—Me—R | S | D | T | L | Pen | W | h | k | NH2)2 | DIG |
| 378 | ((thioether) | 2-Benzyl | N—Me—R | S | D | T | L | Pen | W | F(4-COOH) | k | NH2)2 | DIG |
| 379 | ((thioether) | 2-Benzyl | N—Me—R | S | D | T | L | Pen | W | Tic | k | NH2)2 | DIG |
| 380 | ((thioether) | 2-Benzyl | N—Me—R | S | D | T | L | Pen | W | w | k | NH2)2 | DIG |
| 381 | thioether | Acetyl | N—Me—R | S | D | T | L | Pen | W | k | NH2)2 | | DIG |
| 382 | thioether | Propionyl | N—Me—R | S | D | T | L | Pen | W | k | NH2)2 | | DIG |
| 383 | thioether | Propionyl | N—Me—R | S | D | T | L | hC | W | k | NH2)2 | | DIG |
| 384 | ((thioether) | 2-Benzyl | N—Me—R | S | D | T | L | Pen | Y | e | k | NH2)2 | DIG |

Example 2

Characterization of Thioether Peptide Monomer and Dimer Molecules

The stability, potency, and selectivity of certain thioether peptide monomer and dimers were determined using a variety of assays described herein. Peptides listed in Table 8 can be used as control peptides for all of the assays described herein.

Simulated Intestinal Fluid (SIF) Stability Assay

Studies were carried out in simulated intestinal fluid (SIF) to evaluate intestinal stability of the peptide molecules of the instant invention. To prepare the SIF reagent, blank FASSIF was prepared by dissolving 0.348 g NaOH, 3.954 g sodium phosphate monobasic monohydrate and 6.186 g NaCl in a final volume of 1 liter water (final pH=6.5).

To this solution, 24 g porcine pancreatin (Sigma catalog P7545) was added and stirred for 30 minutes (final pancreatin concentration is 2.4%). The solution was filtered through a cheese cloth and a No. 1 Whatman filter, and 10 ml aliquots were stored at −70° C. To run the reaction, a 10 ml aliquot was thawed at 37° C., and 125 µl aliquots were removed and mixed with an equal volume of blank FASSIF. The peptide stock solution (10 mM in 100% DMSO) was diluted 75-fold in blank FASSIF. A 50 µl aliquot of the diluted peptide was combined with 125 µl pancreatin (2.4%) and 125 µl blank FASSIF to yield final concentrations of 1% pancreatin and 22 µM peptide. The reactions were incubated at 37° C., and at various time points 50 µl aliquots were removed and added to 200 µl of quench solution containing 50% acetonitrile, 50% methanol, 5% formic acid, and 1 µg/ml internal standard. The quenched samples were centrifuged at 10,000 rpm for 10 minutes, and the supernatants were analyzed by LCMS/MS. The percent remaining at each time point was calculated based on the peak area response ratio of test to compound to internal standard. Half-lives were calculated by fitting to a first-order exponential decay equation using GraphPad. A small sampling of the results of these studies is provided and discussed herein and in the accompanying figures.

Simulated Gastric Fluid (SGF) Stability Assays

Studies were carried out in simulated gastric fluid (SGF) to evaluate intestinal stability of the peptide molecules of the instant invention. SGF was prepared by adding 20 mg NaCl, 32 mg porcine pepsin (MP Biochemicals, catalog 02102599), and 70 µl HCl to 10 ml water (final pH=2).

Aliquots of SGF (0.5 ml each) were pre-warmed at 37° C. To start the reaction, 1 µl of peptide stock solution (10 mM in DMSO) was added to 0.5 ml SGF and thoroughly mixed such that the final peptide concentration was 20 µM. The reactions were incubated at 37° C. with gentle shaking. At each time point (0, 15, 30, 60 min) 50 µl aliquots were removed and added to 200 ul acetonitrile containing 0.1% formic acid to quench the reaction. Samples are stored at 4° C. until the end of the experiment and centrifuged at 10,000 rpm for 5 minutes. Aliquots of the supernatant were removed, diluted 1:1 into distilled water containing internal standard, and analyzed by LCMS/MS. Percent remaining at each timepoint was calculated based on the peak area response ratio of test to compound to internal standard. Time 0 was set to 100%, and all later timepoints were calculated relative to time 0. Half-lives were calculated by fitting to a first-order exponential decay equation using GraphPad.

Redox Stability Assays

Studies were carried out under redox conditions to evaluate intestinal stability of the peptide molecules of the instant invention.

Dithiothreitol (DTT) Redox Stability Assay

The DTT stability assay was prepared by adding 5 µl of a 10 mM peptide stock solution in DMSO to 1 ml of 100 mM Tris-Cl, pH 7.5 (final peptide concentration is 50 µM). At time 0 min, 5 ul of a freshly thawed 100 mM DTT solution was added such that the final DTT concentration is 0.5 mM. The reactions were incubated at room temperature. At different time points up to 120 minutes, 50 µl aliquots were removed and the reaction was quenched by adding 10 µl of 5M acetic acid. To measure disappearance of the parent peptide, the quenched samples (30 µl) were analyzed by reverse phase HPLC and UV absorbance at 220 nm. Half-lives were calculated by fitting to a first-order exponential decay equation using Excel.

Cysteine/Cystine Redox Stability Assay

Peptides were diluted to 90 µM by adding 4.545 µl of a 10 mM peptide DMSO stock to 495.45 µl of 100 mM Tris-Cl, pH 7.5. Aliquots of 55 µl were removed and added to 20 µl of 2.5 mM Cystine in 100 mM Tris-Cl, pH 7.5. Cysteine stock solutions in 100 mM Tris-Cl, pH 7.5 were prepared fresh at the following concentrations: 400 mM, 200 mM, 80 mM, 44 mM, 22 mM, 11 mM, 5.5 mM and blank. At time 0, 25 µl of each cysteine stock solution was added to the 55 µl of cystine/peptide solution and the mixture was incubated at room temperature for 40 min. The samples were quenched by adding 20 µl of 5M acetic acid and analyzed by reverse phase HPLC. The fraction of oxidized peptide was calculated and plotted against the calculated oxidation reduction potential (OEP) as defined by the Nernst equation.

α4β7-MAdCAM Competition ELISA

A nickel coated plate (Pierce #15442) was coated with rh integrin α4β7 (R&D Systems #5397-A30) at 800 ng/well and incubated at room temperature with shaking for 1 hr. The solution was then removed by shaking and blocked with assay buffer (50 mM Tris-HCl pH7.6, 150 mM NaCl, 1 mM $MnCl_2$ or $MgCl_2$, 0.05% Tween-20 and 0.5% BSA) at 250 ul/well. The plate was then incubated at room temperature for 1 hr. Each well was washed 3 times with wash buffer (50 mM Tris-HCl pH7.6, 100 mM NaCl, 1 mM $MnCl_2$ or $MgCl_2$, 0.05% Tween-20). To each well was added 25 ul of a serial dilution (3-fold dilutions in assay buffer) of peptides starting at 20 μM. 25 ul of recombinant human MAdCAM-1 (R&D Systems #6056-MC) was then added to each well at a fixed concentration 20 nM. The final starting peptide concentration was 10 μM, and the final MAdCAM-1 concentration was 10 nM. The plates were then incubated at room temperature for 1 hr to reach binding equilibrium. The wells were then washed three times with wash buffer. 50 ul of mouse anti-human IgG1-HRP (Invitrogen #A10648) diluted in 1:2000 in assay buffer was then added to each well. The wells were incubated at room temperature for 45 min with shaking. The wells were then washed 3 times with wash buffer. 100 ul of TMB were then added to each well and closely observe during development time. The reaction was stopped with 2N $H_2SO_4$ and absorbance was read at 450 nm.

α4β1-VCAM Competition ELISA

A Nunc MaxiSorp plate was coated with rh VCAM-1/CD106 Fc chimera (R&D #862-VC) at 400 ng/well in 50 ul per well in 1×PBS and incubated overnight at 4° C. The solution was removed by shaking and then blocked with 250 ul of 1% BSA in 1×PBS per well. The wells were then incubated at room temperature for 1 hr with shaking. Each well was then washed once with wash buffer (50 mM Tris-HCl pH7.6, 100 mM NaCL, 1 mM $MnCl_2$ or $MgCl_2$, 0.05% Tween-20). 25 ul of serial dilutions of peptides starting at 200 μM in assay buffer (Assay buffer: 50 mM Tris-HCl pH7.6, 100 mM NaCl, 1 mM $MnCl_2$ or $MgCl_2$, 0.05% Tween-20) was added to each well. Additionally, 25 ul of α β1 (R&D Systems #5668-A4) was added to each well at a fixed concentration of 120 nM. The final peptide and α β1 concentrations were 100 μM and 60 nM, respectively. The plates were then incubated at 37° C. for 2 hr. The solution was then removed by shaking and each well was washed three times with wash buffer. 50 ul of 9F10 antibody at 4 ug/ml (purified mouse anti-human CD49d, BD Bioscience Cat#555502) was then added to each well, and the plate was incubated at room temperature for 1 hr with shaking. The solution was again removed by shaking, and each well was washed three times with wash buffer. 50 ul of peroxidase-conjugated AffiniPure Goat anti-mouse IgG (Jackson immune research cat #115-035-003) diluted in 1:5000 in assay buffer was added to each well. The plate was incubated at room temperature for 30 min with shaking. Each well was then washed 3 times with wash buffer. 100 ul of TMB was then added to each well and closely observe during developing time. The reaction was stepped with 2N $H_2SO_4$ and absorbance was read at 450 nm.

PBMC Memory T Cell Adhesion Assay

Fresh CD4+/CD45RO+ memory T cells were isolated from human peripheral blood mononuclear cell (PBMC) donors by Aragen Bioscience Inc. (Morgan Hill, Calif.). The assay plate was prepared using IgG Fc capture antibody (donkey anti human) immobilized at 500 ng/well in 50 mM sodium bicarbonate buffer, pH 9.5, ON, 4 C onto a Greiner Fluotrac plate (100 ul per well). The plate was rinsed two time with Blocking Buffer (25 mM Tris HCl, pH7.5, 150 mM NaCl, 1.5% BSA, 0.05% Tween), and blocked with Blocking Buffer for 2 hours at 37 C or 5 hours at RT using 200 ul per well. The Blocking Buffer was removed and either MAdCAM-1 or VCAM-1 at 400 ng/well in Blocking Buffer was added and the plate incubated overnight at 4 C (100 ul per well). The plate was washed two times with Blocking Buffer, and rinsed once with 200 ul Binding Media (DMEM phenol red free, 10 mM HEPES, 1×Na pyruvate, 1x Glutamine, and supplemented with 1 mM MnCl2 prior to use). To prepare cells, approximately 25 million CD4+/CD45RO+ memory T cells were counted by trypan blue exclusion using a haemocytometer to determine viability and cell count. The cells were transferred to a 50 ml conical tube, and centrifuged at 1200 rpm for 10 minute. The media was aspirated and the cell pellet resuspended in 15 ml Binding Media. The cells were centrifuged again and resuspended in the appropriate amount of Binding Media to be used for assays (50 ul of cells per well at 2× the final density). To each well, and equal volume (50 ul) of test compound was added and the plate was incubated for 1.5 hours at 37 C, 5% CO2.

Each well was rinsed 3× with 150 ul per well of Binding Media. CyQuant NF reagent was prepared as suggested by manufacturer), and 100 ul of CyQuant NF reagent was added per well. The plate was incubated at 37 C, 5% CO2, for 45 minutes. The plate was protected from light by using black adhesive seals. Fluorescence intensity was measured using a Molecular Devices Gemini EM Fluorescent Plate Reader (Ex 485/Em530, Bottom Read, Reading Sensitivity=20). IC50 curves are generated using Graph Pad Prism and the curves analyzed using analyzed using a non-linear regression (four parameters) algorithm. The log (concentration) versus RFU (Ex485/Em530) was plotted to determine IC50 values.

α4β7-MAdCAM Cell Adhesion Assay

RPMI 8866 cells (Sigma #95041316) were cultured in RPMI 1640 HEPES medium (Invitrogen #22400-089) supplemented with 10% serum (Fetal Bovine Serum, Invitrogen #16140-071), 1 mM sodium pyruvate (Invitrogen #11360-070), 2 mM L-glutamine (Invitrogen #25030-081) and Penicillin-Streptomycin (Invitrogen #15140-122) at 100 units of penicillin and 100 μg of streptomycin per ml. The cells were washed two times in DMEM medium (ATCC #30-2002) supplemented with 0.1% BSA, 10 mM HEPES pH 7 and 1 mM $MnCl_2$. The cells were re-suspended in supplemented DMEM medium at a density of $4×10^6$ cells/ml.

A Nunc MaxiSorp plate was coated with rh MAdCAM-1/Fc Chimera (R&D #6065-MC) at 200 ng per well in 50 ul per well in 1×PBS and incubated at 4° C. overnight. The solution was then removed by shaking, blocked with 250 ul per well PBS containing 1% BSA, and incubated at 37° C. for 1 hr. The solution was removed by shaking. Peptides were diluted by serial dilution in a final volume of 50 ul per well (2× concentration). To each well, 50 ul of cells (200,000 cells) were added and the plate was incubated at 37° C., 5% $CO_2$ for 30-45 min to allow cell adhesion. The wells were washed manually three times (100 ul per wash) with supplemented DMEM. After the final wash, 100 ul/well of supplemented DMEM and 10 ul/well of MTT reagent (ATTC cat#30-1010K) were added. The plate was incubated at 37° C., 5% CO2 for 2-3 hrs until a purple precipitate is visible. 100 ul of Detergent Reagent (ATTC cat#30-1010K) was added to each well. The plate was covered from the light, wrapped in Parafilm to prevent evaporation, and left overnight at room temperature in the dark. The plate was shaken for 5 min and the absorbance at 570 nm is measured. To calculate the dose response, the absorbance value of control wells not containing cells was subtracted from each test well.

α4β1-VCAM Cell Adhesion Assay

Jurkat E6.1 cells (Sigma #88042803) were cultured in RPMI 1640 HEPES medium (Invitrogen #22400-089) supplemented with 10% serum (Fetal Bovine Serum, Invitrogen #16140-071), 1 mM sodium pyruvate (Invitrogen #11360-070), 2 mM L-glutamine (Invitrogen #25030-081) and Penicillin-Streptomycin (Invitrogen #15140-122) at 100 units of penicillin and 100 μg of streptomycin per ml. The cells were washed two times in DMEM medium (ATCC #30-2002) supplemented with 0.1% BSA, 10 mM HEPES pH 7 and 1 mM $MnCl_2$. The cells were re-suspended in supplemented DMEM medium at a density of $4\times10^6$ cells/ml.

A Nunc MaxiSorp plate was coated with rh VCAM-1/CD106 Fc chimera (R&D #862-VC) at 400 ng per well in 50 ul per well in 1×PBS and incubated at 4° C. overnight. The solution was then removed by shaking, blocked with 250 ul per well PBS containing 1% BSA, and incubated at 37° C. for 1 hr. The solution was removed by shaking. Peptides were diluted by serial dilution in a final volume of 50 ul per well (2× concentration). To each well, 50 ul of cells (200,000 cells) were added and the plate was incubated at 37° C., 5% $CO_2$ for 30-45 min to allow cell adhesion. The wells were washed manually three times (100 ul per wash) with supplemented DMEM. After the final wash, 100 ul/well of supplemented DMEM and 10 ul/well of MTT reagent (ATTC cat#30-1010K) were added. The plate was incubated at 37° C., 5% CO2 for 2-3 hrs until a purple precipitate is visible. 100 ul of Detergent Reagent (ATTC cat#30-1010K) is added to each well. The plate was covered from the light, wrapped in Parafilm to prevent evaporation, and left overnight at room temperature in the dark. The plate was shaken for 5 min and the absorbance at 570 nm is measured. To calculate the dose response, the absorbance value of control wells not containing cells was subtracted from each test well.

The potency, selectivity and stability data for certain illustrative peptide monomers and dimers of the present invention are provided in Tables 6 and 7. These peptides have the structures shown in Tables 4 and 5, which may be identified by their SEQ ID NOs. Table 6 provides potency, selectivity and stability data for representative peptide monomers. Table 7 provides potency, selectivity and stability data for representative peptide dimers. For potency, IC50 values are shown as *<25 nM, =25-100 nM, *=100-1000 nM. Where data not shown, data was not determined, but is expected that these peptides have an IC50<100 nM in α4β7 ELISA and/or cell assays.

TABLE 6

Characterization of Illustrative Thioether Monomer Peptides

| SEQ ID NO | ELISA A4B7 (nM) | ELISA A4B1 (nM) | Cell-Adhesion A4B7 (nM) | PBMC IC50 (nM) | SIF (Porcine) (half-life, min) | SGF (Porcine) (Half-life, Min) |
|---|---|---|---|---|---|---|
| 49 | ** | | >1000 | | | |
| 50 | *** | | | | | |
| 51 | ** | | | | | 6 |
| 52 | >1000 | | | | | |
| 53 | *** | | | | | >180 |
| 54 | >1000 | | | | | second |
| 55 | * | *** | *** | | 25 | |
| 56 | * | *** | *** | | 186 | |
| 57 | *** | | | | <20 | |
| 58 | >1000 | | | | | |
| 59 | *** | | | | <20 | |
| 60 | * | *** | | | >180 | |
| 61 | * | | | | >180 | |
| 62 | * | | | | >180 | |
| 63 | * | | | | >180 | |
| 64 | * | | | | 179 | |
| 65 | * | | ** | | >180 | |
| 66 | ** | | | | >180 | |
| 67 | * | | | | <20 | |
| 68 | * | | | | >180 | |
| 69 | * | | *** | | >180 | |
| 70 | * | | | | >180 | |
| 71 | ** | | | | >180 | |
| 72 | * | | | | >180 | |
| 73 | * | | | | >180 | |
| 74 | * | | | | >180 | |
| 75 | * | | | | >180 | |
| 76 | * | | | | >180 | |
| 77 | * | | | | 88 | |
| 78 | * | | | | 78 | |
| 79 | * | | | | | |
| 80 | * | | ** | | | |
| 81 | * | *** | ** | | | |
| 82 | * | | *** | | | |
| 83 | * | | | | | |
| 84 | * | | | | | |
| 85 | * | | | | | |
| 86 | * | | | | | |
| 87 | * | | | | | |
| 88 | * | | ** | | | |

TABLE 6-continued

Characterization of Illustrative Thioether Monomer Peptides

| SEQ ID NO | ELISA A4B7 (nM) | ELISA A4B1 (nM) | Cell-Adhesion A4B7 (nM) | PBMC IC50 (nM) | SIF (Porcine) (half-life, min) | SGF (Porcine) (Half-life, Min) |
|---|---|---|---|---|---|---|
| 89 | * | | *** | | | |
| 90 | * | | | | | |
| 91 | * | | *** | | | |
| 92 | * | | ** | | | |
| 93 | * | | ** | | | |
| 94 | * | | *** | | >180 | |
| 95 | * | | *** | | >180 | |
| 96 | * | | *** | | 26 | |
| 97 | * | *** | ** | | >180, >180 | >180 |
| 98 | * | *** | ** | *** | >300 | >180 |
| 99 | * | | | | | |
| 100 | * | | ** | | | |
| 101 | * | | *** | *** | | |
| 102 | * | | ** | | | |
| 103 | * | | | | | |
| 104 | * | | ** | | | |
| 105 | * | | | | | |
| 106 | * | | ** | | | |
| 107 | * | | ** | | | |
| 108 | * | | ** | | | |
| 109 | * | | | | | |
| 110 | * | | ** | | | |
| 111 | | | >1000 | | | |
| 112 | | | >1000 | | | |
| 113 | * | | ** | | | |
| 114 | * | ** | ** | | >180 | |
| 115 | * | | | | | |
| 116 | * | | ** | | | |
| 117 | | | *** | | | |
| 118 | | | *** | | | |
| 119 | | | *** | | | |
| 120 | | | *** | | | |
| 121 | | | *** | | | |
| 122 | | | *** | | | |
| 123 | | | ** | | | |
| 124 | | | ** | | | |
| 125 | | | * | *** | >180 | |
| 126 | | | ** | | >180 | |
| 127 | | | ** | | | |
| 128 | | | ** | | | |
| 129 | | | ** | | | |
| 130 | | | *** | | | |
| 131 | | | ** | | | |
| 132 | | | * | *** | >180 | |
| 133 | | | * | *** | >180 | |
| 134 | | | * | ** | >180 (428) | |
| 135 | | | * | *** | | |
| 136 | | | ** | | | |
| 137 | | | ** | | | |
| 138 | | | *** | | | |
| 139 | | | ** | | | |
| 140 | | | >1000 | | | |
| 141 | | | >1000 | | | |
| 142 | | | * | | | |

TABLE 7

Characterization of Illustrative Thioether Peptide Dimers

| SEQ ID NO | ELISA A4B7(nM) | ELISA A4B1 (nM) | Cell-Adhesion A4B7 (nM) | Cell Adhesion A4B1 (nM) | PBMC IC50 (nM) | SIF (Porcine) (half-life, min) | SGF (Porcine) (Half-life, Min) |
|---|---|---|---|---|---|---|---|
| 143 | * | >1000 | *** | | | | |
| 144 | * | >1000 | >1000 | | | <20 | |
| 145 | | *** | ** | | | | |
| 146 | * | ** | * | | | <20 | |
| 147 | | | >1000 | | | | |
| 148 | | | >1000 | | | | |
| 149 | | | >1000 | | | <20 | |
| 150 | * | ** | * | >100,000 | | >180, >180, >300 | >180 |

TABLE 7-continued

Characterization of Illustrative Thioether Peptide Dimers

| SEQ ID NO | ELISA A4B7(nM) | ELISA A4B1 (nM) | Cell-Adhesion A4B7 (nM) | Cell Adhesion A4B1 (nM) | PBMC IC50 (nM) | SIF (Porcine) (half-life, min) | SGF (Porcine) (Half-life, Min) |
|---|---|---|---|---|---|---|---|
| 151 | * | ** | * | | | >180 | |
| 152 | * | ** | * | >100,000 | >180 | | >60 |
| 153 | | *** | * | | | >180 (275) | |
| 154 | * | ** | * | >100,000 | | <20 | |
| 155 | * | *** | * | | ** | >180, >300 | >180 |
| 156 | | ** | ** | >100,000 | | >180 | |
| 157 | | *** | ** | | | <20 | |
| 158 | * | *** | * | >100,000 | | >180 | |
| 159 | * | ** | * | >100,000 | | >180 | >180 |
| 160 | * | | * | | | >180 | >60 |
| 161 | * | ** | * | >100,000 | | >180 | |
| 162 | | *** | | | | >180 | |
| 163 | | | * | | | >180 | |
| 164 | * | ** | * | >100,000 | | >180 | >60 |
| 165 | * | ** | * | >100,000 | | >180 | >60 |
| 166 | * | ** | * | | | 30 | |
| 167 | * | ** | * | >100,000 | | <20 | |
| 168 | * | ** | * | >100,000 | | | |
| 169 | * | *** | * | >100,000 | | >180, >180 | >180 |
| 170 | | | * | | | | |
| 171 | | | * | | | | |
| 172 | | | >1000 | | | | |
| 173 | | | ** | | | | |
| 174 | | | * | | | | |
| 175 | | | * | | | | |
| 176 | | | * | | | | |
| 177 | | | * | | | | |
| 178 | * | *** | * | >1000 | | >180 (375), >180(266), >180 | >180 |
| 179 | | | *** | | | | |
| 180 | | | *** | | | | |
| 181 | | | >1000 | | | | |
| 182 | | | ** | | | | |
| 183 | | | ** | | | | |
| 184 | * | *** | * | >100,000 | ** | >180, >180, >180 | >180 |
| 185 | | | ** | | | | |
| 186 | | | ** | | | | |
| 187 | | | ** | | | | |
| 188 | | | >1000 | | | | |
| 189 | | | >1000 | | | | |
| 190 | | | * | | | | |
| 191 | | | * | >100,000 | | | |
| 192 | | | * | | | | |
| 193 | | | * | | | | |
| 194 | | *** | * | | | | |
| 195 | | | * | | | | |
| 196 | | | * | | | | |
| 197 | | | * | | | | |
| 198 | | | * | | | | |
| 199 | | | * | | | | |
| 200 | | | * | | | | |
| 201 | | | * | | | | |
| 202 | | | *** | | | | |
| 203 | | | *** | | | | |
| 204 | * | *** | * | >100,000 | | >180 | >180 |
| 205 | | | *** | | | | |
| 206 | | | >1000 | | | | |
| 207 | * | *** | * | >100,000 | | >180 | >180 |
| 208 | * | ** | * | >100,000 | | >180 (312) | >180 |
| 209 | * | *** | * | >100,000 | | >180 | |
| 210 | | | *** | | | | |
| 211 | | | * | | | 7 | |
| 212 | | | ** | | | | |
| 213 | | | * | | | >180 (419) | |
| 214 | | | ** | | | | |
| 215 | | | * | | | | |
| 216 | | | * | | | >180 | |
| 217 | | | ** | | | | |
| 218 | | | * | | | | |

TABLE 7-continued

Characterization of Illustrative Thioether Peptide Dimers

| SEQ ID NO | ELISA A4B7(nM) | ELISA A4B1 (nM) | Cell-Adhesion A4B7 (nM) | Cell Adhesion A4B1 (nM) | PBMC IC50 (nM) | SIF (Porcine) (half-life, min) | SGF (Porcine) (Half-life, Min) |
|---|---|---|---|---|---|---|---|
| 219 | | | * | | | >180, 407 | >360 |
| 220 | | | * | | | >180 | |
| 221 | | | ** | | | | |
| 222 | | | * | | * | | |
| 223 | | | * | | * | | |

TABLE 8

Characterization of Illustrative Peptide Monomers

| SEQ ID NO | Peptide sequence | 1 | 2 | 3 | 4 | 5 | 6 | 7 | 8 | 9 | 10 | ELISA A4B7 (nM) | ELISA A4B1(nM) | Cell-Adhesion A4B7(nM) | SIF (Porcine) (half-life, min) | Redox stability (DTT) |
|---|---|---|---|---|---|---|---|---|---|---|---|---|---|---|---|---|
| 385 | Ac | C | R | S | D | T | L | C | G | E | NH2 | 97 | 2020 | 590 | <1 min | ~3 min |
| 386 | Ac | C | R | S | D | T | L | C | NH2 | | | 96.8 | 2880 | 1221 | <1 min | ~3 min |

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:
1. A peptide molecule comprising a structure of Formula (V) (SEQ ID NO: 49):

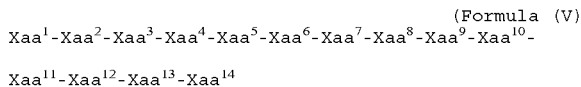

or a pharmaceutically acceptable salt thereof, wherein the peptide comprises a thioether bond between Xaa⁴ and Xaa¹⁰, and wherein:

$Xaa^1$ is absent or any amino acid;
$Xaa^2$ is absent or any amino acid;
$Xaa^3$ is absent or any amino acid;
$Xaa^4$ is a methyl benzoyl moiety capable of forming a thioether bond with $Xaa^{10}$;
$Xaa^5$ is selected from the group consisting of N(alpha)-Me-Arg, Arg, HomoArg, Dap, Dab, Arg-Me-sym, Arg-Me-asym, 4-Guan, Cit, Cav, N-Me-Lys, Phe(4-quanidino), Phe(4-carbamoyl amino), Phe(4-NH₂), N-Me-HomoArg, Tyr, His, and suitable isostere replacements;
$Xaa^6$ is selected from the group consisting of Ser, Gly, Thr, Ile, and suitable isostere replacements;
$Xaa^7$ is selected from the group consisting of Asp, N-Me-Asp, Asp(OMe), D-Asp, and suitable isostere replacements;
$Xaa^8$ is selected from the group consisting of Thr, Gln, Ser, Asp, Pro, Gly, His, Ala, Ile, Phe, Lys, Arg, Asn, Glu, Val, Tyr, Trp, Leu, Met, HomoLeu, Nle, and N-Methyl amino acids including N-Me-Thr;
$Xaa^9$ is selected from the group consisting of Gln, Asn, Asp, Pro, Gly, Ala, Phe, Leu, Glu, Ile, Val, HLeu, n-Butyl Ala, n-Pentyl Ala, n-Hexyl Ala, Nle, cyclobutyl-Ala, Cpa, Cba, Aoc, N-Me-Leu, and suitable isostere replacements;
$Xaa^{10}$ is selected from the group consisting of Cys, N-Me-Cys, D-Cys, HCys, Pen, D-Pen, and Pen(=O);
$Xaa^{11}$ is absent or is selected from the group consisting of: Trp, Phe, 2-Nal, 1-Nal, Tyr, His, Phe(4-F), Phe(4-CF3), Phe (4-CH3), Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe (4-carbomyl), Phe(3-Carbomyl), Phe (2-carbomyl), Tyr (Me), HomoPhe, N-Me-Phe, N-Me-Tyr, Ser, Sar, Dihydro Trp, Ile, Leu, Arg, Thr, aromatic amino acids, substituted aromatic amino acids, Gly, Gln, Asn, Asp, Ala, Ile, Leu, Val, Met, Thr, Lys, Trp, Tyr, His, Glu, Arg, Pro, Phe, Sar, 1-Nal, 2-Nal, D-1-Nal, D-2-Nal, HPhe, D-Phe, D-Tyr, Phe(4-F), O-Me-Tyr, dihydro-Trp, Dap, Dab, Dab(Ac), Orn, D-Orn, N-Me-Orn, N-Me-Dap, D-Dap, D-Dab, Bip, Ala(3,3diphenyl), Biphenyl-Ala, aromatic ring substituted Phe, aromatic ring substituted Trp, aromatic ring substituted His, hetero aromatic amino acids, N-Me-Lys, N-Me-Lys (Ac), 4-Me-Phe, Phe(4-OMe), Phe(CF3), Aic, Bpa, Phe(3-Me), Phe(2-Me), Phe(2-CF3), β-Me-Phe, and corresponding D-amino acids and suitable isostere replacements;
$Xaa^{12}$ is absent or selected from the group consisting of aromatic amino acids, substituted aromatic amino acids, Glu, D-Glu, HomoGlu, Beta-Homo-Glu, Asp, D-HomoGlu, Amide, Lys, COOH, CONH₂, Gln, Pro, Gly, His, Ala, Ile, Phe, Arg, Leu, Val, Tyr, Trp, Met, Gla, Ser, Asn, D-Glu, β-HGlu, 2-Nal, 1-Nal, D-Asp, Bip, β-HPhe, β-Glu, D-Tyr, D-Phe, D-Lys, Dap, Dab, Orn, D-Orn, N-Me-Orn, N-Me-Dap, N-Me-Dab, N-Me Lys, D-Dap, D-Dab, D-His, F(4-COOH), Tic, D-Trp, D-Leu, D-Arg, D-Thr, N-Me-Glu, N-Me-Asp, alpha-H-Glu, isosteres, and corresponding D-amino acids;
$Xaa^{13}$ is absent or any amino acid; and
$Xaa^{14}$ is absent or any amino acid;
wherein if the peptide molecule is a peptide dimer or subunit thereof, then $Xaa^{14}$ is absent or selected from the group consisting of: any amino acid with an amine side chain, Lys, D-Lys, N-Me-Lys, D-N-Me-Lys, Orn, N-Me-Orn, Dab, N-Me-Dab, Dap, N-Me-Dap, Homo-Lys, D-Dap, D-Dab, D-Orn, Gln, Pro, Gly, His, Ala, Ile, Phe, Lys, Arg, Leu, Val, Tyr, Trp, Met, Glu, Ser, Asn, Gla, Cys, HomoCys, COOH, CONH₂, suitable isosteres, corresponding D-amino acids, and corresponding N-Methyl amino acids, and
wherein the peptide molecule comprises a thioether bond between $Xaa^4$ and $Xaa^{10}$.

2. The peptide molecule of claim 1, wherein
$Xaa^1$ is absent or any amino acid;
$Xaa^2$ is absent or any amino acid;
$Xaa^3$ is absent or any amino acid;
$Xaa^4$ is a 2-methyl-benzoyl moiety capable of forming a thioether bond with $Xaa^{10}$;
$Xaa^5$ is selected from the group consisting of: N-Me-Arg, Arg, N-Me-Lys, Phe (4-quanidino), Phe(4-carbamoyl amino), Cit, Phe(4-NH2), N-Me-Homo-Arg, Homo-Arg, Tyr and His;
$Xaa^6$ is Ser, Gly, Thr or Ile;
$Xaa^7$ is Asp or D-Asp;
$Xaa^8$ is selected from the group consisting of: Thr, Val, Ile, Leu, hLeu, Nle, and Val;
$Xaa^9$ is selected from the group consisting of: Leu, Nle, Cpa, Cba, HomoLeu, Aoc, and N-Me-Leu;
$Xaa^{10}$ is Pen, Cys, D-Cys or HomoCys; and
$Xaa^{11}$ is absent or selected from the group consisting of: Trp, Phe, 2-Nal, 1-Nal, Tyr, His, Phe(4-F), Phe(4-CF3), Phe (4-CH3), Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Phe (4-carbomyl), Phe(3-Carbomyl), Phe (2-carbomyl), Tyr (Me), HomoPhe, N-Me-Phe, N-Me-Tyr, Sar, Dihydro Trp, Ile, Leu, Arg, Thr, Bpa, Phe(3-Me), Phe(2-Me), Phe(2-CF3), β-Me-Phe, and Ser;
$Xaa^{12}$ is absent or selected from the group consisting of: any aromatic amino acid, Glu, D-Glu, homoGlu, Asp, D-homoGlu, D-Asp, Gla, beta-homo-Glu, N-Me-Glu, N-Me-Asp, alpha-H-Glu, corresponding D-amino acid, and isosteres;
$Xaa^{13}$ is absent or any amino acid; and
$Xaa^{14}$ is any amino acid.

3. The peptide molecule of claim 1, wherein
$Xaa^1$ is absent or any amino acid;
$Xaa^2$ is absent or any amino acid;
$Xaa^3$ is absent or any amino acid;
$Xaa^4$ is a 2-methylbenzoyl moiety capable of forming a thioether bond with $Xaa^{10}$;
$Xaa^5$ is N-Me-Arg;
$Xaa^6$ is Ser, Gly, Thr, or Ile;
$Xaa^7$ is Asp or D-Asp;
$Xaa^8$ is selected from the group consisting of: Thr, Val, Ile, Leu, hLeu and Nle;
$Xaa^9$ is selected from the group consisting of: Leu, Nle, Cpa, Cba, HomoLeu, Aoc, and N-Me-Leu;
$Xaa^{10}$ is Pen, Cys, D-Cys or HomoCys;
$Xaa^{11}$ is selected from the group consisting of: Trp, Phe, 2-Nal, 1-Nal, Tyr, His, Phe(4-F), Phe(4-CF3), Phe (4-CH3), Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Pge(4-carbomyl), Phe(3-Carbomyl), Tyr(Me), HomoPhe, N-Me-Phe, N-Me-Tyr, Dihydro Trp, Ile, Leu, Ser, Arg, Thr, Sar, Bpa, Phe(3-Me), Phe(2-Me), Phe(2-CF3), β-Me-Phe, and any substituted aromatic amino acid and corresponding D-amino acids;

$Xaa^{12}$ is selected from the group consisting of: any aromatic amino acid, Glu, D-Glu, homoGlu, Asp, D-Asp, D-homoGlu, Gla, beta-homo-Glu, N-Me-Glu, N-Me-Asp, alpha-H-Glu, corresponding D-amino acid and isosteres;

$Xaa^{13}$ is absent; and $Xaa^{14}$ is any amino acid.

4. The peptide molecule of claim 1, wherein $Xaa^1$ is absent or any amino acid;

$Xaa^2$ is absent or any amino acid;

$Xaa^3$ is absent or any amino acid;

$Xaa^4$ is a 2-methylbenzoyl moiety capable of forming a thioether bond with $Xaa^{10}$;

$Xaa^5$ is N-Me-Arg;

$Xaa^6$ is Ser, Gly, Thr, or Ile;

$Xaa^7$ is Asp or D-Asp;

$Xaa^8$ is selected from the group consisting of: Thr, Val, Ile, Leu, hLeu and Nle;

$Xaa^9$ is selected from the group consisting of: Leu, Nle, Cpa, Cba, HomoLeu, Aoc, and N-Me-Leu;

$Xaa^{10}$ is Pen, Cys, D-Cys or HomoCys;

$Xaa^{11}$ is selected from the group consisting of: Trp, Phe, 2-Nal, 1-Nal, Tyr, His, Phe(4-F), Phe(4-CF3), Phe (4-CH3), Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Pge(4-carbomyl), Phe(3-Carbomyl), Tyr(Me), HomoPhe, N-Me-Phe, N-Me-Tyr, Dihydro Trp, Ile, Leu, Arg, Thr, Sar, Bpa, Phe(3-Me), Phe(2-Me), Phe(2-CF3), β-Me-Phe, and Ser;

$Xaa^{12}$ is selected from the group consisting of: any aromatic amino acid, Glu, D-Glu, homoGlu, Asp, D-Asp, D-homoGlu, Gla, beta-homo-Glu, N-Me-Glu, N-Me-Asp, alpha-H-Glu, corresponding D-amino acid and isosteres;

$Xaa^{13}$ is absent or any amino acid; and $Xaa^{14}$ is any amino acid.

5. The peptide molecule of claim 1, wherein:

$Xaa^1$ is absent or any amino acid;

$Xaa^2$ is absent or any amino acid;

$Xaa^3$ is absent or any amino acid;

$Xaa^4$ is a 2-methylbenzoyl moiety capable of forming a thioether bond with $Xaa^{10}$;

$Xaa^5$ is N-Me-Arg;

$Xaa^6$ is Ser;

$Xaa^7$ is Asp or D-Asp;

$Xaa^8$ is Thr or Val;

$Xaa^9$ is selected from the group consisting of: Leu, Nle, Cpa, Cba, HomoLeu, Aoc, and N-Me-Leu;

$Xaa^{10}$ is Pen, Cys, D-Cys or HomoCys;

$Xaa^{11}$ is selected from the group consisting of: Trp, Phe, 2-Nal, 1-Nal, Tyr, His, Phe(4-F), Phe(4-CF3), Phe (4-CH3), Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Pge(4-carbomyl), Phe(3-Carbomyl), Tyr(Me), HomoPhe, N-Me-Phe, N-Me-Tyr, Dihydro Trp, Ile, Leu, Arg, Thr, Sar, Bpa, Phe(3-Me), Phe(2-Me), Phe(2-CF3), β-Me-Phe, and Ser;

$Xaa^{12}$ is absent or selected from the group consisting of: any aromatic amino acid, Glu, D-Glu, homoGlu, Asp, D-Asp, D-homoGlu, Gla, beta-homo-Glu, N-Me-Glu, N-Me-Asp, alpha-H-Glu, corresponding D-amino acid and isosteres;

$Xaa^{13}$ is absent; and $Xaa^{14}$ is any amino acid.

6. The peptide molecule of claim 1, wherein:

$Xaa^1$ is absent or any amino acid;

$Xaa^2$ is absent or any amino acid;

$Xaa^3$ is absent or any amino acid;

$Xaa^4$ is a 2-methylbenzoyl moiety capable of forming a thioether bond with $Xaa^{10}$;

$Xaa^5$ is N-Me-Arg;

$Xaa^6$ is Ser;

$Xaa^7$ is Asp or D-Asp;

$Xaa^8$ is Thr or Val;

$Xaa^9$ is selected from the group consisting of: Leu, Nle, Cpa, Cba, HomoLeu, Aoc, and N-Me-Leu;

$Xaa^{10}$ is Pen, Cys, D-Cys or HomoCys;

$Xaa^{11}$ is selected from the group consisting of: Trp, Phe, 2-Nal, 1-Nal, Tyr, His, Phe(4-F), Phe(4-CF3), Phe (4-CH3), Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Pge(4-carbomyl), Phe(3-Carbomyl), Tyr(Me), HomoPhe, N-Me-Phe, N-Me-Tyr, Dihydro Trp, Ile, Leu, Arg, Thr, Sar, Bpa, Phe(3-Me), Phe(2-Me), Phe(2-CF3), β-Me-Phe, and Ser;

$Xaa^{12}$ is absent or selected from the group consisting of: any aromatic amino acid, Glu, D-Glu, beta-homo-Glu, N-Me-Glu, N-Me-Asp, alpha-H-Glu;

$Xaa^{13}$ is absent; and, $Xaa^{14}$ is any amino acid.

7. The peptide molecule of claim 1, wherein:

$Xaa^1$ is absent or any amino acid;

$Xaa^2$ is absent or any amino acid;

$Xaa^3$ is absent or any amino acid;

$Xaa^4$ is a 2-methylbenzoyl moiety capable of forming a thioether bond with $Xaa^{10}$;

$Xaa^5$ is N-Me-Arg;

$Xaa^6$ is Ser;

$Xaa^7$ is Asp or D-Asp;

$Xaa^8$ is Thr or Val;

$Xaa^9$ is Leu;

$Xaa^{10}$ is Pen, Cys, D-Cys or HomoCys;

$Xaa^{11}$ is selected from the group consisting of: Trp, Phe, 2-Nal, 1-Nal, Tyr, His, Phe(4-F), Phe(4-CF3), Phe (4-CH3), Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Pge(4-carbomyl), Phe(3-Carbomyl), Tyr(Me), HomoPhe, N-Me-Phe, N-Me-Tyr, Dihydro Trp, Ile, Leu, Arg, Thr, Sar, Bpa, Phe(3-Me), Phe(2-Me), Phe(2-CF3), β-Me-Phe, and Ser;

$Xaa^{12}$ is selected from the group consisting of: any aromatic amino acid, Glu, D-Glu, beta-homo-Glu, N-Me-Glu, N-Me-Asp, alpha-H-Glu, corresponding D-amino acid and isosteres;

$Xaa^{13}$ is absent; and $Xaa^{14}$ is any amino acid.

8. The peptide molecule of claim 1, wherein:

$Xaa^1$ is absent or any amino acid;

$Xaa^2$ is absent or any amino acid;

$Xaa^3$ is absent or any amino acid;

$Xaa^4$ is a 2-methylbenzoyl moiety capable of forming a thioether bond with $Xaa^{10}$;

$Xaa^5$ is N-Me-Arg;

Xaa⁶ is Ser;
Xaa⁷ is Asp or D-Asp;
Xaa⁸ is Thr or Val;
Xaa⁹ is Leu;
Xaa¹⁰ is Pen, Cys, D-Cys or HomoCys;
Xaa¹¹ is selected from the group consisting of: Trp, Phe, 2-Nal, 1-Nal, Tyr, His, Phe(4-F), Phe(4-CF3), Phe (4-CH3), Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Pge(4-carbomyl), Phe(3-Carbomyl), Tyr(Me), HomoPhe, N-Me-Phe, N-Me-Tyr, Dihydro Trp, Ile, Leu, Arg, Thr, Sar, Bpa, Phe(3-Me), Phe(2-Me), Phe(2-CF3), β-Me-Phe, and Ser;
Xaa¹² is selected from the group consisting of: any aromatic amino acid, Glu, D-Glu, N-Me-Glu, N-Me-Asp, alpha-H-Glu, and beta-homo-Glu;
Xaa¹³ is absent; and
Xaa¹⁴ is any amino acid.

9. The peptide molecule of claim 1, wherein:
Xaa¹ is absent or any amino acid;
Xaa² is absent or any amino acid;
Xaa³ is absent or any amino acid;
Xaa⁴ is a 2-methylbenzoyl moiety capable of forming a thioether bond with Xaa¹⁰;
Xaa⁵ is N-Me-Arg;
Xaa⁶ is Ser;
Xaa⁷ is Asp;
Xaa⁸ is Thr or Val;
Xaa⁹ is Leu;
Xaa¹⁰ is Pen, Cys, D-Cys or HomoCys;
Xaa¹¹ is selected from the group consisting of: Trp, Phe, 2-Nal, 1-Nal, Tyr, His, Phe(4-F), Phe(4-CF3), Phe (4-CH3), Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Pge(4-carbomyl), Phe(3-Carbomyl), Tyr(Me), HomoPhe, N-Me-Phe, N-Me-Tyr, Dihydro Trp, Ile, Leu, Arg, Thr, Sar, Bpa, Phe(3-Me), Phe(2-Me), Phe(2-CF3), β-Me-Phe, and Ser;
Xaa¹² is selected from the group consisting of: any aromatic amino acid, Glu, D-Glu, N-Me-Glu, N-Me-Asp, alpha-H-Glu, and beta-homo-Glu;
Xaa¹³ is absent; and
Xaa¹⁴ is any amino acid.

10. The peptide molecule of claim 1, wherein:
Xaa¹ is absent or any amino acid;
Xaa² is absent or any amino acid;
Xaa³ is absent or any amino acid;
Xaa⁴ is a 2-methylbenzoyl moiety capable of forming a thioether bond with Xaa¹⁰;
Xaa⁵ is N-Me-Arg;
Xaa⁶ is Ser;
Xaa⁷ is Asp or D-Asp;
Xaa⁸ is Thr or Val;
Xaa⁹ is Leu;
Xaa¹⁰ is Pen, Cys, D-Cys or HomoCys;
Xaa¹¹ is selected from the group consisting of: Trp, Phe, 2-Nal, 1-Nal, Tyr, His, Phe(4-F), Phe(4-CF3), Phe (4-CH3), Phe (4-tBu), Bip, Phe(4-COOH), Gly, 3,3-DiPhenylGly, 3,3 diPhenyl Ala, Tic, b-homo-Trp, D-1-Nal, D-2-Nal, Phe(2,4-diCl), Phe(3,4-diCl), Pge(4-carbomyl), Phe(3-Carbomyl), Tyr(Me), Bpa, Phe(3-Me), Phe(2-Me), Phe(2-CF3), β-Me-Phe, and HomoPhe;
Xaa¹² is selected from the group consisting of: any aromatic amino acid, Glu, D-Glu, N-Me-Glu, N-Me-Asp, alpha-H-Glu, and beta-homo-Glu;
Xaa¹³ is absent; and
Xaa¹⁴ is any amino acid.

11. The peptide molecule of claim 1, wherein Xaa¹, Xaa² and Xaa³ are absent.

12. The peptide molecule of claim 1, wherein Xaa⁵ is N-Me-Arg.

13. The peptide molecule of claim 1, wherein Xaa¹⁴ is selected from the group consisting of: Lys, D-Lys, N-Me-Lys, D-N-Me-Lys, Orn, Dab, Dap, Homo-Lys, D-Dap, D-Dab, Cys, HomoCys, Pen, or D-Orn.

14. The peptide molecule of claim 1, wherein Xaa⁴ is a 2-methyl benzoyl moiety that forms a thioether bond with Xaa¹⁰, Xaa⁵ is N-Me-Arg, Xaa⁶ is Ser, Xaa⁷ is Asp, Xaa⁸ is Thr, Xaa⁹ is Leu, and Xaa¹⁰ is Pen, Cys, D-Cys or HomoCys.

15. The peptide molecule of claim 1, wherein Xaa¹⁴ is selected from the group consisting of: D-Lys, N-Me-Lys, and D-N-Me-Lys.

16. The peptide molecule of claim 1, further comprising a terminal modifying group selected from the group consisting of DIG, PEG4, PEG13, PEG25, PEG1K, PEG2K, PEG4K, PEG5K, Polyethylene glycol having molecular weight from 400 Da to 40,000 Da, IDA, Ac-IDA, ADA, Glutaric acid, Isophthalic acid, 1,3-phenylenediacetic acid, 1,4-phenylenediacetic acid, 1,2-phenylenediacetic acid, AADA, suitable aliphatic acids, suitable aromatic acids, and heteroaromatic acids.

17. The peptide molecule of claim 1, wherein the peptide molecule is a dimer comprising two peptide molecules of claim 1 dimerized by a linker.

18. The peptide molecule of claim 17, wherein the linker is selected from the group consisting of: DIG, PEG4, PEG4-biotin, PEG13, PEG25, PEG1K, PEG2K, PEG3.4K, PEG4K, PEG5K, IDA, ADA, Boc-IDA, Glutaric acid, Isophthalic acid, 1,3-phenylenediacetic acid, 1,4-phenylenediacetic acid, 1,2-phenylenediacetic acid, Triazine, Boc-Triazine, IDA-biotin, PEG4-Biotin, AADA, suitable aliphatics, aromatics, heteroaromatics, and polyethylene glycol based linkers having a molecular weight from approximately 400 Da to approximately 40,000 Da.

19. A pharmaceutical composition comprising a peptide molecule of claim 1 and a pharmaceutically acceptable carrier, diluent or excipient.

20. A method for treating a disease or condition that is associated with a biological function of integrin α4β7, the method comprising providing to a subject in need thereof an effective amount of the peptide molecule of claim 1 or pharmaceutical composition of claim 19, wherein the disease or condition is selected from the group consisting of Inflammatory Bowel Disease (IBD), adult IBD, pediatric IBD, adolescent IBD, ulcerative colitis, Crohn's disease, Celiac disease (nontropical Sprue), enteropathy associated with seronegative arthropathies, microscopic colitis, collagenous colitis, eosinophilic gastroenteritis, radiotherapy, chemotherapy, pouchitis resulting after proctocolectomy and ileoanal anastomosis, gastrointestinal cancer, pancreatitis, insulin-dependent diabetes mellitus, mastitis, cholecystitis, cholangitis, pericholangitis, chronic bronchitis, chronic sinusitis, asthma, primary sclerosing cholangitis, human immunodeficiency virus (HIV) infection in the GI tract, eosinophilic asthma, eosinophilic esophagitis, gastritis, colitis, microscopic colitis and graft versus host disease (GVDH).

21. The peptide molecule of claim 17, wherein the linker is bound to the C-termini of the two peptide molecules of claim 1.

22. The peptide molecule of claim 17, wherein the linker is bound to the N-termini of the two peptide molecules of claim 1.

* * * * *

UNITED STATES PATENT AND TRADEMARK OFFICE
CERTIFICATE OF CORRECTION

PATENT NO. : 9,714,270 B2
APPLICATION NO. : 14/714198
DATED : July 25, 2017
INVENTOR(S) : Ashok Bhandari et al.

It is certified that error appears in the above-identified patent and that said Letters Patent is hereby corrected as shown below:

On the Title Page

"(72) Inventors: Ashok Bhandari, Pleasanton, CA (US);
Dinesh V. Patel, Fremont, CA (US);
Genet Zemede, San Jose, CA (US);
Brian Troy Frederick, Ben Lomond, CA (US);
Larry C. Mattheakis, Cupertino, CA (US)"

Should read:
--(72) Inventors: Ashok Bhandari, Pleasanton, CA (US);
Dinesh V. Patel, Fremont, CA (US);
Genet Zemede, San Jose, CA (US);
Brian Troy Frederick, Ben Lomond, CA (US);
Larry C. Mattheakis, Cupertino, CA (US)
David Liu, Milpitas, CA (US)--

Signed and Sealed this
Sixteenth Day of May, 2023

Katherine Kelly Vidal
*Director of the United States Patent and Trademark Office*